(12) United States Patent
Rueger et al.

(10) Patent No.: US 9,550,796 B2
(45) Date of Patent: Jan. 24, 2017

(54) PYRROLOPYRROLONE DERIVATIVES AND THEIR USE AS BET INHIBITORS

(71) Applicants: Heinrich Rueger, Flueh (CH); Jutta Blank, Binzen (DE); Vincent Bordas, Village-Neuf (FR); Simona Cotesta, Basel (CH); Guido Bold, Gipf-Oberfrick (CH); Vito Guagnano, Lecce (IT); Andrea Vaupel, Riehen (CH)

(72) Inventors: Heinrich Rueger, Flueh (CH); Jutta Blank, Binzen (DE); Vincent Bordas, Village-Neuf (FR); Simona Cotesta, Basel (CH); Guido Bold, Gipf-Oberfrick (CH); Vito Guagnano, Lecce (IT); Andrea Vaupel, Riehen (CH)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 15/037,116

(22) PCT Filed: Nov. 20, 2014

(86) PCT No.: PCT/IB2014/066199
§ 371 (c)(1),
(2) Date: May 17, 2016

(87) PCT Pub. No.: WO2015/075665
PCT Pub. Date: May 28, 2015

(65) Prior Publication Data
US 2016/0280719 A1 Sep. 29, 2016

(30) Foreign Application Priority Data

Nov. 21, 2013 (EP) .................................. 13193825

(51) Int. Cl.
| | | |
|---|---|---|
| C07D 487/04 | (2006.01) |
| A61K 31/407 | (2006.01) |
| A61K 31/44 | (2006.01) |
| A61K 31/5377 | (2006.01) |
| A61K 31/506 | (2006.01) |
| A61K 31/41 | (2006.01) |
| A61K 31/4439 | (2006.01) |
| A61K 45/06 | (2006.01) |
| C07D 519/00 | (2006.01) |
| A61K 31/437 | (2006.01) |
| A61K 31/444 | (2006.01) |
| A61K 31/4192 | (2006.01) |
| A61K 31/513 | (2006.01) |
| A61K 31/5025 | (2006.01) |

(52) U.S. Cl.
CPC ......... *C07D 519/00* (2013.01); *A61K 31/4192* (2013.01); *A61K 31/437* (2013.01); *A61K 31/444* (2013.01); *A61K 31/4439* (2013.01); *A61K 31/506* (2013.01); *A61K 31/5025* (2013.01); *A61K 31/513* (2013.01); *C07D 487/04* (2013.01)

(58) Field of Classification Search
CPC .... C07D 487/04; A61K 31/407; A61K 31/44; A61K 31/5377; A61K 31/506; A61K 31/41; A61K 31/4439; A61K 45/06
See application file for complete search history.

(56) References Cited

U.S. PATENT DOCUMENTS

| | | |
|---|---|---|
| 3,829,420 A | 8/1974 | Inaba et al. |
| 3,865,827 A | 2/1975 | Yamamoto et al. |
| 3,923,710 A | 12/1975 | Ishizumi et al. |
| 4,099,002 A | 7/1978 | Inaba et al. |
| 4,258,187 A | 3/1981 | Middleton |
| 4,335,127 A | 6/1982 | Vandenberk et al. |
| 4,695,633 A | 9/1987 | Berneth et al. |
| 6,479,499 B1 | 11/2002 | Kuo et al. |
| 6,734,302 B2 | 5/2004 | Kong et al. |

(Continued)

FOREIGN PATENT DOCUMENTS

| | | |
|---|---|---|
| EP | 1 657 238 A1 | 5/2006 |
| EP | 2 143 713 A1 | 1/2010 |

(Continued)

OTHER PUBLICATIONS

Acharya, B.P. et al., "Friedel-Crafts Acylation with 2-Isocyanatobenzoyl Chlorides: The Structure of the Intermediate Complex," Journal of Chemical Research, Synopses, (4):96-7 (1987)[Abstract only].

(Continued)

*Primary Examiner* — Yong Chu
(74) *Attorney, Agent, or Firm* — Qian Zhang

(57) ABSTRACT

The present invention provides a compound of formula (I) or a pharmaceutically acceptable salt thereof; a method for manufacturing the compounds of the invention, and its therapeutic uses. The present invention further provides a combination of pharmacologically active agents and a pharmaceutical composition.

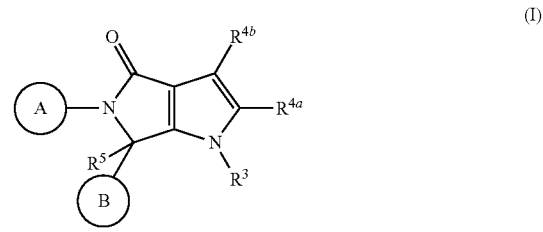

(I)

13 Claims, No Drawings

(56) References Cited

U.S. PATENT DOCUMENTS

| | | |
|---|---|---|
| 7,541,354 B2 | 6/2009 | Fancelli et al. |
| 8,101,644 B2 | 1/2012 | Kai et al. |
| 8,222,288 B2 | 7/2012 | Wang et al. |
| 8,440,693 B2 | 5/2013 | Berghausen et al. |
| 9,365,576 B2 * | 6/2016 | Cotesta ............... A61K 31/407 |
| 2003/0153580 A1 | 8/2003 | Kong et al. |
| 2006/0069085 A1 | 3/2006 | Zhao et al. |
| 2008/0153791 A1 | 6/2008 | Wilckens |
| 2009/0163545 A1 | 6/2009 | Goldfarb |
| 2010/0160356 A1 | 6/2010 | Heinrich et al. |
| 2010/0210632 A1 | 8/2010 | Kai et al. |
| 2011/0183939 A1 | 7/2011 | Kai et al. |
| 2011/0230457 A1 | 9/2011 | Berghausen et al. |
| 2011/0301133 A1 | 12/2011 | Wu et al. |
| 2012/0065210 A1 | 3/2012 | Chu et al. |
| 2013/0245036 A1 | 9/2013 | Berghausen et al. |
| 2013/0281396 A1 | 10/2013 | McLure et al. |
| 2013/0281473 A1 | 10/2013 | Berghausen et al. |
| 2013/0317024 A1 | 11/2013 | Cotesta et al. |
| 2014/0011798 A1 | 1/2014 | Furet et al. |
| 2014/0135306 A1 | 5/2014 | Buschmann et al. |

FOREIGN PATENT DOCUMENTS

| | | |
|---|---|---|
| JP | S5721388 A | 2/1982 |
| JP | 2001-302515 | 10/2001 |
| WO | WO 93/04047 A1 | 3/1993 |
| WO | WO 95/19362 A1 | 7/1995 |
| WO | WO 98/01467 A2 | 1/1998 |
| WO | WO 98/45276 A2 | 10/1998 |
| WO | WO 00/66560 A1 | 11/2000 |
| WO | WO 02/12242 A2 | 2/2002 |
| WO | WO 03/051359 A1 | 6/2003 |
| WO | WO 03/062392 A2 | 7/2003 |
| WO | WO 03/095625 A2 | 11/2003 |
| WO | WO 03/101985 A1 | 12/2003 |
| WO | WO 2004/014916 A1 | 2/2004 |
| WO | WO 2004/094421 A1 | 11/2004 |
| WO | WO 2004/094429 A1 | 11/2004 |
| WO | WO 2004/096134 A2 | 11/2004 |
| WO | WO 2005/027882 A1 | 3/2005 |
| WO | WO 2005/051922 A1 | 6/2005 |
| WO | WO 2005/110996 A1 | 11/2005 |
| WO | WO 2005/117876 A1 | 12/2005 |
| WO | WO 2006/024837 A1 | 3/2006 |
| WO | WO 2006/074262 A1 | 7/2006 |
| WO | WO 2006/097337 A2 | 9/2006 |
| WO | WO 2006/100038 A1 | 9/2006 |
| WO | WO 2006/136606 A2 | 12/2006 |
| WO | WO 2007/068637 A1 | 6/2007 |
| WO | WO 2007/096334 A1 | 8/2007 |
| WO | WO 2007/144384 A1 | 12/2007 |
| WO | WO 2008/034039 A2 | 3/2008 |
| WO | WO 2008/045529 A1 | 4/2008 |
| WO | WO 2008/120725 A1 | 10/2008 |
| WO | WO 2008/130614 A1 | 10/2008 |
| WO | WO 2010/007116 A2 | 1/2010 |
| WO | WO 2010/035727 A1 | 4/2010 |
| WO | WO 2010/047956 A1 | 4/2010 |
| WO | WO 2010/141738 A2 | 12/2010 |
| WO | WO 2011/076786 A1 | 6/2011 |
| WO | WO 2011/161031 A1 | 12/2011 |
| WO | WO 2012/034954 A1 | 3/2012 |
| WO | WO 2012/046030 A2 | 4/2012 |
| WO | WO 2012/065022 A2 | 5/2012 |
| WO | WO 2012/151512 A2 | 11/2012 |
| WO | WO 2012/174487 A2 | 12/2012 |
| WO | WO 2012/175487 A1 | 12/2012 |
| WO | WO 2012/175520 A1 | 12/2012 |
| WO | WO 2013/027168 A1 | 2/2013 |
| WO | WO 2013/033268 A2 | 3/2013 |
| WO | WO 2013/033270 A2 | 3/2013 |
| WO | WO 2013/080141 A1 | 6/2013 |
| WO | WO 2013/097052 A1 | 7/2013 |
| WO | WO 2013/111105 A1 | 8/2013 |
| WO | WO 2013/156869 A1 | 10/2013 |
| WO | WO 2013/158952 A1 | 10/2013 |
| WO | WO 2013/175281 A1 | 11/2013 |
| WO | WO 2013/175417 A1 | 11/2013 |

OTHER PUBLICATIONS

Bahloul, A. et al., "1,3-Dipolar Cycloaddition of Diarylnitrilimines with 4-Arylidene-1,2-Diphenyl-1,4-Dihydro-3(2H)-Isoquinolin-3-Ones," Journal de la Societe Marocaine de Chimie, 2(1):12-17 (French)(1993)[Abstract only].

Chen, R. et al., "Ytterbium(III) Triflate-Catalyzed Stereoselective Synthesis of Beta-lactams via [2+2] Cyclocondensation in Ionic Liquid," Synthetic Communications, 36(21):3167-3174, Taylor & Francis Group, LLC (English)(2006).

Dietz, G. et al.; "Synthesis and Conversion of 3,4-Dihydroquinazolin-4-ols. Part 2: Conversion of 3,4-Dihydroquinazolin-4-ols;" Direktionsber. Forsch. Entwickl., VEB Pharm. Komb. Germed Dresden, Dresden, Ger. Dem. Rep.; Pharmazie; 35(12):751-5 (German)(1980)[Abstract only].

Ishiwaka, N. et al., "o-Aminobenzophenone Derivatives. V. Reactions of 2-Amino-5-Chloro-Benzophenone with Isocyanates and Isothiocyanates," Kagaku Zasshi, 90(9):917-20 (Japanese)(1969)[Abstract only].

Ishiwaka, N. et al., "Reaction of 2-Amino-5-Chlorobenzophenone with P-Substituted Phenyl Isocyanates," Kagaku Zasshi, 91(10):994-7 (Japanese)(1970)[Abstract only].

Ivanov, I. et al., "Polyphosphoric Acid-Induced Construction of Quinazolinone Skeleton from 1-(3,4-Dimethoxyphenyl)-3-Phenylurea and Carboxylic Acids," Heterocycles, 68(7):1443-1449, The Japan Institute of Heterocyclic Chemistry (English)(2006).

Ivanov, I., "Synthesis of 6,7-Dimethoxy-3,4-Diphenyl-2(1H)-Quinazolinone from 1-(3,4-Dimethoxyphenyl)Urea and Benzoic Acid in Polyphosphoric Acid," Molbank M492/1-M492/2 (English)(2006)[Abstract only].

Mollov, N.M. et al., "Internal Alpha-Amidoalkylation Leading to 1,4-Dihydro-3(2H)-Isoquinolinones," Acta Chimica Academiae Scientiarum Hungaricae, 98(3):315-19 (English)(1978).

Mollov, N.M. et al., "Reactivity of Adducts Obtained from Arylacetyl Chloride and Aromatic Schiff Bases," Izvestiya po Khimiya, 10(4):616-20 (English)(1977).

Mollov, N.M. et al., "Synthesis of 3(2H)-isoquinolinones by Means of Inner Alpha-Amidoalkylation," Doklady Bolgarskoi Akademii Nauk, 28(8):1055-7 (English)(1975)[Abstract only].

Mumm, O. et al., "Diacylamides," Berichte der Deutschen Chemischen Gesellschaft, 48:379-91 (1915)[Abstract only].

Pfeiffer, P. et al., "Autoxidation Phenomena in the Anils of the Indandione Series. II," Journal fuer Praktische Chemie (Leipzig), 159:13-35 (1941)[Abstract and Article].

Pfeiffer, P. et al., "Autoxidation Phenomena. VI," Justus Liebigs Annalen der Chemie, 563:73-85 (1949)[Abstract and Article].

Pfeiffer, P. et al., "Autoxidation Reactions. VII," Justus Liebigs Annalen der Chemie, 581:149-59 (1953)[Abstract and Article].

Richter, D., "Anthraquinone Coloring Matters: Ruberythric Acid," Journal of the Chemical Society, 1701-3 (1936).

Richter, P. et al., "Synthesis of Derivatives of 2-Hydrazino-1,4- or 3,4-Dihydroquinazolines," Pharmazie, 45 (10):721-4 (German)(1990)[Abstract only].

Schonberg, A. et al., "Autoxidation Effects in the Indone Series," Naturwissenschaften, 24:620 (1936)[Abstract only].

Schonberg, A. et al., "Autoxidation Phenomena and Valency Tautomerism in the Indone Series," Journal of the Chemical Society, 109-12 (1937).

Venkov, A. et al., "An Improved Synthesis of N-Substituted 1-Aryl-3-Oxo-1,2,3,4-Tetrahydroisoquinolines," Synthesis, 216-17, Stuttgart, New York (English)(1982).

Ventsov, A. et al., "Synthesis of N-Substituted 1,4-Dihydro-3(2H)-Isoquinolinones from 3,4,5-Trimethoxyphenylacety chloride and Schiff Bases," Bolgarskoi Akademii Nauk, 34(10):1405-7 (English)(1981)[Abstract only].

Yamamoto, M. et al., "Synthetic Studies on Quinazoline Derivatives. II. The Reactions of 2-Trichloro- and

(56) References Cited

OTHER PUBLICATIONS

2-Trifluoroacetamidobenzophenones with Primary Amines," Chemical & Pharmaceutical Bulletin, 29(8):2135-56 (English)(1981).
Zhang, Y. et al., "Superacid-Promoted Reactions of N-Acyliminium Ions: An Effective Route to Substituted 3-Oxo-1,2,3,4-Tetrahydroisoquinolines and Related Products," Synthesis (11):1775-1780 (English)(2006).
Zin'kovskaya, V.R. et al., "Ring-chain transformations involving the carbonyl group. XVI. Amides of 2-benzoylphenyl-Alpha,Alpha-dimethylacetic acid," Latvijas PSR Zinatnu, Akademijas Vestis, Kimijas Serija, (1)65-8 (Russian)(1976)[Abstract only].
De Luca et al., "3D Pharmacophore Models for 1,2,3,4-Tetrahydroisoquinoline Derivatives Acting as Anticonvulsant Agents" Arch. Pharm. Chem. Life Sci., 2006, 339, 388-400.
Dudkina, Anna S. et al. "Small Molecule Protein-Protein Inhibitors for the p53-MDM2 Interaction", Current Topics in Medicinal Chemistry, 2007, 7, pp. 952-960.
Shangary, Sanjeev et al., "Targeting the MDM2-p53 Interaction for Cancer Therapy", Clin. Cancer Res., 2008, 14, 5318-5324.
Andreichikov et al., Chemistry of Oxalyl Derivatives of Methyl Ketones XLIV. Synthesis of 4-Aroyl-1,5-Diphenyltetrahydropyrrole-2,3-Diones and their Reaction with Amines and Hydrazine. Journal of Organic Chemistry 1986;22(8):1572-7.
Chung et al., Fragment-based discovery of bromodomain inhibitors part 1: inhibitor binding modes and implications for lead discovery. J Med Chem. Jan. 26, 2012;55(2):576-86.
Dohrn et al., Berichte der Deutschen Chemischen Gesellschaft [Abteilung] B: Abhandlungen. 1931;64B:2863-5.
Filippakopoulos et al., Benzodiazepines and benzotriazepines as protein interaction inhibitors targeting bromodomains of the BET family. Bioorg Med Chem. Mar. 15, 2012;20(6):1878-86.
Filippakopoulos et al., Selective inhibition of BET bromodomains. Nature. Dec. 23, 2010;468(7327):1067-73.
Gein et al., 5-Membered 2,3-Dioxoheterocyclic Compounds. Journal of General Chemistry. 1993;63(10):2324-8.
Gein et al., Reactions of 4-Acyl-1-alkoxyaryl-5-aryl-3-hydroxy-2,5-dihydro-1 H-pyrrol-2-ones with Nucleophilic Reagents. Russian Journal of Organic Chemistry. 2011;47(1):95-9.
Gein et al, "Synthesis and analgesic activity of 5-aryl-4-heteroyl-3-hydroxy-1-(2-thiazolyl)-3-pyrrolin-2-ones and their derivatives" Perm State Pharmaceutical Academy, Perm, 614990, Russia; Pharmaceutical Chemistry Journal (2014), 47(10),539-543.
Jordan, Tamoxifen: a most unlikely pioneering medicine. Nat Rev Drug Discov. Mar. 2003;2(3):205-13.
Hackman et al., Translation of research evidence from animals to humans. JAMA. Oct. 11, 2006;296(14):1731-2.
Lee et al., Novel Pyrrolopyrimidine-Based alpha-Helix Mimetics: Cell Permeable Inhibitors of Protein-Protein Interactions. Journal of the American Chemical Society. 2010;133:676-9.
Miyazaki et al., Lead optimization of novel p53-MDM2 interaction inhibitors possessing dihydroimidazothiazole scaffold. Bioorganic and Medicinal Chemistry Letters. 2013;23:728-32.

No Auhtor Listed, WedMD "Leukemia." Available from: <http://www.webmd.com/cancer/tc/leukemia-prevention?print=true#> @2010.
No Author Listed, American Cancer Society. "Leukemia—Acute Myeloid (Myelogenous)." © 2013. Available from: <http://www.cancer.org/cancer/leukemia-acutemyeloidaml/detailedguide/leukemia-acute-myeloid-myelogenous-whats-aml >.
No Author Listed, Mayo Clinic "Leukemia Medications." Available from: <http://www.drugs.com/condition/leukemia.html> @2013.
No Author Listed, National Cancer Institute. "Drugs Approved for Leukemia." © 2013. Available from: http://www.cancer.gov/cancertopics/druginfo/leukemia/print >.
Richter et al., An Optimised Small-Molecule Stabiliser of the 14-3-3-PMA2 Protein-Protein Interaction. Chem. Eur. J. 2012;18(21):6520-7.
Sun et al., Single-Nucleotide Polymorphisms in p53 Pathway and Aggressiveness of Prostate Cancer in a Caucasian Population. Clin. Cancer Res. 2010;16:5244-51.
Vanotti et al., Cdc7 Kinase Inhibitors: Pyrrolopyrimidinones as Potential Antitumor Agents. 1. Synthesis and Structure-Activity Relationships. Journal of Medicinal Chemistry. 2008;51:487-501.
Wade et al., Targeting Mdm2 and Mdmx in Cancer Therapy: Better Living through Medicinal Chemistry? Mol. Cancer Res. 2009;7:1-11.
Wang et al., Benzimidazole-2-one: A novel anchoring principle for antagonizing p53-Mdm2. Bioorganic & Medicinal Chemistry. 2013;21:3982-95.
Westphal The formation of pyrrolo[3,4-c]pyrazoles. Journal for Practical Chemistry. 1969;311:379-84.
Wu et al., The double bromodomain-containing chromatin adaptor Brd4 and transcriptional regulation. J Biol Chem. May 4, 2007;282(18):13141-5.
Sheng, R. et al, Pharmacophore model construction of p53-MDM2 binding inhibitors, Acta Physico-Chimica Sinica, Aug. 6, 2007, vol. 23, No. 11,p. 1815-1820 (English Abstract included).
Aebi, A. et al, Pharmaceutica Acta Helvetiae, vol. 38, Issue: 7-8, pp. 616-622, Journal, 1963.
Shams El-Dine et al, "Reactions with pyrrolidine-2,4-diones, Part 4: Synthesis of some 3-substituted 1,5-diphenylpyrrolidine-2,4-diones as potential antimicrobial, anti-HIV-1 and antineoplastic agents," Pharmazie. Dec. 2001;56(12):933-7.
Chaudhari, "Preparation and Biological Evaluation of 3-amino-4-aryl-4, 5-dihydro-1-N-tolyl pyrazolo [3, 4-d] pyrimidines Derivative," Oriental Journal of Chemistry (2012), 28(1), 507-512.
Hayat et al., "Synthesis, characterization, antiamoebic activity and cytotoxicity of new pyrazolo[3, 4-d]pyrimidine-6-one derivatives," J Enzyme Inhib Med Chem. Aug. 2011;26(4):472-9.
Akbari et al., "Synthesis and antimicrobial activity of some new pyrazolo[3,4-d]pyrimidines and thiazolo[4,5-d]pyrimidines," Indian Journal of Chemistry, vol. 47B, Mar. 2008, pp. 477-480.
Jarsania et al., "A simple and efficient one pot biginelli condesation of pyrazolo[3,4-d]pyrimidine-ones/thiones," Organic Chemistry: An Indian Journal, Dec. 2007, 3(4),176-179, Sep. 1, 2016.
Kamal et al., "p53-Mdm2 inhibitors: patent review (2009-2010)," Expert Opin Ther Pat. Feb. 2012;22(2):95-105.

* cited by examiner

PYRROLOPYRROLONE DERIVATIVES AND THEIR USE AS BET INHIBITORS

This application is a U.S. National Phase filing of International Application No. PCT/IB2014/066199 filed 20 Nov. 2014, which claims priority to EP Application No. 13193825.0 filed 21 Nov. 2013, the contents of which are incorporated herein by reference in their entirety.

FIELD OF THE INVENTION

The invention provides pyrrolopyrrolone derivatives and their use as BET inhibitors, for the treatment of conditions or diseases such as cancer.

BACKGROUND OF THE INVENTION

BET proteins are proteins encoded by either of the genes BRD2, BRD3, BRD4, or BRDT. Each of these proteins bears two N-terminal bromodomains. Bromodomains comprise of a conserved ~110 amino acid segment found in at least 42 diverse proteins that specifically interact with acetylated lysines that occur for example on histone tails (Filippakopoulos and Knapp, FEBS Letters, 586 (2012), 2692-2704). Histones are a constituent part of chromatin and their covalent modifications including lysine acetylation regulate gene transcription. Bromodomains are thus believed to regulate transcription by recruiting proteins to genes that are marked with specific patterns of lysine acetylation.

Several published reports have linked the BET protein family to diseases including cancer, metabolic disease and inflammation. Oncogenic fusions of BRD4 or BRD3 and the Nuclear protein in Testis (NUT) gene caused by chromosomal translocations are underlying an aggressive cancer named NUT midline carcinoma (French et al., J Clin Oncol, 22 (2004), 4135-9; French et al., J Clin Pathol, 63 (2008), 492-6). The BRD3/4 bromodomains are preserved in these fusion proteins, and their inhibition either by knockdown or with the selective BET bromodomain inhibitor JQ1 leads to death and/or differentiation of these cancer cells both in vitro and in animal tumour models (Filippakopoulos et al., Nature, 468 (2010), 1067-73). JQ1 and several other selective BET inhibitors have been shown to bind to BET bromodomains and thereby prevent acetyl-lysine binding, which prevents BET proteins from interacting with chromatin and thereby regulating transcription. BRD4 was also identified from an RNAi screen as a target in acute myeloid leukemia (AML) (Zuber et al., Nature, 478 (2011), 524-8). This finding was validated in vitro and in vivo using the BET inhibitor JQ1 and another selective BET inhibitor named I-BET151 that is chemically unrelated to JQ1 (Dawson et al., Nature, 478 (2011), 529-33). These and other studies showed that BET inhibitors have broad anti-cancer activity in acute leukemias, multiple myeloma and other hematological malignancies. In several cancer models an acute downregulation of the oncogenic transcription factor Myc upon BET inhibition has been observed (Delmore et al., Cell, 146 (2011), 904-17; Mertz et al., Proc Natl Acad Sci USA, 108 (2011), 16669-74). More recent studies suggest that the therapeutic potential of BET inhibitors extends to other cancer indications, for example lung and brain cancer.

Another BET inhibitor named I-BET762 that is closely related to JQ1 in chemical structure and the manner in which it binds to BET bromodomains, was reported to modulate expression of key inflammatory genes and thereby protect against endotoxic shock and bacteria-induced sepsis in mouse models (Nicodeme et al., Nature, 468 (2010), 1119-23). This body of data has been used to support the clinical evaluation of the BET inhibitor RVX-208 in clinical trials in patients suffering from atherosclerosis, coronary artery disease, dyslipidemia, diabetes, and other cardiovascular diseases (McNeill, Curr Opin Investig Drugs, 3 (2010), 357-64 and www.clinicaltrials.gov), Both RVX-208 and I-BET762 have been shown to upregulate Apolipoprotein A-I, which is critically involved in reducing the tissue levels of cholesterol. Finally, BET proteins have been linked to propagation and transcription regulation of several viruses, and therefore it is believed that BET inhibitors could have anti-viral activity (Weidner-Glunde, Frontiers in Bioscience 15 (2010), 537-549).

In summary, inhibitors of BET bromodomains have therapeutic potential in several human diseases.

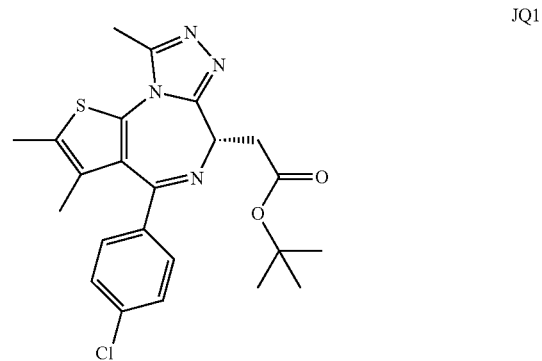

JQ1

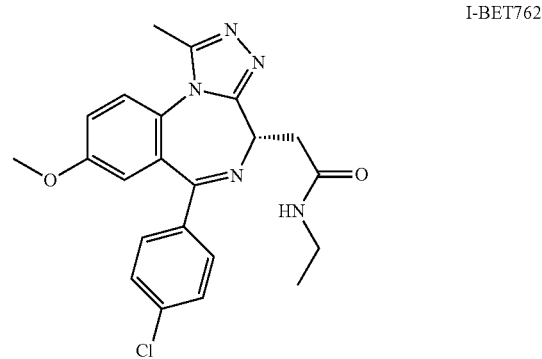

I-BET762

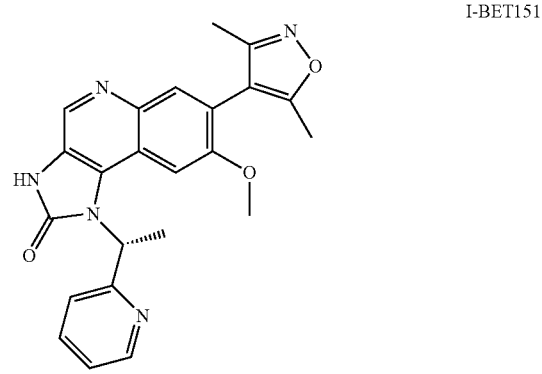

I-BET151

-continued

RVX-208

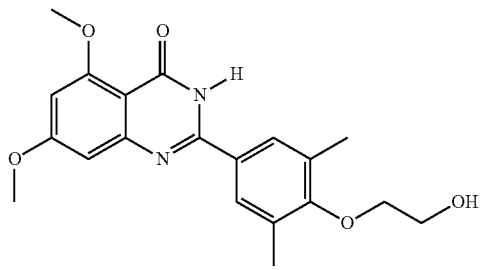

There remains a need for new treatments and therapies for the treatment of cancer. The invention provides compounds as BET inhibitors, pharmaceutically acceptable salts thereof, pharmaceutical compositions thereof and combinations thereof. The invention further provides methods of treating, preventing or ameliorating cancer, comprising administering to a subject in need thereof an effective amount of a BET inhibitor.

Various embodiments of the invention are described herein. Particularly interesting compounds of the invention have good potency in the biological assays described herein. In another aspect they should have a favourable safety profile. In another aspect, they should possess favourable pharmacokinetic properties.

SUMMARY OF THE INVENTION

According to a first aspect of the invention, there is provided a compound of formula (I) or a pharmaceutically acceptable salt thereof,

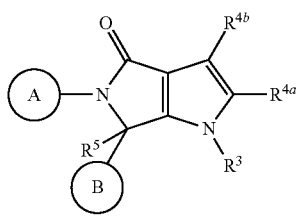

(I)

wherein:
A is selected from

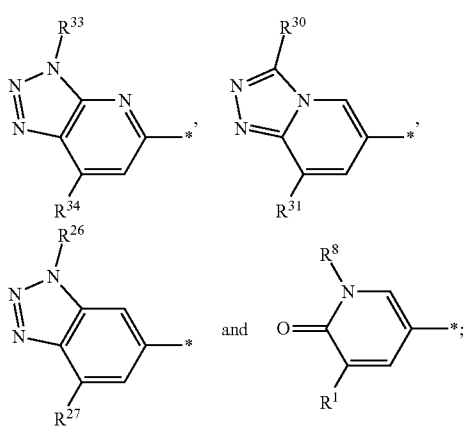

or A is

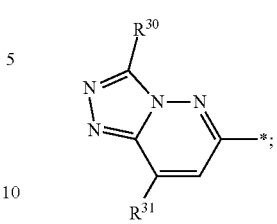

$R^{26}$ is methyl;
$R^{27}$ is methyl;
$R^{30}$ is methyl or $CF_2$;
$R^{31}$ is methyl;
$R^{33}$ is methyl;
$R^{34}$ is methyl;
$R^8$ is $(C_1-C_4)$alkyl;
$R^1$ is selected from H, chloro and methyl;
B is selected from

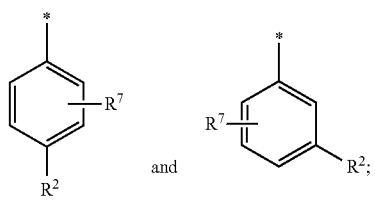

$R^2$ is selected from halo, methoxy, cyano, methyl and H;
$R^5$ is H;
$R^7$ is selected from H and halo;
$R^3$ is selected from H, methyl, ethyl, methoxyethyl, hydroxymethyl, methoxymethyl, hydroxyethyl, —C(O)O—$(C_1-C_2)$alkyl, —C(O)NR$^9$R$^{10}$, cyclopropyl, isopropyl,

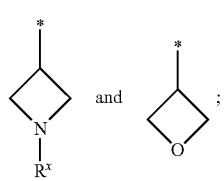

or $R^3$ is selected from —CH$_2$C(O)NR$^9$R$^{10}$, —$(C_1-C_2)$alkyl-NR$^9$R$^{10}$ and

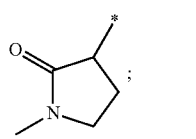 [SMILES: *C1CCN(C)C1=O]

$R^x$ is selected from H, methyl, —C(O)O—$(C_1-C_2)$alkyl, ethyl, isopropyl, —C(O)—$(C_1-C_2)$alkyl, said —C(O)—$(C_1-C_2)$alkyl being optionally substituted by methoxy, or $R^x$ is selected from

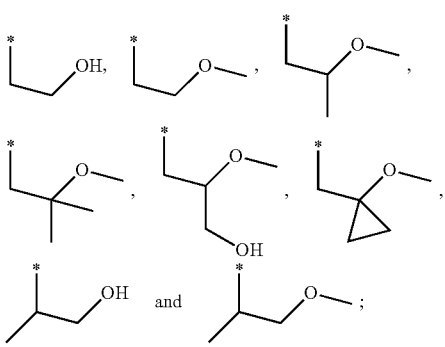

R⁹ is selected from H and methyl;
R¹⁰ is selected from H and methyl;
R⁴ᵃ is selected from H, methyl, cyclopropyl,

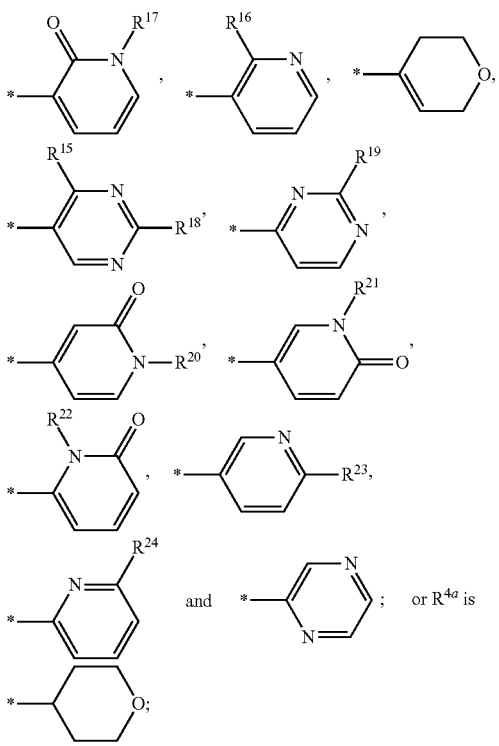

R⁴ᵇ is selected from H, cyclopropyl, methyl, —C(O)NR⁹R¹⁰, —C(O)OH, —NHC(O)—O—(C₁-C₄alkyl), —NHC(O)—(C₁-C₄alkyl) and NR⁹R¹⁰; or R⁴ᵇ is selected from —NHC(O)NR⁹R¹⁰, —C(O)NH(C₁-C₂alkyl)-NR⁹R¹⁰, —NHC(O)—(C₁-C₂alkyl)-NR⁹R¹⁰

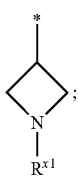

R¹⁵ is selected from methoxy and H;
R¹⁶ is selected from methoxy and hydroxy;
R¹⁷ is methyl;
R¹⁸ is selected from methoxy and —NR⁹R¹⁰;
R¹⁹ is selected from methoxy and CF₃;
R²⁰ is methyl;
R²¹ is methyl;
R²² is methyl;
R²³ is selected from —NR⁹R¹⁰ and methoxy;
R²⁴ is selected from —NR⁹R¹⁰, H and methoxy;
Rˣ¹ is selected from H, methyl and —C(O)—(C₁-C₂)alkyl; and
* indicates the point of attachment to the remainder of the molecule;
with the proviso that
when A is:

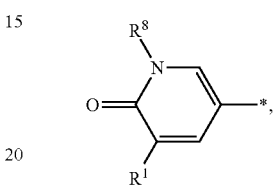

and R³ is selected from ethyl, cyclopropyl and isopropyl, then R⁴ᵃ is selected from

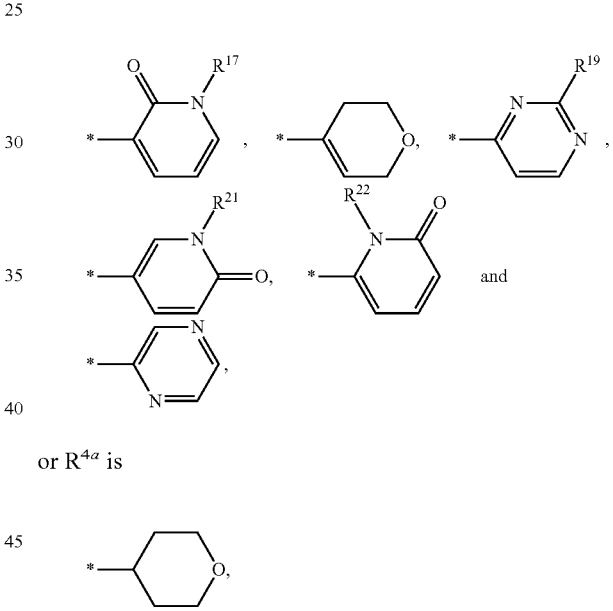

or R⁴ᵃ is

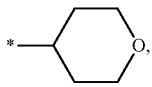

and the remaining substituents are as defined herein.

In another embodiment, the invention provides a pharmaceutical composition comprising a therapeutically effective amount of a compound according to the definition of formula (I), or a pharmaceutically acceptable salt thereof, or subformulae thereof and one or more pharmaceutically acceptable carriers.

In another embodiment, the invention provides a combination, in particular a pharmaceutical combination, comprising a therapeutically effective amount of the compound according to the definition of formula (I), or a pharmaceutically acceptable salt thereof, or subformulae thereof and one or more therapeutically active agent.

DETAILED DESCRIPTION

Described below are a number of embodiments (E) of the first aspect of the invention, where for convenience E1 is identical thereto.

E1 A compound of formula (I) as defined above, or a pharmaceutically acceptable salt thereof.

E1.1 A compound of formula (I) or a pharmaceutically acceptable salt thereof, according to E1, (I)

wherein:

A is selected from $R^{26}$ is methyl;
$R^{27}$ is methyl;
$R^{30}$ is methyl or $CF_2$;
$R^{31}$ is methyl;
$R^{33}$ is methyl;
$R^{34}$ is methyl;
$R^{8}$ is $(C_1$-$C_4)$alkyl;
$R^{1}$ is selected from H, chloro and methyl;
B is selected from $R^{2}$ is selected from halo, methoxy, cyano, methyl and H;
$R^{5}$ is H;
$R^{7}$ is selected from H and halo;
$R^{3}$ is selected from H, methyl, ethyl, methoxyethyl, hydroxymethyl, methoxymethyl, hydroxyethyl, —C(O)O—$(C_1$-$C_2)$alkyl, —C(O)$NR^9R^{10}$, cyclopropyl, isopropyl, $R^x$ is selected from H, methyl, —C(O)O—$(C_1$-$C_2)$alkyl, ethyl, isopropyl, —C(O)—$(C_1$-$C_2)$alkyl, said —C(O)—$(C_1$-$C_2)$alkyl being optionally substituted by methoxy, or $R^x$ is selected from $R^9$ is selected from H and methyl;
$R^{10}$ is selected from H and methyl;
$R^{4a}$ is selected from H, methyl, cyclopropyl, $R^{4b}$ is selected from H, cyclopropyl, methyl, —C(O)$NR^9R^{10}$, —C(O)OH, —NHC(O)—O—$(C_1$-$C_4$alkyl), —NHC(O)—$(C_1$-$C_4$alkyl) and $NR^9R^{10}$;
$R^{15}$ is selected from methoxy and H;
$R^{16}$ is selected from methoxy and hydroxy;
$R^{17}$ is methyl;

$R^{18}$ is selected from methoxy and —$NR^9R^{10}$;
$R^{19}$ is selected from methoxy and $CF_3$;
$R^{20}$ is methyl;
$R^{21}$ is methyl;
$R^{22}$ is methyl;
$R^{23}$ is selected from —$NR^9R^{10}$ and methoxy;
$R^{24}$ is selected from —$NR^9R^{10}$, H and methoxy;
and
* indicates the point of attachment to the remainder of the molecule;
with the proviso that
when A is:

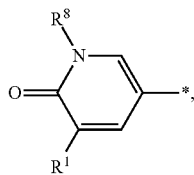

and $R^3$ is selected from ethyl, cyclopropyl and isopropyl, then $R^{4a}$ is selected from

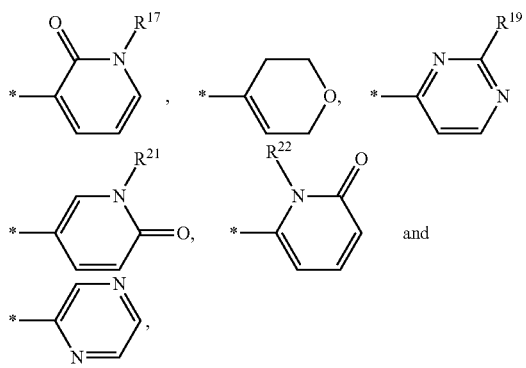

and the remaining substituents are as defined herein.

E2 A compound of formula (I) or a pharmaceutically acceptable salt thereof, according to E1, wherein A is selected from

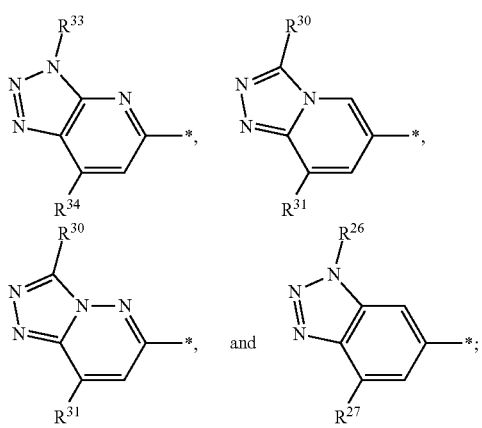

$R^{26}$ is methyl;
$R^{27}$ is methyl;
$R^{30}$ is methyl or $CF_2$;
$R^{31}$ is methyl;
$R^{33}$ is methyl;
$R^{34}$ is methyl;
B is selected from

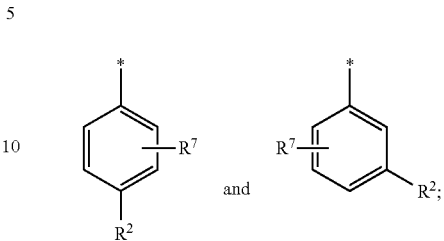

$R^2$ is selected from halo, methoxy, cyano, methyl and H;
$R^5$ is H;
$R^7$ is selected from H and halo;
$R^3$ is selected from H, methyl, ethyl, methoxyethyl, hydroxymethyl, methoxymethyl, hydroxyethyl, —C(O)O—($C_1$-$C_2$)alkyl, —C(O)$NR^9R^{10}$, cyclopropyl, isopropyl,

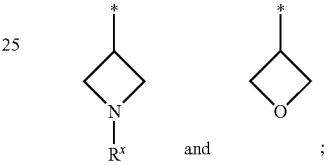

$R^x$ is selected from H, methyl, —C(O)O—($C_1$-$C_2$)alkyl, ethyl, isopropyl, —C(O)—($C_1$-$C_2$)alkyl, said —C(O)—($C_1$-$C_2$)alkyl being optionally substituted by methoxy, or $R^x$ is selected from

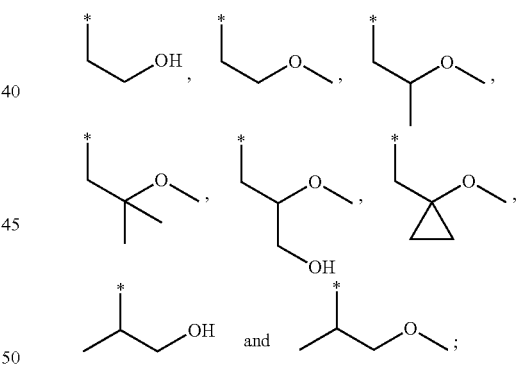

$R^9$ is selected from H and methyl;
$R^{10}$ is selected from H and methyl;
$R^{4a}$ is selected from H, methyl, cyclopropyl,

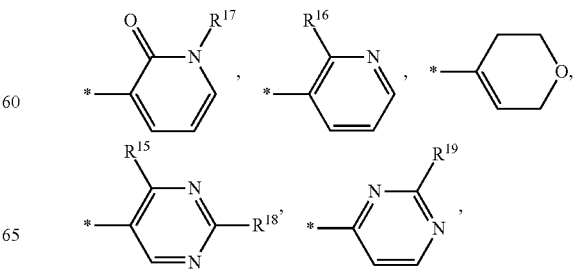

-continued

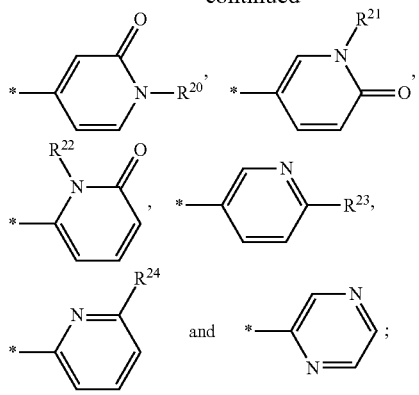

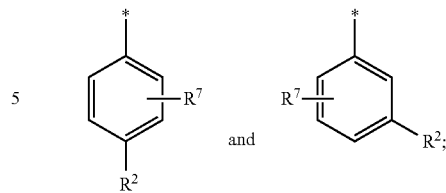

and $R^2$ is selected from halo, methoxy, cyano, methyl and H;
$R^5$ is H;
$R^7$ is selected from H and halo;
$R^3$ is selected from H, methyl, ethyl, methoxyethyl, hydroxymethyl, methoxymethyl, hydroxyethyl, —C(O)O—($C_1$-$C_2$)alkyl, —C(O)$NR^9R^{10}$, cyclopropyl, isopropyl, $R^{4b}$ is selected from H, cyclopropyl, methyl, —C(O)$NR^9R^{10}$, —C(O)OH, —NHC(O)—O—($C_1$-$C_4$alkyl), —C(O)NH($C_1$-$C_2$alkyl)-$NR^9R^{10}$, —NHC(O)—($C_1$-$C_2$alkyl)-$NR^9R^{10}$, —NHC(O)—($C_1$-$C_4$alkyl) and $NR^9R^{10}$;
$R^{15}$ is selected from methoxy and H;
$R^{16}$ is selected from methoxy and hydroxy;
$R^{17}$ is methyl;
$R^{18}$ is selected from methoxy and —$NR^9R^{10}$;
$R^{19}$ is selected from methoxy and $CF_3$;
$R^{20}$ is methyl;
$R^{21}$ is methyl;
$R^{22}$ is methyl;
$R^{23}$ is selected from —$NR^9R^{10}$ and methoxy;
$R^{24}$ is selected from —$NR^9R^{10}$, H and methoxy;
and
* indicates the point of attachment to the remainder of the molecule.

E2.1 A compound of formula (I) or a pharmaceutically acceptable salt thereof, according to any of embodiments E1, E1.1 and E2, wherein
A is selected from

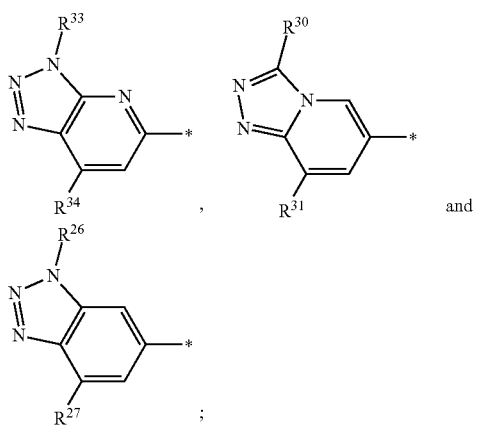

$R^{26}$ is methyl;
$R^{27}$ is methyl;
$R^{30}$ is methyl or $CF_2$;
$R^{31}$ is methyl;
$R^{33}$ is methyl;
$R^{34}$ is methyl;
B is selected from

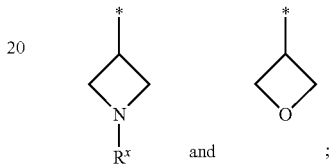

$R^x$ is selected from H, methyl, —C(O)O—($C_1$-$C_2$)alkyl, ethyl, isopropyl, —C(O)—($C_1$-$C_2$)alkyl, said —C(O)—($C_1$-$C_2$)alkyl being optionally substituted by methoxy, or $R^x$ is selected from

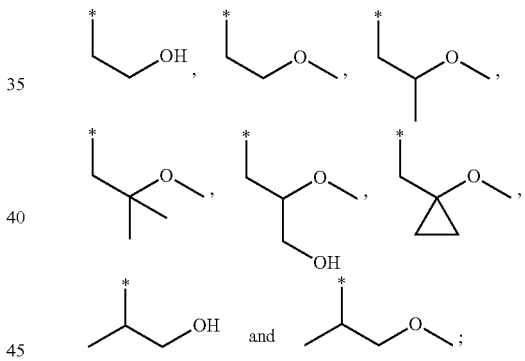

$R^9$ is selected from H and methyl;
$R^{10}$ is selected from H and methyl;
$R^{4a}$ is selected from H, methyl, cyclopropyl,

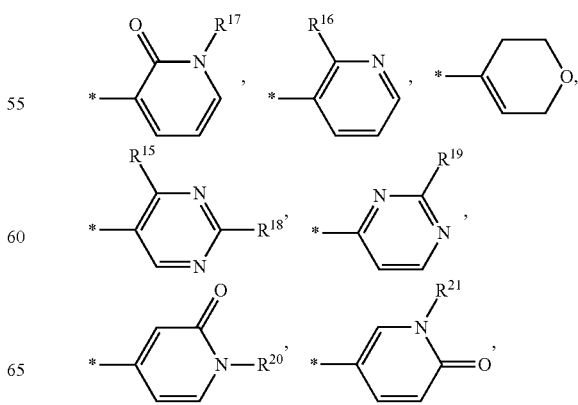

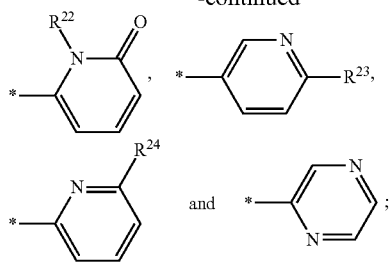

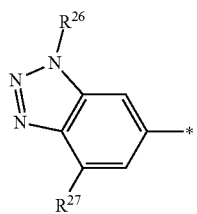

R⁴ᵇ is selected from H, cyclopropyl, methyl, —C(O)NR⁹R¹⁰, —C(O)OH, —NHC(O)—O—(C₁-C₄alkyl), —NHC(O)—(C₁-C₄alkyl) and NR⁹R¹⁰;

R¹⁵ is selected from methoxy and H;

R¹⁶ is selected from methoxy and hydroxy;

R¹⁷ is methyl;

R¹⁸ is selected from methoxy and —NR⁹R¹⁰;

R¹⁹ is selected from methoxy and CF₃;

R²⁰ is methyl;

R²¹ is methyl;

R²² is methyl;

R²³ is selected from —NR⁹R¹⁰ and methoxy;

R²⁴ is selected from —NR⁹R¹⁰, H and methoxy;

and

* indicates the point of attachment to the remainder of the molecule.

E3 A compound of formula (I) or a pharmaceutically acceptable salt thereof, according to E1 or E2 wherein A is selected from:

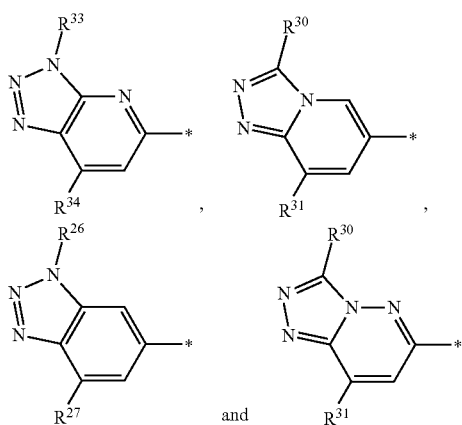

E3.1 A compound of formula (I) or a pharmaceutically acceptable salt thereof, according to any of E1, E1.1 E2, E2.1 and E3, wherein A is selected from:

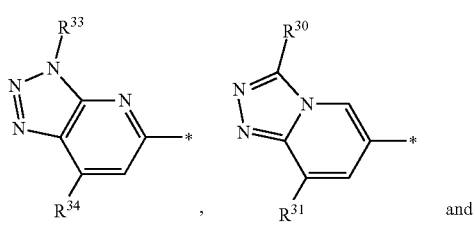

E4 A compound of formula (I) or a pharmaceutically acceptable salt thereof, according to E1, wherein A is selected from:

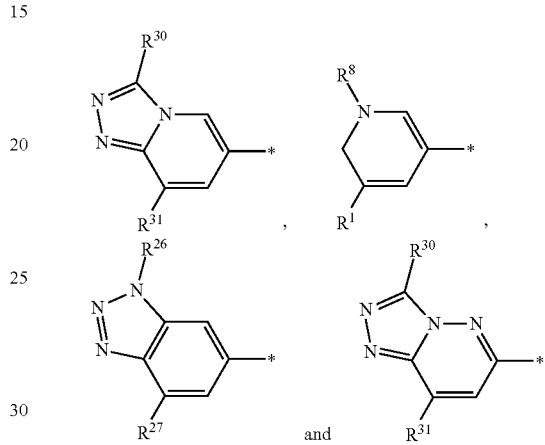

E4.1 A compound of formula (I) or a pharmaceutically acceptable salt thereof, according to E1 or E1.1, wherein A is selected from:

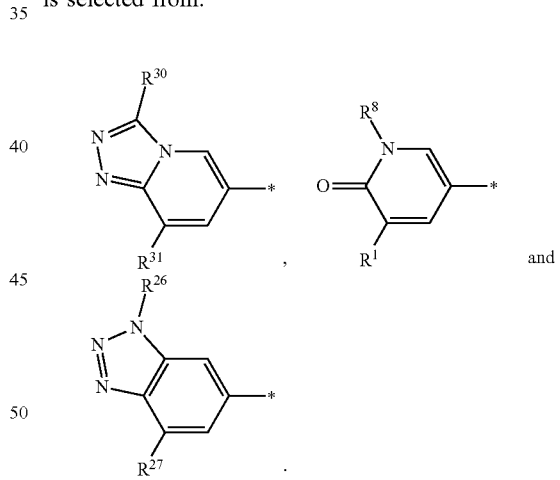

E5 A compound of formula (I) or a pharmaceutically acceptable salt thereof, according to any of E1, E1.1 and E4, wherein A is:

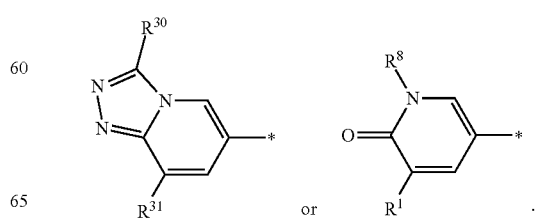

E6 A compound of formula (I) or a pharmaceutically acceptable salt thereof, according to any of E1, E1.1, E2, E2.1, E3, E3.1, E4, E4.1 and E5, wherein A is:

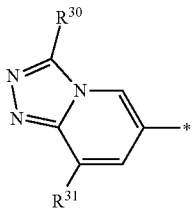

E7 A compound of formula (I) or a pharmaceutically acceptable salt thereof, according to any of E1, E1.1, E2, E2.1, E3, E3.1, E4, E4.1, E5 and E6 wherein A is:

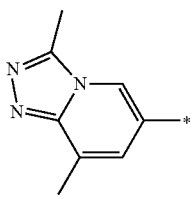

E8 A compound of formula (I) or a pharmaceutically acceptable salt thereof, according to any of E1, E1.1 E4, E4.1 and E5, wherein A is:

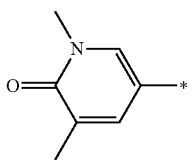

E9 A compound of formula (I) or a pharmaceutically acceptable salt thereof, according to any of E1 to E8, wherein B is:

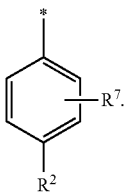

E10 A compound of formula (I) or a pharmaceutically acceptable salt thereof, according to any of E1 to E9, wherein B is:

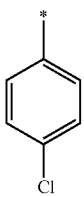

E11 A compound of formula (I) or a pharmaceutically acceptable salt thereof, according to any of E1 to E10, wherein $R^3$ is methyl, —C(O)O—CH$_2$CH$_3$,

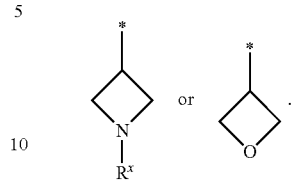

E11.1 A compound of formula (I) or a pharmaceutically acceptable salt thereof, according to any of E1 to E11, wherein $R^3$ is methyl or

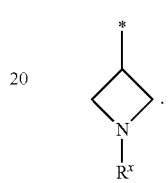

E12 A compound of formula (I) or a pharmaceutically acceptable salt thereof, according to any of E1 to E11.1, wherein $R^x$ is selected from H, methyl, —C(O)O—(C$_1$-C$_2$)alkyl, —C(O)—(C$_1$-C$_2$)alkyl, said —C(O)—(C$_1$-C$_2$)alkyl being optionally substituted by methoxy.

E13 A compound of formula (I) or a pharmaceutically acceptable salt thereof, according to any of E1 to E12, wherein $R^x$ is selected from methyl, —C(O)—CH$_3$ and —C(O)O—CH$_2$CH$_3$.

E14 A compound of formula (I) or a pharmaceutically acceptable salt thereof, according to any of E1 to E13, wherein $R^{4a}$ is selected from H,

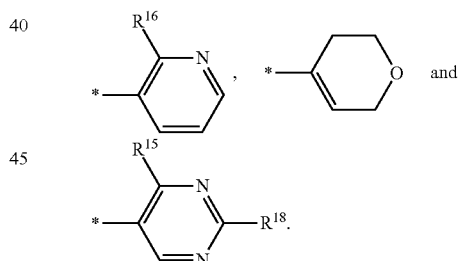

E15 A compound of formula (I) or a pharmaceutically acceptable salt thereof, according to any of E1 to E14, wherein $R^{4a}$ is selected from H,

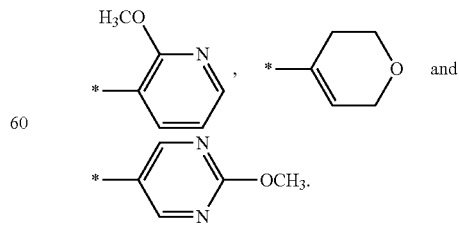

E16 A compound of formula (I) or a pharmaceutically acceptable salt thereof, according to any of E1 to E15, wherein $R^{4b}$ is selected from —C(O)NR$^9$R$^{10}$, cyclopropyl, methyl, H, —NHC(O)—(C$_1$-C$_4$alkyl), —C(O)NH(C$_1$-C$_2$alkyl)-NR$^9$R$^{10}$ and —NHC(O)—(C$_1$-C$_2$alkyl)-NR$^9$R$^{10}$.

E16.1 A compound of formula (I) or a pharmaceutically acceptable salt thereof, according to any of E1 to E16, wherein $R^{4b}$ is selected from —C(O)NR$^9$R$^{10}$, cyclopropyl, methyl, H and —NHC(O)—(C$_1$-C$_4$alkyl).

E17 A compound of formula (I) or a pharmaceutically acceptable salt thereof, according to any of E1 to E16, wherein $R^{4b}$ is selected from —C(O)—NHCH$_3$, cyclopropyl, methyl, H, —NHC(O)—CH$_3$, —C(O)NH—CH$_2$CH$_2$—N(CH$_3$)$_2$ and —NHC(O)—CH$_2$CH$_2$—N(CH$_3$)$_2$.

E18 A compound of formula (I) or a pharmaceutically acceptable salt thereof, according to any of E1 to E17, wherein the compound of formula (I) is formula (Ia):

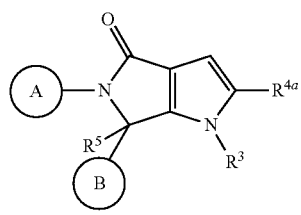

(Ia)

E19 A compound of formula (I) or a pharmaceutically acceptable salt thereof, according to any of E1 to E17, wherein the compound of formula (I) is formula (Ib):

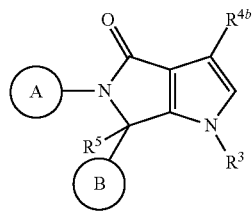

(Ib)

E20 A compound of formula (I) or a pharmaceutically acceptable salt thereof, according to any of E1 to E19, wherein the compound of formula (I) has the stereochemistry of formula (Ic):

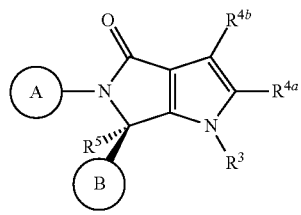

(Ic)

E21 A compound of formula (I) or a pharmaceutically acceptable salt thereof according to E1, wherein A is:

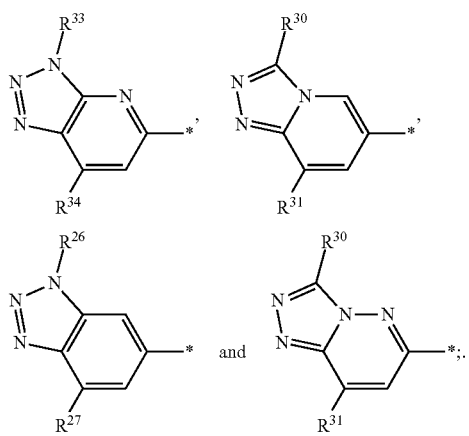

B is:

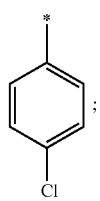

$R^3$ is methyl, —C(O)O—CH$_2$CH$_3$,

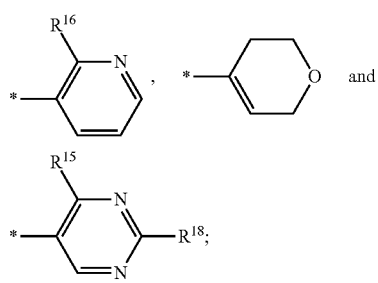

$R^x$ is selected from methyl, —C(O)—CH$_3$ and —C(O)O—CH$_2$CH$_3$;

$R^{4a}$ is selected from H, and $R^{4b}$ is selected from —C(O)NR$^9$R$^{10}$, cyclopropyl, methyl, H, —NHC(O)—(C$_1$-C$_4$alkyl), —C(O)NH(C$_1$-C$_2$alkyl)-NR$^9$R$^{10}$ and —NHC(O)—(C$_1$-C$_2$alkyl)-NR$^9$R$^{10}$.

E21. A compound of formula (I) or a pharmaceutically acceptable salt thereof, according to E1 or E1.1, wherein A is:

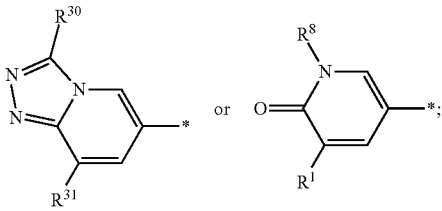

B is:

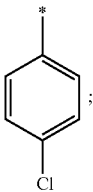

$R^3$ is methyl or

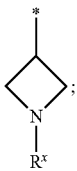

$R^x$ is selected from methyl, —C(O)—CH₃ and —C(O)O—CH₂CH₃;
$R^{4a}$ is selected from H,

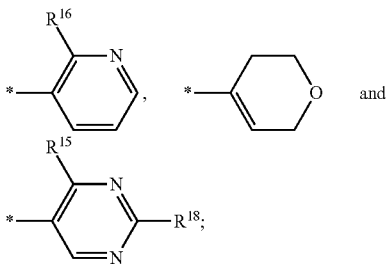

and
$R^{4b}$ is selected from —C(O)NR⁹R¹⁰, cyclopropyl, methyl, H and —NHC(O)—(C₁-C₄alkyl).

E22 A compound of formula (I) according to E1, selected from:

Example 1: 6-(4-chlorophenyl)-3-cyclopropyl-5-(3,7-dimethyl-3H[1,2,3]triazolo[4,5-b]pyridin-5-yl)-1-(hydroxymethyl)-5,6-dihydropyrrolo[3,4-b]pyrrol-4(1H)-one Example 2: 6-(4-chlorophenyl)-5-(3,7-dimethyl-3H-[1,2,3]triazolo[4,5-b]pyridin-5-yl)-1-(methoxymethyl)-3-methyl-5,6-dihydropyrrolo[3,4-b]pyrrol-4(1H)-one Example 3: 6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one Example 4: 1-(azetidin-3-yl)-6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one Example 5: 6-(4-chlorophenyl)-5-(3,8-dimethyl-[1,2,4]triazolo[4,3-a]pyridin-6-yl)-3-methyl-1-(1-methylazetidin-3-yl)-5,6-dihydropyrrolo[3,4-b]pyrrol-4(1H)-one Example 6: 6-(4-chlorophenyl)-5-(3,8-dimethyl-[1,2,4]triazolo[4,3-a]pyridin-6-yl)-3-methyl-1-(oxetan-3-yl)-5,6-dihydropyrrolo[3,4-b]pyrrol-4(1H)-one Example 7: 1-(1-acetylazetidin-3-yl)-6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one Example 8: Ethyl 3-(6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrol-1(4H)-yl)azetidine-1-carboxylate Example 9: 6-(4-chlorophenyl)-5-(3,8-dimethyl-[1,2,4]triazolo[4,3-a]pyridin-6-yl)-N,3-dimethyl-4-oxo-5,6-dihydropyrrolo[3,4-b]pyrrole-1(4H)-carboxamide Example 10: 6-(4-chlorophenyl)-5-(3,8-dimethyl-[1,2,4]triazolo[4,3-a]pyridin-6-yl)-N,N,3-trimethyl-4-oxo-5,6-dihydropyrrolo[3,4-b]pyrrole-1(4H)-carboxamide Example 11: Ethyl 6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrole-1(4H)-carboxylate Example 12: 6-(4-chlorophenyl)-5-(3,8-dimethyl-[1,2,4]triazolo[4,3-a]pyridin-6-yl)-1-(1-(2-methoxyacetyl)azetidin-3-yl)-3-methyl-5,6-dihydropyrrolo[3,4-b]pyrrol-4(1H)-one Example 13: 6-(4-chlorophenyl)-5-(3,8-dimethyl-[1,2,4]triazolo[4,3-a]pyridin-6-yl)-1-(2-methoxyethyl)-3-methyl-5,6-dihydropyrrolo[3,4-b]pyrrol-4(1H)-one Example 14: 6-(4-chlorophenyl)-5-(3,8-dimethyl-[1,2,4]triazolo[4,3-a]pyridin-6-yl)-1-(2-hydroxyethyl)-3-methyl-5,6-dihydropyrrolo[3,4-b]pyrrol-4(1H)-one Example 15: 1-(azetidin-3-yl)-6-(4-chlorophenyl)-3-cyclopropyl-5-(3,8-dimethyl-[1,2,4]triazolo[4,3-a]pyridin-6-yl)-5,6-dihydropyrrolo[3,4-b]pyrrol-4(1H)-one Example 16: 6-(4-chlorophenyl)-3-cyclopropyl-5-(3,8-dimethyl-[1,2,4]triazolo[4,3-a]pyridin-6-yl)-1-(1-methylazetidin-3-yl)-5,6-dihydropyrrolo[3,4-b]pyrrol-4(1H)-one Example 17: 1-(1-acetylazetidin-3-yl)-6-(4-chlorophenyl)-3-cyclopropyl-5-(3,8-dimethyl-[1,2,4]triazolo[4,3-a]pyridin-6-yl)-5,6-dihydropyrrolo[3,4-b]pyrrol-4(1H)-one Example 18: 6-(4-chlorophenyl)-3-cyclopropyl-5-(3,8-dimethyl-[1,2,4]triazolo[4,3-a]pyridin-6-yl)-1-(oxetan-3-yl)-5,6-dihydropyrrolo[3,4-b]pyrrol-4(1H)-one Example 19: 1-(azetidin-3-yl)-6-(4-chlorophenyl)-5-(3,7-dimethyl-3H-[1,2,3]triazolo[4,5-b]pyridin-5-yl)-3-methyl-5,6-dihydropyrrolo[3,4-b]pyrrol-4(1H)-one Example 20: 6-(4-chlorophenyl)-5-(3,7-dimethyl-3H-[1,2,3]triazolo[4,5-b]pyridin-5-yl)-3-methyl-1-(1-methylazetidin-3-yl)-5,6-dihydropyrrolo[3,4-b]pyrrol-4(1H)-one Example 21: 6-(4-chlorophenyl)-5-(3,8-dimethyl-[1,2,4]triazolo[4,3-a]pyridin-6-yl)-5,6-dihydropyrrolo[3,4-b]pyrrol-4(1H)-one Example 22: Ethyl 6-(4-chlorophenyl)-5-(3,8-dimethyl-[1,2,4]triazolo[4,3-a]pyridin-6-yl)-4-oxo-5,6-dihydropyrrolo[3,4-b]pyrrole-1(4H)-carboxylate Example 23: 6-(4-chlorophenyl)-5-(3,8-dimethyl-[1,2,4]triazolo[4,3-a]pyridin-6-yl)-N-methyl-4-oxo-5,6-dihydropyrrolo[3,4-b]pyrrole-1(4H)-carboxamide Example 24: 6-(4-chlorophenyl)-5-(3,8-dimethyl-[1,2,4]triazolo[4,3-a]pyridin-6-yl)-N,N-dimethyl-4-oxo-5,6-dihydropyrrolo[3,4-b]pyrrole-1(4H)-carboxamide Example 25: 6-(4-chlorophenyl)-5-(3,8-dimethyl-[1,2,4]triazolo[4,3-a]pyridin-6-yl)-2-(1-methyl-2-oxo-1,2-dihydropyridin-3-yl)-5,6-dihydropyrrolo[3,4-b]pyrrol-4(1H)-one Example 26: 6-(4-chlorophenyl)-5-(3,8-dimethyl-[1,2,4]triazolo[4,3-a]pyridin-6-yl)-2-(2-hydroxypyridin-3-yl)-5,6-dihydropyrrolo[3,4-b]pyrrol-4(1H)-one Example 27: 6-(4-chlorophenyl)-5-(3,8-dimethyl-[1,2,4]triazolo[4,3-a]pyridin-6-yl)-2-(2-methoxypyridin-3-yl)-5,6-dihydropyrrolo[3,4-b]pyrrol-4(1H)-one Example 28: 6-(4-chlorophenyl)-5-(1,4-dimethyl-1H-benzo[d][1,2,3]triazol-6-yl)-1,3-dimethyl-5,6-dihydropyrrolo[3,4-b]pyrrol-4(1H)-one Example 29: 6-(4-chlorophenyl)-5-(3,8-dimethyl-[1,2,4]triazolo[4,3-a]pyridin-6-yl)-1-methyl-5,6-dihydropyrrolo[3,4-b]pyrrol-4(1H)-one Example 30: 6-(4-chlorophenyl)-5-(3,8-dimethyl-[1,2,4]triazolo[4,3-a]pyridin-6-yl)-2-(2-methoxypyridin-3-yl)-1-methyl-5,6-dihydropyrrolo[3,4-b]pyrrol-4(1H)-one Example 31: 6-(4-chlorophenyl)-2-(3,6-dihydro-2H-pyran-4-yl)-5-(3,8-dimethyl-[1,2,4]triazolo[4,3-a]pyridin-6-yl)-1-methyl-5,6-dihydropyrrolo[3,4-b]pyrrol-4(1H)-one Example 32: 6-(4-chlorophenyl)-5-(3,7-dimethyl-3H-[1,2,3]triazolo[4,5-a]pyridin-5-yl)-1,3-dimethyl-5,6-dihydropyrrolo[3,4-b]pyrrol-4(1H)-one Example 33: 6-(4-chlorophenyl)-5-(3,8-dimethyl-[1,2,4]triazolo[4,3-a]pyridin-6-yl)-1,3-dimethyl-5,6-dihydropyrrolo[3,4-b]pyrrol-4(1H)-one Example 34: 6-(4-chlorophenyl)-5-(1,5-dimethyl-6-oxo-1,6-dihydropyridin-3-yl)-1,3-dimethyl-5,6-dihydropyrrolo[3,4-b]pyrrol-4(1H)-one Example 35: 6-(4-chlorophenyl)-3-cyclopropyl-5-(3,8-dimethyl-[1,2,4]triazolo[4,3-a]pyridin-6-yl)-1-methyl-5,6-dihydropyrrolo[3,4-b]pyrrol-4(1H)-one Example 36: (R)-6-(4-chlorophenyl)-3-cyclopropyl-5-(3,8-dimethyl-[1,2,4]triazolo[4,3-a]pyridin-6-yl)-1-methyl-5,6-dihydropyrrolo[3,4-b]pyrrol-4(1H)-one Example 37: 6-(4-chlorophenyl)-3-cyclopropyl-5-(1,5-dimethyl-6-oxo-1,6-dihydropyridin-3-yl)-1-methyl-5,6-dihydropyrrolo[3,4-b]pyrrol-4(1H)-one Example 38: 5-(5-chloro-1-methyl-6-oxo-1,6-dihydropyridin-3-yl)-6-(4-chlorophenyl)-2-(2,4-dimethoxypyrimidin-5-yl)-1-methyl-5,6-dihydropyrrolo[3,4-b]pyrrol-4(1H)-one Example 39: 5-(5-chloro-1-methyl-6-oxo-1,6-dihydropyridin-3-yl)-6-(4-chlorophenyl)-2-(2-methoxypyrimidin-4-yl)-1-methyl-5,6-dihydropyrrolo[3,4-b]pyrrol-4(1H)-one Example 40: 5-(5-chloro-1-methyl-6-oxo-1,6-dihydropyridin-3-yl)-6-(4-chlorophenyl)-2-(2-methoxypyrimidin-5-yl)-1-methyl-5,6-dihydropyrrolo[3,4-b]pyrrol-4(1H)-one Example 41: 5-(5-chloro-1-methyl-6-oxo-1,6-dihydropyridin-3-yl)-6-(4-chlorophenyl)-1-methyl-2-(1-methyl-2-oxo-1,2-dihydropyridin-4-yl)-5,6-dihydropyrrolo[3,4-b]pyrrol-4(1H)-one Example 42: 5-(5-chloro-1-methyl-6-oxo-1,6-dihydropyridin-3-yl)-6-(4-chlorophenyl)-1-methyl-2-(1-methyl-6-oxo-1,6-dihydropyridin-3-yl)-5,6-dihydropyrrolo[3,4-b]pyrrol-4(1H)-one Example 43: 5-(5-chloro-1-methyl-6-oxo-1,6-dihydropyridin-3-yl)-6-(4-chlorophenyl)-1-methyl-2-(1-methyl-2-oxo-1,2-dihydropyridin-3-yl)-5,6-dihydropyrrolo[3,4-b]pyrrol-4(1H)-one Example 44: 5-(5-chloro-1-methyl-6-oxo-1,6-dihydropyridin-3-yl)-6-(4-chlorophenyl)-1-methyl-2-(1-methyl-6-oxo-1,6-dihydropyridin-2-yl)-5,6-dihydropyrrolo[3,4-b]pyrrol-4(1H)-one Example 45: 6-(4-chlorophenyl)-5-(1,5-dimethyl-6-oxo-1,6-dihydropyridin-3-yl)-1-methyl-2-(1-methyl-2-oxo-1,2-dihydropyridin-4-yl)-5,6-dihydropyrrolo[3,4-b]pyrrol-4(1H)-one Example 46: 6-(4-chlorophenyl)-5-(1,5-dimethyl-6-oxo-1,6-dihydropyridin-3-yl)-1-methyl-2-(1-methyl-6-oxo-1,6-dihydropyridin-3-yl)-5,6-dihydropyrrolo[3,4-b]pyrrol-4(1H)-one Example 47: 6-(4-chlorophenyl)-5-(1,5-dimethyl-6-oxo-1,6-dihydropyridin-3-yl)-1-methyl-2-(1-methyl-2-oxo-1,2-dihydropyridin-3-yl)-5,6-dihydropyrrolo[3,4-b]pyrrol-4(1H)-one Example 48: 6-(4-chlorophenyl)-5-(1,5-dimethyl-6-oxo-1,6-dihydropyridin-3-yl)-1-methyl-2-(1-methyl-6-oxo-1,6-dihydropyridin-2-yl)-5,6-dihydropyrrolo[3,4-b]pyrrol-4(1H)-one Example 49: 6-(4-chlorophenyl)-5-(1,5-dimethyl-6-oxo-1,6-dihydropyridin-3-yl)-1-methyl-2-(2-(trifluoromethyl)pyrimidin-4-yl)-5,6-dihydropyrrolo[3,4-b]pyrrol-4(1H)-one Example 50: 6-(4-chlorophenyl)-5-(1,5-dimethyl-6-oxo-1,6-dihydropyridin-3-yl)-2-(6-(dimethylamino)pyridin-3-yl)-1-methyl-5,6-dihydropyrrolo[3,4-b]pyrrol-4(1H)-one Example 51: 6-(4-chlorophenyl)-5-(1,5-dimethyl-6-oxo-1,6-dihydropyridin-3-yl)-2-(6-(dimethylamino)pyridin-2-yl)-1-methyl-5,6-dihydropyrrolo[3,4-b]pyrrol-4(1H)-one Example 52: 6-(4-chlorophenyl)-5-(1,5-dimethyl-6-oxo-1,6-dihydropyridin-3-yl)-1-methyl-2-(pyridin-2-yl)-5,6-dihydropyrrolo[3,4-b]pyrrol-4(1H)-one Example 53: 6-(4-chlorophenyl)-2-(2,4-dimethoxypyrimidin-5-yl)-5-(1,5-dimethyl-6-oxo-1,6-dihydropyridin-3-yl)-1-methyl-5,6-dihydropyrrolo[3,4-b]pyrrol-4(1H)-one Example 54: (R)-6-(4-chlorophenyl)-2-(2,4-dimethoxypyrimidin-5-yl)-5-(1,5-dimethyl-6-oxo-1,6-dihydropyridin-3-yl)-1-methyl-5,6-dihydropyrrolo[3,4-b]pyrrol-4(1H)-one Example 55: 6-(4-chlorophenyl)-5-(1,5-dimethyl-6-oxo-1,6-dihydropyridin-3-yl)-2-(2-methoxypyrimidin-5-yl)-1-methyl-5,6-dihydropyrrolo[3,4-b]pyrrol-4(1H)-one Example 56: (R)-6-(4-chlorophenyl)-5-(1,5-dimethyl-6-oxo-1,6-dihydropyridin-3-yl)-2-(2-methoxypyrimidin-5-yl)-1-methyl-5,6-dihydropyrrolo[3,4-b]pyrrol-4(1H)-one Example 57: 6-(4-chlorophenyl)-5-(1,5-dimethyl-6-oxo-1,6-dihydropyridin-3-yl)-2-(2-(dimethylamino)pyrimidin-5-yl)-1-methyl-5,6-dihydropyrrolo[3,4-b]pyrrol-4(1H)-one Example 58: 6-(4-chlorophenyl)-5-(1,5-dimethyl-6-oxo-1,6-dihydropyridin-3-yl)-2-(6-methoxypyridin-3-yl)-1-methyl-5,6-dihydropyrrolo[3,4-b]pyrrol-4(1H)-one Example 59: 6-(4-chlorophenyl)-5-(1,5-dimethyl-6-oxo-1,6-dihydropyridin-3-yl)-2-(6-methoxypyridin-2-yl)-1-methyl-5,6-dihydropyrrolo[3,4-b]pyrrol-4(1H)-one Example 62: 5-(5-chloro-1-methyl-6-oxo-1,6-dihydropyridin-3-yl)-6-(4-chlorophenyl)-1-cyclopropyl-2-(1-methyl-6-oxo-1,6-dihydropyridin-2-yl)-5,6-dihydropyrrolo[3,4-b]pyrrol-4(1H)-one Example 63: 6-(4-chlorophenyl)-1-cyclopropyl-5-(1,5-dimethyl-6-oxo-1,6-dihydropyridin-3-yl)-2-(1-methyl-6-oxo-1,6-dihydropyridin-2-yl)-5,6-dihydropyrrolo[3,4-b]pyrrol-4(1H)-one Example 64: 5-(5-chloro-1-methyl-6-oxo-1,6-dihydropyridin-3-yl)-6-(4-chlorophenyl)-1-cyclopropyl-2-(1-methyl-2-oxo-1,2-dihydropyridin-3-yl)-5,6-dihydropyrrolo[3,4-b]pyrrol-4(1H)-one Example 65: 6-(4-chlorophenyl)-1-cyclopropyl-5-(1,5-dimethyl-6-oxo-1,6-dihydropyridin-3-yl)-2-(1-methyl-2-oxo-1,2-dihydropyridin-3-yl)-5,6-dihydropyrrolo[3,4-b]pyrrol-4(1H)-one Example 66: 5-(5-chloro-1-methyl-6-oxo-1,6-dihydropyridin-3-yl)-6-(4-chlorophenyl)-1-cyclopropyl-2-(1-methyl-6-oxo-1,6-dihydropyridin-3-yl)-5,6-dihydropyrrolo[3,4-b]pyrrol-4(1H)-one Example 67: 6-(4-chlorophenyl)-1-cyclopropyl-5-(1,5-dimethyl-6-oxo-1,6-dihydropyridin-3-yl)-2-(1-methyl-6-oxo-1,6-dihydropyridin-3-yl)-5,6-dihydropyrrolo[3,4-b]pyrrol-4(1H)-one Example 68: 6-(4-chlorophenyl)-2-cyclopropyl-5-(1,5-dimethyl-6-oxo-1,6-dihydropyridin-3-yl)-1-methyl-5,6-dihydropyrrolo[3,4-b]pyrrol-4(1H)-one Example 69: 6-(4-chlorophenyl)-5-(1,5-dimethyl-6-oxo-1,6-dihydropyridin-3-yl)-1,2-dimethyl-5,6-dihydropyrrolo[3,4-b]pyrrol-4(1H)-one Example 72: 6-(4-chlorophenyl)-5-(1,5-dimethyl-6-oxo-1,6-dihydropyridin-3-yl)-1-methyl-5,6-dihydropyrrolo[3,4-b]pyrrol-4(1H)-one Example 74: 5-(5-chloro-1-methyl-6-oxo-1,6-dihydropyridin-3-yl)-6-(4-chlorophenyl)-1,2-dimethyl-5,6-dihydropyrrolo[3,4-b]pyrrol-4(1H)-one Example 75: (R)-5-(5-chloro-1-methyl-6-oxo-1,6-dihydropyridin-3-yl)-6-(4-chlorophenyl)-1,2-dimethyl-5,6-dihydropyrrolo[3,4-b]pyrrol-4(1H)-one Example 76: 5-(5-chloro-1-methyl-6-oxo-1,6-dihydropyridin-3-yl)-6-(4-chlorophenyl)-1-methyl-5,6-dihydropyrrolo[3,4-b]pyrrol-4(1H)-one Example 77: (R)-5-(5-chloro-1-methyl-6-oxo-1,6-dihydropyridin-3-yl)-6-(4-chlorophenyl)-1-methyl-5,6-dihydropyrrolo[3,4-b]pyrrol-4(1H)-one Example 78: 6-(4-chlorophenyl)-1-methyl-5-(1-methyl-6-oxo-1,6-dihydropyridin-3-yl)-5,6-dihydropyrrolo[3,4-b]pyrrol-4(1H)-one Example 79: 5-(1,5-dimethyl-6-oxo-1,6-dihydropyridin-3-yl)-1-methyl-6-phenyl-5,6-dihydropyrrolo[3,4-b]pyrrol-4(1H)-one Example 80: 6-(4-chloro-3-fluorophenyl)-5-(1,5-dimethyl-6-oxo-1,6-dihydropyridin-3-yl)-1-methyl-5,6-dihydropyrrolo[3,4-b]pyrrol-4(1H)-one Example 81: 5-(1,5-dimethyl-6-oxo-1,6-dihydropyridin-3-yl)-1-methyl-6-(p-tolyl)-5,6-dihydropyrrolo[3,4-b]pyrrol-4(1H)-one Example 82: 5-(1,5-dimethyl-6-oxo-1,6-dihydropyridin-3-yl)-6-(4-fluorophenyl)-1-methyl-5,6-dihydropyrrolo[3,4-b]pyrrol-4(1H)-one Example 83: 4-(5-(1,5-dimethyl-6-oxo-1,6-dihydropyridin-3-yl)-1-methyl-4-oxo-1,4,5,6-tetrahydropyrrolo[3,4-b]pyrrol-6-yl)benzonitrile Example 84: 5-(1,5-dimethyl-6-oxo-1,6-dihydropyridin-3-yl)-6-(4-methoxyphenyl)-1-methyl-5,6-dihydropyrrolo[3,4-b]pyrrol-4(1H)-one Example 85: 5-(1,5-dimethyl-6-oxo-1,6-dihydropyridin-3-yl)-6-(3-methoxyphenyl)-1-methyl-5,6-dihydropyrrolo[3,4-b]pyrrol-4(1H)-one Example 86: 5-(5-chloro-1-methyl-6-oxo-1,6-dihydropyridin-3-yl)-1-methyl-6-phenyl-5,6-dihydropyrrolo[3,4-b]pyrrol-4(1H)-one Example 87: 5-(5-chloro-1-methyl-6-oxo-1,6-dihydropyridin-3-yl)-1-methyl-6-(p-tolyl)-5,6-dihydropyrrolo[3,4-b]pyrrol-4(1H)-one Example 88: 5-(5-chloro-1-methyl-6-oxo-1,6-dihydropyridin-3-yl)-6-(4-fluorophenyl)-1-methyl-5,6-dihydropyrrolo[3,4-b]pyrrol-4(1H)-one Example 89: 4-(5-(5-chloro-1-methyl-6-oxo-1,6-dihydropyridin-3-yl)-1-methyl-4-oxo-1,4,5,6-tetrahydropyrrolo[3,4-b]pyrrol-6-yl)benzonitrile Example 90: 5-(5-chloro-1-methyl-6-oxo-1,6-dihydropyridin-3-yl)-6-(4-chloro-3-fluorophenyl)-1-methyl-5,6-dihydropyrrolo[3,4-b]pyrrol-4(1H)-one Example 91: 5-(5-chloro-1-methyl-6-oxo-1,6-dihydropyridin-3-yl)-6-(3-methoxyphenyl)-1-methyl-5,6-dihydropyrrolo[3,4-b]pyrrol-4(1H)-one Example 92: 5-(5-chloro-1-methyl-6-oxo-1,6-dihydropyridin-3-yl)-6-(4-methoxyphenyl)-1-methyl-5,6-dihydropyrrolo[3,4-b]pyrrol-4(1H)-one Example 93: 6-(4-chlorophenyl)-5-(3,7-dimethyl-3H-[1,2,3]triazolo[4,5-b]pyridin-5-yl)-N,1-dimethyl-4-oxo-1,4,5,6-tetrahydropyrrolo[3,4-b]pyrrole-3-carboxamide Example 94: 6-(4-chlorophenyl)-5-(3,7-dimethyl-3H-[1,2,3]triazolo[4,5-b]pyridin-5-yl)-N,N,1-trimethyl-4-oxo-1,4,5,6-tetrahydropyrrolo[3,4-b]pyrrole-3-carboxamide Example 95: Tert-butyl (6-(4-chlorophenyl)-5-(3,7-dimethyl-3H-[1,2,3]triazolo[4,5-b]pyridin-5-yl)-1-methyl-4-oxo-1,4,5,6-tetrahydropyrrolo[3,4-b]pyrrol-3-yl)carbamate Example 96: N-(6-(4-chlorophenyl)-5-(3,7-dimethyl-3H-[1,2,3]triazolo[4,5-b]pyridin-5-yl)-1-methyl-4-oxo-1,4,5,6-tetrahydropyrrolo[3,4-b]pyrrol-3-yl)acetamide Example 97: Ethyl (6-(4-chlorophenyl)-5-(3,7-dimethyl-3H-[1,2,3]triazolo[4,5-b]pyridin-5-yl)-1-methyl-4-oxo-1,4,5,6-tetrahydropyrrolo[3,4-b]pyrrol-3-yl)carbamate Example 98: 6-(4-chlorophenyl)-5-(1,4-dimethyl-1H-benzo[d][1,2,3]triazol-6-yl)-N,1-dimethyl-4-oxo-1,4,5,6-tetrahydropyrrolo[3,4-b]pyrrole-3-carboxamide Example 99: 6-(4-chlorophenyl)-5-(3,8-dimethyl-[1,2,4]triazolo[4,3-a]pyridin-6-yl)-N,1-dimethyl-4-oxo-1,4,5,6-tetrahydropyrrolo[3,4-b]pyrrole-3-carboxamide Example 100: 6-(4-chlorophenyl)-5-(3,8-dimethyl-[1,2,4]triazolo[4,3-a]pyridin-6-yl)-N,N,1-trimethyl-4-oxo-1,4,5,6-tetrahydropyrrolo[3,4-b]pyrrole-3-carboxamide Example 101: 6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrole-3-carboxamide Example 102: Tert-butyl (6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)carbamate Example 103: N-(6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)acetamide Example 104: 6-(4-chlorophenyl)-3-cyclopropyl-5-(3,7-dimethyl-3H-[1,2,3]triazolo[4,5-b]pyridin-5-yl)-1-(oxetan-3-yl)-5,6-dihydropyrrolo[3,4-b]pyrrol-4(1H)-one Example 105: 1-(1-acetylazetidin-3-yl)-6-(4-chlorophenyl)-3-cyclopropyl-5-(3,7-dimethyl-3H-[1,2,3]triazolo[4,5-b]pyridin-5-yl)-5,6-dihydropyrrolo[3,4-b]pyrrol-4(1H)-one Example 106: 6-(4-chlorophenyl)-3-cyclopropyl-5-(3,7-dimethyl-3H-[1,2,3]triazolo[4,5-b]pyridin-5-yl)-1-(1-methylazetidin-3-yl)-5,6-dihydropyrrolo[3,4-b]pyrrol-4(1H)-one, Example 107: 6-(4-chlorophenyl)-5-(3-(difluoromethyl)-8-methyl-[1,2,4]triazolo[4,3-a]pyridin-6-yl)-1,3-dimethyl-5,6-dihydropyrrolo[3,4-b]pyrrol-4(1H)-one, Example 108: 6-(4-chlorophenyl)-5-(3-(difluoromethyl)-8-methyl-[1,2,4]triazolo[4,3-b]pyridazin-6-yl)-N,1-dimethyl-4-oxo-1,4,5,6-tetrahydropyrrolo[3,4-b]pyrrole-3-carboxamide Example 109: N-(6-(4-chlorophenyl)-5-(3-(difluoromethyl)-8-methyl-[1,2,4]triazolo[4,3-b]pyridazin-6-yl)-1-methyl-4-oxo-1,4,5,6-tetrahydropyrrolo[3,4-b]pyrrol-3-yl)acetamide Example 110: N-(6-(4-chlorophenyl)-5-(3-(difluoromethyl)-8-methyl-[1,2,4]triazolo[4,3-b]pyridazin-6-yl)-1-methyl-4-oxo-1,4,5,6-tetrahydropyrrolo[3,4-b]pyrrol-3-yl)-3-(dimethylamino)propanamide Example 111: 1-(6-(4-chlorophenyl)-5-(3-(difluoromethyl)-8-methyl-[1,2,4]triazolo[4,3-b]pyridazin-6-yl)-1-methyl-4-oxo-1,4,5,6-tetrahydropyrrolo[3,4-b]pyrrol-3-yl)-3-methylurea Example 112: 6-(4-chlorophenyl)-5-(1,4-dimethyl-1H-benzo[d][1,2,3]triazol-6-yl)-N-(2-(dimethylamino)ethyl)-1-methyl-4-oxo-1,4,5,6-tetrahydropyrrolo[3,4-b]pyrrole-3-carboxamide Example 113: N-(6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrol-3-yl)acetamide Example 114: 1-(6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrol-3-yl)-3-methylurea Example 115: N-(6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrol-3-yl)-3-(dimethylamino)propanamide Example 116: N-(6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)-2-(dimethylamino)acetamide Example 117: 3-(1-acetylazetidin-3-yl)-6-(4-chlorophenyl)-5-(3,8-dimethyl-[1,2,4]triazolo[4,3-a]pyridin-6-yl)-1-methyl-5,6-dihydropyrrolo[3,4-b]pyrrol-4(1H)-one Example 118: 6-(4-chlorophenyl)-5-(3,8-dimethyl-[1,2,4]triazolo[4,3-a]pyridin-6-yl)-1-methyl-3-(1-methylazetidin-3-yl)-5,6-dihydropyrrolo[3,4-b]pyrrol-4(1H)-one Example 119: 6-(4-chlorophenyl)-3-cyclopropyl-2-(3,6-dihydro-2H-pyran-4-yl)-5-(3,8-dimethyl-[1,2,4]triazolo[4,3-a]pyridin-6-yl)-1-methyl-5,6-dihydropyrrolo[3,4-b]pyrrol-4(1H)-one Example 120: 6-(4-chlorophenyl)-3-cyclopropyl-5-(3,8-dimethyl-[1,2,4]triazolo[4,3-a]pyridin-6-yl)-2-(2-methoxypyridin-3-yl)-1-methyl-5,6-dihydropyrrolo[3,4-b]pyrrol-4(1H)-one Example 121: 6-(4-chlorophenyl)-5-(3,8-dimethyl-[1,2,4]triazolo[4,3-a]pyridin-6-yl)-1-methyl-2-(tetrahydro-2H-pyran-4-yl)-5,6-dihydropyrrolo[3,4-b]pyrrol-4(1H)-one Example 122: 6-(4-chlorophenyl)-3-cyclopropyl-5-(3,8-dimethyl-[1,2,4]triazolo[4,3-a]pyridin-6-yl)-1,2-dimethyl-5,6-dihydropyrrolo[3,4-b]pyrrol-4(1H)-one Example 123: Ethyl 6-(4-chlorophenyl)-2-(3,6-dihydro-2H-pyran-4-yl)-5-(3,8-dimethyl-[1,2,4]triazolo[4,3-a]pyridin-6-yl)-3-methyl-4-oxo-5,6-dihydropyrrolo[3,4-b]pyrrole-1(4H)-carboxylate Example 124: Ethyl 6-(4-chlorophenyl)-5-(3,8-dimethyl-[1,2,4]triazolo[4,3-a]pyridin-6-yl)-2-(2-methoxypyridin-3-yl)-3-methyl-4-oxo-5,6-dihydropyrrolo[3,4-b]pyrrole-1(4H)-carboxylate Example 125: Ethyl 6-(4-chlorophenyl)-3-cyclopropyl-5-(3,8-dimethyl-[1,2,4]triazolo[4,3-a]pyridin-6-yl)-4-oxo-5,6-dihydropyrrolo[3,4-b]pyrrole-1(4H)-carboxylate Example 126: 6-(4-chlorophenyl)-5-(3,8-dimethyl-[1,2,4]triazolo[4,3-a]pyridin-6-yl)-3-methyl-1-(1-methyl-2-oxopyrrolidin-3-yl)-5,6-dihydropyrrolo[3,4-b]pyrrol-4(1H)-one Example 127: 2-(6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrol-1(4H)-yl)-N-methylacetamide Example 128: 6-(4-chlorophenyl)-5-(3,8-dimethyl-[1,2,4]triazolo[4,3-a]pyridin-6-yl)-1-(2-(dimethylamino)ethyl)-3-methyl-5,6-dihydropyrrolo[3,4-b]pyrrol-4(1H)-one Example 129: 2-(6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrol-1(4H)-yl)-N,N-dimethylacetamide Example 130: 3-(azetidin-3-yl)-6-(4-chlorophenyl)-5-(3,7-dimethyl-3H-[1,2,3]triazolo[4,5-b]pyridin-5-yl)-1-methyl-5,6-dihydropyrrolo[3,4-b]pyrrol-4(1H)-one Example 131: 6-(4-chlorophenyl)-5-(3,8-dimethyl-[1,2,4]triazolo[4,3-b]pyridazin-6-yl)-1-methyl-5,6-dihydropyrrolo[3,4-b]pyrrol-4(1H)-one Example 132: 6-(4-chlorophenyl)-5-(3-(difluoromethyl)-8-methyl-[1,2,4]triazolo[4,3-a]pyridin-6-yl)-N,1-dimethyl-4-oxo-1,4,5,6-tetrahydropyrrolo[3,4-b]pyrrole-3-carboxamide Example 133: N-(6-(4-chlorophenyl)-5-(3-(difluoromethyl)-8-methyl-[1,2,4]triazolo[4,3-a]pyridin-6-yl)-1-methyl-4-oxo-1,4,5,6-tetrahydropyrrolo[3,4-b]pyrrol-3-yl)acetamide Example 134: N-(6-(4-chlorophenyl)-5-(3-(difluoromethyl)-8-methyl-[1,2,4]triazolo[4,3-a]pyridin-6-yl)-1-methyl-4-oxo-1,4,5,6-tetrahydropyrrolo[3,4-b]pyrrol-3-yl)-2-(dimethylamino)acetamide Example 135: (R)-6-(4-chlorophenyl)-5-(3,8-dimethyl-[1,2,4]triazolo[4,3-a]pyridin-6-yl)-2-(2-methoxypyridin-3-yl)-1-methyl-5,6-dihydropyrrolo[3,4-b]pyrrol-4(1H)-one Example 136: (R)—N-(6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)acetamide and Example 137: (R)-6-(4-chlorophenyl)-2-(3,6-dihydro-2H-pyran-4-yl)-5-(3,8-dimethyl-[1,2,4]triazolo[4,3-a]pyridin-6-yl)-1-methyl-5,6-dihydropyrrolo[3,4-b]pyrrol-4(1H)-one, or a pharmaceutically acceptable salt thereof.

E23 A compound of formula (I) or a pharmaceutically acceptable salt thereof, according to E1, selected from:

Example 99: 6-(4-chlorophenyl)-5-(3,8-dimethyl-[1,2,4]triazolo[4,3-a]pyridin-6-yl)-N,1-dimethyl-4-oxo-1,4,5,6-tetrahydropyrrolo[3,4-b]pyrrole-3-carboxamide Example 16: 6-(4-chlorophenyl)-3-cyclopropyl-5-(3,8-dimethyl-[1,2,4]triazolo[4,3-a]pyridin-6-yl)-1-(1-methylazetidin-3-yl)-5,6-dihydropyrrolo[3,4-b]pyrrol-4(1H)-one Example 17: 1-(1-acetylazetidin-3-yl)-6-(4-chlorophenyl)-3-cyclopropyl-5-(3,8-dimethyl-[1,2,4]triazolo[4,3-a]pyridin-6-yl)-5,6-dihydropyrrolo[3,4-b]pyrrol-4(1H)-one Example 11: Ethyl 6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrole-1(4H)-carboxylate Example 8: Ethyl 3-(6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrol-1(4H)-yl)azetidine-1-carboxylate Example 5: 6-(4-chlorophenyl)-5-(3,8-dimethyl-[1,2,4]triazolo[4,3-a]pyridin-6-yl)-3-methyl-1-(1-methylazetidin-3-yl)-5,6-dihydropyrrolo[3,4-b]pyrrol-4(1H)-one Example 6: 6-(4-chlorophenyl)-5-(3,8-dimethyl-[1,2,4]triazolo[4,3-a]pyridin-6-yl)-3-methyl-1-(oxetan-3-yl)-5,6-dihydropyrrolo[3,4-b]pyrrol-4(1H)-one Example 30: 6-(4-chlorophenyl)-5-(3,8-dimethyl-[1,2,4]triazolo[4,3-a]pyridin-6-yl)-2-(2-methoxypyridin-3-yl)-1-methyl-5,6-dihydropyrrolo[3,4-b]pyrrol-4(1H)-one Example 31: 6-(4-chlorophenyl)-2-(3,6-dihydro-2H-pyran-4-yl)-5-(3,8-dimethyl-[1,2,4]triazolo[4,3-a]pyridin-6-yl)-1-methyl-5,6-dihydropyrrolo[3,4-b]pyrrol-4(1H)-one Example 56: (R)-6-(4-chlorophenyl)-5-(1,5-dimethyl-6-oxo-1,6-dihydropyridin-3-yl)-2-(2-methoxypyrimidin-5-yl)-1-methyl-5,6-dihydropyrrolo[3,4-b]pyrrol-4(1H)-one, and Example 103: N-(6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)acetamide, Example 33: 6-(4-chlorophenyl)-5-(3,8-dimethyl-[1,2,4]triazolo[4,3-a]pyridin-6-yl)-1,3-dimethyl-5,6-dihydropyrrolo[3,4-b]pyrrol-4(1H)-one Example 36: (R)-6-(4-chlorophenyl)-3-cyclopropyl-5-(3,8-dimethyl-[1,2,4]triazolo[4,3-a]pyridin-6-yl)-1-methyl-5,6-dihydropyrrolo[3,4-b]pyrrol-4(1H)-one Example 93: 6-(4-chlorophenyl)-5-(3,7-dimethyl-3H-[1,2,3]triazolo[4,5-b]pyridin-5-yl)-N,1-dimethyl-4-oxo-1,4,5,6-tetrahydropyrrolo[3,4-b]pyrrole-3-carboxamide Example 98: 6-(4-chlorophenyl)-5-(1,4-dimethyl-1H-benzo[d][1,2,3]triazol-6-yl)-N,1-dimethyl-4-oxo-1,4,5,6-tetrahydropyrrolo[3,4-b]pyrrole-3-carboxamide Example 112: 6-(4-chlorophenyl)-5-(1,4-dimethyl-1H-benzo[d][1,2,3]triazol-6-yl)-N-(2-(dimethylamino)ethyl)-1-methyl-4-oxo-1,4,5,6-tetrahydropyrrolo[3,4-b]pyrrole-3-carboxamide, Example 115: N-(6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrol-3-yl)-3-(dimethylamino)propanamide, Example 131: 6-(4-chlorophenyl)-5-(3,8-dimethyl-[1,2,4]triazolo[4,3-b]pyridazin-6-yl)-1-methyl-5,6-dihydropyrrolo[3,4-b]pyrrol-4(1H)-one, Example 132: 6-(4-chlorophenyl)-5-(3-(difluoromethyl)-8-methyl-[1,2,4]triazolo[4,3-a]pyridin-6-yl)-N,1-dimethyl-4-oxo-1,4,5,6-tetrahydropyrrolo[3,4-b]pyrrole-3-carboxamide, Example 135: (R)-6-(4-chlorophenyl)-5-(3,8-dimethyl-[1,2,4]triazolo[4,3-a]pyridin-6-yl)-2-(2-methoxypyridin-3-yl)-1-methyl-5,6-dihydropyrrolo[3,4-b]pyrrol-4(1H)-one, Example 136: (R)—N-(6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)acetamide, Example 137: (R)-6-(4-chlorophenyl)-2-(3,6-dihydro-2H-pyran-4-yl)-5-(3,8-dimethyl-[1,2,4]triazolo[4,3-a]pyridin-6-yl)-1-methyl-5,6-dihydropyrrolo[3,4-b]pyrrol-4(1H)-one, or a pharmaceutically acceptable salt thereof.

E24 A compound of formula (I), according to E1, selected from:

Example 99: 6-(4-chlorophenyl)-5-(3,8-dimethyl-[1,2,4]triazolo[4,3-a]pyridin-6-yl)-N,1-dimethyl-4-oxo-1,4,5,6-tetrahydropyrrolo[3,4-b]pyrrole-3-carboxamide Example 11: Ethyl 6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrole-1(4H)-carboxylate Example 5: 6-(4-chlorophenyl)-5-(3,8-dimethyl-[1,2,4]triazolo[4,3-a]pyridin-6-yl)-3-methyl-1-(1-methylazetidin-3-yl)-5,6-dihydropyrrolo[3,4-b]pyrrol-4(1H)-one Example 6: 6-(4-chlorophenyl)-5-(3,8-dimethyl-[1,2,4]triazolo[4,3-a]pyridin-6-yl)-3-methyl-1-(oxetan-3-yl)-5,6-dihydropyrrolo[3,4-b]pyrrol-4(1H)-one Example 33: 6-(4-chlorophenyl)-5-(3,8-dimethyl-[1,2,4]triazolo[4,3-a]pyridin-6-yl)-1,3-dimethyl-5,6-dihydropyrrolo[3,4-b]pyrrol-4(1H)-one Example 36: (R)-6-(4-chlorophenyl)-3-cyclopropyl-5-(3,8-dimethyl-[1,2,4]triazolo[4,3-a]pyridin-6-yl)-1-methyl-5,6-dihydropyrrolo[3,4-b]pyrrol-4(1H)-one Example 93: 6-(4-chlorophenyl)-5-(3,7-dimethyl-3H-[1,2,3]triazolo[4,5-b]pyridin-5-yl)-N,1-dimethyl-4-oxo-1,4,5,6-tetrahydropyrrolo[3,4-b]pyrrole-3-carboxamide Example 98: 6-(4-chlorophenyl)-5-(1,4-dimethyl-1H-benzo[d][1,2,3]triazol-6-yl)-N,1-dimethyl-4-oxo-1,4,5,6-tetrahydropyrrolo[3,4-b]pyrrole-3-carboxamide Example 112: 6-(4-chlorophenyl)-5-(1,4-dimethyl-1H-benzo[d][1,2,3]triazol-6-yl)-N-(2-(dimethylamino)ethyl)-1-methyl-4-oxo-1,4,5,6-tetrahydropyrrolo[3,4-b]pyrrole-3-carboxamide, Example 115: N-(6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrol-3-yl)-3-(dimethylamino)propanamide, Example 131: 6-(4-chlorophenyl)-5-(3,8-dimethyl-[1,2,4]triazolo[4,3-b]pyridazin-6-yl)-1-methyl-5,6-dihydropyrrolo[3,4-b]pyrrol-4(1H)-one, Example 132: 6-(4-chlorophenyl)-5-(3-(difluoromethyl)-8-methyl-[1,2,4]triazolo[4,3-a]pyridin-6-yl)-N,1-dimethyl-4-oxo-1,4,5,6-tetrahydropyrrolo[3,4-b]pyrrole-3-carboxamide, Example 135: (R)-6-(4-chlorophenyl)-5-(3,8-dimethyl-[1,2,4]triazolo[4,3-a]pyridin-6-yl)-2-(2-methoxypyridin-3-yl)-1-methyl-5,6-dihydropyrrolo[3,4-b]pyrrol-4(1H)-one, Example 136: (R)—N-(6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)acetamide, Example 137: (R)-6-(4-chlorophenyl)-2-(3,6-dihydro-2H-pyran-4-yl)-5-(3,8-dimethyl-[1,2,4]triazolo[4,3-a]pyridin-6-yl)-1-methyl-5,6-dihydropyrrolo[3,4-b]pyrrol-4(1H)-one, or a pharmaceutically acceptable salt thereof.

The present disclosure includes compounds of stereochemistry as shown in formula (Id):

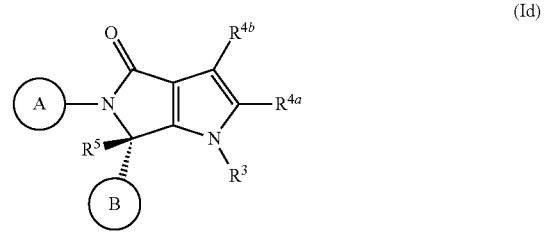

Unless specified otherwise, the term "compounds of the present invention" refers to compounds of formula (I) and subformulae thereof, and salts thereof, as well as all stereoisomers (including diastereoisomers and enantiomers), rotamers, tautomers and isotopically labeled compounds (including deuterium substitutions), as well as inherently formed moieties.

Various embodiments of the invention are described herein. It will be recognized that features specified in each embodiment may be combined with other specified features to provide further embodiments of the present invention.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

In another aspect, the present invention provides compounds of formula I in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$, $^{31}P$, $^{32}P$, $^{35}S$, $^{36}Cl$, $^{123}I$, $^{124}I$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labelled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by BET proteins, or (ii) associated with BET protein activity, or (iii) characterized by activity (normal or abnormal) of BET proteins; or (2) reduce or inhibit the activity of BET proteins; or (3) reduce or inhibit the expression of BET. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of BET proteins; or at least partially reducing or inhibiting the expression of BET proteins.

A "BET protein" is a protein encoded by either of the genes BRD2, BRD3, BRD4, or BRDT". Unless indicated otherwise "BET proteins" or "BET protein" are used herein in the singular and plural forms interchangeably, and the use of either is not limiting. Unless indicated otherwise "BET proteins" includes all, or any combination of, such encoded proteins.

As used herein, the term "($C_3$-$C_6$)cycloalkyl" refers to saturated monocyclic hydrocarbon groups of 3-6 carbon atoms. Exemplary $C_{3-6}$cycloalkyl groups include, but are not limited to, cyclopropyl, cyclobutyl, cyclopentyl and cyclohexyl.

As used herein, the term "($C_1$-$C_4$)alkyl" refers to a fully saturated branched or unbranched hydrocarbon moiety having 1 to 4 carbon atoms. Representative examples of $C_{1-4}$alkyl include methyl, ethyl, n-propyl, iso-propyl, n-butyl, sec-butyl, iso-butyl and tert-butyl.

"halo" or "halogen" means fluoro, chloro, bromo, in particular fluoro and chloro.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

Compositions:

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. For purposes of the present invention, unless designated otherwise, solvates and hydrates are generally considered compositions. Preferably, pharmaceutically acceptable carriers are sterile. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The compounds of formula I in free form or in pharmaceutically acceptable salt form, exhibit valuable pharmacological properties, e.g. BET protein modulating properties, e.g. as indicated in tests as provided in the next sections, and are therefore indicated for therapy or for use as research chemicals, e.g. as tool compounds.

Having regard to their activity as BET inhibitors, compounds of the formula (I) in free or pharmaceutically acceptable salt form, are useful in the treatment of conditions which are mediated by the activity of BET proteins, such as cancer, and/or that are responsive (meaning especially in a therapeutically beneficial way) to inhibition of a BET protein, most especially a disease or disorder as mentioned herein below.

Compounds of the invention are believed to be useful in the treatment of diseases or disorders such as cancer. In particular, such cancers include benign or malignant tumours, a soft tissue sarcoma or a sarcoma such as liposarcoma, rhabdomyosarcoma or bone cancer, e.g. osteosarcoma, a carcinoma, such as of the brain, kidney, liver, adrenal gland, bladder, breast, gastric, ovary, colon, rectum, prostate, pancreas, lung (including small cell lung cancer), vagina or thyroid, a glioblastoma, meningioma, glioma, mesothelioma, a neuroendocrine tumor such as neuroblastoma, a multiple myeloma, a gastrointestinal cancer, especially colon carcinoma or colorectal adenoma, a tumor of the head and neck, a melanoma, a prostate hyperplasia, a neoplasia, a neoplasia of epithelial character, a neoplasia originating from blood or bone marrow, a leukemia such as acute myeloid leukemia (AML) or acute lymphoblastic leukemia (ALL) or B-cell chronic lymphocytic leukemia, a lymphoma, such as of B- or T-cell origin, such as diffuse large B cell lymphoma (DLBCL), NUT midline carcinoma or any other neoplasia with chromosomal rearrangements of the BET genes, and metastases in other organs.

Compounds of the invention may also be of use in the treatment of atherosclerosis, coronary artery disease, dyslipidemia, diabetes, and other cardiovascular diseases, and/or as antiviral agents.

Thus, as a further embodiment, the present invention provides the use of a compound of formula (I) or a salt thereof, in therapy. In a further embodiment, the therapy is selected from a disease which may be treated by inhibition of BET proteins. In another embodiment, the disease is a cancer disease selected from the afore-mentioned list.

Thus, as a further embodiment, the present invention provides a compound of formula (I) or a salt thereof, for use in therapy. In a further embodiment, the therapy is selected from a disease which may be treated by inhibition of a BET protein. In another embodiment, the disease is a cancer disease selected from the afore-mentioned list.

In another embodiment, the invention provides a method of treating a disease which is treated by inhibition of a BET protein, comprising administration of a therapeutically acceptable amount of a compound of formula (I) or salt thereof. In a further embodiment, the disease is a cancer disease selected from the afore-mentioned list.

Thus, as a further embodiment, the present invention provides the use of a compound of formula (I) or salt thereof, for the manufacture of a medicament. In a further embodiment, the medicament is for treatment of a disease which may be treated by inhibition of a BET protein. In another embodiment, the disease is a cancer disease selected from the afore-mentioned list.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

Combinations

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by a BET protein. Products provided as a combined preparation include a composition comprising the compound of formula (I) and the other therapeutic agent(s) together in the same pharmaceutical composition, or the compound of formula (I) and the other therapeutic agent(s) in separate form, e.g. in the form of a kit.

In one embodiment, the invention provides a pharmaceutical composition comprising a compound of formula (I) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of formula (I) for treating a disease or condition mediated by a BET protein, wherein the medicament is prepared for administration with another therapeutic agent. The invention also provides the use of another therapeutic agent for treating a disease or condition mediated by a BET protein, wherein the medicament is administered with a compound of formula (I).

The invention also provides a compound of formula (I) for use in a method of treating a disease or condition mediated by a BET protein, wherein the compound of formula (I) is prepared for administration with another therapeutic agent. The invention also provides another therapeutic agent for use in a method of treating a disease or condition mediated by a BET protein, wherein the other therapeutic agent is prepared for administration with a compound of formula (I). The invention also provides a compound of formula (I) for use in a method of treating a disease or condition mediated by a BET protein, wherein the compound of formula (I) is administered with another therapeutic agent. The invention also provides another therapeutic agent for use in a method of treating a disease or condition mediated by a BET protein, wherein the other therapeutic agent is administered with a compound of formula (I).

The invention also provides the use of a compound of formula (I) for treating a disease or condition mediated by a BET protein, wherein the patient has previously (e.g. within 24 hours) been treated with another therapeutic agent. The invention also provides the use of another therapeutic agent for treating a disease or condition mediated by a BET protein, wherein the patient has previously (e.g. within 24 hours) been treated with a compound of formula (I).

In one embodiment, the other therapeutic agent is an anticancer agent.

In a further embodiment, the other therapeutic agent is a modulator of a target in the field of epigenetics, such as an inhibitor of histone deacetylase (HDAC), or an inhibitor of histone methyltransferase (HMT).

Generic Schemes

Typically, the compounds of formula (I) can be prepared according to the Schemes provided infra.

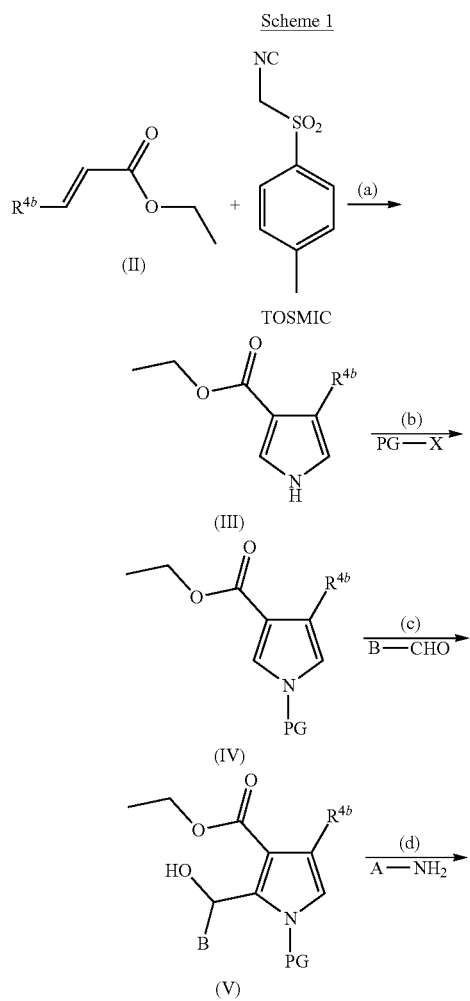

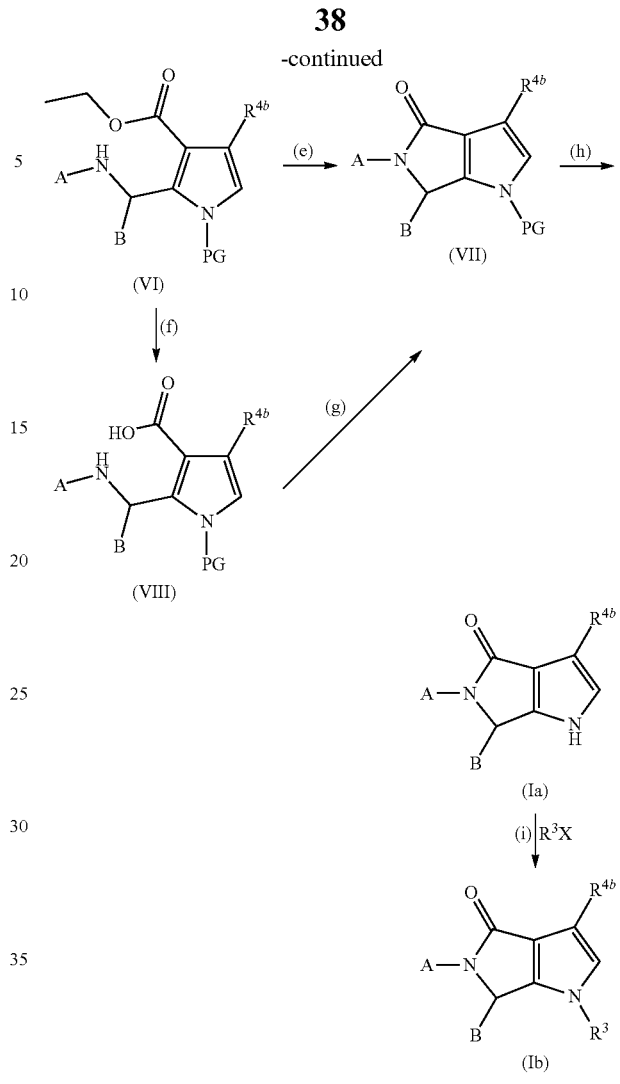

PG = protecting group

Scheme 1 illustrates one method for preparing compounds of the present invention (e.g. Example 1) when $R^{4a}$ is H.

Step (a) involves reaction of an ethyl acrylate with p-tolylsulfonylmethyl isocyanide (TOSMIC) in the presence of sodium hydride and in a suitable solvent mixture such as diethyl ether/dimethyl sulfoxide. Step (b) involves the protection of a pyrrole with a suitable protecting group (PG), a step well known in the art. When the PG is SEM, the pyrrole is treated with a suitable base such as sodium hydride and with SEMCl (2-(Trimethylsilyl)ethoxymethyl chloride) in a suitable solvent such as DMF at a suitable temperature (0°—room temperature (rt)). Step (c) involves the deprotonation of a protected pyrrole with a suitable base such as LDA, followed by addition of an aldehyde in a suitable solvent such as THF at −78° C. Step (d) involves the conversion of an alcohol into a leaving group. When the leaving group is a mesylate, methanesulfonic anhydride in the presence of an organic base such as triethylamine is used. When the leaving group is a chloride, 1-chloro-N,N,2-trimethylpropenylamine is used in the presence of an organic base such as triethylamine in a suitable solvent such as DCM at a suitable temperature (0°—rt). Step (e) involves the reaction with dimethyl aluminium chloride in a suitable solvent such as toluene at a suitable temperature (100-120° C.). Step (f) involves the saponification of the ester group on treatment with a base such as an alkali metal hydroxide (e.g. lithium hydroxide or sodium hydroxide) in a solvent such as wet cycloalkylether or alcohol (e.g. dioxane/water or methanol/water), at room temperature. Step (g) involves the formation of a lactam by treatment of an amino acid with 1-chloro-N,N,2-trimethylpropenylamine in a suitable solvent such as DCM at room temperature. Step (h) involves the removal of a suitable protecting group PG, a step well known in the art. For example, when PG is SEM, a compound is treated with TFA or aqueous HCl at a suitable temperature such as room temperature and subsequently with an aqueous solution of NaOH. Step (i) involves alkylation (e.g. Example 4) or formation of ureas and carbamates (e.g. Examples 9-11) with suitable reagents and according to methods well known in the art.

Step (b) involves the reduction of an azide to the corresponding amine by catalytic hydrogenation using a suitable catalyst such as Ra—Ni and a suitable solvent such as ethanol.

Step (c) involves the reaction with dimethyl aluminium chloride in a suitable solvent such as toluene at a suitable temperature (100-120° C.).

Step (d) involves the coupling reaction with a suitable halide in the presence of CuI, N,N'-dimethylethylenediamine and potassium triphosphate in a suitable solvent such as dioxane and at a suitable temperature such as 100° C.

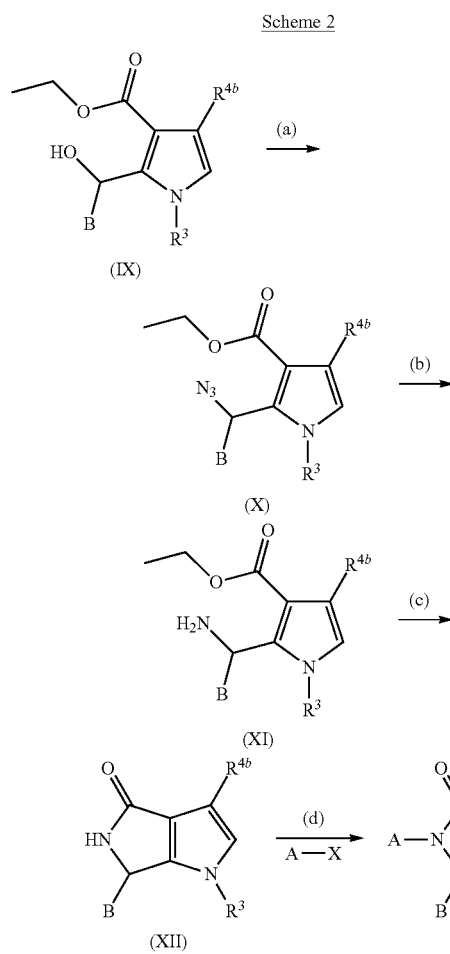

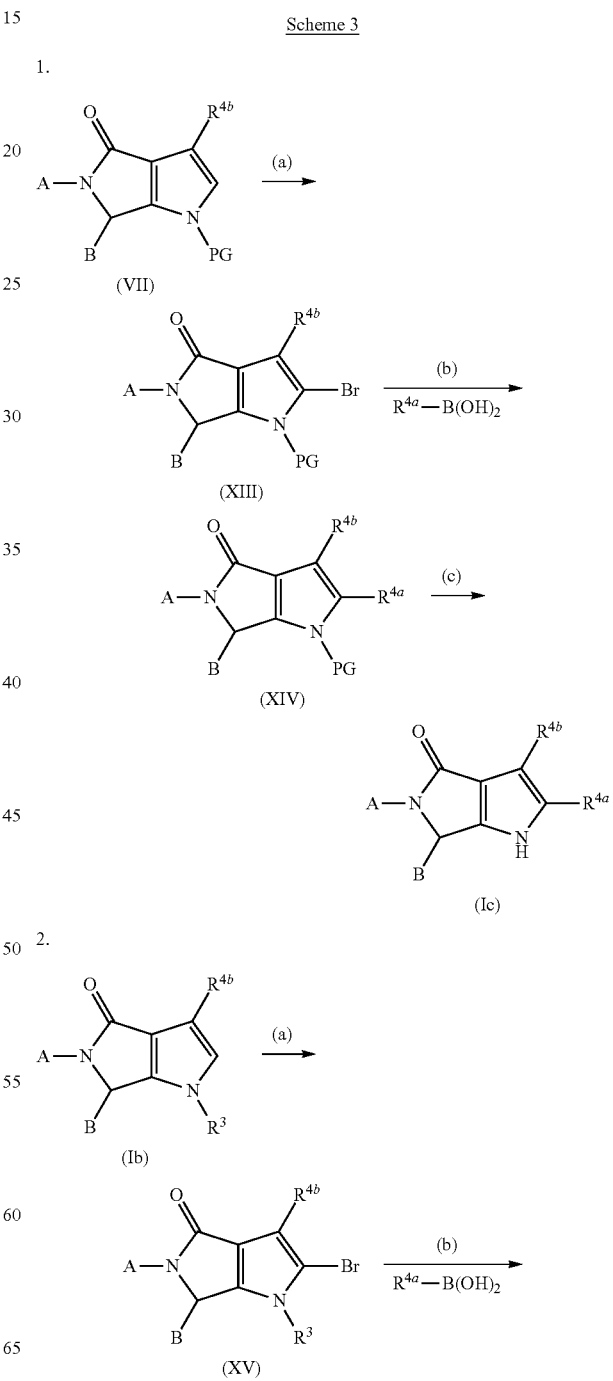

Scheme 2 illustrates an alternative method for preparing compounds of the present invention (e.g. Example 28) using alcohol IX which can be prepared in analogy to the methods described for the synthesis of alcohol V in Scheme 1.

Step (a) involves the conversion of an alcohol into the corresponding chloride by treatment with 1-chloro-N,N,2-trimethylpropenylamine in DCM at room temperature, and the subsequent displacement of the chlorine atom by the azido group upon treatment with tetra-n-butylammonium azide in the presence of an organic base such as triethylamine at a suitable temperature such as room temperature.

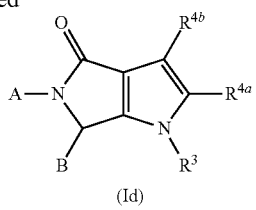

(Id)

3.

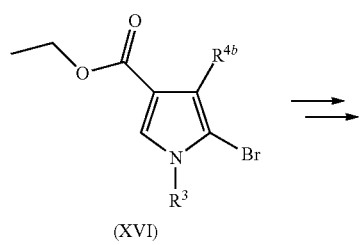

(XVI)

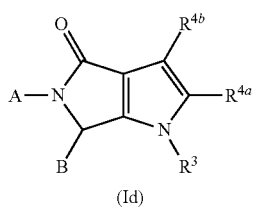

(Id)

The first synthetic sequence of Scheme 3 illustrates one method for preparing compounds of the present invention (e.g. Example 25) when R3 is H. Similar methods can be applied using Ib instead of VII to prepare compounds of the present invention (e.g. Example 30) when R3 is not H (Sequence 2, Scheme 3). Alternatively (Sequence 3, Scheme 3), the bromination step can be conducted on the starting pyrrole and the resulting product (XVI, which can be prepared according to methods known in the art) can be converted into compounds of the present invention (e.g. Example 31) according to the methods described in Scheme 1.

Step (a) involves the bromination of the protected pyrrolo-pyrrolidinone VII (Scheme 1) with NBS in a suitable solvent such as chloroform or carbon tetrachloride at a suitable temperature (0° C.—rt).

Step (b) involves the coupling reaction with a boronic acid in the presence of 1,1'-bis(diphenylphosphino)ferrocene-palladium(II)dichloride dichloromethane complex and potassium triphosphate in a suitable solvent mixture such as dioxane/water at a suitable temperature (80-110° C.).

Step (c) involves the removal of a suitable protecting group PG, a step well known in the art. For example, when PG is SEM, a compound is treated with TFA or aqueous HCl at a suitable temperature such as room temperature and subsequently with an aqueous solution of NaOH.

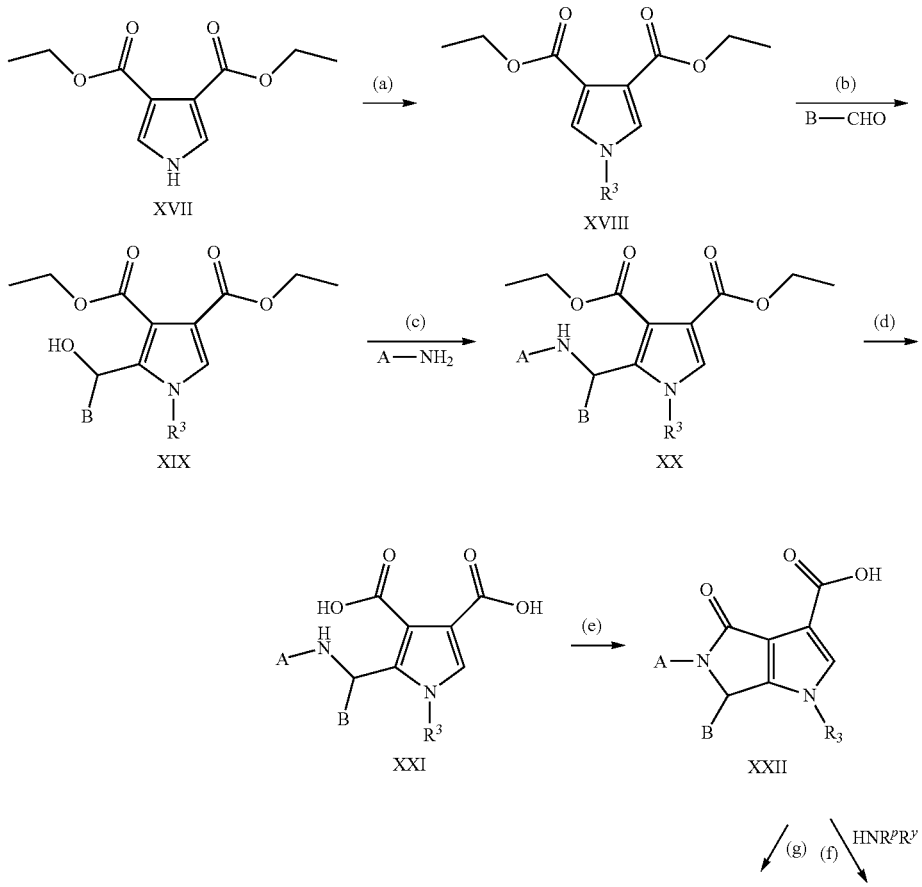

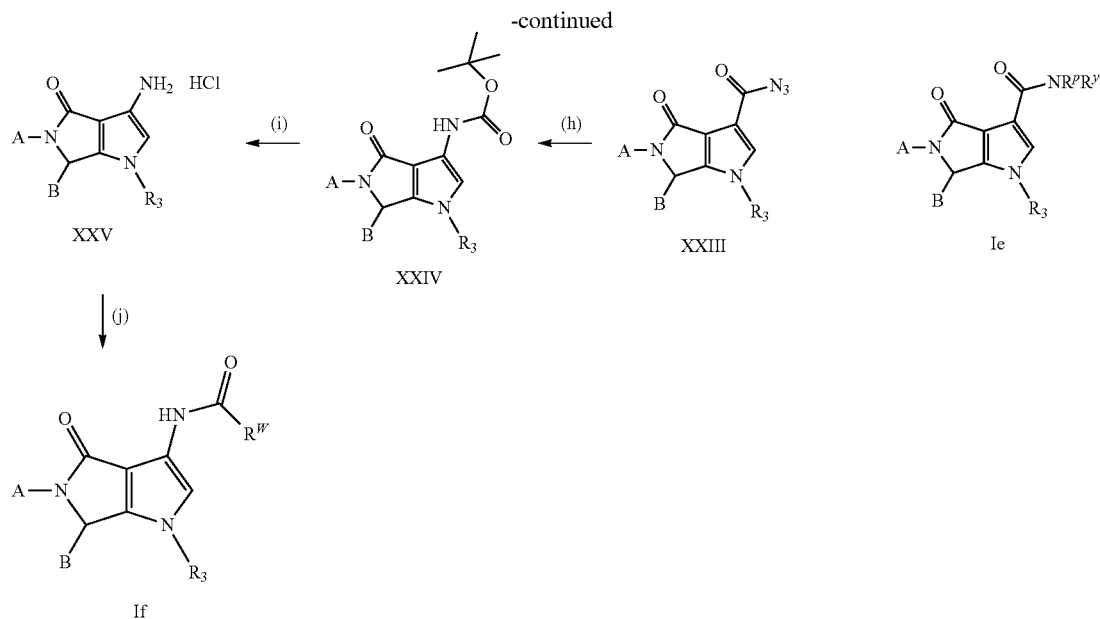

Scheme 4 illustrates one method for preparing compounds of the invention (e.g. Example 93, 96).

Steps (a)-(e) are in analogy to those described in Scheme 1.

Step (f) involves the reaction of a carboxylic acid with amines HNR$^p$R$^y$ according to methods well known in the art.

Step (g) involves the reaction of a carboxylic acid with sodium azide in the presence of TBTU and an organic amine such as DIEA in a suitable solvent such as DMF at a suitable temperature such as room temperature.

Step (h) involves the Curtius rearrangement of an acyl azide to the corresponding isocyanate which reacts with tert-butanol to provide the corresponding BOC-protected amine. The reaction is carried out in a suitable solvent mixture such as toluene/tert-butanol and at a suitable temperature such as 100° C.

Step (i) involves the removal of BOC by reaction with 4N HCl in dioxane at a suitable temperature such as room temperature.

Step (j) involves acylation of an amine to the corresponding amides/carbamates R$^w$ (eg. Examples 96, 97) with suitable reagents and according to methods well known in the art.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material. Compounds of the invention and intermediates can also be converted into each other according to methods generally known to those skilled in the art.

Synthetic Methods

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

Instrumentation

Achiral SFC were performed on Thar-Waters prep SFC 100 (UV and/or MS detection).

NMR spectra were run on Oxford As 400 (400 MHz) or Bruker Ultrashield 600 PLUS (600 MHz) NMR spectrometers.

LC-MS 1

| | |
|---|---|
| Instrument | Waters Acquity UPLC/SQD |
| Column | Acquity HSS T3 2.1 × 50 mm, 1.8 µmm |
| Column Temperature | 60° C. |
| Eluents | A: water + 0.05% formic acid + 3.75 mM ammonium acetate |
| | B: Acetonitrile + 0.04% formic Acid |
| Flow Rate | 1.0 mL/min |
| Gradient | 5% to 98% B in 1.4 min, 0.4 min 98% B, to 5% B in 0.1 min, 0.1 min 5% B |

LC-MS 2

| | |
|---|---|
| Instrument | Waters Acquity UPLC/SQD |
| Column | Acquity HSS T3 2.1 × 50 mm, 1.8 µmm |
| Column Temperature | 50° C. |
| Eluents | A: water + 0.05% formic acid + 3.75 mM ammonium acetate |
| | B: Acetonitrile + 0.04% formic Acid |

| | |
|---|---|
| Flow Rate | 1.2 mL/min |
| Gradient | 2% to 98% B in 1.4 min, 0.4 min 98% B, to 2% B in 0.1 min, 0.1 min 2% B |

ABBREVIATIONS

Ac$_2$O acetic anhydride
app apparent
Ar argon
ATP adenosine 5'-triphosphate
BINAP racemic 2,2'-bis(diphenylphosphino)-1,1'-binaphthyl
BOC tertiary butyl carboxy
br. broad
brine saturated (at rt) sodium chloride solution
BSA bovine serum albumin
d doublet
dd doublet of doublets
CH$_3$CN acetonitrile
CuI Copper(I) iodide
DCM dichloromethane
DIEA diethylisopropylamine
DME 1,4-dimethoxyethane
DMF N,N-dimethylformamide
DMSO dimethylsulfoxide
EDTA ethylenediamine tetraacetic acid
EP ethylpyridine
eq equivalent(s)
ESI electrospray ionization
Et$_2$O diethyl ether
EtOAc ethyl acetate
EtOH ethanol
h hour(s)
HBTU O-Benzotriazole-N,N,N',N'-tetramethyl-uronium-hexafluoro-phosphate
HOBt 1-hydroxy-7-azabenzotriazole
HPLC high pressure liquid chromatography
KOH potassium hydroxide
KOtBu potassium tert-butoxide
K$_3$PO$_4$ potassium phosphate
LCMS liquid chromatography and mass spectrometry
LDA lithium diisopropylamide
m multiplet
Me methyl
MeOH methanol
MgSO$_4$ magnesium sulfate
min minute(s)
mL milliliter(s)
mmol millimol
MS mass spectrometry
Ms$_2$O methanesulfonic anhydride
MTBE methyl tert-butyl ether
m/z mass to charge ratio
MW microwave
NaB(OAc)$_3$H sodium triacetoxyborohydride
NaH sodium hydride
NaHCO$_3$ sodium bicarbonate
NaNO$_2$ sodium nitrite
NaOAc sodium acetate
NaOH sodium hydroxide
Na$_2$SO$_4$ sodium sulfate
n-BuPAd$_2$ Di(1-adamantyl)-n-butylphosphine
NBS N-Bromosuccinimide
NEt$_3$ triethylamine
NH$_4$Cl ammonium chloride
NH$_4$OH ammonium hydroxide
NMR nuclear magnetic resonance
PdCl$_2$(dppf)-CH$_2$Cl$_2$ 1,1'-Bis(diphenylphosphino)ferrocene-palladium(II)dichloride dichloromethane complex
Pd$_2$dba$_3$ Tris(dibenzylideneacetone)dipalladium(0)
Pd(PPh$_3$)$_4$ tetrakis(triphenylphosphine)palladium(0)
ppm parts per million
PPU propyl-pyridyl-urea
rac racemic
Ra—Ni Raney Nickel
Rf ratio of fronts
Rt retention time
s singlet
scCO2 supercritical carbon dioxide
SFC supercritical fluid chromatography
SEMCl 2-(Trimethylsilyl)ethoxymethyl chloride
t triplet
TBTU O-(Benzotriazol-1-yl)-N,N,N',N'-tetramethyluronium tetrafluoroborate
TFA trifluoroacetic acid
TFAA trifluoroacetic anhydride
THF tetrahydrofuran
Tris.HCl aminotris(hydroxymethyl)methane hydrochloride
Xantphos 4,5-bis(diphenylphosphino)-9,9-dimethyxanthene Example 1

6-(4-chlorophenyl)-3-cyclopropyl-5-(3,7-dimethyl-3H-[1,2,3]triazolo[4,5-b]pyridin-5-yl)-1-(hydroxymethyl)-5,6-dihydropyrrolo[3,4-b]pyrrol-4(1H)-one

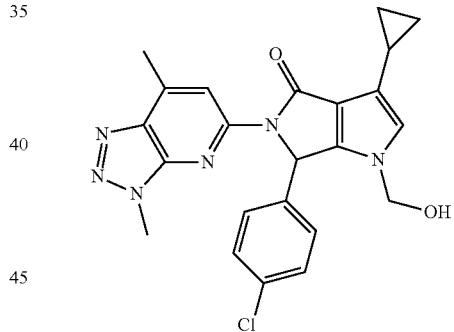

Step 1: 2,6-dichloro-4-methyl-3-nitropyridine 2,6-Dichloro-4-methylpyridine (238 g, 1469 mmol) was dissolved in TFA (1.9 L) and fuming nitric acid (197 mL, 4407 mmol). TFAA was added while maintaining the temperature below 30° C. using an ice/water bath. The reaction mixture was stirred for 4 h at rt and poured into ice water (8 L). The resulting suspension was filtered. The filter cake was washed with water (2 L) and dried in vacuo at 30° C. to afford the title compound (256 g) as colorless crystals. Rt: 1.06 min (LC-MS 1); MS m/z: 207.0 [M]$^+$ (LC-MS 1).

Step 2: 6-chloro-N,4-dimethyl-3-nitropyridin-2-amine

Methylamine (2M in THF, 1.5 L, 3000 mmol) was added to a solution of 2,6-dichloro-4-methyl-3-nitropyridine (Step 1 of Example 1, 295 g, 1425 mmol) THF (4.5 L) while maintaining the temperature at 20° C. The reaction mixture stirred for 2 h at rt, diluted with EtOAc (3 L) and water (5 L). The organic layer was separated and the aqueous layer was extracted with EtOAc (2 L). The combined organic extracts were washed with brine (5 L), dried ($Na_2SO_4$), filtered and the filtrate was evaporated in vacuo at 30° C. to afford the title compound (285 g, purity 81%) as yellow crystals. Rt: 1.07 min (LC-MS 1); MS m/z: 201.0 $[M]^+$ (LC-MS 1).

Step 3: 6-chloro-N2,4-dimethylpyridine-2,3-diamine

A mixture of 6-chloro-N,4-dimethyl-3-nitropyridin-2-amine (Step 2 of Example 1, 285 g, 1417 mmol) and Ra—Ni ($H_2O$) (29 g, Fluka 83440) in EtOH (2.7 L) was shaken for 24 h at 25° C. under a hydrogen atmosphere (0.1 bar). The reaction mixture filtered over hyflo and the filtrate was evaporated in vacuo at 30° C. to provide the title compound (250 g, purity 72%) as a red oil. Rt: 0.74 min (LC-MS 1); MS m/z: 171.0 $[M]^+$ (LC-MS 1).

Step 4: 5-chloro-3,7-dimethyl-3H-[1,2,3]triazolo[4,5-b]pyridine

6-Chloro-N2,4-dimethylpyridine-2,3-diamine (Step 3 of Example 1, 250 g, 1457 mmol) was dissolved in aqueous HCl (2N, 3 L) and cooled to 0° C. $NaNO_2$ (101 g, 1457 mmol) was added (the temperature rised to 10° C.). The reaction mixture was stirred at 0° C. for 30 minutes, basified with aqueous NaOH (2N, 4.5 L) (the temperature raised to 15° C.) and extracted twice with DCM (3 L). The combined organic layers were washed with brine (5 L), dried ($Na_2SO_4$), filtered and the filtrate was evaporated in vacuo at 30° C. The residue was purified by silica gel column chromatography (eluent: EtOAc/heptane; gradient: 7% to 100% EtOAc in 38 min, 22 min 100% EtOAc; flow: 1 L/min) followed by crystallization of the resulting material from hexane (1 L) to afford the title compound (95 g). Rt: 0.79 min (LC-MS 1); MS m/z: 182.0 $[M]^+$ (LC-MS 1).

Step 5: 3,7-dimethyl-3H-[1,2,3]triazolo[4,5-b]pyridin-5-amine

In a sealed tube was introduced 5-chloro-3,7-dimethyl-3H-[1,2,3]triazolo[4,5-b]pyridine (Step 4 of Example 1, 3 g, 16.43 mmol) and $NH_4OH$ (45.7 mL, 329 mmol). The reaction mixture was stirred for 7 h at 120° C. under MW irradiation, allowed to cool to rt, and concentrated. The residue was purified by silica gel chromatography on Combiflash Isco (eluent: MeOH/DCM; gradient: 2.5 min 0% MeOH, 0% to 8.4% MeOH in 15.1 min; flow: 40 mL/min) to afford the title compound (1.7 g) as a brown solid. Rf=0.49 (10% DCM/MeOH); Rt: 0.43 min (LC-MS 1); MS m/z: 164.1 $[M+H]^+$ (LC-MS 1).

Step 6: Ethyl 4-cyclopropyl-1H-pyrrole-3-carboxylate

To a stirred solution of ethyl 3-cyclopropylate (Aldrich, 3 g, 21.40 mmol) and p-toluenesulphonylmethyl isocyanide (Aldrich, 4.73 g, 26.1 mmol) in $Et_2O$ (100 mL) and DMSO (50 mL) was added NaH (1.156 g, 28.9 mmol) portionwise under Ar. The reaction mixture was stirred for 1 h at rt. p-Toluenesulphonylmethyl isocyanide (4.73 g, 26.1 mmol) and NaH (1.156 g, 28.9 mmol) were added. The reaction mixture was stirred for 1 h at rt, quenched with brine (100 mL), and extracted with $Et_2O$ (2×100 mL). The combined organic layers were washed with brine (100 mL), dried ($Na_2SO_4$), filtered and the filtrate was concentrated. The residue was purified by silica gel chromatography on Combiflash Isco (eluent: EtOAc/hexane; gradient: 0% to 34.5% EtOAc in 20 min; flow: 60 mL/min) followed by trituration of the resulting material in hexane/$Et_2O$ (1:1) to afford the title compound (3.45 g, purity 90%) as a yellow oil. Rf=0.79 (50% EtOAc/hexane); Rt: 0.87 min (LC-MS 1); MS m/z: 180.1 $[M+H]^+$ (LC-MS 1).

Step 7: Ethyl 4-cyclopropyl-1-((2-(trimethylsilyl)ethoxy)methyl)-1H-pyrrole-3-carboxylate To a stirred solution of ethyl 4-cyclopropyl-1H-pyrrole-3-carboxylate (Step 6 of Example 1, 3.45 g, 19.25 mmol) in DMF (30 mL) was added NaH (0.924 g, 23.10 mmol) at 0° C. under Ar. The reaction mixture was stirred for 30 min at 0° C. SEMCl (3.76 mL, 21.18 mmol) was added portionwise. The reaction mixture was stirred for 30 min at rt, quenched by addition of a saturated aqueous solution of $NaHCO_3$ (150 mL), and extracted with EtOAc (2×150 mL). The combined organic layers were washed with a saturated aqueous solution of $NaHCO_3$ (150 mL), dried ($Na_2SO_4$), filtered and the filtrate was concentrated. The residue was purified by silica gel chromatography on Combiflash Isco (eluent: EtOAc/hexane; gradient: 0% to 8.7% EtOAc in 24.3 min; flow: 60 mL/min) to afford the title compound (5.47 g) as a colorless oil. Rf=0.36 (10% EtOAc/hexane); Rt: 1.39 min (LC-MS 1); MS m/z: 310.2 $[M+H]^+$ (LC-MS 1).

Step 8: Ethyl 2-((4-chlorophenyl)(hydroxy)methyl)-4-cyclopropyl-1-((2-(trimethylsilyl)ethoxy)methyl)-1H-pyrrole-3-carboxylate To a stirred solution of ethyl 4-cyclopropyl-1-((2-(trimethylsilyl)ethoxy)methyl)-1H-pyrrole-3-carboxylate (Step 7 of Example 1, 5.45 g, 17.61 mmol) in THF (100 mL) was added LDA (2M in THF/heptane/ethylbenzene, 11.45 mL, 22.89 mmol) at −78° C. under Ar. The reaction mixture was stirred for 30 min at −78° C. 4-Chlorobenzaldehyde (3.22 g, 22.89 mmol) in THF (10 mL) was added. The reaction mixture was stirred for 30 min at −78° C., quenched by addition of brine (100 mL), and extracted with EtOAc (2×100 mL). The combined organic layers were washed with brine (1×100 mL), dried ($Na_2SO_4$), filtered and the filtrate was concentrated. The residue was purified by silica gel chromatography on Combiflash Isco (eluent: EtOAc/hexane; gradient: 0% to 10% EtOAc in 30 min, 3.9 min 10% EtOAc; flow: 85 mL/min) to afford the title compound (6.95 g, purity 80%) as a yellow oil. Rf=0.23 (10% EtOAc/hexane); Rt: 1.54 min (LC-MS 1); MS m/z: 432.2 $[M-17]^+$ (LC-MS 1).

Step 9: Ethyl 2-((4-chlorophenyl)((3,7-dimethyl-3H-[1,2,3]triazolo[4,5-b]pyridin-5-yl)amino)methyl)-4-cyclopropyl-1-((2-(trimethylsilyl)ethoxy)methyl)-1H-pyrrole-3-carboxylate To a stirred solution of ethyl 2-((4-chlorophenyl)(hydroxy)methyl)-4-cyclopropyl-14(2-(trimethylsilyl)ethoxy)methyl)-1H-pyrrole-3-carboxylate (Step 8 of Example 1, 2 g, 4.44 mmol) in DCM (40 mL) was added 1-chloro-N,N,2-trimethyl-1-propenylamine (0.878 mL, 6.67 mmol) at rt under Ar. The reaction mixture was stirred for 5 h at rt and cooled to 0° C. Triethylamine (1.858 mL, 13.33 mmol) and 3,7-dimethyl-3H-[1,2,3]triazolo[4,5-b]pyridin-5-amine (Step 5 of Example 1, 0.798 g, 4.89 mmol) were added at 0°

C. The reaction mixture was stirred for 16 h at rt, quenched by addition of a saturated aqueous solution of NaHCO$_3$ (100 mL), and extracted with DCM (100 mL). The combined organic layers were washed with brine (100 mL), dried (Na$_2$SO$_4$), filtered and the filtrate was concentrated. The residue was purified by silica gel chromatography on Combiflash Isco (eluent: EtOAc/hexane; gradient: 0% to 65.5% EtOAc in 15.3 min; flow: 40 mL/min) to afford the title compound (1.67 g) as a yellow solid. Rf=0.76 (50% EtOAc/hexane); Rt: 1.57 min (LC-MS 1); MS m/z: 595.4 [M+H]$^+$ (LC-MS 1).

Step 10: 6-(4-chlorophenyl)-3-cyclopropyl-5-(3,7-dimethyl-3H-[1,2,3]triazolo[4,5-b]pyridin-5-yl)-1-(hydroxymethyl)-5,6-dihydropyrrolo[3,4-b]pyrrol-4(1H)-one To a stirred solution of ethyl 2-((4-chlorophenyl)((3,7-dimethyl-3H-[1,2,3]triazolo[4,5-b]pyridin-5-yl)amino)methyl)-4-cyclopropyl-1-((2-(trimethylsilyl)ethoxy)methyl)-1H-pyrrole-3-carboxylate (Step 9 of Example 1, 1.67 g, 2.81 mmol) in toluene (30 mL) was added dimethylaluminium chloride (1M in hexane, 16.83 mL, 16.83 mmol) at rt under Ar. The reaction mixture was stirred for 8 h at 120° C., diluted with a saturated aqueous solution of Rochelle salt (100 mL), and extracted with EtOAC (2×100 mL). The combined organic layers were washed with water (100 mL), dried (Na$_2$SO$_4$), filtered and the filtrate was concentrated. The residue was purified by silica gel chromatography on Combiflash Isco (eluent: EtOAc/DCM; gradient: 0% to 7.8% EtOAc in 15.6 min, 7.8% to 7.9% EtOAc in 0.2 min, 7.9% to 38.1% EtOAc in 15.2 min; flow: 35 mL/min) to afford the title compound (492 mg, purity 90%) as a yellow solid. Rf=0.24 (10% EtOAc/DCM); Rt: 1.13 min (LC-MS 1); MS m/z: 449.3 [M+H]$^+$ (LC-MS 1).

Example 2

6-(4-chlorophenyl)-5-(3,7-dimethyl-3H-[1,2,3]triazolo[4,5-b]pyridin-5-yl)-1-(methoxymethyl)-3-methyl-5,6-dihydropyrrolo[3,4-b]pyrrol-4(1H)-one

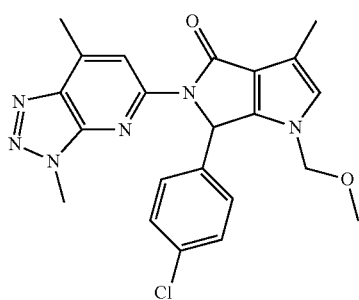 [SMILES: COCn1cc(C)c2c1C(c1ccc(Cl)cc1)N(c1cc(C)c3nnn(C)c3n1)C2=O]

Step 1: Ethyl 1-(methoxymethyl)-4-methyl-1H-pyrrole-3-carboxylate

To a stirred solution of ethyl 4-methylpyrrole-3-carboxylate (Alfa Aesar, 1 g, 6.53 mmol) in DMF (10 mL) was added NaH (0.313 g, 7.83 mmol) at 0° C. under Ar. The reaction mixture was stirred for 30 min at 0° C. Chloromethyl methylether (Aldrich, 0.595 mL, 7.83 mmol) was added portionwise. The reaction mixture was stirred for 1 h at rt, quenched by addition of a saturated aqueous solution of NaHCO$_3$ (75 mL), and extracted with EtOAc (2×75 mL). The combined organic layers were washed with a saturated aqueous solution of NaHCO$_3$ (75 mL), dried (Na$_2$SO$_4$), filtered and the filtrate was concentrated. The residue was purified by silica gel chromatography on Combiflash Isco (eluent: EtOAc/hexane; gradient: 1.2 min 0% EtOAc, 0% to 33.7% EtOAc in 12.2 min; flow: 35 mL/min) to afford the title compound (1.25 g, purity 85%) as a colorless oil. Rf=0.82 (50% EtOAc/hexane); Rt: 0.91 min (LC-MS 1); MS m/z: 198.2 [M+H]$^+$ (LC-MS 1).

Step 2: Ethyl 2-((4-chlorophenyl)(hydroxy)methyl)-1-(methoxymethyl)-4-methyl-1H-pyrrole-3-carboxylate To a stirred solution of ethyl 1-(methoxymethyl)-4-methyl-1H-pyrrole-3-carboxylate (Step 1 of Example 2, 1.25 g, 6.34 mmol) in THF (25 mL) was added LDA (2M in THF/heptane/ethylbenzene, 4.12 mL, 8.24 mmol) at −78° C. under Ar. The reaction mixture was stirred for 30 min at −78° C. 4-Chlorobenzaldehyde (1.158 g, 8.24 mmol) in THF (3 mL) was added. The reaction mixture was stirred for 30 min at −78° C., quenched by addition of brine (100 mL), and extracted with EtOAc (2×100 mL). The combined organic layers were washed with brine (100 mL), dried (Na$_2$SO$_4$), filtered and the filtrate was concentrated. The residue was purified by silica gel chromatography on Combiflash Isco (eluent: EtOAc/hexane; gradient: 1.5 min 0% EtOAc, 0% to 20% EtOAc in 21 min, 0.2 min 20% EtOAc; flow: 40 mL/min) to afford the title compound (1.25 g, purity 86%) as a colorless oil. Rf=0.11 (10% EtOAc/hexane); Rt: 1.21 min (LC-MS 1); MS m/z: 320.2 [M-17]$^+$ (LC-MS 1).

Step 3: Ethyl 2-((4-chlorophenyl)((3,7-dimethyl-3H-[1,2,3]triazolo[4,5-b]pyridin-5-yl)amino)methyl)-1-(methoxymethyl)-4-methyl-1H-pyrrole-3-carboxylate The title compound was prepared using an analogous procedure to that described in Step 9 of Example 1 using ethyl 2-((4-chlorophenyl)(hydroxy)methyl)-1-(methoxymethyl)-4-methyl-1H-pyrrole-3-carboxylate (Step 2 of Example 2, 1 g, 2.96 mmol) and 3,7-dimethyl-3H-[1,2,3]triazolo[4,5-b]pyridin-5-amine (Step 5 of Example 1, 0.531 g, 3.26 mmol). The crude product was purified by silica gel chromatography on Combiflash Isco (eluent: EtOAc/DCM; gradient: 0% to 6.2% EtOAc in 18.2 min; flow: 35 mL/min) to afford the title compound (1.25 g) as a colorless oil. Rf=0.31 (10% EtOAc/DCM); Rt: 1.32 min (LC-MS 1); MS m/z: 483.32 [M+H]$^+$ (LC-MS 1).

Step 4: 2-((4-chlorophenyl)((3,7-dimethyl-3H-[1,2,3]triazolo[4,5-b]pyridin-5-yl)amino)methyl)-1-(methoxymethyl)-4-methyl-1H-pyrrole-3-carboxylic acid To a stirred solution of ethyl 2-((4-chlorophenyl)((3,7-dimethyl-3H-[1,2,3]triazolo[4,5-b]pyridin-5-yl)amino)methyl)-1-(methoxymethyl)-4-methyl-1H-pyrrole-3-carboxylate (Step 3 of Example 2, 690 mg, 1.429 mmol) in THF (10 mL) and MeOH (10 mL) was added aqueous NaOH (2N, 7.14 mL, 14.29 mmol). The reaction mixture was stirred for 20 h at 100° C., quenched by addition of aqueous HCl (1M, 100 mL), and extracted with EtOAc (2×100 mL). The combined organic layers were dried (Na$_2$SO$_4$), filtered and the filtrate was concentrated to afford the title compound (637 mg) as a colorless solid. Rt: 1.07 min (LC-MS 1); MS m/z: 455.2 [M+1]⁺ (LC-MS 1).

Step 5: 6-(4-chlorophenyl)-5-(3,7-dimethyl-3H-[1,2,3]triazolo[4,5-b]pyridin-5-yl)-1-(methoxymethyl)-3-methyl-5,6-dihydropyrrolo[3,4-b]pyrrol-4(1H)-one To a stirred solution of 2-((4-chlorophenyl)((3,7-dimethyl-3H-[1,2,3]triazolo[4,5-b]pyridin-5-yl)amino)methyl)-1-(methoxymethyl)-4-methyl-1H-pyrrole-3-carboxylic acid (Step 4 of Experiment 2, 630 mg, 1.385 mmol) in DCM (10 mL) was added 1-chloro-N,N,2-trimethyl-1-propenylamine (0.255 mL, 1.939 mmol) at rt under Ar. The reaction mixture was stirred for 2 h at rt, quenched by addition of a saturated aqueous solution of NaHCO$_3$ (100 mL), and extracted with DCM (2×100 mL). The combined organic layers were washed with a saturated aqueous solution of NaHCO$_3$ (100 mL), dried (Na$_2$SO$_4$), filtered and the filtrate was concentrated. The residue was purified by silica gel chromatography on Combiflash Isco (eluent: EtOAc/hexane; gradient: 0% to 77.6% EtOAc in 10.9 min; flow: 30 mL/min) followed by trituration of the resulting material in Et$_2$O to afford the title compound (470 mg) as a colorless solid. Rf=0.40 (50% EtOAc/hexane); Rt: 1.20 min (LC-MS 1); MS m/z: 437.2 [M+H]⁺ (LC-MS 1); ¹H NMR (400 MHz, DMSO-d6) δ 8.27 (d, J=1.2 Hz, 1H), 7.51-7.37 (m, 2H), 7.36-7.27 (m, 2H), 6.84 (d, J=1.3 Hz, 1H), 6.60 (s, 1H), 4.97 (d, J=10.5 Hz, 1H), 4.75 (d, J=10.5 Hz, 1H), 4.09 (s, 3H), 2.90 (s, 3H), 2.64 (s, 3H), 2.19 (s, 3H).

Example 3

6-(4-chlorophenyl)-5-(3,8-di methyl-[1,2,4]triazolo[4,3-a]pyridin-6-yl)-3-methyl-5,6-dihydropyrrolo[3,4-b]pyrrol-4(1H)-one

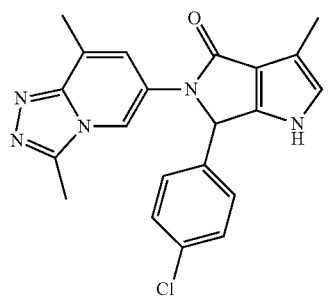 [SMILES: Cc1c[nH]c2c1C(=O)N(c1cc(C)c3nnc(C)n3c1)C2c1ccc(Cl)cc1]

Step 1: 2-hydrazinyl-3-methyl-5-nitropyridine

Hydrazine hydrate (Sigma Aldrich, 268 mL, 5517 mmol) was added within 15 min to a yellow suspension of 2-chloro-3-methyl-5-nitropyridine (AOBChem, 200 g, 1159 mmol) and ethanol (2700 mL) at rt. After addition of ~180 mL of hydrazine, the reaction became slight exothermic and the reaction mixture changed to a dark red solution. The internal temperature raised slowly up to 35° C. and the reaction mixture was cooled with a dry ice/aceton bath to 20° C. The brown suspension was cooled down to −5° C. and stirred for 30 min. The suspension was filtered. The filter cake was washed twice with MTBE and dried over night at rt under vacuum to afford the title compound (274.2 g, purity 71%) as a yellow solid. Rt: 0.46 min (LC-MS 1); MS m/z: 169.1 [M+H]⁺ (LC-MS 1);

Step 2: N'-(3-methyl-5-nitropyridin-2-yl)acetohydrazide

To a yellow suspension of 2-hydrazinyl-3-methyl-5-nitropyridine (Step 1 of Experiment 3, 273.2 g, 1154 mmol) in DCM (3600 mL) was added triethylamine (640 mL, 4614 mmol). Acetic anhydride (239 mL, 2538 mmol) was added dropwise within 30 min. The resulting red suspension was stirred for 2 h at rt. Acetic anhydride (0.42 eq) was added. The mixture was warmed to 30° C. and stirred for 1 h. Acetic anhydride (0.5 eq) was added. The reaction mixture was stirred for 15 min, poured onto a 3.5% aqueous solution of NaHCO$_3$(7.7 L), and diluted with acetonitrile. The red suspension was stirred for 30 min and filtered. The filter cake was washed with water (3×1 L) and twice with MTBE, and dried at 35° C. under vacuum to afford the title compound (272 g, purity 89%). Rt: 0.47 min (LC-MS 1); MS m/z: 210.2 [M+H]⁺ (LC-MS 1).

Step 3: 3,8-dimethyl-6-nitro-[1,2,4]triazolo[4,3-a]pyridine

AcOH (315 mL, 5508 mmol) was added to a suspension of N'-(3-methyl-5-nitropyridin-2-yl)acetohydrazide (Step 2 of Experiment 3, 227 g, 1080 mmol) in dioxane (2 L). The resulting brown suspension was heated to reflux, stirred at reflux over night and allowed to cool. Acetic anhydride (102 mL, 1 eq) was added within 10 min. The brown reaction solution was heated again to reflux and stirred for 8 h and 45 min, allowed to cool to rt, stirred at rt 15.5 h, and concentrated in vacuo. The brown residue was suspended in MTBE, stirred and filtered. The resulting brown material (180 g) was suspended in EtOAc (350 mL) and heated to reflux. The brown solution was stirred for 15 min at reflux. MTBE (180 mL) was then added. The suspension was allowed to cool to rt, then cooled to 0° C. with an ice/water bath, and filtered. The filter cake was washed with MTBE and dried over night at 40° C. under vacuum to provide the title compound (150.6 g). Rt: 0.54 min (LC-MS 1); MS m/z: 192.2 [M+H]⁺ (LC-MS 1).

Step 4: 3,8-dimethyl-[1,2,4]triazolo[4,3-a]pyridin-6-amine

A mixture of 3,8-dimethyl-6-nitro-[1,2,4]triazolo[4,3-a]pyridine (216.3 g, 1126 mmol) and 10% Pd/C (80 g) in MeOH (10 L) was stirred for 25 min under an hydrogen atmosphere (4 bar), filtered and the filtrate was concentrated in vacuo. The residue was purified by silica gel column chromatography (10-20% MeOH/DCM) followed by trituration of the resulting material in MTBE/petrol ether to afford the title compound (124.7 g) as a beige solid. Rt: 0.31 min (LC-MS 1); MS m/z: 162.2 [M+H]⁺ (LC-MS 1).

Step 5: Ethyl 4-methyl-1-((2-(trimethylsilyl)ethoxy)methyl)-1H-pyrrole-3-carboxylate The title compound was prepared using an analogous procedure to that described in Step 7 of Example 1 using ethyl 4-methylpyrrole-3-carboxylate (Alfa Aesar, 3 g, 19.59 mmol). The crude product was purified by silica gel chromatography on Combiflash Isco (eluent: EtOAc/hexane; gradient: 2.8 min 0% EtOAc, 0% to 5.8% EtOAc in 28.5 min; flow: 85 mL/min) to afford the title compound (3.02 g) as a colorless oil. Rf=0.42 (10% EtOAc/hexane); Rt: 1.34 min (LC-MS 1); MS m/z: 284.2 [M+H]$^+$ (LC-MS 1).

Step 6: Ethyl 2-((4-chlorophenyl)(hydroxy)methyl)-4-methyl-1-((2-(trimethylsilyl)ethoxy)methyl)-1H-pyrrole-3-carboxylate The title compound was prepared using an analogous procedure to that described in Step 8 of Example 1 using ethyl 4-methyl-1-((2-(trimethylsilyl)ethoxy)methyl)-1H-pyrrole-3-carboxylate (Step 5 of Example 3, 3.01 g, 10.62 mmol). The crude product was purified by silica gel chromatography on Combiflash Isco (eluent: EtOAc/hexane; gradient: 2.5 min 0% EtOAc, 0% to 6.5% EtOAc in 21.3 min, 12.3 min 6.5% EtOAc, 6.5% to 7.5 EtOAc in 3.4 min, 7.5% to 9.6% EtOAc in 2.9 min; flow: 60 mL/min) to afford the title compound (3.67 g) as a colorless oil. Rf=0.25 (10% EtOAc/hexane); Rt: 1.50 min (LC-MS 1); MS m/z: 406.2 [M-17]$^+$ (LC-MS 1).

Step 7: Ethyl 2-((4-chlorophenyl)((3,8-dimethyl-[1,2,4]triazolo[4,3-a]pyridin-6-yl)amino)methyl)-4-methyl-1-((2-(trimethylsilyl)ethoxy)methyl)-1H-pyrrole-3-carboxylate The title compound was prepared using an analogous procedure to that described in Step 9 of Example 1 using ethyl 2-((4-chlorophenyl)(hydroxy)methyl)-4-methyl-1-((2-(trimethylsilyl)ethoxy)methyl)-1H-pyrrole-3-carboxylate (Step 6 of Example 3, 2 g, 4.72 mmol) and 3,8-dimethyl-[1,2,4]triazolo[4,3-a]pyridin-6-amine (Step 4 of example 3, 0.842 g, 5.19 mmol). The crude product was purified by silica gel chromatography on Combiflash Isco (eluent: MeOH/DCM; gradient: 2.3 min 0% MeOH, 0% to 3.1% MeOH in 17.7 min, 5.7 min 3.1% MeOH, 3.1% to 3.6 MeOH in 2.8 min; flow: 60 mL/min) to afford the title compound (1.67 g) as a colorless oil. Rf=0.58 (10% MeOH/DCM); Rt: 1.43 min (LC-MS 1); MS m/z: 568.3 [M+H]$^+$ (LC-MS 1).

Step 8: 2-((4-chlorophenyl)((3,8-dimethyl-[1,2,4]triazolo[4,3-a]pyridin-6-yl)amino)methyl)-4-methyl-1-((2-(trimethylsilyl)ethoxy)methyl)-1H-pyrrole-3-carboxylic acid The title compound was prepared using an analogous procedure to that described in Step 4 of Example 2 using ethyl 2-((4-chlorophenyl)((3,8-dimethyl-[1,2,4]triazolo[4,3-a]pyridin-6-yl)amino)methyl)-4-methyl-1-((2-(trimethylsilyl)ethoxy)methyl)-1H-pyrrole-3-carboxylate (Step 7 of Example 3, 500 mg, 0.880 mmol) and stirring the reaction mixture for 5 h at 100° C. The crude product (545 mg) was used without purification. Rt: 1.23 min (LC-MS 1); MS m/z: 540.2 [M+H]$^+$ (LC-MS 1).

Step 9: 6-(4-chlorophenyl)-5-(3,8-dimethyl-[1,2,4]triazolo[4,3-a]pyridin-6-yl)-3-methyl-1-((2-(trimethylsilyl)ethoxy)methyl)-5,6-dihydropyrrolo[3,4-b]pyrrol-4(1H)-one The title compound was prepared using an analogous procedure to that described in Step 5 of Example 2 using 2-((4-chlorophenyl)((3,8-dimethyl-[1,2,4]triazolo[4,3-a]pyridin-6-yl)amino)methyl)-4-methyl-1-((2-(trimethylsilyl)ethoxy)methyl)-1H-pyrrole-3-carboxylic acid (Step 8 of Example 3, 966 mg, 1.788 mmol) and stirring the reaction mixture for 16 h at rt. The crude product was purified by silica gel chromatography on Combiflash Isco (eluent: MeOH/DCM; gradient: 1% to 4.1% MeOH in 18.5 min, 8 min 4.2% MeOH; flow: 40 mL/min) to afford the title compound (552 mg) as a yellow solid. Rf=0.49 (10% MeOH/DCM); Rt: 1.25 min (LC-MS 1); MS m/z: 522.2 [M+H]$^+$ (LC-MS 1).

Step 10: 6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one A mixture of 6-(4-chlorophenyl)-5-(3,8-dimethyl-[1,2,4]triazolo[4,3-a]pyridin-6-yl)-3-methyl-14(2-(trimethylsilyl)ethoxy)methyl)-5,6-dihydropyrrolo[3,4-b]pyrrol-4(1H)-one (Step 9 of Example 3, 550 mg, 1.053 mmol) and TFA (0.812 mL, 10.53 mmol) was stirred for 1 h at rt. The mixture was cooled to 0° C. Aqueous NaOH (4N, 6.58 mL, 26.3 mmol) and THF (5 mL) were added. The reaction mixture was stirred for 1 h at rt, quenched by addition of brine (50 mL), and extracted with EtOAc (2×100 mL). The combined organic layers were washed with brine (75 mL), dried (Na$_2$SO$_4$), filtered and the filtrate was concentrated. The residue was purified by silica gel chromatography on Combiflash Isco (eluent: MeOH/DCM; gradient: 2.5 min 0% MeOH, 0% to 9.7% MeOH in 30.9 min; flow: 35 mL/min) to afford the title compound (71 mg) as a colorless solid. Rf=0.45 (10% DCM/MeOH); Rt: 0.83 min (LC-MS 1); MS m/z: 392.1 [M+H]$^+$ (LC-MS 1); $^1$H NMR (400 MHz, DMSO-d6) δ 2.15 (s, 3H) 2.41 (s, 3H) 2.59 (s, 3H) 6.40 (s, 1H) 6.68 (s, 1H) 7.17-7.48 (m, 5H) 8.36 (s, 1H) 11.34 (s, 1H).

Example 4

1-(azetidin-3-yl)-6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one

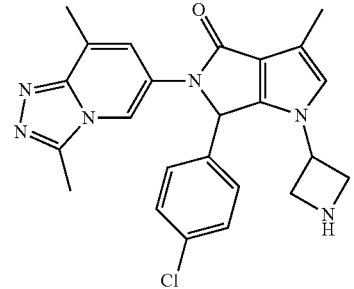 [SMILES: Cc1cn(C2CNC2)c2c1C(=O)N(c1cc(C)c3nnc(C)n3c1)C2c1ccc(Cl)cc1]

Step 1: 6-(4-chlorophenyl)-5-(3,8-dimethyl-[1,2,4]triazolo[4,3-a]pyridin-6-yl)-1-(hydroxymethyl)-3-methyl-5,6-dihydropyrrolo[3,4-b]pyrrol-4(1H)-one The title compound was prepared using an analogous procedure to that described in Step 10 of Example 1 using ethyl 2-((4-chlorophenyl)((3,8-dimethyl-[1,2,4]triazolo[4,3-a]pyridin-6-yl)amino)methyl)-4-methyl-1-((2-(trimethylsilyl)ethoxy)methyl)-1H-pyrrole-3-carboxylate (Step 7 of Example 3, 1.24 g, 2.182 mmol) and stirring the reaction mixture for 3 h at 120° C. The crude product was purified by silica gel chromatography on Combiflash Isco (eluent:

MeOH/DCM; gradient: 1.5 to 7% MeOH in 28.3 min, 3.2 min 7% MeOH; flow: 35 mL/min) to afford the title compound (588 mg, purity 85%) as a yellow solid. Rf=0.41 (10% DCM/MeOH); Rt: 0.80 min (LC-MS 1); MS m/z: 422.2 [M+H]+ (LC-MS 1).

Step 2: 6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one To a stirred solution of 6-(4-chlorophenyl)-5-(3,8-dimethyl-[1,2,4]triazolo[4,3-a]pyridin-6-yl)-1-(hydroxymethyl)-3-methyl-5,6-dihydropyrrolo[3,4-b]pyrrol-4(1H)-one (Step 1 of Example 4, 580 mg, 1.375 mmol) in THF (20 mL) was added aqueous NaOH (1N, 13.75 mL, 13.75 mmol). The reaction mixture was stirred for 1 h at rt, quenched by addition of aqueous NaOH (0.1N, 75 mL), and extracted with EtOAc (2×100 mL). The combined organic layers were dried (Na₂SO₄), filtered and the filtrate was concentrated. The residue was purified by silica gel chromatography on Combiflash Isco (eluent: MeOH/DCM; gradient: 3% to 9.6% MeOH in 18.9 min; flow: 35 mL/min) to afford the title compound (369 mg, purity 75%) as a yellow solid. Rf=0.45 (10% EtOAc/hexane); Rt: 0.83 min (LC-MS 1); MS m/z: 392.2 [M+H]+ (LC-MS 1).

Step 3: Tert-butyl 3-(6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrol-1(4H)-yl)azetidine-1-carboxylate To a stirred solution of 6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one (Step 2 of Example 4, 365 mg, 0.931 mmol) in DMF (12 mL) was added NaH (48.4 mg, 1.211 mmol) under Ar. The reaction mixture was stirred for 30 min at rt. and N-Boc-3-iodoazetidine (Apollo, 316 mg, 1.118 mmol) was added. The reaction mixture was heated to 80° C., stirred for 1 h, allowed to cool, quenched by addition of a saturated aqueous solution of NaHCO₃ (50 mL), and extracted with EtOAc (2×100 mL). The combined organic layers were washed with a saturated aqueous solution of NaHCO₃ (75 mL), dried (Na₂SO₄), filtered and the filtrate was concentrated. The residue was purified by silica gel chromatography on Combiflash Isco (eluent: MeOH/DCM; gradient: 1.5% to 8% MeOH in 23.3 min; flow: 35 mL/min) to afford the title compound (333 mg, purity 93%) as a yellow solid. Rf=0.45 (10% MeOH/DCM); Rt: 1.08 min (LC-MS 1); MS m/z: 547.3 [M+H]+ (LC-MS 1).

Step 4: 1-(azetidin-3-yl)-6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one To a stirred solution of tert-butyl 3-(6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrol-1(4H)-yl)azetidine-1-carboxylate (Step 3 of Example 4, 330 mg, 0.603 mmol) in DCM (4 mL) was added TFA (0.930 mL, 12.06 mmol). The reaction mixture was stirred for 30 min at rt, quenched by addition of a saturated aqueous solution of NaHCO₃, and extracted with DCM (2×100 mL). The combined organic layers were dried (Na₂SO₄), filtered and the filtrate was concentrated. The residue was purified by silica gel chromatography on Combiflash Isco (eluent: MeOH/DCM; gradient: 1.6 min 0% MeOH, 0% to 9.9% MeOH in 23.3 min, 2.7 min 9.9% MeOH; flow: 30 mL/min) to afford the title compound (160 mg) as a brown solid. Rf=0.16 (10% MeOH/DCM); Rt: 0.56 min (LC-MS 1); MS m/z: 447.3 [M+H]+ (LC-MS 1).

Example 5

6-(4-chlorophenyl)-5-(3,8-di methyl-[1,2,4]triazolo[4,3-a]pyridin-6-yl)-3-methyl-1-(1-methylazetidin-3-yl)-5,6-dihydropyrrolo[3,4-b]pyrrol-4(1H)-one

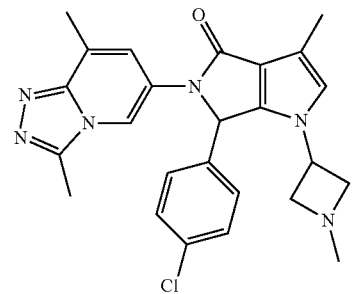 [SMILES: Cc1cn(C2CN(C)C2)c2c1C(=O)N(c1cc(C)c3nnc(C)n3c1)C2c1ccc(Cl)cc1]

To a stirred solution of 1-(azetidin-3-yl)-6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one (Step 4 of Example 4, 80 mg, 0.179 mmol) in MeOH (2 mL) was added formaldehyde (0.049 mL, 0.537 mmol). The mixture was stirred for 5 min at rt. NaB(OAc)₃H (190 mg, 0.895 mmol) was added. The reaction mixture was stirred for 1 h at rt, quenched by addition of a saturated aqueous solution of NaHCO₃ (50 mL), and extracted with EtOAc (2×100 mL). The combined organic layers were washed with a saturated aqueous solution of NaHCO₃ (75 mL), dried (Na₂SO₄), filtered and the filtrate was concentrated. The residue was purified by silica gel chromatography on Combiflash Isco (eluent: MeOH/DCM; gradient: 0% to 8% MeOH in 13.9 min; flow: 18 mL/min) to afford the title compound (47 mg) as a colorless solid. Rf=0.43 (10% MeOH/DCM); Rt: 0.57 min (LC-MS 1); MS m/z: 461.3 [M+H]+ (LC-MS 1); ¹H NMR (400 MHz, DMSO-d6) δ 2.09-2.22 (m, 6H) 2.41 (s, 3H) 2.60 (s, 3H) 2.80-2.89 (m, 1H) 2.96-3.03 (m, 1H) 3.09-3.16 (m, 1H) 3.43-3.53 (m, 1H) 4.19-4.30 (m, 1H) 6.45 (s, 1H) 7.01 (s, 1H) 7.26-7.39 (m, 5H) 8.30 (s, 1H).

Example 6

6-(4-chlorophenyl)-5-(3,8-dimethyl-[1,2,4]triazolo[4,3-a]pyridin-6-yl)-3-methyl-1-(oxetan-3-yl)-5,6-dihydropyrrolo[3,4-b]pyrrol-4(1H)-one

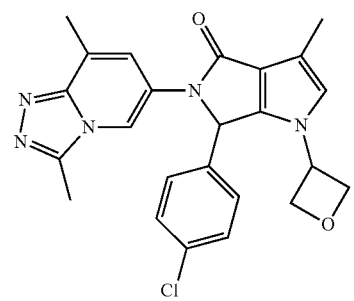 [SMILES: Cc1cn(C2COC2)c2c1C(=O)N(c1cc(C)c3nnc(C)n3c1)C2c1ccc(Cl)cc1]

To a stirred solution of 6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one (Step 10 of Example 3, 55 mg, 0.140 mmol) in DMF (2 mL) was added NaH (7.30 mg, 0.182 mmol) under Ar. The reaction mixture was stirred for 30 min at rt. and 3-Iodooxetane (Aldrich, 31.0 mg, 0.168 mmol) was added. The reaction mixture was stirred for 1 h at 80° C., quenched by addition of a saturated aqueous solution of NaHCO₃ (50 mL), and extracted with EtOAc (2×100 mL). The combined organic layers were washed with a saturated aqueous solution of NaHCO₃ (75 mL), dried (Na₂SO₄), filtered and the filtrate was concentrated. The residue was purified by silica gel chromatography on Combiflash Isco (eluent: MeOH/DCM; gradient: 2.5% to 10% MeOH in 23 min, 0.4 min 10% MeOH; flow: 18 mL/min). The resulting material was further purified by preparative achiral SFC (column: Diol, 250×30 mm, 5 μm, 100 A, Princeton; eluent: MeOH/scCO₂; gradient: 1 min 23% MeOH, 23% to 28% MeOH in 6 min, 28% to 50% MeOH, in 1 min, 1.5 min 50% MeOH; flow: 100 mL/min) to afford the title compound (20 mg) as a colorless solid. Rf=0.39 (10% MeOH/DCM); Rt: 0.87 min (LC-MS 1); MS m/z: 448.2 [M+H]⁺ (LC-MS 1); ¹H NMR (400 MHz, DMSO-d6) δ 2.19 (s, 3H) 2.41 (s, 3H) 2.60 (s, 3H) 4.33-4.39 (m, 1H) 4.46-4.51 (m, 2H) 4.69-4.74 (m, 1H) 4.91-5.00 (m, 1H) 6.50 (s, 1H) 7.11 (s, 1H) 7.28-7.37 (m, 5H) 8.31 (s, 1H).

Example 7

1-(1-acetylazetidin-3-yl)-6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one

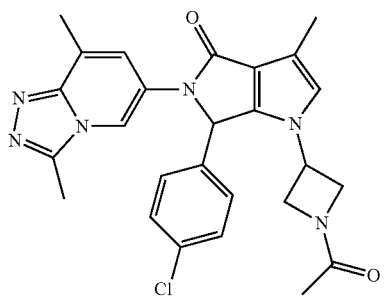 [SMILES: CC(=O)N1CC(n2cc(C)c3c2C(c2ccc(Cl)cc2)N(c2cc(C)c4nnc(C)n4c2)C3=O)C1]

To a stirred solution of 1-(azetidin-3-yl)-6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one (Step 4 of Example 4, 80 mg, 0.179 mmol) in DCM (1 mL) were added triethylamine (0.100 mL, 0.716 mmol) and Ac₂O (0.034 mL, 0.358 mmol) under Ar. The reaction mixture was stirred for 1 h at rt, diluted with water (75 mL), and extracted with EtOAc (2×100 mL). The combined organic layers were washed with water (100 mL), dried (Na₂SO₄), filtered and the filtrate was concentrated. The residue was purified by silica gel chromatography on Combiflash Isco (eluent: MeOH/DCM; gradient: 0% to 4.8% MeOH in 18.9 min; flow: 18 mL/min) followed by trituration of the resulting material in Et₂O to provide the title compound (52 mg) as a colorless solid. Rf=0.41 (10% MeOH/DCM); Rt: 0.76 min (LC-MS 1); MS m/z: 489.3 [M+H]⁺ (LC-MS 1); ¹H NMR (400 MHz, DMSO-d6) δ ppm [1.57 (s), 1.72 (s), 3H] 2.17 (s, 3H) 2.41 (s, 3H) 2.58-2.63 (m, 3H) 3.54-3.64 (m, 1H) 3.75-3.92 (m, 1H) 3.99-4.32 (m, 2H) 4.58-4.81 (m, 1H) [6.54 (s) 6.58 (s), 1H] 6.99 (s) 7.02 (s), 1H] 7.25-7.38 (m, 5H) 8.28-8.34 (m, 1H).

Example 8

Ethyl 3-(6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrol-1(4H)-yl)azetidine-1-carboxylate

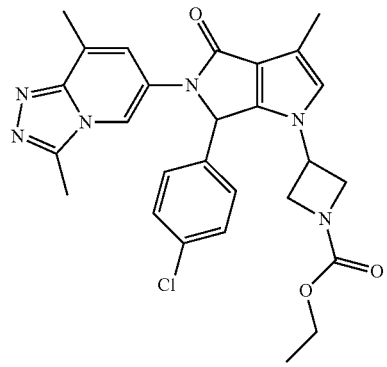 [SMILES: CCOC(=O)N1CC(n2cc(C)c3c2C(c2ccc(Cl)cc2)N(c2cc(C)c4nnc(C)n4c2)C3=O)C1]

To a stirred solution of 1-(azetidin-3-yl)-6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one (Step 4 of Example 4, 80 mg, 0.179 mmol) in DCM (2 mL) were added triethylamine (0.075 mL, 0.537 mmol) and ethyl chloroformate (0.026 mL, 0.268 mmol) under Ar. The reaction mixture was stirred for 16 h at rt, diluted with water (75 mL), and extracted with EtOAc (2×100 mL). The combined organic layers were washed with water (100 mL), dried (Na₂SO₄), filtered and the filtrate was concentrated. The residue was purified by silica gel chromatography on Combiflash Isco (eluent: MeOH/DCM; gradient: 1% to 6.3% MeOH in 18.3 min; flow: 18 mL/min) followed by trituration of the resulting material in Et₂O to provide the title compound (62 mg) as a yellow solid. Rf=0.50 (10% MeOH/DCM); Rt: 0.94 min (LC-MS 1); MS m/z: 519.2 [M+H]⁺ (LC-MS 1); ¹H NMR (400 MHz, DMSO-d6) δ ppm 1.13 (t, J=7.23 Hz, 3H) 2.16 (s, 3H) 2.41 (s, 3H) 2.60 (s, 3H) 3.83-4.11 (m, 6H) 4.73 (br. s., 1H) 6.57 (s, 1H) 6.98 (br. s., 1H) 7.26-7.44 (m, 5H) 8.31 (s, 1H).

Example 9

6-(4-chlorophenyl)-5-(3,8-dimethyl-[1,2,4]triazolo[4,3-a]pyridin-6-yl)-N,3-dimethyl-4-oxo-5,6-dihydropyrrolo[3,4-b]pyrrole-1(4H)-carboxamide

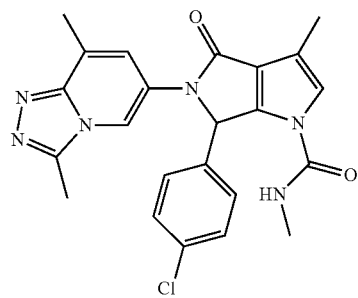 [SMILES: CNC(=O)n1cc(C)c2c1C(c1ccc(Cl)cc1)N(c1cc(C)c3nnc(C)n3c1)C2=O]

Step 1: N-methyl-1H-imidazole-1-carboxamide

A mixture of 1,1'-carbonyl diimidazole (5 g, 30.8 mmol) and methylamine (2N in THF, 25 mL, 50 mmol) Reactants were stirred for 3 h at rt and concentrated. The residue was purified by silica gel column chromatography (5% MeOH/DCM) to afford the title compound (2.44 g) as a colorless solid. Rt: 0.24 min (LC-MS 1); MS m/z: 126.1 [M+H]+ (LC-MS 1);

Step 2: 6-(4-chlorophenyl)-5-(3,8-dimethyl-[1,2,4]triazolo[4,3-a]pyridin-6-yl)-N,3-dimethyl-4-oxo-5,6-dihydropyrrolo[3,4-b]pyrrole-1(4H)-carboxamide To a stirred solution of 6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one (Step 2 of Example 4, 100 mg, 0.255 mmol) and triethylamine (0.107 mL, 0.766 mmol) in DCM (3 mL) was added N-methyl-1H-imidazole-1-carboxamide (Step 1 of Example 9, 63.9 mg, 0.510 mmol). The reaction mixture was stirred for 40 h at rt under Ar, concentrated, quenched by addition of a saturated aqueous solution of NaHCO$_3$ (100 mL), and extracted with EtOAc (2×100 mL). The combined organic layers were washed with a saturated aqueous solution of NaHCO$_3$ (50 mL), dried (Na$_2$SO$_4$), filtered and the filtrate was concentrated. The residue was purified by silica gel chromatography on Combiflash Isco (eluent: MeOH/DCM; gradient: 2.5% to 10% MeOH in 23 min, 0.4 min 10% MeOH; flow: 18 mL/min). The resulting material was further purified by preparative achiral SFC (column: PPU, 250×30 mm, 5 μm, 100 A, Princeton; eluent: MeOH/scCO$_2$; gradient: 1 min 20% MeOH, 20% to 25% MeOH in 6 min, 25% to 50% MeOH, in 1 min, 1.5 min 50% MeOH; flow: 100 mL/min) to afford the title compound (18 mg) as a colorless solid. Rf=0.52 (50% EtOAc/hexane); Rt: 0.82 min (LC-MS 1); MS m/z: 449.2 [M+H]+ (LC-MS 1); $^1$H NMR (400 MHz, DMSO-d6) δ 2.19 (s, 3H) 2.40 (s, 3H) 2.60 (s, 3H) 2.65 (d, J=4.30 Hz, 3H) 6.60 (s, 1H) 7.18-7.27 (m, 4H) 7.30 (s, 1H) 7.34 (s, 1H) 8.15-8.26 (m, 1H) 8.41 (d, J=0.78 Hz, 1H).

Example 10

6-(4-chlorophenyl)-5-(3,8-dimethyl-[1,2,4]triazolo[4,3-a]pyridin-6-yl)-N,N,3-trimethyl-4-oxo-5,6-dihydropyrrolo[3,4-b]pyrrole-1(4H)-carboxamide

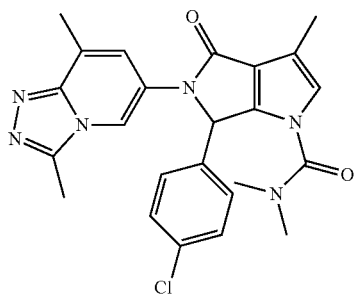 [SMILES: Cc1cn(C(=O)N(C)C)c2c1C(=O)N(c1cc(C)c3nnc(C)n3c1)C2c1ccc(Cl)cc1]

To a stirred solution of 6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one (Step 2 of Example 4, 100 mg, 0.255 mmol) in pyridine (2 mL) was added dimethylcarbamoyl chloride (Fluka, 0.047 mL, 0.510 mmol) under Ar. The reaction mixture was stirred for 16 h at 100° C., concentrated, quenched by addition of a saturated aqueous solution of NaHCO$_3$ (100 mL), and extracted with EtOAc (2×100 mL). The combined organic layers were washed with a saturated aqueous solution of NaHCO$_3$ (50 mL), dried (Na$_2$SO$_4$), filtered and the filtrate was concentrated. The residue was purified by silica gel chromatography on Combiflash Isco (eluent: MeOH/DCM; gradient: 0% to 8% MeOH in 14.9 min, 1.3 min 8% MeOH; flow: 18 mL/min). The resulting material was further purified by preparative achiral SFC (column: PPU, 250×30 mm, 5 μm, 100 A, Princeton; eluent: MeOH/scCO$_2$; gradient: 1 min 14% MeOH, 14% to 19% MeOH in 6 min, 19% to 50% MeOH, in 1 min, 1.5 min 50% MeOH; flow: 100 mL/min) followed by trituration of the product in Et$_2$O to afford the title compound (16 mg) as a colorless solid. Rf=0.44 (10% MeOH/DCM); Rt: 0.88 min (LC-MS 1); MS m/z: 463.2 [M+H]+ (LC-MS 1); $^1$H NMR (400 MHz, DMSO-d6) δ 8.43 (s, 1H), 7.38 (s, 1H), 7.29 (d, J=8.1 Hz, 2H), 7.21 (d, J=8.2 Hz, 2H), 7.10 (s, 1H), 6.55 (s, 1H), 2.81 (s, 6H), 2.60 (s, 3H), 2.41 (s, 3H), 2.19 (s, 3H).

Example 11

Ethyl 6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrole-1(4H)-carboxylate

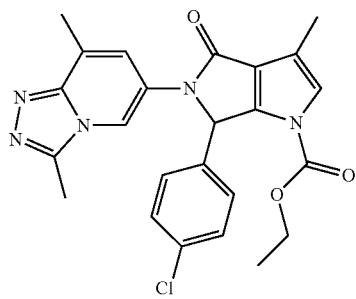 [SMILES: CCOC(=O)n1cc(C)c2c1C(c1ccc(Cl)cc1)N(c1cc(C)c3nnc(C)n3c1)C2=O]

The title compound was prepared using an analogous procedure to that described in Step 10 of Example 1 using 6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one (Step 2 of Example 4, 100 mg, 0.255 mmol). The crude product was purified by preparative HPLC (Gilson gx-281. Column: Sunfire C18, 30×100 mm, 5 μm. Flow: 30 mL/min. Gradient: 5% to 100% B in 20 min; A=0.1% TFA in H$_2$O, B=CH$_3$CN. Detection: UV) to afford the title compound (79 mg) as a colorless solid. Rf=0.38 (10% DCM/MeOH); Rt: 1.04 min (LC-MS 1); MS m/z: 464.1 [M+H]+ (LC-MS 1); $^1$H NMR (400 MHz, DMSO-d6) δ 8.39 (d, J=1.9 Hz, 1H), 7.35-7.15 (m, 6H), 6.57 (s, 1H), 4.31-4.00 (m, 2H), 2.61 (s, 3H), 2.40 (s, 3H), 2.20 (s, 3H), 1.07 (t, J=7.0 Hz, 3H).

Example 12

6-(4-chlorophenyl)-5-(3,8-dimethyl-[1,2,4]triazolo[4,3-a]pyridin-6-yl)-1-(1-(2-methoxyacetyl)azetidin-3-yl)-3-methyl-5,6-dihydropyrrolo[3,4-b]pyrrol-4(1H)-one

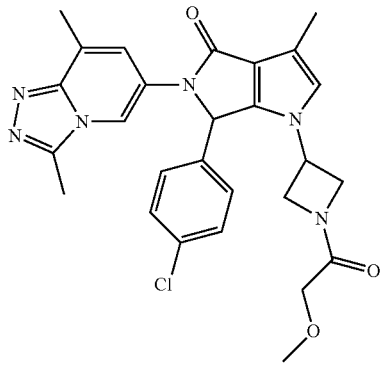 [SMILES: COCC(=O)N1CC(n2cc(C)c3c2C(c2ccc(Cl)cc2)N(c2cc(C)c4nnc(C)n4c2)C3=O)C1]

To a stirred solution of 1-(azetidin-3-yl)-6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one (Step 4 of Example 4, 91 mg, 0.204 mmol) in DMF (2 mL) was added DIEA (0.107 mL, 0.611 mmol), TBTU (131 mg, 0.407 mmol) and methoxyacetic acid (Aldrich, 0.023 mL, 0.305 mmol) under Ar. The reaction mixture was stirred for 16 h at rt, diluted with water (75 mL), and extracted with EtOAc (2×100 mL). The combined organic layers were washed with water (100 mL), dried (Na$_2$SO$_4$), filtered and the filtrate was concentrated. The residue was purified by silica gel chromatography on Combiflash Isco (eluent: MeOH/DCM; gradient: 2.5% to 9% MeOH in 17.2 min; flow: 18 mL/min) to afford the title compound (14 mg) as a brown solid. Rf=0.46 (10% MeOH/DCM); Rt: 0.78 min (LC-MS 1); MS m/z: 519.3 [M+H]$^+$ (LC-MS 1); $^1$H NMR (400 MHz, DMSO-d6) δ 8.42-8.18 (m, 1H), 7.43-7.21 (m, 5H), 7.10-6.92 (m, 1H), 6.66-6.40 (m, 1H), 4.84-4.58 (m, 1H), 4.43-3.57 (m, 5H), 3.28-3.26 (m, 1H), 3.25-3.16 (m, 3H), 2.60 (d, J=1.9 Hz, 3H), 2.41 (s, 3H), 2.17 (s, 3H).

Example 13

6-(4-chlorophenyl)-5-(3,8-dimethyl-[1,2,4]triazolo[4,3-a]pyridin-6-yl)-1-(2-methoxyethyl)-3-methyl-5,6-dihydropyrrolo[3,4-b]pyrrol-4(1H)-one

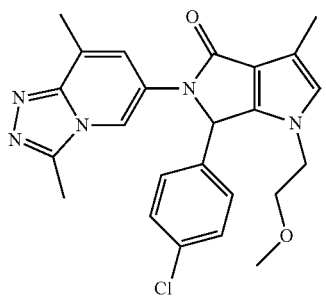 [SMILES: COCCn1cc(C)c2c1C(c1ccc(Cl)cc1)N(c1cc(C)c3nnc(C)n3c1)C2=O]

The title compound was prepared using an analogous procedure to that described in Step 1 of Example 2 using 6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one (Step 2 of Example 4, 80 mg, 0.204 mmol) and (2-bromomethyl)-methyl ether (Aldrich, 0.023 mL, 0.245 mmol). After addition of (2-bromomethyl)-methyl ether, the reaction mixture was stirred for 30 min at rt before quenching. The crude product was purified by silica gel chromatography on Combiflash Isco (eluent: MeOH/DCM; gradient: 1% to 6.7% MeOH in 18.7 min; flow: 18 mL/min). The resulting material was further purified by preparative achiral SFC (column: PPU, 250×30 mm, 5 μm, 100 A, Princeton; eluent: MeOH/scCO$_2$; gradient: 1 min 16% MeOH, 16% to 21% MeOH in 6 min, 21% to 50% MeOH, in 1 min, 1.5 min 50% MeOH; flow: 100 mL/min) followed by trituration of the product in Et$_2$O to afford the title compound (17 mg) as a yellow solid. Rf=0.53 (10% MeOH/DCM); Rt: 0.95 min (LC-MS 1); MS m/z: 450.2 [M+H]$^+$ (LC-MS 1); $^1$H NMR (400 MHz, DMSO-d6) δ 8.32 (s, 1H), 7.39-7.27 (m, 5H), 6.69 (s, 1H), 6.40 (s, 1H), 3.80-3.69 (m, 1H), 3.58-3.47 (m, 1H), 3.34-3.27 (m, 1H), 3.25-3.15 (m, 1H), 3.12 (s, 3H), 2.59 (s, 3H), 2.41 (s, 3H), 2.14 (s, 3H).

Example 14

6-(4-chlorophenyl)-5-(3,8-dimethyl-[1,2,4]triazolo[4,3-a]pyridin-6-yl)-1-(2-hydroxyethyl)-3-methyl-5,6-dihydropyrrolo[3,4-b]pyrrol-4(1H)-one

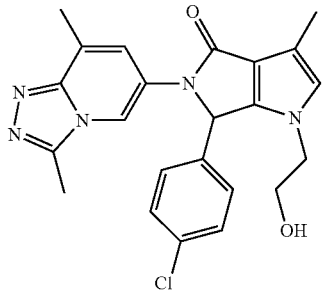 [SMILES: Cc1cn(CCO)c2c1C(=O)N(c1cc(C)c3nnc(C)n3c1)C2c1ccc(Cl)cc1]

The title compound was prepared using an analogous procedure to that described in Step 10 of Example 1 using 6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one (Step 2 of Example 4, 200 mg, 0.510 mmol) and (Fluka, 0.067 mL, 0.612 mmol). After addition 2-bromoethyl acetate, the reaction mixture was stirred for 30 min at rt, quenched by addition of aqueous NaOH (1N, 50 mL) and stirred for 1 h at rt before extraction. The crude product was purified by silica gel chromatography on Combiflash Isco (eluent: MeOH/DCM; gradient: 3% to 8.8% MeOH in 14.9 min; flow: 18 mL/min). The resulting material was further purified by preparative achiral SFC (column: reprosil 70 NH2, 250×30 mm, 5 μm, 70 A, Dr Maisch; eluent: MeOH/scCO$_2$; gradient: 1 min 22% MeOH, 22% to 27% MeOH in 6 min, 27% to 50% MeOH in 1 min, 1.5 min 50% MeOH; flow: 100 mL/min) followed by trituration of the product in Et$_2$O to afford the title compound (33 mg) as a colorless solid. Rf=0.36 (10% MeOH/DCM); Rt: 0.80 min (LC-MS 1); MS m/z: 436.2 [M+H]$^+$ (LC-MS 1); $^1$H NMR (400 MHz, DMSO-d6) δ 8.32 (s, 1H), 7.48-7.22 (m, 5H), 6.69 (s, 1H), 6.41 (s, 1H), 4.91 (t, J=5.0 Hz, 1H), 3.71-3.59 (m, 1H), 3.48-3.30 (m, 3H), 2.59 (s, 3H), 2.41 (s, 3H), 2.15 (s, 3H).

Example 15

1-(azetidin-3-yl)-6-(4-chlorophenyl)-3-cyclopropyl-5-(3,8-dimethyl-[1,2,4]triazolo[4,3-a]pyridin-6-yl)-5,6-dihydropyrrolo[3,4-b]pyrrol-4(1H)-one

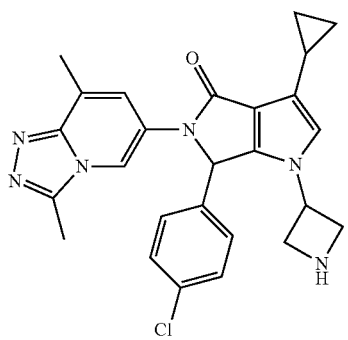

Step 1: Ethyl 2-((4-chlorophenyl)((3,8-dimethyl-[1,2,4]triazolo[4,3-a]pyridin-6-yl)amino)methyl)-4-cyclopropyl-1-((2-(trimethylsilyl)ethoxy)methyl)-1H-pyrrole-3-carboxylate The title compound was prepared using an analogous procedure to that described in Step 9 of Example 1 using 3,8-dimethyl-[1,2,4]triazolo[4,3-a]pyridin-6-amine (Step 4 of Example 3, 0.793 g, 4.89 mmol, 1.1 eq). The crude product was purified by silica gel chromatography on Combiflash Isco (eluent: MeOH/DCM; gradient: 0% to 6.2% MeOH in 17.6 min; flow: 40 mL/min) to afford the title compound (1.81 g) as a yellow solid. Rf=0.62 (10% MeOH/DCM); Rt: 1.48 min (LC-MS 1); MS m/z: 594.3 [M+H]+ (LC-MS 1).

Step 2: 6-(4-chlorophenyl)-3-cyclopropyl-5-(3,8-dimethyl-[1,2,4]triazolo[4,3-a]pyridin-6-yl)-1-(hydroxymethyl)-5,6-dihydropyrrolo[3,4-b]pyrrol-4(1H)-one The title compound was prepared using an analogous procedure to that described in Step 10 of Example 1 using ethyl 2-((4-chlorophenyl)((3,8-dimethyl-[1,2,4]triazolo[4,3-a]pyridin-6-yl)amino)methyl)-4-cyclopropyl-1-((2-(trimethylsilyl)ethoxy)methyl)-1H-pyrrole-3-carboxylate (Step 1 of Example 15, 1.81 g, 3.05 mmol) and stirring the reaction mixture for 16 h at 120° C. The crude product was purified by silica gel chromatography on Combiflash Isco (eluent: MeOH/DCM; gradient: 0% to 10% MeOH in 22.9 min, 0.7 min 10% MeOH; flow: 35 mL/min) to afford the title compound (516 mg) as a yellow solid. Rf=0.48 (10% MeOH/DCM); Rt: 0.88 min (LC-MS 1); MS m/z: 448.2 [M+H]+ (LC-MS 1).

Step 3: 6-(4-chlorophenyl)-3-cyclopropyl-5-(3,8-dimethyl-[1,2,4]triazolo[4,3-a]pyridin-6-yl)-5,6-dihydropyrrolo[3,4-b]pyrrol-4(1H)-one The title compound was prepared using an analogous procedure to that described in Step 2 of Example 4 using 6-(4-chlorophenyl)-3-cyclopropyl-5-(3,8-dimethyl-[1,2,4]triazolo[4,3-a]pyridin-6-yl)-1-(hydroxymethyl)-5,6-dihydropyrrolo[3,4-b]pyrrol-4(1H)-one (Step 2 of Example 15, 516 mg, 1.152 mmol). The crude product was purified by silica gel chromatography on Combiflash Isco (eluent: MeOH/DCM; gradient: 0% to 8.7% MeOH in 18.7 min; flow: 30 mL/min) to afford the title compound (370 mg, purity 80%) as a brown solid. Rf=0.50 (10% MeOH/DCM); Rt: 0.92 min (LC-MS 1); MS m/z: 418.2 [M+H]+ (LC-MS 1).

Step 4: Tert-butyl 3-(6-(4-chlorophenyl)-3-cyclopropyl-5-(3,8-dimethyl-[1,2,4]triazolo[4,3-a]pyridin-6-yl)-4-oxo-5,6-dihydropyrrolo[3,4-b]pyrrol-1(4H)-yl)azetidine-1-carboxylate The title compound was prepared using an analogous procedure to that described in Step 3 of Example 4 using 6-(4-chlorophenyl)-3-cyclopropyl-5-(3,8-dimethyl-[1,2,4]triazolo[4,3-a]pyridin-6-yl)-5,6-dihydropyrrolo[3,4-b]pyrrol-4(1H)-one (Step 3 of Example 15, 280 mg, 0.670 mmol) and stirring the reaction mixture for 2 h at 80° C. The crude product was purified by silica gel chromatography on Combiflash Isco (eluent: MeOH/EtOAc; gradient: 0% to 10% MeOH in 18 min, 2 min 10% MeOH; flow: 30 mL/min) to afford the title compound (157 mg, purity 75%) as a yellow solid. Rf=1.14 (10% MeOH/EtOAc); Rt: 0.92 min (LC-MS 1); MS m/z: 573.4 [M+H]+ (LC-MS 1).

Step 5: 1-(azetidin-3-yl)-6-(4-chlorophenyl)-3-cyclopropyl-5-(3,8-dimethyl-[1,2,4]triazolo[4,3-a]pyridin-6-yl)-5,6-dihydropyrrolo[3,4-b]pyrrol-4(1H)-one The title compound was prepared using an analogous procedure to that described in Step 4 of Example 4 using tert-butyl 3-(6-(4-chlorophenyl)-3-cyclopropyl-5-(3,8-dimethyl-[1,2,4]triazolo[4,3-a]pyridin-6-yl)-4-oxo-5,6-dihydropyrrolo[3,4-b]pyrrol-1(4H)-yl)azetidine-1-carboxylate (Step 4 of Example 15, 155 mg, 0.270 mmol). The crude product was purified by silica gel chromatography on Combiflash Isco (eluent: (MeOH/NH4OH, 4:1)/EtOAc; gradient: 0% to 9.4% MeOH/NH4OH in 15.9 min; flow: 18 mL/min) to afford the title compound (75 mg) as a brown solid. Rf=0.13 (10% MeOH/DCM); Rt: 0.62 min (LC-MS 1); MS m/z: 473.3 [M+H]+ (LC-MS 1).

Example 16

6-(4-chlorophenyl)-3-cyclopropyl-5-(3,8-dimethyl-[1,2,4]triazolo[4,3-a]pyridin-6-yl)-1-(1-methylazetidin-3-yl)-5,6-dihydropyrrolo[3,4-b]pyrrol-4(1H)-one

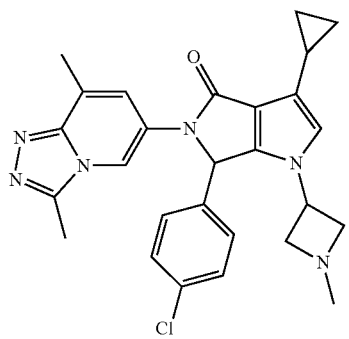 [SMILES: Cc1cc(N2C(=O)c3c(C4CC4)cn(C4CN(C)C4)c3C2c2ccc(Cl)cc2)cn2c(C)nnc12]

The title compound was prepared using an analogous procedure to that described in Example 5 using 1-(azetidin-3-yl)-6-(4-chlorophenyl)-3-cyclopropyl-5-(3,8-dimethyl-[1,2,4]triazolo[4,3-a]pyridin-6-yl)-5,6-dihydropyrrolo[3,4-b]pyrrol-4(1H)-one (Step 5 of Example 15, 35 mg, 0.074 mmol) and stirring the reaction mixture for 1 h at rt. The crude product was purified by silica gel chromatography on Combiflash Isco (eluent: MeOH/DCM; gradient: 1.5% to 10% MeOH in 19 min, 2.3 min 10% MeOH; flow: 18 mL/min) to afford the title compound (18 mg) as a colorless solid. Rf=0.39 (10% MeOH/DCM); Rt: 0.64 min (LC-MS 1); MS m/z: 487.3 [M+H]$^+$ (LC-MS 1). $^1$H NMR (400 MHz, DMSO-d6) δ 8.29 (d, J=1.7 Hz, 1H), 7.43-7.17 (m, 5H), 7.09 (s, 1H), 6.43 (s, 1H), 4.27-4.11 (m, 1H), 3.55-3.39 (m, 1H), 3.16 (t, J=6.8 Hz, 1H), 3.02-2.88 (m, 1H), 2.83 (t, J=6.8 Hz, 1H), 2.60 (s, 3H), 2.41 (s, 3H), 2.16 (s, 3H), 1.92-1.71 (m, 1H), 0.98-0.74 (m, 4H).

Example 17

1-(1-acetylazetidin-3-yl)-6-(4-chlorophenyl)-3-cyclopropyl-5-(3,8-dimethyl-[1,2,4]triazolo[4,3-a]pyridin-6-yl)-5,6-dihydropyrrolo[3,4-b]pyrrol-4(1H)-one

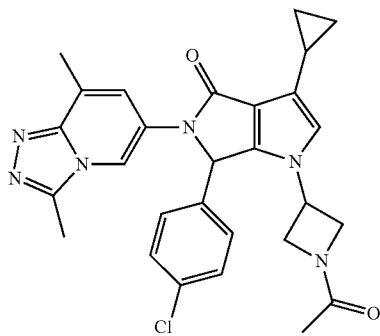 [SMILES: CC(=O)N1CC(n2cc(C3CC3)c3c2C(c2ccc(Cl)cc2)N(c2cc(C)c4nnc(C)n4c2)C3=O)C1]

The title compound was prepared using an analogous procedure to that described in Example 7 using 1-(azetidin-3-yl)-6-(4-chlorophenyl)-3-cyclopropyl-5-(3,8-dimethyl-[1,2,4]triazolo[4,3-a]pyridin-6-yl)-5,6-dihydropyrrolo[3,4-b]pyrrol-4(1H)-one (Step 5 of Example 15, 35 mg, 0.074 mmol). The crude product was purified by silica gel chromatography on Combiflash Isco (eluent: MeOH/DCM; gradient: 2% to 9.3% MeOH in 17.4 min; flow: 18 mL/min) to afford the title compound (24 mg) as a colorless solid. Rf=0.38 (10% MeOH/DCM); Rt: 0.84 min (LC-MS 1); MS m/z: 515.3 [M+H]$^+$ (LC-MS 1). $^1$H NMR (400 MHz, DMSO-d6) δ 8.37-8.17 (m, 1H), 7.46-7.16 (m, 5H), 7.16-6.99 (m, 1H), 6.62-6.40 (m, 1H), 4.81-4.50 (m, 1H), 4.35-3.95 (m, 2H), 3.90-3.57 (m, 2H), 2.60 (d, J=2.3 Hz, 3H), 2.41 (s, 3H), 1.88-1.79 (m, 1H), 1.76-1.51 (m, 3H), 0.96-0.76 (m, 4H).

Example 18

6-(4-chlorophenyl)-3-cyclopropyl-5-(3,8-dimethyl-[1,2,4]triazolo[4,3-a]pyridin-6-yl)-1-(oxetan-3-yl)-5,6-dihydropyrrolo[3,4-b]pyrrol-4(1H)-one

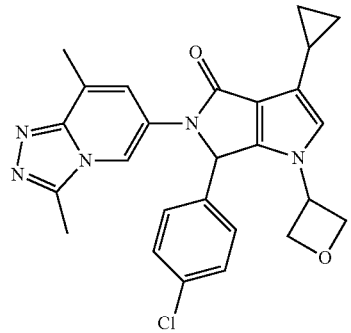 [SMILES: Cc1cc(N2C(=O)c3c(C4CC4)cn(C4COC4)c3C2c2ccc(Cl)cc2)cn2c(C)nnc12]

The title compound was prepared using an analogous procedure to that described in Example 6 using 6-(4-chlorophenyl)-3-cyclopropyl-5-(3,8-dimethyl-[1,2,4]triazolo[4,3-a]pyridin-6-yl)-5,6-dihydropyrrolo[3,4-b]pyrrol-4(1H)-one (Step 3 of Example 15, 80 mg, 0.191 mmol). The crude product was purified by silica gel chromatography on Combiflash Isco (eluent: MeOH/DCM; gradient: 1.5% to 8.7% MeOH in 13.8 min; flow: 18 mL/min). The resulting material was further purified by preparative achiral SFC (column: 4-EP, 250×30 mm, 5 μm, 60 A, Princeton; eluent: MeOH/scCO$_2$; gradient: 1 min 17% MeOH, 17% to 22% MeOH in 6 min, 22% to 50% MeOH in 1 min, 1.5 min 50% MeOH; flow: 100 mL/min) followed by trituration of the resulting material in Et$_2$O to afford the title compound (20 mg) as a colorless solid. Rf=0.48 (10% MeOH/DCM); Rt: 0.94 min (LC-MS 1); MS m/z: 474.3 [M+H]$^+$ (LC-MS 1). $^1$H NMR (400 MHz, DMSO-d6) δ 8.30 (s, 1H), 7.45-7.26 (m, 5H), 7.19 (s, 1H), 6.47 (s, 1H), 5.07-4.82 (m, 1H), 4.72 (t, J=7.3 Hz, 1H), 4.55 (t, J=6.6 Hz, 1H), 4.47 (t, J=6.6 Hz, 1H), 4.32 (t, J=7.2 Hz, 1H), 2.60 (s, 3H), 2.41 (s, 3H), 1.91-1.80 (m, 1H), 0.98-0.78 (m, 4H).

Example 19

1-(azetidin-3-yl)-6-(4-chlorophenyl)-5-(3,7-dimethyl-3H-[1,2,3]triazolo[4,5-b]pyridin-5-yl)-3-methyl-5,6-dihydropyrrolo[3,4-b]pyrrol-4(1H)-one

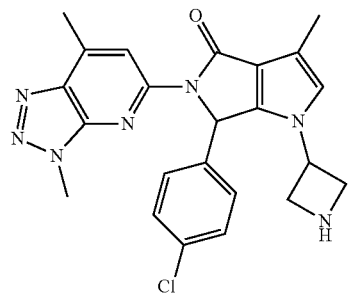 [SMILES: Cc1cn(C2CNC2)c2c1C(=O)N(c1cc(C)c3nnn(C)c3n1)C2c1ccc(Cl)cc1]

Step 1: Ethyl 2-((4-chlorophenyl)((3,7-dimethyl-3H-[1,2,3]triazolo[4,5-b]pyridin-5-yl)amino)methyl)-4-methyl-14(2-(trimethylsilyl)ethoxy)methyl)-1H-pyrrole-3-carboxylate The title compound was prepared using an analogous procedure to that described in Step 9 of Example 1 using ethyl 2-((4-chlorophenyl)(hydroxy)methyl)-4-methyl-1-((2-(trimethylsilyl)ethoxy)methyl)-1H-pyrrole-3-carboxylate (Step 6 of Example 3, 2 g, 4.72 mmol). The crude product was purified by silica gel chromatography on Combiflash Isco (eluent: EtOAc/hexane; gradient: 0% to 36.5% EtOAc in 18.3 min; flow: 40 mL/min) to afford the title compound (1.87 g) as a yellow solid. Rf=0.79 (50% EtOAc/hexane); Rt: 1.56 min (LC-MS 1); MS m/z: 569.3 [M+H]$^+$ (LC-MS 1).

Step 2: 6-(4-chlorophenyl)-5-(3,7-dimethyl-3H-[1,2,3]triazolo[4,5-b]pyridin-5-yl)-1-(hydroxymethyl)-3-methyl-5,6-dihydropyrrolo[3,4-b]pyrrol-4(1H)-one The title compound was prepared using an analogous procedure to that described in Step 10 of Example 1 using of ethyl 2-((4-chlorophenyl)((3,7-dimethyl-3H-[1,2,3]triazolo[4,5-b]pyridin-5-yl)amino)methyl)-4-methyl-1-((2-(trimethylsilyl)ethoxy)methyl)-1H-pyrrole-3-carboxylate (Step 1 of Example 19, 1.87 g, 3.29 mmol) and stirring the reaction mixture was stirred for 20 h at 120° C. The crude product was purified by silica gel chromatography on Combiflash Isco (eluent: EtOAc/hexane; gradient: 1.3 min 0% EtOAc, 0% to 100% EtOAc in 16 min, 17.7 min 100% EtOAc; flow: 35 mL/min). to afford the title compound (317 mg, purity 70%) as a yellow solid. Rf=0.45 (50% EtOAc/hexane); Rt: 1.04 min (LC-MS 1); MS m/z: 423.2 [M+H]$^+$ (LC-MS 1).

Step 3: 6-(4-chlorophenyl)-5-(3,7-dimethyl-3H-[1,2,3]triazolo[4,5-b]pyridin-5-yl)-3-methyl-5,6-dihydropyrrolo[3,4-b]pyrrol-4(1H)-one The title compound was prepared using an analogous procedure to that described in Step 2 of Example 4 using 6-(4-chlorophenyl)-5-(3,7-dimethyl-3H-[1,2,3]triazolo[4,5-b]pyridin-5-yl)-1-(hydroxymethyl)-3-methyl-5,6-dihydropyrrolo[3,4-b]pyrrol-4(1H)-one (Step 2 of Example 19, 310 mg, 0.733 mmol). The crude product was purified by silica gel chromatography on Combiflash Isco (eluent: MeOH/DCM; gradient: 0% to 6% MeOH in 12.4; flow: 30 mL/min) to afford the title compound (223 mg, purity 75%) as a brown solid. Rf=0.78 (10% MeOH/DCM); Rt: 1.07 min (LC-MS 1); MS m/z: 393.2 [M+H]$^+$ (LC-MS 1).

Step 4: Tert-butyl 3-(6-(4-chlorophenyl)-5-(3,7-dimethyl-3H-[1,2,3]triazolo[4,5-b]pyridin-5-yl)-3-methyl-4-oxo-5,6-dihydropyrrolo[3,4-b]pyrrol-1(4H)-yl)azetidine-1-carboxylate The title compound was prepared using an analogous procedure to that described in Step 3 of Example 4 using 6-(4-chlorophenyl)-5-(3,7-dimethyl-3H-[1,2,3]triazolo[4,5-b]pyridin-5-yl)-3-methyl-5,6-dihydropyrrolo[3,4-b]pyrrol-4(1H)-one (Step 3 of Example 19, 140 mg, 0.356 mmol). The crude product was purified by silica gel chromatography on Combiflash Isco (eluent: EtOAc/hexane; gradient: 0% to 99.5% EtOAc in 16 min, 15.1 min; flow: 30 mL/min). to afford the title compound (105 mg, purity 90%) as a yellow solid. Rf=0.31 (50% EtOAc/hexane); Rt: 1.32 min (LC-MS 1); MS m/z: 548.2 [M+H]$^+$ (LC-MS 1).

Step 5: 1-(azetidin-3-yl)-6-(4-chlorophenyl)-5-(3,7-dimethyl-3H-[1,2,3]triazolo[4,5-b]pyridin-5-yl)-3-methyl-5,6-dihydropyrrolo[3,4-b]pyrrol-4(1H)-one The title compound was prepared using an analogous procedure to that described in Step 4 of Example 4 using tert-butyl 3-(6-(4-chlorophenyl)-5-(3,7-dimethyl-3H-[1,2,3]triazolo[4,5-b]pyridin-5-yl)-3-methyl-4-oxo-5,6-dihydropyrrolo[3,4-b]pyrrol-1(4H)-yl)azetidine-1-carboxylate (Step 4 of Example 19, 100 mg, 0.182 mmol) and stirring the reaction mixture for 2 h at rt. The crude product was purified by silica gel chromatography on Combiflash Isco (eluent: MeOH/DCM; gradient: 0% to 6.8% MeOH in 10.5; flow: 18 mL/min) to afford the title compound (55 mg) as a brown solid. Rf=0.30 (10% MeOH/DCM); Rt: 0.76 min (LC-MS 1); MS m/z: 448.3 [M+H]$^+$ (LC-MS 1).

Example 20

6-(4-chlorophenyl)-5-(3,7-di methyl-3H-[1,2,3]triazolo[4,5-b]pyridin-5-yl)-3-methyl-1-(1-methylazetidin-3-yl)-5,6-dihydropyrrolo[3,4-b]pyrrol-4(1H)-one

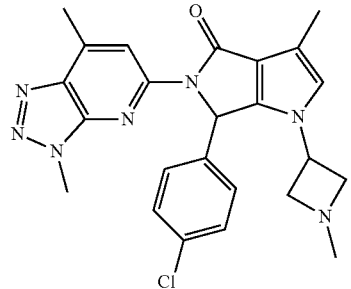 [SMILES: Cc1cn(C2CN(C)C2)c2c1C(=O)N(c1cc(C)c3nnn(C)c3n1)C2c1ccc(Cl)cc1]

The title compound was prepared using an analogous procedure to that described in Example 5 using 1-(azetidin-3-yl)-6-(4-chlorophenyl)-5-(3,7-dimethyl-3H-[1,2,3]triazolo[4,5-b]pyridin-5-yl)-3-methyl-5,6-dihydropyrrolo[3,4-b]pyrrol-4(1H)-one (Step 5 of Example 19, 50 mg, 0.112 mmol). The crude product was purified by silica gel chromatography on Combiflash Isco (eluent: MeOH/DCM; gradient: 0% to 5.3% MeOH in 10.5; flow: 18 mL/min) followed by trituration in Et$_2$O to afford the title compound (36 mg) as a colorless solid. Rf=0.59 (10% MeOH/DCM); Rt: 0.77 min (LC-MS 1); MS m/z: 462.3 [M+H]$^+$ (LC-MS 1); $^1$H NMR (400 MHz, DMSO-d6) δ 8.26 (s, 1H), 7.46-7.26 (m, 4H), 7.07 (s, 1H), 6.65 (s, 1H), 4.40-4.28 (m, 1H), 4.11 (s, 3H), 3.54-3.47 (m, 1H), 3.23-3.16 (m, 1H), 2.84-2.77 (m, 1H), 2.69-2.64 (m, 1H), 2.63 (s, 3H), 2.20 (s, 3H), 2.16 (s, 3H).

Example 21

6-(4-chlorophenyl)-5-(3,8-dimethyl-[1,2,4]triazolo[4,3-a]pyridin-6-yl)-5,6-dihydropyrrolo[3,4-b]pyrrol-4(1H)-one

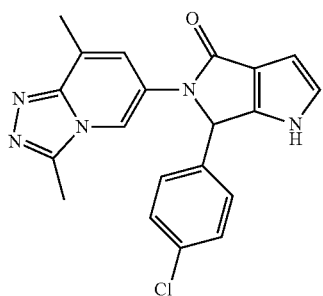 [SMILES: Cc1cc(N2C(=O)c3cc[nH]c3C2c2ccc(Cl)cc2)cn2c(C)nnc12]

Step 1: Methyl 1-((2-(trimethylsilyl)ethoxy)methyl)-1H-pyrrole-3-carboxylate The title compound was prepared using an analogous procedure to that described in Step 7 of Example 1 using methyl 1H-pyrrole-3-carboxylate (Ace Synthesis, 8.67 g, 69.3 mmol) and 1.3 eq of NaH, stirring the reaction mixture for 3 h at rt and quenching it with water. The crude product was purified by silica gel column chromatography (10% EtOAc/hexane) to afford the title compound (12.2 g) as a yellow oil. Rf=0.19 (10% EtOAc/hexane); Rt: 1.20 min (LC-MS 1); MS m/z: 256.2 [M+H]$^+$ (LC-MS 1).

Step 2: Methyl 2-((4-chlorophenyl)(hydroxy)methyl)-14(2-(trimethylsilyl)ethoxy)methyl)-1H-pyrrole-3-carboxylate To a stirred suspension of methyl 1-((2-(trimethylsilyl)ethoxy)methyl)-1H-pyrrole-3-carboxylate (Step 1 of Example 21, 12.2 g, 47.7 mmol) in THF (200 mL) was added LDA (2M, 31 mL, 61.9 mmol) at −78° C. under Ar. The reaction mixture was stirred for 1 h at −78° C. 4-Chlorobenzaldehyde (7.37 g, 52.4 mmol) in THF (50 mL) was added. The reaction mixture was stirred for 1.5 h at −78° C., quenched by addition of a saturated aqueous solution of ammonium chloride, diluted with a saturated aqueous solution of ammonium chloride and EtOAc, and extracted twice with EtOAc. The combined organic extracts were washed with water and brine, dried (Na$_2$SO$_4$), filtered and the filtrate was concentrated. The residue was purified by silica gel column chromatography (20% EtOAc/hexane) to afford the title compound (15.2 g, purity 93%) as a yellow oil. Rf=0.23 (20% EtOAc/hexane); Rt: 1.40 min (LC-MS 1); MS m/z: 378.1 [M-17]$^+$ (LC-MS 1).

Step 3: Methyl 2-((4-chlorophenyl)((3,8-dimethyl-[1,2,4]triazolo[4,3-a]pyridin-6-yl)amino)methyl)-1-((2-(trimethylsilyl)ethoxy)methyl)-1H-pyrrole-3-carboxylate The title compound was prepared using an analogous procedure to that described in Step 9 of Example 1 using methyl 2-((4-chlorophenyl)(hydroxy)methyl)-1-((2-(trimethylsilyl)ethoxy)methyl)-1H-pyrrole-3-carboxylate (Step 2 of Example 21, 8.1 g, 19.03 mmol) and 3,8-dimethyl-[1,2,4]triazolo[4,3-a]pyridin-6-amine (Step 4 of Example 3, 3.39 g, 20.93 mmol), and quenching the reaction mixture with water. The residue was purified by silica gel column chromatography (5% MeOH/DCM) to afford the title compound (8.6 g, purity 90%) as a yellow oil. Rf=0.20 (5% MeOH/DCM); Rt: 1.33 min (LC-MS 1); MS m/z: 540.3 [M+H]$^+$ (LC-MS 1).

Step 4: 2-((4-chlorophenyl)((3,8-dimethyl-[1,2,4]triazolo[4,3-a]pyridin-6-yl)amino)methyl)-1-((2-(trimethylsilyl)ethoxy)methyl)-1H-pyrrole-3-carboxylic acid To a stirred solution of methyl 2-((4-chlorophenyl)((3,8-dimethyl-[1,2,4]triazolo[4,3-a]pyridin-6-yl)amino)methyl)-1-((2-(trimethylsilyl)ethoxy)methyl)-1H-pyrrole-3-carboxylate (Step 3 of Example 21, 8.57 g, 12.38 mmol) in THF (60 mL) and MeOH (60 mL) was added aqueous NaOH (2N, 60 mL, 120 mmol). The reaction mixture was stirred for 4 h at 100° C. and allowed to cool. THF and MeOH were evaporated. The resulting aqueous residue was acidified to pH 5 by addition of 6N HCl. The mixture was diluted in EtOAc/water and extracted twice with EtOAc. The combined organic extracts were dried (Na$_2$SO$_4$), filtered and the filtrate was concentrated to afford the title compound (8 g, purity 79%) as a brown oil. Rt: 1.17 min (LC-MS 1); MS m/z: 526.2 [M+H]$^+$ (LC-MS 1).

Step 5: 6-(4-chlorophenyl)-5-(3,8-dimethyl-[1,2,4]triazolo[4,3-a]pyridin-6-yl)-1-((2-(trimethylsilyl)ethoxy)methyl)-5,6-dihydropyrrolo[3,4-b]pyrrol-4(1H)-one The title compound was prepared using an analogous procedure to that described in Step 5 of Example 2 using 2-((4-chlorophenyl)((3,8-dimethyl-[1,2,4]triazolo[4,3-a]pyridin-6-yl)amino)methyl)-1-((2-(trimethylsilyl)ethoxy)methyl)-1H-pyrrole-3-carboxylic acid (Step 4 of Example 21, 8 g, 12 mmol) and quenching the reaction mixture with water. The residue was purified by silica gel column chromatography (5% MeOH/DCM) followed by trituration of the resulting material in Et$_2$O to afford the title compound (3.78 g) as a colorless solid. Rf=0.25 (5% MeOH/DCM); Rt: 1.19 min (LC-MS 1); MS m/z: 508.2 [M+H]$^+$ (LC-MS 1).

Step 6: 6-(4-chlorophenyl)-5-(3,8-dimethyl-[1,2,4]triazolo[4,3-a]pyridin-6-yl)-5,6-dihydropyrrolo[3,4-b]pyrrol-4(1H)-one A mixture of 6-(4-chlorophenyl)-5-(3,8-dimethyl-[1,2,4]triazolo[4,3-a]pyridin-6-yl)-1-((2-(trimethylsilyl)ethoxy)methyl)-5,6-dihydropyrrolo[3,4-b]pyrrol-4(1H)-one (Step 5 of Example 21, 1 g, 1.968 mmol), EtOH (10 mL) and HCl (6N, 9.84 mL, 59 mmol) was stirred for 7 h at 65° C. The reaction mixture was diluted with DCM/water, basified with aqueous 2N NaOH and extracted twice with DCM. The combined organic extracts were dried (Na$_2$SO$_4$), filtered and the filtrate was concentrated. The residue was purified by silica gel column chromatography (1% ammonia/7.5% MeOH/DCM). The resulting material was triturated in Et$_2$O to provide the title compound (460 mg) as a colorless solid. Rf=0.23 (1% ammonia/7.5% MeOH/DCM); Rt: 0.77 min (LC-MS 1); MS m/z: 378.2 [M+H]$^+$ (LC-MS 1); $^1$H NMR (400 MHz, DMSO-d6) δ 2.42 (s, 3H) 2.60 (s, 3H) 6.31 (d, J=3.13 Hz, 1H) 6.47 (s, 1H) 6.96 (d, J=2.74 Hz, 1H) 7.20-7.42 (m, 5H) 8.35 (s, 1H) 11.69 (s, 1H).

Example 22

Ethyl 6-(4-chlorophenyl)-5-(3,8-dimethyl-[1,2,4]triazolo[4,3-a]pyridin-6-yl)-4-oxo-5,6-dihydropyrrolo[3,4-b]pyrrole-1(4H)-carboxylate

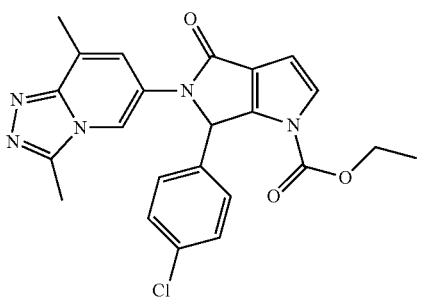 [SMILES: CCOC(=O)n1ccc2c1C(c1ccc(Cl)cc1)N(c1cc(C)c3nnc(C)n3c1)C2=O]

Ethyl chloroformate (0.013 mL, 0.135 mmol) was added to a stirred suspension of 6-(4-chlorophenyl)-5-(3,8-dimethyl-[1,2,4]triazolo[4,3-a]pyridin-6-yl)-5,6-dihydropyrrolo[3,4-b]pyrrol-4(1H)-one (Step 6 of Example 21, 34 mg, 0.090 mmol) and triethylamine (0.038 mL, 0.270 mmol) in DCM (3 mL) at rt. The reaction mixture was stirred for 30 min at rt, diluted in DCM/water, and extracted twice with DCM. The combined organic extracts were washed with water and brine, dried (Na$_2$SO$_4$), filtered and the filtrate was concentrated. The residue was purified by silica gel chromatography on Combiflash Isco (eluent: MeOH/DCM; gradient: 1.6 min 0% MeOH, 0% to 8.6% MeOH in 17 min; flow: 18 mL/min) followed by trituration in Et$_2$O to afford the title compound (30 mg) as a colorless solid. Rf=0.31 (5% MeOH/DCM); Rt: 0.95 min (LC-MS 1); MS m/z: 450.2 [M+H]$^+$ (LC-MS 1); $^1$H NMR (400 MHz, DMSO-d6) δ 1.04-1.14 (m, 3H) 2.41 (s, 3H) 2.62 (s, 3H) 4.21 (q, J=7.04 Hz, 2H) 6.56-6.72 (m, 2H) 7.16-7.37 (m, 5H) 7.51 (d, J=3.52 Hz, 1H) 8.40 (s, 1H).

Example 23

6-(4-chlorophenyl)-5-(3,8-dimethyl-[1,2,4]triazolo[4,3-a]pyridin-6-yl)-N-methyl-4-oxo-5,6-dihydropyrrolo[3,4-b]pyrrole-1(4H)-carboxamide

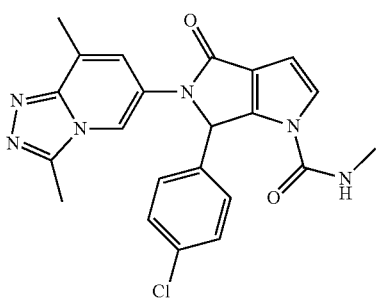 [SMILES: CNC(=O)n1ccc2c1C(c1ccc(Cl)cc1)N(c1cc(C)c3nnc(C)n3c1)C2=O]

A mixture of 6-(4-chlorophenyl)-5-(3,8-dimethyl-[1,2,4]triazolo[4,3-a]pyridin-6-yl)-5,6-dihydropyrrolo[3,4-b]pyrrol-4(1H)-one (Step 6 of Example 21, 60 mg, 0.159 mmol), N-methyl-1H-imidazole-1-carboxamide (Step 1 of Example 9, 39.7 mg, 0.318 mmol) and triethylamine (0.046 mL, 0.333 mmol) in DCM (3 mL) was stirred for 24 h at rt, diluted in DCM/water, and extracted twice with DCM. The combined organic extracts were washed with water and brine, dried (Na$_2$SO$_4$), filtered and the filtrate was concentrated. The residue was purified by silica gel chromatography on Combiflash Isco (eluent: (MeOH/NH$_4$OH 4:1)/DCM; gradient: 1.7 min 0% MeOH/NH$_4$OH, 0% to 9.4% MeOH/NH$_4$OH in 20 min; flow: 35 mL/min) followed by trituration in Et$_2$O. The resulting material was further purified by preparative achiral SFC (column: 2-EP, 250×30 mm, 5 μm, 60 A, Princeton; eluent: MeOH/scCO$_2$; gradient: 1 min 18% MeOH, 18% to 23% MeOH in 6 min, 23% to 50% MeOH in 1 min, 1.5 min 50% MeOH; flow: 100 mL/min) followed by trituration of the product in Et$_2$O to afford the title compound (32 mg) as a colorless solid. Rf=0.21 (1% ammonia/7.5% MeOH/DCM); Rt: 0.76 min (LC-MS 1); MS m/z: 435.2 [M+H]$^+$ (LC-MS 1); $^1$H NMR (400 MHz, DMSO-d6) δ 2.40 (s, 3H) 2.56-2.74 (m, 6H) 6.59 (d, J=3.52 Hz, 1H) 6.66 (s, 1H) 7.13-7.29 (m, 4H) 7.33 (s, 1H) 7.56 (d, J=3.13 Hz, 1H) 8.26-8.48 (m, 2H).

Example 24

6-(4-chlorophenyl)-5-(3,8-dimethyl-[1,2,4]triazolo[4,3-a]pyridin-6-yl)-N,N-dimethyl-4-oxo-5,6-dihydropyrrolo[3,4-b]pyrrole-1(4H)-carboxamide

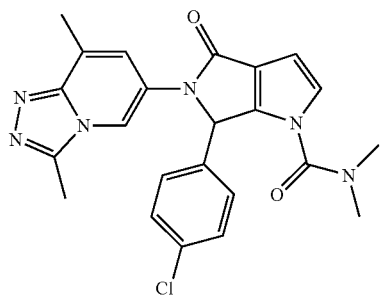 [SMILES: Cc1cc(N2C(=O)c3ccn(C(=O)N(C)C)c3C2c2ccc(Cl)cc2)cn2c(C)nnc12]

A mixture of 6-(4-chlorophenyl)-5-(3,8-dimethyl-[1,2,4]triazolo[4,3-a]pyridin-6-yl)-5,6-dihydropyrrolo[3,4-b]pyrrol-4(1H)-one (Step 6 of Example 21, 60 mg, 0.159 mmol) and dimethylcarbamoyl chloride (Fluka, 0.018 mL, 0.191 mmol) in pyridine (2 mL) was stirred for 14 h at 100° C., diluted in EtOAc/water, and extracted twice with EtOAc. The combined organic extracts were washed with brine, dried (Na$_2$SO$_4$), filtered and the filtrate was concentrated. The residue was purified by silica gel chromatography on Combiflash Isco (eluent: (MeOH/NH$_4$OH 4:1)/DCM; gradient: 1.3 min 0% MeOH/NH$_4$OH, 0% to 6.2% MeOH/NH$_4$OH in 13.7 min, 6.2% to 6.6% MeOH/NH$_4$OH in 1.8 min, 6.6% to 8% MeOH/NH$_4$OH in 6.6 min; flow: 35 mL/min). The resulting material was triturated in Et$_2$O to afford the title compound (35 mg) as a colorless solid. Rf=0.24 (1% ammonia/5% MeOH/DCM); Rt: 0.80 min (LC-MS 1); MS m/z: 449.2 [M+H]$^+$ (LC-MS 1); $^1$H NMR (400 MHz, DMSO-d6) δ 2.41 (s, 3H) 2.60 (s, 3H) 2.81 (s, 6H) 6.54 (d, J=3.13 Hz, 1H) 6.60 (s, 1H) 7.16-7.26 (m, 2H) 7.26-7.41 (m, 4H) 8.44 (s, 1H).

Example 25

6-(4-chlorophenyl)-5-(3,8-dimethyl-[1,2,4]triazolo
[4,3-a]pyridin-6-yl)-2-(1-methyl-2-oxo-1,2-dihydro-
pyridin-3-yl)-5,6-dihydropyrrolo[3,4-b]pyrrol-4
(1H)-one

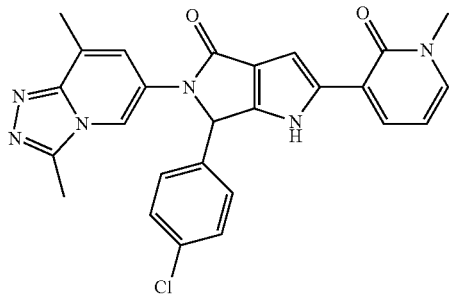 [SMILES: Cc1cc(N2C(=O)c3cc(-c4cccn(C)c4=O)[nH]c3C2c2ccc(Cl)cc2)cn2c(C)nnc12]

Step 1: 3-bromo-1-methylpyridin-2(1H)-one

A mixture of 2-hydroxy-3-bromopyridine (Aldrich, 967 mg, 5.56 mmol), potassium carbonate (1536 mg, 11.12 mmol) and iodomethane (0.521 mL, 8.34 mmol) in DMF (10 mL) was stirred for 1 h at rt, diluted in EtOAc/water, and extracted twice with EtOAc. The combined organic extracts were washed with brine, dried ($Na_2SO_4$), filtered and the filtrate was concentrated. The residue was purified by silica gel column chromatography (50% EtOAc/hexane) to afford the title compound (757 mg) as a yellow oil. Rf=0.11 (50% EtOAc/hexane); Rt: 0.50 min (LC-MS 1); MS m/z: 188.0 $[M]^+$ (LC-MS 1).

Step 2: 1-methyl-3-(4,4,5,5-tetramethyl-1,3,2-dioxa-borolan-2-yl)pyridin-2(1H)-one A mixture of 3-bromo-1-methylpyridin-2(1H)-one (Step 1 of Example 25, 770 mg, 4.1 mmol), bis(pinacolato)diboron (1248 mg, 4.91 mmol), $PdCl_2$(dppf)$CH_2Cl_2$ complex (401 mg, 0.491 mmol) and potassium acetate (1206 mg, 12.29 mmol) in dioxane (16 mL) was stirred for 2 h at 110° C. The reaction mixture was diluted with toluene, sonicated for 30 min at 40° C. and filtered (the filter cake was rinsed with hot toluene). The filtrate was concentrated to afford the title compound (1.7 g, purity 40%) as a brown oil. Rt: 0.38 min (LC-MS 1); MS m/z: 154.0 $[M]^+$ (boronic acid) (LC-MS 1).

Step 3: 2-bromo-6-(4-chlorophenyl)-5-(3,8-dimethyl-[1,2,4]triazolo[4,3-a]pyridin-6-yl)-14(2-(trimethylsilyl)ethoxy)methyl)-5,6-dihydropyrrolo[3,4-b]pyrrol-4(1H)-one NBS (299 mg, 1.678 mmol) was added to a stirred solution of 6-(4-chlorophenyl)-5-(3,8-dimethyl-[1,2,4]triazolo[4,3-a]pyridin-6-yl)-14(2-(trimethylsilyl)ethoxy)methyl)-5,6-dihydropyrrolo[3,4-b]pyrrol-4(1H)-one (Step 5 of Example 21, 656 mg, 1.291 mmol) in carbon tetrachloride (30 mL) at 0° C. The reaction mixture was stirred for 3 days at rt and cooled to 0° C. NBS (120 mg) was added. After 30 min, the mixture was diluted in EtOAc/water and extracted with EtOAc. The combined organic extracts were washed with brine, dried ($Na_2SO_4$), filtered and the filtrate was concentrated. The residue was purified by silica gel chromatography on Combiflash Isco (eluent: MeOH/DCM; gradient: 1.6 min 0% MeOH, 0% to 6% MeOH in 19.6 min, 0.2 min 6% MeOH; flow: 35 mL/min) to afford the title compound (243 mg, purity 90%) as a beige foam. Rf=0.26 (5% MeOH/DCM); Rt: 1.31 min (LC-MS 1); MS m/z: 586.3/588.2 $[M+H]^+$ (LC-MS 1).

Step 4: 6-(4-chlorophenyl)-5-(3,8-dimethyl-[1,2,4]triazolo[4,3-a]pyridin-6-yl)-2-(1-methyl-2-oxo-1,2-dihydropyridin-3-yl)-1-((2-(trimethylsilyl)ethoxy)methyl)-5,6-dihydropyrrolo[3,4-b]pyrrol-4(1H)-one $PdCl_2$(dppf).$CH_2Cl_2$ complex (30.1 mg, 0.037 mmol) was added to a stirred mixture of 2-bromo-6-(4-chlorophenyl)-5-(3,8-dimethyl-[1,2,4]triazolo[4,3-a]pyridin-6-yl)-14(2-(trimethylsilyl)ethoxy)methyl)-5,6-dihydropyrrolo[3,4-b]pyrrol-4(1H)-one (Step 3 of Example 25, 240 mg, 0.368 mmol) and $K_3PO_4$ (312 mg, 1.472 mmol) in dioxane (3 mL) and water (1 mL) at 80° C. and then heated up to 110° C. 1-Methyl-3-(4,4,5,5-tetramethyl-1,3,2-dioxaborolan-2-yl)pyridin-2(1H)-one (Step 2 of Example 25, 541 mg, 0.920 mmol) was added. The reaction mixture was stirred at 110° C. for 10 min, diluted in EtOAc/water, and extracted twice with EtOAc. The combined organic extracts were washed with brine, dried ($Na_2SO_4$), filtered and the filtrate was concentrated. The residue was loaded onto a Varian PL-Thiol MP SPE cartridge (to remove metals traces) and eluted with MeOH. The resulting filtrate was concentrated. The residue was purified by silica gel chromatography on Combiflash Isco (eluent: MeOH/DCM; gradient: 1.6 min 0% MeOH, 0% to 7.6% MeOH in 17.7 min, 7.6% to 9.4% MeOH in 8.2 min; flow: 40 mL/min) to afford the title compound (187 mg) as a beige solid. Rf=0.12 (5% MeOH/DCM); Rt: 1.11 min (LC-MS 1); MS m/z: 615.3 $[M+H]^+$ (LC-MS 1).

Step 5: 6-(4-chlorophenyl)-5-(3,8-dimethyl-[1,2,4]triazolo[4,3-a]pyridin-6-yl)-2-(1-methyl-2-oxo-1,2-dihydropyridin-3-yl)-5,6-dihydropyrrolo[3,4-b]pyrrol-4(1H)-one A mixture of 6-(4-chlorophenyl)-5-(3,8-dimethyl-[1,2,4]triazolo[4,3-a]pyridin-6-yl)-2-(1-methyl-2-oxo-1,2-dihydropyridin-3-yl)-1-((2-(trimethylsilyl)ethoxy)methyl)-5,6-dihydropyrrolo[3,4-b]pyrrol-4(1H)-one (Step 4 of Example 25, 185 mg, 0.292 mmol), HCl (6N, 2 mL) and EtOH (2 mL) was stirred for 5.5 h at 70° C. and cooled to rt. NaOH (4N, 4 mL) was added. The mixture was stirred for 30 min at rt, diluted in DCM/water, and extracted twice with DCM. The combined organic extracts were washed with brine, dried ($Na_2SO_4$), filtered and the filtrate was concentrated. The residue was purified by silica gel chromatography on Combiflash Isco (eluent: MeOH/DCM; gradient: 1.6 min 0% MeOH, 0% to 10.1% MeOH in 22.1 min, 4.7 min 10.1% MeOH; flow: 40 mL/min) followed by trituration of the resulting material in $Et_2O$ to afford the title compound (106 mg) as an off-white solid. Rf=0.21 (1% ammonia/5% MeOH/DCM); Rt: 0.85 min (LC-MS 1); MS m/z: 485.2 $[M+H]^+$ (LC-MS 1).

Example 26

6-(4-chlorophenyl)-5-(3,8-dimethyl-[1,2,4]triazolo[4,3-a]pyridin-6-yl)-2-(2-hydroxypyridin-3-yl)-5,6-dihydropyrrolo[3,4-b]pyrrol-4(1H)-one

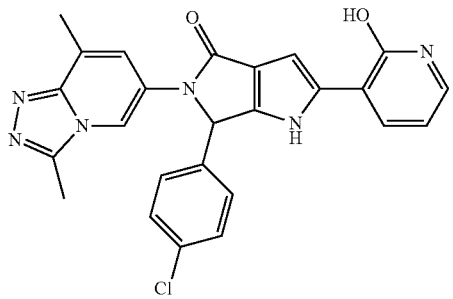 [SMILES: Cc1cc(N2C(=O)c3cc(-c4cccnc4O)[nH]c3C2c2ccc(Cl)cc2)cn2c(C)nnc12]

Step 1: 6-(4-chlorophenyl)-5-(3,8-dimethyl-[1,2,4]triazolo[4,3-a]pyridin-6-yl)-2-(2-methoxypyridin-3-yl)-14(2-(trimethylsilyl)ethoxy)methyl)-5,6-dihydropyrrolo[3,4-b]pyrrol-4(1H)-one The title compound was prepared using an analogous procedure to that described in Step 4 of Example 25 using (2-methoxypyridin-3-yl)boronic acid (60.9 mg, 0.398 mmol, 1.5 eq). The crude product was purified by silica gel column chromatography (5% MeOH/DCM) to afford the title compound (106 mg, purity 90%) as a beige solid. Rf=0.20 (5% MeOH/DCM); Rt: 1.29 min (LC-MS 1); MS m/z: 615.3 [M+H]+ (LC-MS 1).

Step 2: 6-(4-chlorophenyl)-5-(3,8-dimethyl-[1,2,4]triazolo[4,3-a]pyridin-6-yl)-2-(2-hydroxypyridin-3-yl)-5,6-dihydropyrrolo[3,4-b]pyrrol-4(1H)-one The title compound was prepared using an analogous procedure to that described in Step 5 of Example 25 using 6-(4-chlorophenyl)-5-(3,8-dimethyl-[1,2,4]triazolo[4,3-a]pyridin-6-yl)-2-(2-methoxypyridin-3-yl)-14(2-(trimethylsilyl)ethoxy)methyl)-5,6-dihydropyrrolo[3,4-b]pyrrol-4(1H)-one (Step 1 of Example 26, 56 mg, 0.091 mmol) and stirring the reaction mixture for 15 h at 65° C. The crude product was purified by silica gel column chromatography (1% ammonia/7.5% MeOH/DCM) to afford the title compound (9 mg) as an off-white solid. Rf=0.22 (1% ammonia/7.5% MeOH/DCM); Rt: 0.75 min (LC-MS 1); MS m/z: 471.2 [M+H]+ (LC-MS 1); 1H NMR (400 MHz, DMSO-d6) δ 2.42 (s, 3H) 2.61 (s, 3H) 6.32 (t, J=6.84 Hz, 1H) 6.45 (s, 1H) 7.03 (s, 1H) 7.22-7.48 (m, 6H) 7.87-8.00 (m, 1H) 8.40 (s, 1H) 12.03 (s, 2H)

Example 27

6-(4-chlorophenyl)-5-(3,8-di methyl-[1,2,4]triazolo[4,3-a]pyridin-6-yl)-2-(2-methoxypyridin-3-yl)-5,6-dihydropyrrolo[3,4-b]pyrrol-4(1H)-one

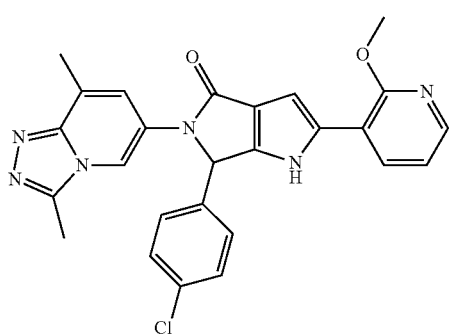 [SMILES: COc1ncccc1-c1cc2c([nH]1)C(c1ccc(Cl)cc1)N(c1cc(C)c3nnc(C)n3c1)C2=O]

Step 1: 2-bromo-6-(4-chlorophenyl)-5-(3,8-dimethyl-[1,2,4]triazolo[4,3-a]pyridin-6-yl)-5,6-dihydropyrrolo[3,4-b]pyrrol-4(1H)-one TFA (1 mL, 12.98 mmol) was added to a stirred mixture of 2-bromo-6-(4-chlorophenyl)-5-(3,8-dimethyl-[1,2,4]triazolo[4,3-a]pyridin-6-yl)-14(2-(trimethylsilyl)ethoxy)methyl)-5,6-dihydropyrrolo[3,4-b]pyrrol-4(1H)-one (Step 3 of Example 25, 262 mg, 0.446 mmol). The reaction mixture was stirred for 1 h at rt, concentrated, and diluted with DCM/water. NaOH (4N, 4 mL) was added. The resulting mixture was stirred for 2 h at rt and washed twice with DCM. The pH of the aqueous layer was adjusted to 9 by addition of aqueous 1N HCl. The resulting beige precipitate was collected by filtration to afford the title compound (148 mg). Rt: 0.86 min (LC-MS 1); MS m/z: 456.2 [M+H]+ (LC-MS 1).

Step 2: 6-(4-chlorophenyl)-5-(3,8-dimethyl-[1,2,4]triazolo[4,3-a]pyridin-6-yl)-2-(2-methoxypyridin-3-yl)-5,6-dihydropyrrolo[3,4-b]pyrrol-4(1H)-one The title compound was prepared using an analogous procedure to that described in Step 4 of Example 25 using 2-bromo-6-(4-chlorophenyl)-5-(3,8-dimethyl-[1,2,4]triazolo[4,3-a]pyridin-6-yl)-5,6-dihydropyrrolo[3,4-b]pyrrol-4(1H)-one (Step 1 of Example 27, 145 mg, 0.317 mmol) and (2-methoxypyridin-3-yl)boronic acid (72.8 mg, 0.476 mmol, 1.5 eq). The crude product was purified by silica gel chromatography on Combiflash Isco (eluent: MeOH/DCM; gradient: 1.6 min 0% MeOH, 0% to 10.1% MeOH in 20.3 min, 1.5 min 10.1% MeOH; flow: 30 mL/min) followed by trituration of the resulting material in Et2O to afford the title compound (36 mg) as a colorless solid. Rf=0.17 (1% ammonia/5% MeOH/DCM); Rt: 0.96 min (LC-MS 1); MS m/z: 485.2 [M+H]+ (LC-MS 1); 1H NMR (400 MHz, DMSO-d6) δ 2.43 (s, 3H) 2.61 (s, 3H) 3.97 (s, 3H) 6.53 (s, 1H) 6.93 (s, 1H) 7.04 (dd, J=7.62, 4.89 Hz, 1H) 7.24-7.45 (m, 5H) 7.94-8.15 (m, 2H) 8.38 (s, 1H) 11.96 (s, 1H).

Example 28

6-(4-chlorophenyl)-5-(1,4-dimethyl-1H-benzo[d][1,2,3]triazol-6-yl)-1,3-dimethyl-5,6-dihydropyrrolo[3,4-b]pyrrol-4(1H)-one

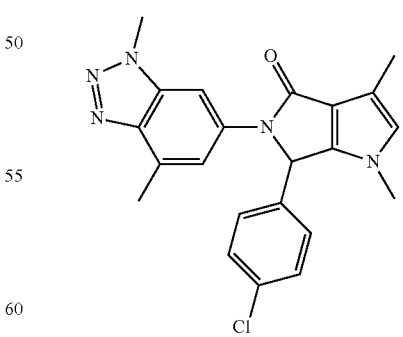

Step 1: 5-bromo-N,3-dimethyl-2-nitroaniline

A mixture of 5-bromo-1-fluoro-3-methyl-2-nitrobenzene (Matrix Scientific, 8 g, 34.2 mmol) and methylamine (2N in THF, 103 mL, 205 mmol) was stirred for 1 h at 100° C. in a sealed tube. The reaction mixture was concentrated, diluted with water (100 mL), and extracted with EtOAc (2×100 mL). The combined organic extracts were washed with brine (1×100 mL), dried (Na$_2$SO$_4$), filtered and the filtrate was evaporated to afford the title compound (8.4 g) as an orange solid. Rt: 1.18 min (LC-MS 1); MS m/z: 245.1 [M+H]$^+$ (LC-MS 1); $^1$H NMR (400 MHz, DMSO-d6) δ 6.84 (d, J=1.9 Hz, 1H), 6.77-6.67 (m, 2H), 2.75 (d, J=4.8 Hz, 3H), 2.26 (s, 3H).

Step 2: 5-bromo-N1,3-dimethylbenzene-1,2-diamine

A mixture of 5-bromo-N,3-dimethyl-2-nitroaniline (Step 1 of Example 28, 8.4 g, 34.3 mmol) and Ra—Ni (Fluka, 1.5 g) in MeOH (150 mL) and THF (150 mL) was stirred for 9 h at rt under a hydrogen atmosphere (0.1 bar). The reaction mixture was filtered over celite and concentrated. The residue was purified by silica gel chromatography on Combiflash Isco (eluent: EtOAc/hexane; gradient: 0% to 66.8% EtOAc in 13.6 min; flow: 85 mL/min) to afford the title compound (6.85 g) as a brown solid. Rf=0.66 (50% EtOAc/hexane); Rt: 0.93 min (LC-MS 1); MS m/z: 215.0/217.0 [M+H]$^+$ (LC-MS 1).

Step 3: 6-bromo-1,4-dimethyl-1H-benzo[d][1,2,3]triazole

To a stirred solution of 5-bromo-N1,3-dimethylbenzene-1,2-diamine (Step 2 of Example 28, 6.87 g, 31.9 mmol) in HCl conc. (38.8 mL, 1278 mmol) was added sodium nitrite (2.64 g, 38.3 mmol) in water (30 mL) at 0° C. The reaction mixture was stirred for 2 h at rt, basified by addition of aqueous NaOH (2N). The resulting precipitate was collected by filtration and purified by silica gel chromatography on Combiflash Isco (eluent: EtOAc/hexane; gradient: 0% to 36.2% EtOAc in 21.7 min; flow: 85 mL/min) to afford the title compound (6.85 g, purity 88%) as a brown solid. Rf=0.71 (50% EtOAc/hexane); Rt: 0.92 min (LC-MS 1); MS m/z: 226.0/228.0 [M+H]$^+$ (LC-MS 1).

Step 4: Ethyl 1,4-dimethyl-1H-pyrrole-3-carboxylate

To a stirred solution of ethyl 4-methylpyrrole-3-carboxylate (Alfa Aesar, 5 g, 32.6 mmol) in DMF (100 mL) was added NaH (1.567 g, 39.2 mmol) at 0° C. under Ar. The reaction mixture was stirred for 30 min at rt. MeI (2.449 mL, 39.2 mmol) was added. The reaction mixture was stirred for 30 min at rt, quenched by addition of a saturated aqueous solution of NaHCO$_3$ (75 mL), and extracted with EtOAc (2×75 mL). The combined organic extracts were washed with a saturated aqueous solution of NaHCO$_3$ (75 mL), dried (Na$_2$SO$_4$), filtered and the filtrate was concentrated. The residue was purified by silica gel column chromatography (2.5-12.5% EtOAc/hexane) to afford the title compound (4.9 g) as a colorless oil. Rf=0.23 (10% EtOAc/hexane); Rt: 0.92 min (LC-MS 1); MS m/z: 168.1 [M+H]$^+$ (LC-MS 1).

Step 5: Ethyl 2-((4-chlorophenyl)(hydroxy)methyl)-1,4-dimethyl-1H-pyrrole-3-carboxylate The title compound was prepared using an analogous procedure to that described in Step 8 of Example 1 using ethyl 1,4-dimethyl-1H-pyrrole-3-carboxylate (Step 4 of Example 28, 4.90 g, 29.3 mmol). The crude product was purified by silica gel column chromatography (5-15% EtOAc/hexane) followed by trituration of the resulting material in Et$_2$O to provide the title compound (3.62 g) as a colorless solid. Rf=0.10 (10% EtOAc/hexane); Rt: 1.22 min (LC-MS 1); MS m/z: 290.1 [M-17]$^+$ (LC-MS 1).

Step 6: Ethyl 2-(azido(4-chlorophenyl)methyl)-1,4-dimethyl-1H-pyrrole-3-carboxylate To a stirred solution of ethyl 2-((4-chlorophenyl)(hydroxy)methyl)-1,4-dimethyl-1H-pyrrole-3-carboxylate (Step 5 of Example 28, 500 mg, 1.625 mmol) in DCM (10 mL) was added 1-chloro-N,N,2-trimethyl-1-propenylamine (0.321 mL, 2.437 mmol) at rt under Ar. The reaction mixture was stirred for 2 h at rt. Triethylamine (0.679 mL, 4.87 mmol) and tetra-n-butylammonium azide (555 mg, 1.949 mmol) were added. The reaction mixture was stirred for 16 h at rt, quenched with brine (100 mL), and extracted with EtOAc (2×100 mL). The combined organic extracts were washed with brine (100 mL), dried (Na$_2$SO$_4$), filtered and the filtrate was concentrated. The residue was purified by silica gel chromatography on Combiflash Isco (eluent: EtOAc/hexane; gradient: 1 min 0% EtOAc, 0% to 10% EtOAc in 13 min, 1 min 10% EtOAc; flow: 30 mL/min) to provide the title compound (369 mg) as a colorless oil. Rf=0.67 (10% EtOAc/hexane); Rt: 1.42 min (LC-MS 1); MS m/z: 305.1 [M-27]$^+$ (LC-MS 1).

Step 7: Ethyl 2-(amino(4-chlorophenyl)methyl)-1,4-dimethyl-1H-pyrrole-3-carboxylate A mixture of ethyl 2-(azido(4-chlorophenyl)methyl)-1,4-dimethyl-1H-pyrrole-3-carboxylate (Step 6 of Example 28, 365 mg, 1.097 mmol) and Ra—Ni (Degussa, 0.1 g) in EtOH (10 mL) was stirred for 12.5 h at rt under a hydrogen atmosphere (0.1 bar). The reaction mixture was filtered over celite and concentrated. The residue was purified by silica gel chromatography on Combiflash Isco (eluent: EtOAc/hexane; gradient: 29.9% to 76.5% EtOAc in 8 min; flow: 30 mL/min) to afford the title compound (317 mg) as a colorless oil. Rf=0.19 (50% EtOAc/hexane); Rt: 0.85 min (LC-MS 1); MS m/z: 307.1 [M+H]$^+$ (LC-MS 1).

Step 8: 6-(4-chlorophenyl)-1,3-dimethyl-5,6-dihydropyrrolo[3,4-b]pyrrol-4(1H)-one The title compound was prepared using an analogous procedure to that described in Step 10 of Example 1 using ethyl 2-(amino(4-chlorophenyl)methyl)-1,4-dimethyl-1H-pyrrole-3-carboxylate (Step 7 of Example 28, 100 mg, 0.326 mmol). The crude product was purified by silica gel chromatography on Combiflash Isco (eluent: MeOH/DCM; gradient: 0% to 2.1% MeOH in 6 min, 1.1 min 2.1% MeOH, 2.1% to 3.7% MeOH in 4.5 min; flow: 18 mL/min) to afford the title compound (82 mg) as a colorless solid. Rf=0.66 (10% MeOH/DCM); Rt: 0.89 min (LC-MS 1); MS m/z: 261.1 [M+H]$^+$ (LC-MS 1).

Step 9: 6-(4-chlorophenyl)-5-(1,4-dimethyl-1H-benzo[d][1,2,3]triazol-6-yl)-1,3-dimethyl-5,6-dihydropyrrolo[3,4-b]pyrrol-4(1H)-one In a 2-mL screw cap vial was introduced 6-(4-chlorophenyl)-1,3-dimethyl-5,6-dihydropyrrolo[3,4-b]pyrrol-4(1H)-one (Step 8 of Example 28, 80 mg, 0.307 mmol), 6-bromo-1,4-dimethyl-1H-benzo[d][1,2,3]triazole (Step 3 of Example 28, 76 mg, 0.338 mmol), K$_3$PO$_4$ (130 mg, 0.614 mmol), CuI (58.4 mg, 0.307 mmol) and N,N'-dimethylethylenediamine (0.050 mL, 0.460 mmol) in dioxane (2 mL). The reaction mixture was stirred for 16 h at 100° C., allowed to cool, diluted with water (75 mL) and extracted with EtOAc (2×100 mL). The combined organic extracts were washed with water (100 mL), dried (Na$_2$SO$_4$), filtered and the filtrate was concentrated. The residue was purified by silica gel chromatography on Combiflash Isco (eluent: EtOAc/hexane; gradient: 20% to 98.6% EtOAc in 14.7; flow: 18 mL/min) followed by trituration of the resulting material in Et$_2$O to provide the title compound (32 mg) as a colorless solid. Rf=0.14 (50% EtOAc/hexane); Rt: 1.06 min (LC-MS 1); MS m/z: 406.2 [M+H]$^+$ (LC-MS 1); $^1$H NMR (400 MHz, DMSO-d6) δ 7.71 (d, J=1.7 Hz, 1H), 7.43-7.20 (m, 5H), 6.64 (s, 1H), 6.54 (s, 1H), 4.16 (s, 3H), 3.25 (s, 3H), 2.56 (s, 3H), 2.14 (s, 3H).

Example 29

6-(4-chlorophenyl)-5-(3,8-di methyl-[1,2,4]triazolo [4,3-a]pyridin-6-yl)-1-methyl-5,6-dihydropyrrolo[3,4-b]pyrrol-4(1H)-one

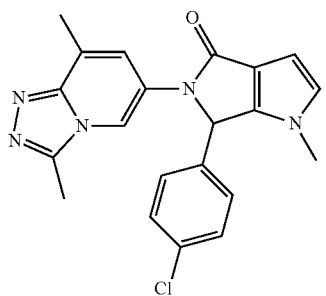 [SMILES: Cc1cc(N2C(=O)c3ccn(C)c3C2c2ccc(Cl)cc2)cn2c(C)nnc12]

Step 1: Methyl 1-methyl-1H-pyrrole-3-carboxylate

To a stirred solution of methyl pyrrole-3-carboxylate (ABCR, 2.5 g, 19.98 mmol) in DMSO (20 mL) was added KOH (1.681 g, 30.0 mmol) under Ar. The mixture was stirred for 10 min. MeI (1.874 mL, 30.0 mmol) was added. The reaction mixture was stirred for 1 h at rt, quenched by addition of aqueous HCl (1N, 200 mL), and extracted with EtOAc (2×200 mL). The combined organic extracts were washed with brine (200 mL), dried (Na$_2$SO$_4$), filtered and the filtrate was concentrated. The residue was purified by silica gel chromatography on Combiflash Isco (eluent: EtOAc/hexane; gradient: 0% to 3.3% EtOAc in 5.6 min, 3.3% to 15.8% EtOAc in 15.7 min, 1.7 min 15.8% EtOAc, 15.8 to 16.3% EtOAc in 0.6 min, 3.2 min 16.3% EtOAc, 16.3% to 16.6% EtOAc in 0.4 min; flow: 85 mL/min) to provide the title compound (2.74 g) as a colorless oil. Rf=0.70 (50% EtOAc/hexane); Rt: 0.65 min (LC-MS 1); MS m/z: 140.1 [M+H]$^+$ (LC-MS 1).

Step 2: Methyl 2-((4-chlorophenyl)(hydroxy) methyl)-1-methyl-1H-pyrrole-3-carboxylate The title compound was prepared using an analogous procedure to that described in Step 8 of Example 1 using methyl 1-methyl-1H-pyrrole-3-carboxylate (Step 1 of Example 29, 2.74 g, 19.69 mmol). The crude product was purified by silica gel chromatography on Combiflash Isco (eluent: EtOAc/hexane; gradient: 0% to 2% EtOAc in 2 min, 2% to 9.4% EtOAc in 9.8 min, 9.4% to 20.8% EtOAc in 6 min, 0.5 min 20.8% EtOAc, 20.8% to 25% EtOAc in 2.2 min, 2.2 min 25% EtOAc; flow: 85 mL/min). Rf=0.10 (10% EtOAc/hexane); Rt: 1.06 min (LC-MS 1); MS m/z: 262.1 [M-17]$^+$ (LC-MS 1).

Step 3: Methyl 2-((4-chlorophenyl)((3,8-dimethyl-[1,2,4]triazolo[4,3-a]pyridin-6-yl)amino)methyl)-1-methyl-1H-pyrrole-3-carboxylate The title compound was prepared using an analogous procedure to that described in Step 9 of Example 1 using methyl 2-((4-chlorophenyl)(hydroxy)methyl)-1-methyl-1H-pyrrole-3-carboxylate (Step 2 of Example 29, 2 g, 7.15 mmol) and 3,8-dimethyl-[1,2,4]triazolo[4,3-a]pyridin-6-amine (Step 4 of Example 3, 1.276 g, 7.87 mmol). The reaction mixture was quenched with a saturated aqueous solution of NaHCO$_3$ (100 mL) and diluted with DCM (100 mL). The resulting precipitate was collected by filtration to afford the title compound (1.55 g) as a colorless solid. Rt: 1.02 min (LC-MS 1); MS m/z: 424.2 [M+H]$^+$ (LC-MS 1).

Step 4: 6-(4-chlorophenyl)-5-(3,8-dimethyl-[1,2,4] triazolo[4,3-a]pyridin-6-yl)-1-methyl-5,6-dihydropyrrolo[3,4-b]pyrrol-4(1H)-one The title compound was prepared using an analogous procedure to that described in Step 9 of Example 1 using methyl 2-((4-chlorophenyl)((3,8-dimethyl-[1,2,4]triazolo[4,3-a]pyridin-6-yl)amino)methyl)-1-methyl-1H-pyrrole-3-carboxylate (Step 3 of Example 29, 1.55 g, 3.66 mmol) and stirring the reaction mixture for 20 h at 120° C. The crude product was purified by silica gel chromatography on Combiflash Isco (eluent: MeOH/DCM; gradient: 1 min 0% MeOH, 0% to 7% MeOH in 14 min, 8 min 7% MeOH; flow: 40 mL/min) to afford the title compound (1.11 g) as a colorless solid. Rf=0.63 (10% MeOH/DCM); Rt: 0.83 min (LC-MS 1); MS m/z: 392.2 [M+H]$^+$ (LC-MS 1).

Example 30

6-(4-chlorophenyl)-5-(3,8-di methyl-[1,2,4]triazolo [4,3-a]pyridin-6-yl)-2-(2-methoxypyridin-3-yl)-1-methyl-5,6-dihydropyrrolo[3,4-b]pyrrol-4(1H)-one

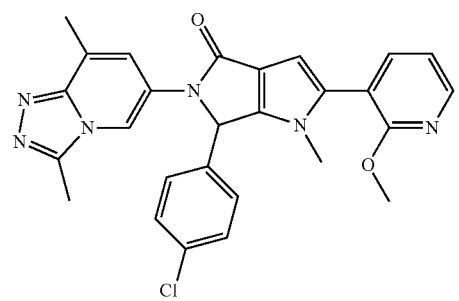 [SMILES: COc1ncccc1-c1cc2c(n1C)C(c1ccc(Cl)cc1)N(c1cc(C)c3nnc(C)n3c1)C2=O]

Step 1: 2-bromo-6-(4-chlorophenyl)-5-(3,8-dimethyl-[1,2,4]triazolo[4,3-a]pyridin-6-yl)-1-methyl-5,6-dihydropyrrolo[3,4-b]pyrrol-4(1H)-one To a stirred solution of 6-(4-chlorophenyl)-5-(3,8-dimethyl-[1,2,4]triazolo[4,3-a]pyridin-6-yl)-1-methyl-5,6-dihydropyrrolo[3,4-b]pyrrol-4(1H)-one (Step 4 of Example 29, 840 mg, 2.144 mmol) in CHCl$_3$ (15 mL) was added NBS (382 mg, 2.144 mmol) under Ar. The reaction mixture was stirred for 16 hr at rt, quenched by addition of brine (50 mL), and extracted with DCM (2×75 mL). The combined organic extracts were washed with brine (50 mL), dried (Na$_2$SO$_4$), filtered and the filtrate was concentrated. The residue was purified by silica gel chromatography on Combiflash Isco (eluent: MeOH/DCM; gradient: 1 min 0% MeOH, 0% to 4.9% MeOH in 11.4 min, 0.5 min 4.9% MeOH, 4.9% to 5.4% MeOH in 1.2 min, 5.4% to 7% MeOH in 1.9 min, 6.8 min 7% MeOH; flow: 40 mL/min) to provide the title compound (833 mg) as a brown solid. Rf=0.53 (10% MeOH/DCM); Rt: 0.97 min (LC-MS 1); MS m/z: 470.0/472.0 [M+H]$^+$ (LC-MS 1).

Step 2: 6-(4-chlorophenyl)-5-(3,8-dimethyl-[1,2,4]triazolo[4,3-a]pyridin-6-yl)-2-(2-methoxypyridin-3-yl)-1-methyl-5,6-dihydropyrrolo[3,4-b]pyrrol-4(1H)-one The title compound was prepared using an analogous procedure to that described in Step 4 of Example 25 using 2-bromo-6-(4-chlorophenyl)-5-(3,8-dimethyl-[1,2,4]triazolo[4,3-a]pyridin-6-yl)-1-methyl-5,6-dihydropyrrolo[3,4-b]pyrrol-4(1H)-one (Step 1 of Example 30, 200 mg, 0.425 mmol), 2-methoxy-3-pyridinylboronic acid (84 mg, 0.552 mmol), and 0.2 eq of PdCl$_2$(dppf).CH$_2$Cl$_2$ complex. The reaction mixture was stirred for 3 h at 110° C. The crude product was purified by silica gel chromatography on Combiflash Isco (eluent: MeOH/DCM; gradient: 2 min 0% MeOH, 0% to 7% MeOH in 22.7 min, 2.6 min 7% MeOH; flow: 18 mL/min). The resulting material was further purified by preparative achiral SFC (column: Diol, 250×30 mm, 5 µm, 60 A, Princeton; eluent: MeOH/scCO$_2$; gradient: 1 min 23% MeOH, 23% to 28% MeOH in 6 min, 28% to 50% MeOH, in 1 min, 1.5 min 50% MeOH; flow: 100 mL/min) to afford the title compound (88 mg) as a colorless solid. Rf=0.54 (10% MeOH/DCM); Rt: 0.97 min (LC-MS 1); MS m/z: 499.2 [M+H]$^+$ (LC-MS 1); $^1$H NMR (400 MHz, DMSO-d6) δ 2.43 (s, 3H) 2.61 (s, 3H) 3.14 (s, 3H) 3.85 (s, 3H) 6.44 (s, 1H) 6.60 (s, 1H) 7.08 (dd, J=7.04, 5.08 Hz, 1H) 7.34 (s, 1H) 7.36-7.43 (m, 4H) 7.72 (dd, J=7.23, 1.76 Hz, 1H) 8.23 (dd, J=5.08, 1.95 Hz, 1H) 8.32 (s, 1H).

Example 31

6-(4-chlorophenyl)-2-(3,6-dihydro-2H-pyran-4-yl)-5-(3,8-dimethyl-[1,2,4]triazolo[4,3-a]pyridin-6-yl)-1-methyl-5,6-dihydropyrrolo[3,4-b]pyrrol-4(1H)-one

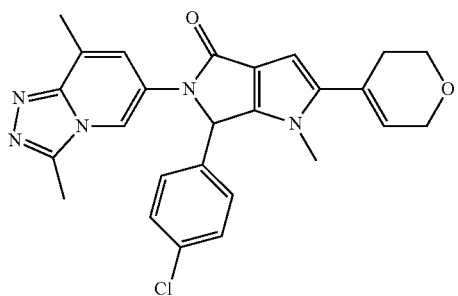 [SMILES: Cc1cc(N2C(=O)c3cc(C4=CCOCC4)n(C)c3C2c2ccc(Cl)cc2)cn2c(C)nnc12]

Step 1: Methyl 1-methyl-1H-pyrrole-3-carboxylate

To a stirred solution of pyrrole-3-carboxylic acid (AstaTech, 5 g, 45.0 mmol) in DMSO (75 mL) was added KOH (7.58 g, 135 mmol) under Ar. The mixture was stirred for 10 min. MeI (8.44 mL, 135 mmol) was added. The reaction mixture was stirred for 1 h at rt, quenched by addition of aqueous HCl (1N, 200 mL), and extracted with EtOAc (2×200 mL). The combined organic extracts were washed with brine (200 mL), dried (Na$_2$SO$_4$), filtered and the filtrate was concentrated. The residue was purified by silica gel column chromatography (5-15% EtOAc/hexane) to provide the title compound (5.98 g) as a colorless oil. Rf=0.70 (50% EtOAc/hexane); Rt: 0.65 min (LC-MS 1); MS m/z: 140.1 [M+H]$^+$ (LC-MS 1).

Step 2: Methyl 5-bromo-1-methyl-1H-pyrrole-3-carboxylate

To a stirred solution of methyl 1-methyl-1H-pyrrole-3-carboxylate (Step 1 of Example 31, 5.98 g, 43.0 mmol) in CHCl$_3$ (100 mL) was added NBS (8.03 g, 45.1 mmol) at 0° C. under Ar. The reaction mixture was allowed to warm to rt, stirred for 16 h, quenched by addition of brine (100 mL), and extracted with DCM (2×100 mL). The combined organic extracts were washed with brine (100 mL), dried (Na$_2$SO$_4$), filtered and the filtrate was concentrated. The residue was purified by silica gel column chromatography (2.5-10% EtOAc/hexane) to provide the title compound (7.1 g) as a colorless solid. Rf=0.30 (10% EtOAc/hexane); Rt: 0.89 min (LC-MS 1); MS m/z: 218.0/220.0 [M+H]$^+$ (LC-MS 1).

Step 3: Methyl 5-bromo-2-((4-chlorophenyl)(hydroxy)methyl)-1-methyl-1H-pyrrole-3-carboxylate To a stirred solution of methyl 5-bromo-1-methyl-1H-pyrrole-3-carboxylate (Step 2 of Example 31, 7.1 g, 32.6 mmol) in THF (100 mL) was added LDA (2N in THF/heptane/ethylbenzene, 21.17 mL, 42.3 mmol) at −78° C. under Ar. The reaction mixture was stirred for 30 min at −78° C. 4-Chlorobenzaldehyde (5.95 g, 42.3 mmol) in THF (50 mL) was added. The reaction mixture was stirred for 30 min at −78° C., quenched by addition of brine (100 mL), and extracted with EtOAc (2×100 mL). The combined organic extracts were washed with brine (100 mL), dried (Na$_2$SO$_4$), filtered and the filtrate was concentrated. The residue was purified by silica gel column chromatography (2.5-9% EtOAc/hexane) followed by crystallization of the resulting material in Et$_2$O/hexane (1:1) to provide the title compound (9.11 g) as a colorless solid. Rf=0.18 (10% EtOAc/hexane); Rt: 1.23 min (LC-MS 1); MS m/z: 339.9/341.9 [M-17]$^+$ (LC-MS 1).

Step 4: Methyl 5-bromo-2-(((4-chlorophenyl)((3,8-dimethyl-[1,2,4]triazolo[4,3-a]pyridin-6-yl)amino) methyl)-1-methyl-1H-pyrrole-3-carboxylate To a stirred solution of methyl 5-bromo-2-((4-chlorophenyl)(hydroxy)methyl)-1-methyl-1H-pyrrole-3-carboxylate (Step 3 of Example 31, 2 g, 5.58 mmol) and triethylamine (3.89 mL, 27.9 mmol) in DCM (25 mL) was added Ms$_2$O (2.91 g, 16.73 mmol) at −40° C. under Ar. The mixture was stirred for 1 h at −40. 3,8-Dimethyl-[1,2,4]triazolo[4,3-a]pyridin-6-amine (Step 4 of Example 3, 0.995 g, 6.13 mmol) was added. The reaction mixture was allowed to warm to rt, stirred for 1 h, quenched by addition of brine (100 mL), and extracted with EtOAc (2×100 mL). The combined organic extracts were washed with brine (100 mL), dried (Na$_2$SO$_4$), filtered and the filtrate was concentrated. The residue was purified by silica gel column chromatography (1-4% MeOH/

DCM) to afford the title compound (812 mg, purity 70%) as a yellow solid. Rf=0.47 (10% MeOH/DCM); Rt: 1.16 min (LC-MS 1); MS m/z: 502.1/504.1 [M+H]+ (LC-MS 1).

Step 5: 2-bromo-6-(4-chlorophenyl)-5-(3,8-dimethyl-[1,2,4]triazolo[4,3-a]pyridin-6-yl)-1-methyl-5,6-dihydropyrrolo[3,4-b]pyrrol-4(1H)-one The title compound was prepared using an analogous procedure to that described in Step 10 of Example 1 using methyl 5-bromo-2-((4-chlorophenyl)((3,8-dimethyl-[1,2,4]triazolo[4,3-a]pyridin-6-yl)amino)methyl)-1-methyl-1H-pyrrole-3-carboxylate (Step 4 of Example 31, 812 mg, 1.615 mmol) and stirring the reaction mixture for 16 h at 120° C. The crude product was purified by silica gel column chromatography (1-4.5% MeOH/DCM) to afford the title compound (161 mg, purity 92%) as a brown solid. Rf=0.51 (10% MeOH/DCM); Rt: 0.97 min (LC-MS 1); MS m/z: 470.1/472.1 [M+H]+ (LC-MS 1).

Step 6: 6-(4-chlorophenyl)-2-(3,6-dihydro-2H-pyran-4-yl)-5-(3,8-dimethyl-[1,2,4]triazolo[4,3-a]pyridin-6-yl)-1-methyl-5,6-dihydropyrrolo[3,4-b]pyrrol-4(1H)-one A mixture of 2-bromo-6-(4-chlorophenyl)-5-(3,8-dimethyl-[1,2,4]triazolo[4,3-a]pyridin-6-yl)-1-methyl-5,6-dihydropyrrolo[3,4-b]pyrrol-4(1H)-one (Step 5 of Example 31, 160 mg, 0.340 mmol), 3,6-dihydro-2H-pyran-4-boronic acid pinacol (Aldrich, 143 mg, 0.680 mmol), $K_3PO_4$ (289 mg, 1.360 mmol) and $PdCl_2(dppf)CH_2Cl_2$ complex (55.5 mg, 0.068 mmol) in 1,4-dioxane (2 mL) and water (2 mL) was stirred for 3 h at 100° C., concentrated, diluted with a saturated aqueous solution of $NaHCO_3$, and extracted with EtOAc (2×100 mL). The combined organic extracts were dried ($Na_2SO_4$), filtered and the filtrate was concentrated. The residue was purified by silica gel column chromatography (0.5-5.5% MeOH/DCM). The resulting material was further purified by preparative achiral SFC (column: Diol, 250×30 mm, 5 μm, 60 A, Princeton; eluent: MeOH/sc$CO_2$; gradient: 1 min 25% MeOH, 25% to 30% MeOH in 6 min, 30% to 50% MeOH, in 1 min, 1.5 min 50% MeOH; flow: 100 mL/min) to afford the title compound (51 mg) as a colorless solid. Rf=0.45 (10% MeOH/DCM); Rt: 0.90 min (LC-MS 1); MS m/z: 474.2 [M+H]+ (LC-MS 1); 1H NMR (400 MHz, DMSO-d6) δ 2.27-2.40 (m, 2H) 2.42 (s, 3H) 2.60 (s, 3H) 3.35 (s, 3H) 3.70-3.83 (m, 2H) 4.15-4.21 (m, 2H) 5.92 (s, 1H) 6.40 (s, 1H) 6.54 (s, 1H) 7.33 (s, 1H) 7.37 (s, 4H) 8.31 (d, J=0.78 Hz, 1H).

Example 32

6-(4-chlorophenyl)-5-(3,7-dimethyl-3H-[1,2,3]triazolo[4,5-b]pyridin-5-yl)-1,3-dimethyl-5,6-dihydropyrrolo[3,4-b]pyrrol-4(1H)-one

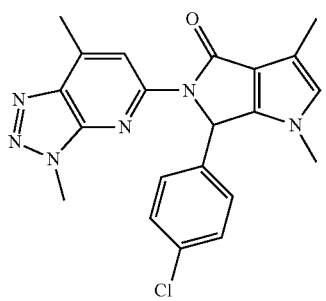 [SMILES: Cc1cn(C)c2c1C(=O)N(c1cc(C)c3nnn(C)c3n1)C2c1ccc(Cl)cc1]

Step 1: Ethyl 2-((4-chlorophenyl)((3,7-dimethyl-3H-[1,2,3]triazolo[4,5-b]pyridin-5-yl)amino)methyl)-1,4-dimethyl-1H-pyrrole-3-carboxylate The title compound was prepared using an analogous procedure to that described in Step 9 of Example 1 using ethyl 2-((4-chlorophenyl)(hydroxy)methyl)-1,4-dimethyl-1H-pyrrole-3-carboxylate (Step 5 of Example 28, 500 mg, 1.625 mmol), quenching the reaction mixture with brine, and extracting it with EtOAc. The crude product was purified by silica gel column chromatography (15-35% EtOAc/hexane) to afford the title compound (340 mg) as a colorless solid. Rf=0.43 (50% EtOAc/hexane); Rt: 1.33 min (LC-MS 1); MS m/z: 453.1 [M+H]+ (LC-MS 1).

Step 2: 6-(4-chlorophenyl)-5-(3,7-dimethyl-3H-[1,2,3]triazolo[4,5-b]pyridin-5-yl)-1,3-dimethyl-5,6-dihydropyrrolo[3,4-b]pyrrol-4(1H)-one The title compound was prepared using an analogous procedure to that described in Step 10 of Example 1 using ethyl 2-((4-chlorophenyl)((3,7-dimethyl-3H-[1,2,3]triazolo[4,5-b]pyridin-5-yl)amino)methyl)-1,4-dimethyl-1H-pyrrole-3-carboxylate (Step 1 of Example 32, 100 mg, 0.221 mmol) and stirring the reaction mixture for 20 h at 120° C. The crude product was purified by silica gel column chromatography (40-60% EtOAc/hexane) followed by trituration of the resulting material in $Et_2O$ to afford the title compound (53 mg) as a colorless solid. Rf=0.36 (50% EtOAc/hexane); Rt: 1.19 min (LC-MS 1); MS m/z: 407.1 [M+H]+ (LC-MS 1); 1H NMR (400 MHz, DMSO-d6) δ 2.15 (d, J=0.78 Hz, 3H) 2.63 (d, J=0.78 Hz, 3H) 3.24 (s, 3H) 4.08 (s, 3H) 6.63 (s, 1H) 6.67 (d, J=0.78 Hz, 1H) 7.31-7.37 (m, 2H) 7.37-7.43 (m, 2H) 8.28 (d, J=0.78 Hz, 1H).

Example 33

6-(4-chlorophenyl)-5-(3,8-di methyl-[1,2,4]triazolo[4,3-a]pyridin-6-yl)-1,3-di methyl-5,6-dihydropyrrolo[3,4-b]pyrrol-4(1H)-one

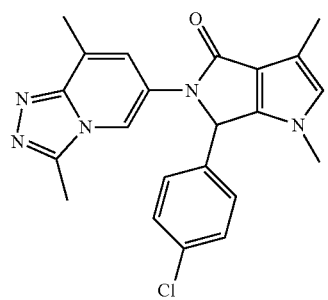 [SMILES: Cc1cn(C)c2c1C(=O)N(c1cc(C)c3nnc(C)n3c1)C2c1ccc(Cl)cc1]

Step 1: Ethyl 2-((4-chlorophenyl)((3,8-dimethyl-[1,2,4]triazolo[4,3-a]pyridin-6-yl)amino)methyl)-1,4-dimethyl-1H-pyrrole-3-carboxylate The title compound was prepared using an analogous procedure to that described in Step 9 of Example 1 using ethyl 2-((4-chlorophenyl)(hydroxy)methyl)-1,4-dimethyl-1H-pyrrole-3-carboxylate (Step 5 of Example 28, 500 mg, 1.625 mmol) and 3,8-dimethyl-[1,2,4]triazolo[4,3-a]pyridin-6-amine (Step 4 of Example 3, 290 mg, 1.787 mmol), quenching the reaction mixture with brine, and extracting it with EtOAc. The crude product was purified by silica gel column chromatography (1-4% MeOH/DCM) to afford the title compound (405 mg) as a colorless solid. Rf=0.41 (10% MeOH/DCM); Rt: 1.16 min (LC-MS 1); MS m/z: 452.1 [M+H]+ (LC-MS 1).

Step 2: 6-(4-chlorophenyl)-5-(3,8-dimethyl-[1,2,4]triazolo[4,3-a]pyridin-6-yl)-1,3-dimethyl-5,6-dihydropyrrolo[3,4-b]pyrrol-4(1H)-one The title compound was prepared using an analogous procedure to that described in Step 10 of Example 1 using ethyl 2-((4-chlorophenyl)((3,8-dimethyl-[1,2,4]triazolo[4,3-a]pyridin-6-yl)amino)methyl)-1,4-dimethyl-1H-pyrrole-3-carboxylate (Step 1 of Example 33, 200 mg, 0.443 mmol), stirring the reaction mixture for 20 h at 120° C., and quenching the reaction mixture with water. The crude product was purified by silica gel column chromatography (1% NH$_3$/DCM/1-3% MeOH). The resulting material was further purified by preparative achiral SFC (column: Reprosil 100 NH2, 250×30 mm, 5 µm, 100 A, Dr Maisch; eluent: MeOH/scCO$_2$; gradient: 1 min 14% MeOH, 14% to 19% MeOH in 6 min, 19% to 50% MeOH, in 1 min, 1.5 min 50% MeOH; flow: 100 mL/min) to afford the title compound (95 mg) as a colorless solid. Rf=0.44 (10% MeOH/DCM); Rt: 0.92 min (LC-MS 1); MS m/z: 406.1 [M+H]+ (LC-MS 1); $^1$H NMR (400 MHz, DMSO-d6) δ 2.14 (s, 3H) 2.41 (s, 3H) 2.59 (s, 3H) 3.25 (s, 3H) 6.44 (s, 1H) 6.66 (s, 1H) 7.28-7.39 (m, 5H) 8.32 (d, J=0.78 Hz, 1H).

Example 34

6-(4-chlorophenyl)-5-(1,5-dimethyl-6-oxo-1,6-dihydropyridin-3-yl)-1,3-dimethyl-5,6-dihydropyrrolo[3,4-b]pyrrol-4(1H)-one

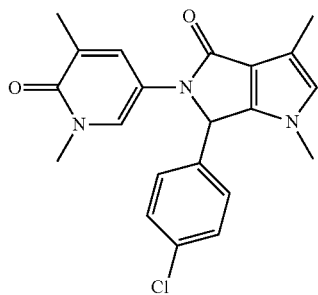 [SMILES: Cc1cn(C)c2c1C(=O)N(c1cc(C)c(=O)n(C)c1)C2c1ccc(Cl)cc1]

Step 1: 1,3-dimethyl-5-nitropyridin-2(1H)-one

To a stirred suspension of 3-methyl-5-nitropyridin-2-ol (Sigma-Aldrich, 15 g, 97 mmol) and K$_2$CO$_3$ (26.9 g, 195 mmol) in DMF (100 mL) was added MeI (9.13 mL, 146 mmol) at 0° C. under Ar. The reaction mixture was stirred for 2 h at rt and filtered. The filtrate was concentrated, dried, diluted with water and extracted with EtOAc. The combined organic layers were washed with brine, dried (Na$_2$SO$_4$), and evaporated to afford the title product (16.4 g) as a yellow solid. Rt: 0.59 min (LC-MS 1); ESI-MS: 169.1 [M+H]+ (LC-MS 1).

Step 2: 5-amino-1,3-dimethylpyridin-2(1H)-one

A mixture of 1,3-dimethyl-5-nitropyridin-2(1H)-one (Step 1 of Example 34, 16.4 g, 98 mmol), Pd/C 10% (2.0 g), THF (200 mL) and MeOH (200 mL) was stirred for 3 h at rt under a hydrogen atmosphere (0.1 bar). The reaction mixture was filtered over celite and concentrated. The crude material was purified by silica gel column chromatography (1% NH$_3$/DCM/1% MeOH) to afford the title product (10.3 g) as a green oil. The green oil was tritured in diethyl ether to afford a powder. Rf=0.35 (1% MeOH/DCM); Rt: 0.21 min (LC-MS 1); ESI-MS: 139.1 [M+H]+ (LC-MS 1).

Step 3: Ethyl 2-((4-chlorophenyl)((1,5-dimethyl-6-oxo-1,6-dihydropyridin-3-yl)amino)methyl)-1,4-dimethyl-1H-pyrrole-3-carboxylate The title compound was prepared using an analogous procedure to that described in Step 9 of Example 1 ethyl 2-((4-chlorophenyl)(hydroxy)methyl)-1,4-dimethyl-1H-pyrrole-3-carboxylate (Step 5 of Example 28, 500 mg, 1.625 mmol) and 5-amino-1,3-dimethylpyridin-2(1H)-one (Step 2 of Example 34, 247 mg, 1.787 mmol), quenching the reaction mixture with brine, and extracting it with EtOAc. The crude product was purified by silica gel column chromatography (0-1% MeOH/EtOAc) to afford the title compound (517 mg, purity 90%) as a brown solid. Rf=0.17 (EtOAc); Rt: 1.17 min (LC-MS 1); MS m/z: 428.1 [M+H]+ (LC-MS 1).

Step 4: 6-(4-chlorophenyl)-5-(1,5-dimethyl-6-oxo-1,6-dihydropyridin-3-yl)-1,3-dimethyl-5,6-dihydropyrrolo[3,4-b]pyrrol-4(1H)-one The title compound was prepared using an analogous procedure to that described in Step 10 of Example 1 using ethyl 2-((4-chlorophenyl)((1,5-dimethyl-6-oxo-1,6-dihydropyridin-3-yl)amino)methyl)-1,4-dimethyl-1H-pyrrole-3-carboxylate (Step 3 of Example 34, 250 mg, 0.584 mmol), stirring the reaction mixture for 2 h at 120° C., and quenching the reaction mixture with water. The crude product was purified by silica gel column chromatography (2-4% MeOH/DCM). The resulting material was triturated in Et$_2$O to afford the title compound (79 mg) as a colorless solid. Rf=0.40 (10% MeOH/DCM); Rt: 0.93 min (LC-MS 1); MS m/z: 382.1 [M+H]+ (LC-MS 1); $^1$H NMR (400 MHz, DMSO-d6) δ 1.90 (s, 3H) 2.10 (s, 3H) 3.21 (s, 3H) 3.33 (s, 3H) 6.05 (s, 1H) 6.61 (s, 1H) 7.23 (d, J=8.60 Hz, 2H) 7.32 (d, J=1.56 Hz, 1H) 7.38 (d, J=8.21 Hz, 2H) 7.58 (d, J=2.74 Hz, 1H).

Example 35

6-(4-chlorophenyl)-3-cyclopropyl-5-(3,8-dimethyl-[1,2,4]triazolo[4,3-a]pyridin-6-yl)-1-methyl-5,6-dihydropyrrolo[3,4-b]pyrrol-4(1H)-one

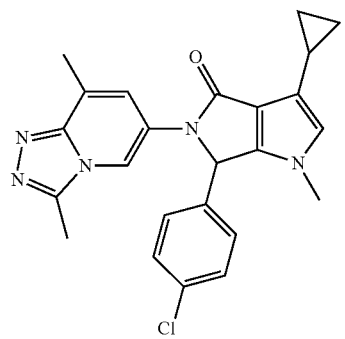 [SMILES: Cc1cc(N2C(=O)c3c(C4CC4)cn(C)c3C2c2ccc(Cl)cc2)cn2c(C)nnc12]

Step 1: Ethyl 4-cyclopropyl-1-methyl-1H-pyrrole-3-carboxylate

The title compound was prepared using an analogous procedure to that described in Step 1 of Example 2 using ethyl 4-cyclopropyl-1H-pyrrole-3-carboxylate (Step 6 of Example 1, 500 mg, 2.79 mmol) and MeI (0.209 mL, 3.35 mmol). The reaction mixture was stirred for 30 min at rt. The crude product was purified by silica gel column chromatography (5-15% EtOAc/hexane) to afford the title compound (475 mg) as a colorless oil. Rf=0.78 (10% EtOAc/hexane); Rt: 1.01 min (LC-MS 1); MS m/z: 194.1 [M+H]$^+$ (LC-MS 1).

Step 2: Ethyl 2-((4-chlorophenyl)(hydroxy)methyl)-4-cyclopropyl-1-methyl-1H-pyrrole-3-carboxylate The title compound was prepared using an analogous procedure to that described in Step 8 of Example 1 using ethyl 4-cyclopropyl-1-methyl-1H-pyrrole-3-carboxylate (Step 1 of Example 35, 475 mg, 2.458 mmol). The crude product was purified by silica gel column chromatography (2.5-15% EtOAc/hexane) to afford the title compound (535 mg) as a colorless oil. Rf=0.15 (10% EtOAc/hexane); Rt: 1.28 min (LC-MS 1); MS m/z: 316.1 [M-17]$^+$ (LC-MS 1).

Step 3: Ethyl 2-((4-chlorophenyl)((3,8-dimethyl-[1,2,4]triazolo[4,3-a]pyridin-6-yl)amino)methyl)-4-cyclopropyl-1-methyl-1H-pyrrole-3-carboxylate The title compound was prepared using an analogous procedure to that described in Step 9 of Example 1 using ethyl 2-((4-chlorophenyl)(hydroxy)methyl)-4-cyclopropyl-1-methyl-1H-pyrrole-3-carboxylate (Step 2 of Example 35, 265 mg, 0.794 mmol) and 3,8-dimethyl-[1,2,4]triazolo[4,3-a]pyridin-6-amine (Step 4 of Example 3, 142 mg, 0.873 mmol). The reaction mixture was quenched with brine and extracted with EtOAc. The crude product was purified by silica gel column chromatography (1-3.5 MeOH/DCM) to afford the title compound (294 mg) as a yellow solid. Rf=0.61 (10% MeOH/DCM); Rt: 1.20 min (LC-MS 1); MS m/z: 478.1 [M+H]$^+$ (LC-MS 1).

Step 4: 6-(4-chlorophenyl)-3-cyclopropyl-5-(3,8-dimethyl-[1,2,4]triazolo[4,3-a]pyridin-6-yl)-1-methyl-5,6-dihydropyrrolo[3,4-b]pyrrol-4(1H)-one The title compound was prepared using an analogous procedure to that described in Step 10 of Example 1 using ethyl 2-((4-chlorophenyl)((3,8-dimethyl-[1,2,4]triazolo[4,3-a]pyridin-6-yl)amino)methyl)-4-cyclopropyl-1-methyl-1H-pyrrole-3-carboxylate (Step 3 of Example 35, 290 mg, 0.607 mmol) and stirring the reaction mixture for 20 h at 120° C. The crude product was purified by silica gel column chromatography (1-4.5% MeOH/DCM). The resulting material was triturated in Et$_2$O to afford the title compound (107 mg) as a colorless solid. Rf=0.47 (10% MeOH/DCM); Rt: 1.01 min (LC-MS 1); MS m/z: 432.1 [M+H]$^+$ (LC-MS 1); $^1$H NMR (400 MHz, DMSO-d6) δ 0.75-0.93 (m, 4H) 1.73-1.83 (m, 1H) 2.41 (s, 3H) 2.59 (s, 3H) 3.23 (s, 3H) 6.43 (s, 1H) 6.72 (s, 1H) 7.27-7.40 (m, 5H) 8.31 (s, 1H).

Example 36

(R)-6-(4-chlorophenyl)-3-cyclopropyl-5-(3,8-dimethyl-[1,2,4]triazolo[4,3-a]pyridin-6-yl)-1-methyl-5,6-dihydropyrrolo[3,4-b]pyrrol-4(1H)-one

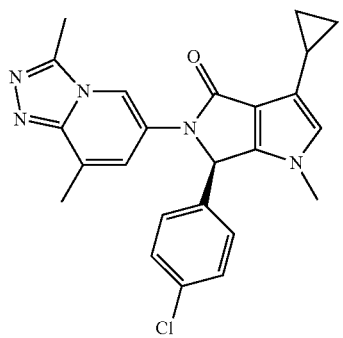 [SMILES: Cc1cc(N2C(=O)c3c(C4CC4)cn(C)c3[C@H]2c2ccc(Cl)cc2)cn2c(C)nnc12]

The title compound (39 mg, 42% yield) was obtained enantiomerically pure (>99% ee) after chiral preparative chromatography (system: Gilson PLC 2020; column: Chiracel OD-H 5 μm, 20×250 mm; mobile phase: heptane/EtOH/MeOH 60:20:20; flow: 10 mL/min; detection UV: 210 nm) of the racemic mixture of 6-(4-chlorophenyl)-3-cyclopropyl-5-(3,8-dimethyl-[1,2,4]triazolo[4,3-a]pyridin-6-yl)-1-methyl-5,6-dihydropyrrolo[3,4-b]pyrrol-4(1H)-one (Step 4 of Example 35).

(R)-6-(4-chlorophenyl)-3-cyclopropyl-5-(3,8-dimethyl-[1,2,4]triazolo[4,3-a]pyridin-6-yl)-1-methyl-5,6-dihydropyrrolo[3,4-b]pyrrol-4(1H)-one Rt: 6.39 min (system: Agilent HPLC; column: Chiracel OD-H 5 μm, 4.6×250 mm; mobile phase: heptane/EtOH/MeOH 60:20:20 (isocratic); flow: 1 mL/min; detection UV: 210 nm).

(S)-6-(4-chlorophenyl)-3-cyclopropyl-5-(3,8-dimethyl-[1,2,4]triazolo[4,3-a]pyridin-6-yl)-1-methyl-5,6-dihydropyrrolo[3,4-b]pyrrol-4(1H)-one. Rt: 4.52 min (system: Agilent HPLC; column: Chiracel OD-H 5 μm, 4.6×250 mm; mobile phase: heptane/EtOH/MeOH 60:20:20 (isocratic); flow: 1 mL/min; detection UV: 210 nm).

Example 37

6-(4-chlorophenyl)-3-cyclopropyl-5-(1,5-dimethyl-6-oxo-1,6-dihydropyridin-3-yl)-1-methyl-5,6-dihydropyrrolo[3,4-b]pyrrol-4(1H)-one

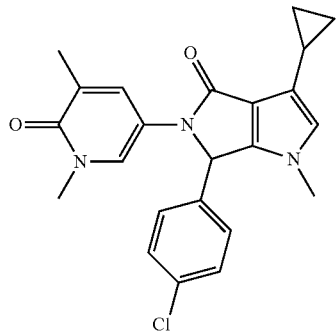 [SMILES: Cc1cc(N2C(=O)c3c(C4CC4)cn(C)c3C2c2ccc(Cl)cc2)cn(C)c1=O]

Step 1: Ethyl 2-((4-chlorophenyl)((1,5-dimethyl-6-oxo-1,6-dihydropyridin-3-yl)amino)methyl)-4-cyclopropyl-1-methyl-1H-pyrrole-3-carboxylate The title compound was prepared using an analogous procedure to that described in Step 9 of Example 1 using ethyl 2-((4-chlorophenyl)(hydroxy)methyl)-4-cyclopropyl-1-methyl-1H-pyrrole-3-carboxylate (Step 2 of Example 35, 265 mg, 0.794 mmol) and 5-amino-1,3-dimethylpyridin-2(1H)-one (Step 2 of Example 34, 121 mg, 0.873 mmol). The reaction mixture was quenched with brine and extracted with EtOAc. The crude product was purified by silica gel column chromatography (1-2.5 MeOH/DCM) to afford the title compound (189 mg, purity 85%) as a brown solid. Rf=0.37 (10% MeOH/DCM); Rt: 1.22 min (LC-MS 1); MS m/z: 454.2 [M+H]$^+$ (LC-MS 1).

Step 2: 6-(4-chlorophenyl)-3-cyclopropyl-5-(1,5-dimethyl-6-oxo-1,6-dihydropyridin-3-yl)-1-methyl-5,6-dihydropyrrolo[3,4-b]pyrrol-4(1H)-one The title compound was prepared using an analogous procedure to that described in Step 10 of Example 1 using ethyl 2-((4-chlorophenyl)((1,5-dimethyl-6-oxo-1,6-dihydropyridin-3-yl)amino)methyl)-4-cyclopropyl-1-methyl-1H-pyrrole-3-carboxylate (Step 1 of Example 37, 189 mg, 0.416 mmol) and stirring the reaction mixture for 2 h at 120° C. The crude product was purified by silica gel column chromatography (1-3.5% MeOH/DCM). The resulting material was triturated in Et$_2$O to afford the title compound (84 mg) as a colorless solid. Rf=0.62 (10% MeOH/DCM); Rt: 1.01 min (LC-MS 1); MS m/z: 408.1 [M+H]$^+$ (LC-MS 1); $^1$H NMR (400 MHz, DMSO-d6) δ 0.71-0.90 (m, 4H) 1.69-1.81 (m, 1H) 1.90 (s, 3H) 3.19 (s, 3H) 3.33 (s, 3H) 6.04 (s, 1H) 6.68 (s, 1H) 7.21 (d, J=8.21 Hz, 2H) 7.29-7.33 (m, 1H) 7.38 (d, J=8.21 Hz, 2H) 7.58 (d, J=1.95 Hz, 1H).

Example 38

5-(5-chloro-1-methyl-6-oxo-1,6-dihydropyridin-3-yl)-6-(4-chlorophenyl)-2-(2,4-dimethoxypyrimidin-5-yl)-1-methyl-5,6-dihydropyrrolo[3,4-b]pyrrol-4(1H)-one

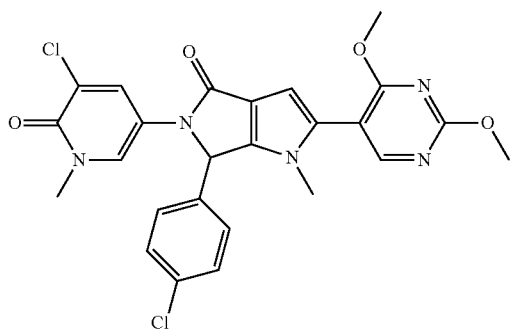 [SMILES: COc1ncc(-c2cc3c(n2C)C(c2ccc(Cl)cc2)N(c2cc(Cl)c(=O)n(C)c2)C3=O)c(OC)n1]

Step 1: 3-chloro-1-methyl-5-nitropyridin-2(1H)-one

To a stirred suspension of 3-chloro-2-hydroxy-5-nitropyridine (10 g, 57.3 mmol) and K$_2$CO$_3$ (15.84 g, 115 mmol) in DMF (100 mL) was added MeI (5.37 mL, 86 mmol) at 0° C. under Ar. The reaction mixture was stirred for 1 h at rt, concentrated, diluted with water (100 mL), and extracted with EtOAc (2×150 mL). The combined organic layers were washed with water (100 mL), dried (Na$_2$SO$_4$), and evaporated to afford the title product (10.38 g) as a yellow solid. $^1$H NMR (400 MHz, DMSO-d6) δ 9.22 (d, J=3.2 Hz, 1H) 8.44 (d, J=2.8 Hz, 1H) 3.61 (s, 3H).

Step 2: 5-amino-3-chloro-1-methylpyridin-2(1H)-one

To a stirred solution of 3-chloro-1-methyl-5-nitropyridin-2(1H)-one (Step 1 of Example 38, 10.38 g, 55.0 mmol), EtOH (200 mL) and ammonium chloride (79 mL, 550 mmol) was added iron (9.22 g, 165 mmol). The reaction mixture was stirred for 1 h at 85° C., filtered through a pad of celite, and concentrated. The crude material was purified by silica gel column chromatography (2-10% MeOH/DCM) to afford the title product (6.77 g) as a black solid. Rf=0.28 (10% MeOH/DCM); $^1$H NMR (400 MHz, DMSO-d6) δ 7.36 (d, J=2.7 Hz, 1H) 6.89 (d, J=2.8 Hz, 1H) 4.41 (br. s, 2H) 3.38 (s, 3H).

Step 3: Methyl 5-bromo-2-(((5-chloro-1-methyl-6-oxo-1,6-dihydropyridin-3-yl)amino)(4-chlorophenyl)methyl)-1-methyl-1H-pyrrole-3-carboxylate To a stirred solution of methyl 5-bromo-2-((4-chlorophenyl)(hydroxy)methyl)-1-methyl-1H-pyrrole-3-carboxylate (Step 3 of Example 31, 5 g, 13.94 mmol) and triethylamine (9.72 mL, 69.7 mmol) in DCM (25 mL) was added Ms$_2$O (4.86 g, 27.9 mmol) at −40° C. under Ar. The mixture was stirred for 15 min at −40. 5-Amino-3-chloro-1-methylpyridin-2(1H)-one (Step 2 of Example 38, 2.87 g, 18.13 mmol) was added. The reaction mixture was allowed to warm to rt, stirred for 3 days, diluted with DCM/water, and extracted twice with DCM. The combined organic extracts were washed with brine (100 mL), dried (Na$_2$SO$_4$), filtered and the filtrate was concentrated. The residue was purified by silica gel column chromatography (50% EtOAc/DCM) to afford the title compound (4.29 g) as a off-white solid. Rf=0.39 (50% EtOAc/DCM); Rt: 1.21 min (LC-MS 1); MS m/z: 498.0/500.0 [M+H]$^+$ (LC-MS 1).

Step 4: 5-bromo-2-(((5-chloro-1-methyl-6-oxo-1,6-dihydropyridin-3-yl)amino)(4-chlorophenyl)methyl)-1-methyl-1H-pyrrole-3-carboxylic acid A mixture of methyl 5-bromo-2-(((5-chloro-1-methyl-6-oxo-1,6-dihydropyridin-3-yl)amino)(4-chlorophenyl)methyl)-1-methyl-1H-pyrrole-3-carboxylate (Step 3 of Example 38, 4.29 g, 8.59 mmol) and NaOH (2N, 40 mL, 80 mmol) in THF (40 mL) and MeOH (40 mL) was stirred for 1.5 h at 70° C. THF and MeOH were evaporated. The resulting aqueous mixture was acidified with aqueous 2N HCl to pH 5 and extracted twice with EtOAc. The combined organic extracts were washed with brine, dried (Na$_2$SO$_4$), filtered and the filtrate was concentrated. The residue was triturated in EtOAc to afford the title compound (4.1 g) as a colorless solid. Rt: 1.02 min (LC-MS 1); MS m/z: 484.0/486.0 [M+H]$^+$ (LC-MS 1).

Step 5: 2-bromo-5-(5-chloro-1-methyl-6-oxo-1,6-dihydropyridin-3-yl)-6-(4-chlorophenyl)-1-methyl-5,6-dihydropyrrolo[3,4-b]pyrrol-4(1H)-one The title compound was prepared using an analogous procedure to that described in Step 5 of Example 2 using 5-bromo-2-(((5-chloro-1-methyl-6-oxo-1,6-dihydropyridin-3-yl)amino)(4-chlorophenyl)methyl)-1-methyl-1H-pyrrole-3-carboxylic acid (Step 4 of Example 38, 4.1 g, 8.03 mmol) and stirring the reaction mixture for 1 h at rt. The crude product was purified by silica gel column chromatography (5% MeOH/DCM) followed by trituration of the resulting material in EtOAc to afford the title compound (3.6 g) as a colorless solid. Rf: 0.24 (5% MeOH/DCM). Rt: 1.02 min (LC-MS 1); MS m/z: 466.0/468.0 [M+H]$^+$ (LC-MS 1).

Step 6: 5-(5-chloro-1-methyl-6-oxo-1,6-dihydropyridin-3-yl)-6-(4-chlorophenyl)-2-(2,4-dimethoxypyrimidin-5-yl)-1-methyl-5,6-dihydropyrrolo[3,4-b]pyrrol-4(1H)-one The title compound was prepared using an analogous procedure to that described in Step 4 of Example 25 using 2-bromo-5-(5-chloro-1-methyl-6-oxo-1,6-dihydropyridin-3-yl)-6-(4-chlorophenyl)-1-methyl-5,6-dihydropyrrolo[3,4-b]pyrrol-4(1H)-one (Step 5 of Example 38, 150 mg, 0.321 mmol) and (2,4-dimethoxypyrimidin-5-yl)boronic acid (Frontier Scientific, 118 mg, 0.642 mmol). DCM was used instead of EtOAc in the workup. The crude was loaded onto a Varian PL-Thiol MP SPE cartridge (to remove metals traces) and eluted with MeOH. After concentration, the residue was purified by silica gel column chromatography (1% ammonia/5% MeOH/DCM) to afford a yellow foam. This foam was purified by preparative achiral SFC (column: CN-Diol, 100×30 mm, 5 µm, 100 A, Princeton; eluent: MeOH/scCO$_2$; gradient: 1 min 14% MeOH, 14% to 19% MeOH in 6 min, 19% to 50% MeOH, in 1 min, 1.5 min 50% MeOH; flow: 100 mL/min). Trituration of the resulting material in Et$_2$O afforded the title compound (31 mg) as a colorless solid. Rf=0.30 (1% ammonia/5% MeOH/DCM); Rt: 1.01 min (LC-MS 1); MS m/z: 526.1 [M+H]$^+$ (LC-MS 1); $^1$H NMR (400 MHz, DMSO-d6) δ 3.09 (s, 3H) 3.42 (s, 3H) 3.91 (s, 3H) 3.88 (s, 3H) 6.24 (s, 1H) 6.39 (s, 1H) 7.31 (m, J=8.60 Hz, 2H) 7.41 (m, J=8.60 Hz, 2H) 7.77-7.88 (m, 2H) 8.20-8.34 (m, 1H).

Example 39

5-(5-chloro-1-methyl-6-oxo-1,6-dihydropyridin-3-yl)-6-(4-chlorophenyl)-2-(2-methoxypyrimidin-4-yl)-1-methyl-5,6-dihydropyrrolo[3,4-b]pyrrol-4(1H)-one

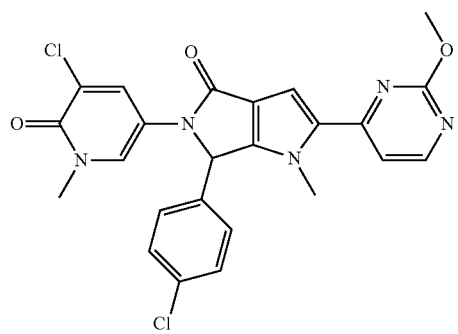 [SMILES: COc1nccc(-c2cc3c(n2C)C(c2ccc(Cl)cc2)N(c2cc(Cl)c(=O)n(C)c2)C3=O)n1]

Step 1: 2-methoxy-4-(4,4,5,5-tetramethyl-1,3,2-dioxaborolan-2-yl)pyrimidine

The title compound was prepared using an analogous procedure to that described in Step 2 of Example 25 using 4-bromo-2-methoxypyridine (ABCR, 1.03 g, 5.45 mmol) and stirring the reaction mixture for 18 h at 120° C. The title compound (2.2 g, purity 20%) could not be characterized due to the low level of purity.

Step 2: 5-(5-chloro-1-methyl-6-oxo-1,6-dihydropyridin-3-yl)-6-(4-chlorophenyl)-2-(2-methoxypyrimidin-4-yl)-1-methyl-5,6-dihydropyrrolo[3,4-b]pyrrol-4(1H)-one The title compound was prepared using an analogous procedure to that described in Step 4 of Example 25 using 2-bromo-5-(5-chloro-1-methyl-6-oxo-1,6-dihydropyridin-3-yl)-6-(4-chlorophenyl)-1-methyl-5,6-dihydropyrrolo[3,4-b]pyrrol-4(1H)-one (Step 5 of Example 38, 200 mg, 0.428 mmol) and 2-methoxy-4-(4,4,5,5-tetramethyl-1,3,2-dioxaborolan-2-yl)pyrimidine (Step 1 of Example 39, 1011 mg, 0.856 mmol). DCM was used instead of EtOAc in the workup. The crude was loaded onto a Varian PL-Thiol MP SPE cartridge (to remove metals traces) and eluted with MeOH. After concentration, the residue was purified by chromatography (1% ammonia/5% MeOH/DCM) to afford a yellow foam. This foam was purified by preparative achiral SFC (silica gel; eluent: MeOH/scCO$_2$; gradient: 25% to 30% MeOH in 11 min; flow: 100 mL/min). Trituration of the resulting material in Et$_2$O afforded the title compound (15 mg) as a colorless solid. Rf=0.32 (1% ammonia/5% MeOH/DCM); Rt: 0.99 min (LC-MS 1); MS m/z: 496.0 [M+H]$^+$ (LC-MS 1); $^1$H NMR (400 MHz, DMSO-d6) δ 3.36 (s, 3H) 3.65 (s, 3H) 3.79 (s, 3H) 6.27 (s, 1H) 7.25 (d, J=8.60 Hz, 2H) 7.30-7.38 (m, 3H) 7.45 (d, J=5.08 Hz, 1H) 7.78 (d, J=1.96 Hz, 2H) 8.43 (d, J=5.47 Hz, 1H).

Example 40

5-(5-chloro-1-methyl-6-oxo-1,6-dihydropyridin-3-yl)-6-(4-chlorophenyl)-2-(2-methoxypyrimidin-5-yl)-1-methyl-5,6-dihydropyrrolo[3,4-b]pyrrol-4(1H)-one

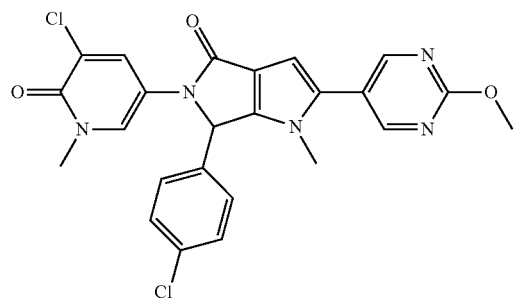 [SMILES: COc1ncc(-c2cc3c(n2C)C(c2ccc(Cl)cc2)N(c2cc(Cl)c(=O)n(C)c2)C3=O)cn1]

The title compound was prepared using an analogous procedure to that described in Step 4 of Example 25 using 2-bromo-5-(5-chloro-1-methyl-6-oxo-1,6-dihydropyridin-3-yl)-6-(4-chlorophenyl)-1-methyl-5,6-dihydropyrrolo[3,4-b]pyrrol-4(1H)-one (Step 5 of Example 38, 150 mg, 0.321 mmol) and (2-methoxypyrimidin-5-yl)boronic acid (Frontier Scientific, 99 mg, 0.642 mmol). DCM was used instead of EtOAc in the workup. The crude was loaded onto a Varian PL-Thiol MP SPE cartridge (to remove metals traces) and eluted with MeOH. After concentration, the residue was purified by silica gel column chromatography (1% ammonia/5% MeOH/DCM) to afford a yellow foam. This foam was purified by preparative achiral SFC (silica gel; eluent: MeOH/scCO$_2$; gradient: 20 min 12% MeOH; flow: 100 mL/min). Trituration of the resulting material in Et$_2$O afforded the title compound (47 mg) as a colorless solid. Rf=0.32 (1% ammonia/5% MeOH/DCM); Rt: 0.94 min (LC-MS 1); MS m/z: 496.1 [M+H]$^+$ (LC-MS 1); $^1$H NMR (400 MHz, DMSO-d6) δ 3.32 (s, 3H) 3.42 (s, 3H) 3.93 (s, 3H) 6.27 (s, 1H) 6.61 (s, 1H) 7.25-7.37 (m, 2H) 7.37-7.46 (m, 2H) 7.85 (s, 2H) 8.73 (s, 2H).

Example 41

5-(5-chloro-1-methyl-6-oxo-1,6-dihydropyridin-3-yl)-6-(4-chlorophenyl)-1-methyl-2-(1-methyl-2-oxo-1,2-dihydropyridin-4-yl)-5,6-dihydropyrrolo[3,4-b]pyrrol-4(1H)-one

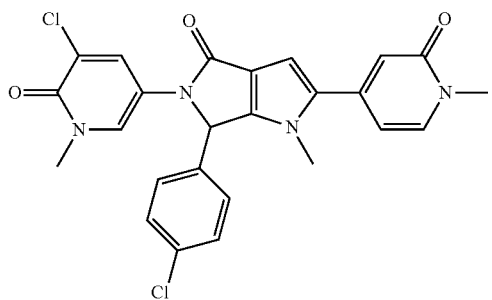 [SMILES: Cn1c(-c2ccn(C)c(=O)c2)cc2c1C(c1ccc(Cl)cc1)N(c1cc(Cl)c(=O)n(C)c1)C2=O]

Step 1: 1-methyl-4-(4,4,5,5-tetramethyl-1,3,2-dioxaborolan-2-yl)pyridin-2(1H)-one The title compound was prepared using an analogous procedure to that described in Step 2 of Example 25 using 4-bromo-1-methylpyridin-2(1H)-one (ABCR, 1.11 g, 5.90 mmol). The title compound (2.9 g, purity 40%) was used without purification. Rt: 0.29 min (LC-MS 1); MS m/z: 154.1 [M+H]$^+$ (boronic acid) (LC-MS 1).

Step 2: 5-(5-chloro-1-methyl-6-oxo-1,6-dihydropyridin-3-yl)-6-(4-chlorophenyl)-1-methyl-2-(1-methyl-2-oxo-1,2-dihydropyridin-4-yl)-5,6-dihydropyrrolo[3,4-b]pyrrol-4(1H)-one The title compound was prepared using an analogous procedure to that described in Step 4 of Example 25 using 2-bromo-5-(5-chloro-1-methyl-6-oxo-1,6-dihydropyridin-3-yl)-6-(4-chlorophenyl)-1-methyl-5,6-dihydropyrrolo[3,4-b]pyrrol-4(1H)-one (Step 5 of Example 38, 150 mg, 0.321 mmol) and 1-methyl-4-(4,4,5,5-tetramethyl-1,3,2-dioxaborolan-2-yl)pyridin-2(1H)-one (Step 1 of Example 41, 377 mg, 0.642 mmol). DCM was used instead of EtOAc in the workup. The crude was loaded onto a Varian PL-Thiol MP SPE cartridge (to remove metals traces) and eluted with MeOH. After concentration, the residue was purified by silica gel column chromatography (1% ammonia/5% MeOH/DCM) to afford a beige foam. This foam was purified by preparative achiral SFC (column: 4-EP, 250×30 mm, 5 μm, 60 A, Princeton; eluent: MeOH/scCO$_2$; gradient: 1 min 20% MeOH, 20% to 25% MeOH in 6 min, 25% to 50% MeOH in 1 min, 1.5 min 50% MeOH; flow: 100 mL/min). Trituration of the resulting material in Et$_2$O afforded the title compound (58 mg) as a colorless solid. Rf=0.22 (1% ammonia/5% MeOH/DCM); Rt: 0.79 min (LC-MS 1); MS m/z: 495.1 [M+H]$^+$ (LC-MS 1); $^1$H NMR (400 MHz, DMSO-d6) δ 3.33-3.46 (m, 9H) 6.26 (s, 1H) 6.37 (dd, J=7.23, 2.15 Hz, 1H) 6.43 (d, J=1.56 Hz, 1H) 6.72 (s, 1H) 7.31 (m, J=8.60 Hz, 2H) 7.40 (m, J=8.21 Hz, 2H) 7.68 (d, J=7.04 Hz, 1H) 7.83 (s, 2H).

Example 42

5-(5-chloro-1-methyl-6-oxo-1,6-dihydropyridin-3-yl)-6-(4-chlorophenyl)-1-methyl-2-(1-methyl-6-oxo-1,6-dihydropyridin-3-yl)-5,6-dihydropyrrolo[3,4-b]pyrrol-4(1H)-one

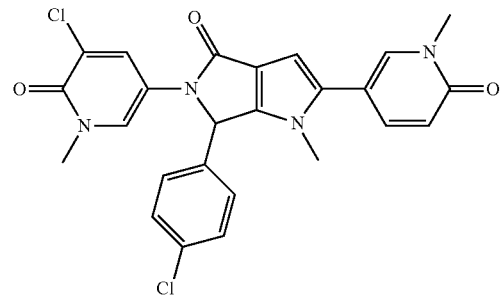 [SMILES: Cn1c(-c2ccc(=O)n(C)c2)cc2c1C(c1ccc(Cl)cc1)N(c1cc(Cl)c(=O)n(C)c1)C2=O]

Step 1: 1-methyl-5-(4,4,5,5-tetramethyl-1,3,2-dioxaborolan-2-yl)pyridin-2(1H)-one The title compound was prepared using an analogous procedure to that described in Step 2 of Example 25 using 5-bromo-1-methylpyridin-2(1H)-one (ABCR, 1.05 g, 5.58 mmol) and stirring the reaction mixture for 30 min at 110° C. The title compound (2.75 g, purity 30%) was used without purification. Rt: 0.83 min (LC-MS 1); MS m/z: 236.2 [M+H]$^+$ (boronic acid) (LC-MS 1).

Step 2: 5-(5-chloro-1-methyl-6-oxo-1,6-dihydropyridin-3-yl)-6-(4-chlorophenyl)-1-methyl-2-(1-methyl-6-oxo-1,6-dihydropyridin-3-yl)-5,6-dihydropyrrolo[3,4-b]pyrrol-4(1H)-one The title compound was prepared using an analogous procedure to that described in Step 4 of Example 25 using 2-bromo-5-(5-chloro-1-methyl-6-oxo-1,6-dihydropyridin-3-yl)-6-(4-chlorophenyl)-1-methyl-5,6-dihydropyrrolo[3,4-b]pyrrol-4(1H)-one (Step 5 of Example 38, 150 mg, 0.321 mmol) and 1-methyl-5-(4,4,5,5-tetramethyl-1,3,2-dioxaborolan-2-yl)pyridin-2(1H)-one (Step 1 of Example 42, 377 mg, 0.642 mmol). The reaction mixture was stirred for 5 min at 110° C. DCM was used instead of EtOAc in the workup. The crude was loaded onto a Varian PL-Thiol MP SPE cartridge (to remove metals traces) and eluted with MeOH. After concentration, the residue was purified by chromatography (1% ammonia/5% MeOH/DCM) to afford a beige foam. This foam was purified by preparative achiral SFC (column: 4-EP, 250×30 mm, 5 μm, 60 A, Princeton; eluent: MeOH/scCO$_2$; gradient: 1 min 20% MeOH, 20% to 25% MeOH in 6 min, 25% to 50% MeOH in 1 min, 1.5 min 50% MeOH; flow: 100 mL/min). Trituration of the resulting material in Et$_2$O afforded the title compound (14 mg) as a colorless solid. Rf=0.24 (1% ammonia/5% MeOH/DCM); Rt: 0.79 min (LC-MS 1); MS m/z: 495.1 [M+H]$^+$ (LC-MS 1); $^1$H NMR (400 MHz, DMSO-d6) δ 3.25 (s, 3H) 3.42 (s, 6H) 6.23 (s, 1H) 6.30-6.45 (m, 2H) 7.30 (m, J=8.60 Hz, 2H) 7.41 (m, J=8.60 Hz, 2H) 7.52 (dd, J=9.38, 2.74 Hz, 1H) 7.78-7.91 (m, 3H).

Example 43

5-(5-chloro-1-methyl-6-oxo-1,6-dihydropyridin-3-yl)-6-(4-chlorophenyl)-1-methyl-2-(1-methyl-2-oxo-1,2-dihydropyridin-3-yl)-5,6-dihydropyrrolo[3,4-b]pyrrol-4(1H)-one

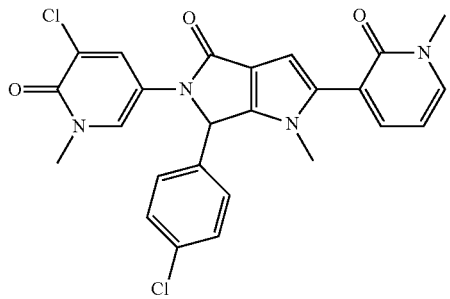 [SMILES: Cn1c(-c2cccn(C)c2=O)cc2c1C(c1ccc(Cl)cc1)N(c1cc(Cl)c(=O)n(C)c1)C2=O]

The title compound was prepared using an analogous procedure to that described in Step 4 of Example 25 using 2-bromo-5-(5-chloro-1-methyl-6-oxo-1,6-dihydropyridin-3-yl)-6-(4-chlorophenyl)-1-methyl-5,6-dihydropyrrolo[3,4-b]pyrrol-4(1H)-one (Step 5 of Example 38, 150 mg, 0.321 mmol) and 1-methyl-3-(4,4,5,5-tetramethyl-1,3,2-dioxaborolan-2-yl)pyridin-2(1H)-one (Step 2 of Example 25, 377 mg, 0.642 mmol). DCM was used instead of EtOAc in the workup. The crude was loaded onto a Varian PL-Thiol MP SPE cartridge (to remove metals traces) and eluted with MeOH. After concentration, the residue was purified by chromatography (1% ammonia/5% MeOH/DCM) to afford a beige foam. This foam was purified by preparative achiral SFC (column: 4-EP, 250×30 mm, 5 μm, 60 A, Princeton; eluent: MeOH/scCO$_2$; gradient: 1 min 19% MeOH, 19% to 24% MeOH in 6 min, 24% to 50% MeOH in 1 min, 1.5 min 50% MeOH; flow: 100 mL/min). Trituration of the resulting material in Et$_2$O afforded the title compound (83 mg) as a colorless solid. Rf=0.31 (1% ammonia/5% MeOH/DCM); Rt: 0.85 min (LC-MS 1); MS m/z: 495.1 [M+H]$^+$ (LC-MS 1); $^1$H NMR (400 MHz, DMSO-d6) δ 3.14 (s, 3H) 3.45 (s, 3H) 3.42 (s, 3H) 6.17-6.36 (m, 3H) 7.30 (m, J=8.60 Hz, 2H) 7.40 (m, J=8.60 Hz, 2H) 7.50 (dd, J=6.84, 2.15 Hz, 1H) 7.73-7.90 (m, 3H).

Example 44

5-(5-chloro-1-methyl-6-oxo-1,6-dihydropyridin-3-yl)-6-(4-chlorophenyl)-1-methyl-2-(1-methyl-6-oxo-1,6-dihydropyridin-2-yl)-5,6-dihydropyrrolo[3,4-b]pyrrol-4(1H)-one

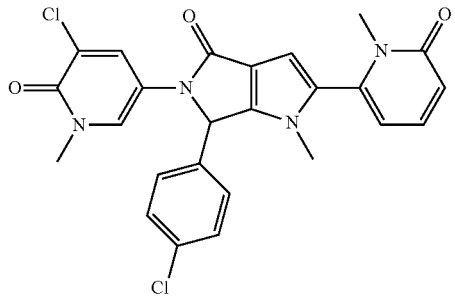

Step 1: 6-bromo-1-methylpyridin-2(1H)-one

The title compound was prepared using an analogous procedure to that described in Step 1 of Example 43 using 6-bromo-2-hydroxypyridine (Combi-Blocks, 10 g, 57.5 mmol). The crude product was purified by silica gel column chromatography (40-60% EtOAc/hexane) to afford the title compound (6.2 g) as a colorless solid. Rf=0.37 (50% EtOAc/hexane); Rt: 0.55 min (LC-MS 1); MS m/z: 188.0/190.0 [M+H]$^+$ (LC-MS 1).

Step 2: 1-methyl-6-(4,4,5,5-tetramethyl-1,3,2-dioxaborolan-2-yl)pyridin-2(1H)-one The title compound was prepared using an analogous procedure to that described in Step 2 of Example 25 using 6-bromo-1-methylpyridin-2(1H)-one (Step 1 of Example 44, 1 g, 5.32 mmol) and stirring the reaction mixture for 3 h at 110° C. The title compound (2.6 g, purity 40%) was used without purification. Rt: 0.37 min (LC-MS 1); MS m/z: 154.1 [M+H]$^+$ (boronic acid) (LC-MS 1).

Step 3: 5-(5-chloro-1-methyl-6-oxo-1,6-dihydropyridin-3-yl)-6-(4-chlorophenyl)-1-methyl-2-(1-methyl-6-oxo-1,6-dihydropyridin-2-yl)-5,6-dihydropyrrolo[3,4-b]pyrrol-4(1H)-one The title compound was prepared using an analogous procedure to that described in Step 4 of Example 25 using 2-bromo-5-(5-chloro-1-methyl-6-oxo-1,6-dihydropyridin-3-yl)-6-(4-chlorophenyl)-1-methyl-5,6-dihydropyrrolo[3,4-b]pyrrol-4(1H)-one (Step 5 of Example 38, 150 mg, 0.321 mmol) and 1-methyl-6-(4,4,5,5-tetramethyl-1,3,2-dioxaborolan-2-yl)pyridin-2(1H)-one (Step 2 of Example 44, 377 mg, 0.642 mmol). The reaction mixture was stirred for 20 min at 110° C. DCM was used instead of EtOAc in the workup. The crude was loaded onto a Varian PL-Thiol MP SPE cartridge (to remove metals traces) and eluted with MeOH. After concentration, the residue was purified by silica gel column chromatography (1% ammonia/5% MeOH/DCM) to afford a beige foam. This foam was purified by preparative achiral SFC (column: 4-EP, 250×30 mm, 6 μm, 60 A, Princeton; eluent: MeOH/scCO$_2$; gradient: 1 min 18% MeOH, 18% to 23% MeOH in 6 min, 23% to 50% MeOH in 1 min, 1.5 min 50% MeOH; flow: 100 mL/min). Trituration of the resulting material in Et$_2$O afforded the title compound (29 mg) as a colorless solid. Rf=0.24 (1% ammonia/5% MeOH/DCM); Rt: 0.81 min (LC-MS 1); MS m/z: 495.1 [M+H]$^+$ (LC-MS 1); $^1$H NMR (400 MHz, DMSO-d6) δ 3.14 (s, 3H) 3.12 (s, 3H) 3.42 (s, 3H) 6.15-6.35 (m, 2H) 6.48 (d, J=8.99 Hz, 1H) 6.61 (s, 1H) 7.31 (d, J=8.60 Hz, 2H) 7.36-7.49 (m, 3H) 7.82 (s, 2H).

Example 45

6-(4-chlorophenyl)-5-(1,5-dimethyl-6-oxo-1,6-dihydropyridin-3-yl)-1-methyl-2-(1-methyl-2-oxo-1,2-dihydropyridin-4-yl)-5,6-dihydropyrrolo[3,4-b]pyrrol-4(1H)-one

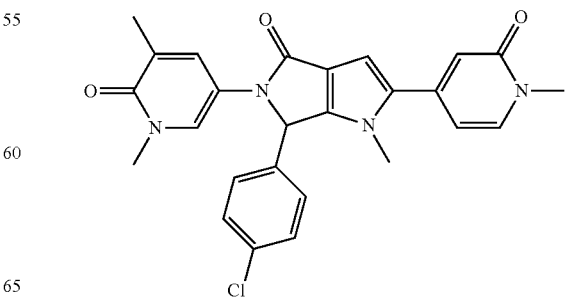

Step 1: Methyl 5-bromo-2-((4-chlorophenyl)((1,5-dimethyl-6-oxo-1,6-dihydropyridin-3-yl)amino)methyl)-1-methyl-1H-pyrrole-3-carboxylate To a stirred solution of methyl 5-bromo-2-((4-chlorophenyl)(hydroxy)methyl)-1-methyl-1H-pyrrole-3-carboxylate (Step 3 of Example 31, 3 g, 8.37 mmol) and triethylamine (5.83 mL, 41.8 mmol) in DCM (60 mL) was added Ms$_2$O (2.91 g, 16.73 mmol) at −40° C. under Ar. The mixture was stirred for 15 min at −40. 5-Amino-1,3-dimethylpyridin-2(1H)-one (Step 2 of Example 34, 1.5 g, 10.88 mmol) was added. The reaction mixture was allowed to warm to rt over 14 h, diluted with DCM/water, and extracted twice with DCM. The combined organic extracts were washed with brine (100 mL), dried (Na$_2$SO$_4$), filtered and the filtrate was concentrated. The residue was purified by silica gel column chromatography (5% MeOH/DCM) followed by trituration of the resulting material in EtOAc to afford the title compound (2.2 g) as a beige solid. Rf=0.41 (5% MeOH/DCM); Rt: 1.18 min (LC-MS 1); MS m/z: 478.0/480.0 [M+H]$^+$ (LC-MS 1).

Step 2: 5-bromo-2-((4-chlorophenyl)((1,5-dimethyl-6-oxo-1,6-dihydropyridin-3-yl)amino)methyl)-1-methyl-1H-pyrrole-3-carboxylic acid A mixture of methyl 5-bromo-2-((4-chlorophenyl)((1,5-dimethyl-6-oxo-1,6-dihydropyridin-3-yl)amino)methyl)-1-methyl-1H-pyrrole-3-carboxylate (Step 1 of Example 45, 2.2 g, 4.6 mmol) and NaOH (2N, 20.7 mL, 41.4 mmol) in THF (10 mL) and MeOH (10 mL) was stirred for 1.5 h at 70° C. and concentrated. The aqueous residue was acidified with aqueous 2N HCl to pH 5 and extracted twice with EtOAc. The combined organic extracts were washed with brine, dried (Na$_2$SO$_4$), filtered and the filtrate was concentrated to afford the title compound (1.22 g, purity 90%) as a yellow foam. Rt: 1.00 min (LC-MS 1); MS m/z: 464.0/466.0 [M+H]$^+$ (LC-MS 1).

Step 3: 2-bromo-6-(4-chlorophenyl)-5-(1,5-dimethyl-6-oxo-1,6-dihydropyridin-3-yl)-1-methyl-5,6-dihydropyrrolo[3,4-b]pyrrol-4(1H)-one 1-Chloro-N,N,2-trimethyl-1-propenyl-amine (0.72 mL, 5.42 mmol) was added to a stirred suspension of 5-bromo-2-((4-chlorophenyl)((1,5-dimethyl-6-oxo-1,6-dihydropyridin-3-yl)amino)methyl)-1-methyl-1H-pyrrole-3-carboxylic acid (Step 2 of Example 45, 2 g, 3.87 mmol) and in DCM (24 mL) at 0° C. The reaction mixture was stirred for 30 min at rt, diluted in DCM/saturated aqueous solution of NaHCO$_3$ and extracted twice with DCM. The combined organic extracts were washed with brine, dried (Na$_2$SO$_4$), filtered and the filtrate was concentrated. The residue was purified by silica gel column chromatography (5% MeOH/DCM) followed by trituration of the resulting material in EtOAc to afford the title compound (1.22 g) as a colorless solid. Rf: 0.22 (5% MeOH/DCM). Rt: 0.98 min (LC-MS 1); MS m/z: 446.0/448.0 [M+H]$^+$ (LC-MS 1).

Step 4: 6-(4-chlorophenyl)-5-(1,5-dimethyl-6-oxo-1,6-dihydropyridin-3-yl)-1-methyl-2-(1-methyl-2-oxo-1,2-dihydropyridin-4-yl)-5,6-dihydropyrrolo[3,4-b]pyrrol-4(1H)-one The title compound was prepared using an analogous procedure to that described in Step 4 of Example 25 using 2-bromo-6-(4-chlorophenyl)-5-(1,5-dimethyl-6-oxo-1,6-dihydropyridin-3-yl)-1-methyl-5,6-dihydropyrrolo[3,4-b]pyrrol-4(1H)-one (Step 3 of Example 45, 150 mg, 0.336 mmol) and 1-methyl-4-(4,4,5,5-tetramethyl-1,3,2-dioxaborolan-2-yl)pyridin-2(1H)-one (Step 1 of Example 41, 395 mg, 0.672 mmol). DCM was used instead of EtOAc in the workup. The crude was loaded onto a Varian PL-Thiol MP SPE cartridge (to remove metals traces) and eluted with MeOH. After concentration, the residue was purified by silica gel column chromatography (1% ammonia/5% MeOH/DCM) to afford a beige foam. This foam was purified by preparative achiral SFC (column: 4-EP, 250×30 mm, 6 μm, 60 A, Princeton; eluent: MeOH/scCO$_2$; gradient: 1 min 16% MeOH, 16% to 21% MeOH in 6 min, 21% to 50% MeOH in 1 min, 1.5 min 50% MeOH; flow: 100 mL/min). Trituration of the resulting material in Et$_2$O afforded the title compound (76 mg) as a colorless solid. Rf=0.20 (1% ammonia/5% MeOH/DCM); Rt: 0.76 min (LC-MS 1); MS m/z: 475.1 [M+H]$^+$ (LC-MS 1); $^1$H NMR (400 MHz, DMSO-d6) δ 1.90 (s, 3H) 3.31-3.42 (m, 9H) 6.22 (s, 1H) 6.32-6.46 (m, 2H) 6.71 (s, 1H) 7.19-7.35 (m, 3H) 7.35-7.44 (m, 2H) 7.60 (d, J=2.74 Hz, 1H) 7.68 (d, J=7.43 Hz, 1H).

Example 46

6-(4-chlorophenyl)-5-(1,5-dimethyl-6-oxo-1,6-dihydropyridin-3-yl)-1-methyl-2-(1-methyl-6-oxo-1,6-dihydropyridin-3-yl)-5,6-dihydropyrrolo[3,4-b]pyrrol-4(1H)-one

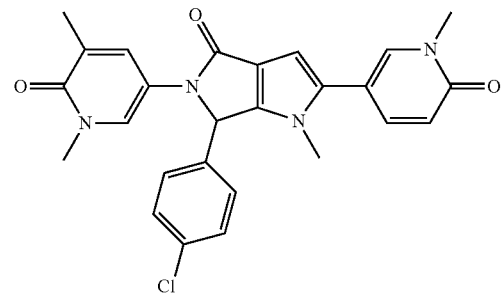 [SMILES: Cc1cc(N2C(=O)c3cc(-c4ccc(=O)n(C)c4)n(C)c3C2c2ccc(Cl)cc2)cn(C)c1=O]

The title compound was prepared using an analogous procedure to that described in Step 4 of Example 25 using 2-bromo-6-(4-chlorophenyl)-5-(1,5-dimethyl-6-oxo-1,6-dihydropyridin-3-yl)-1-methyl-5,6-dihydropyrrolo[3,4-b]pyrrol-4(1H)-one (Step 3 of Example 45, 150 mg, 0.336 mmol) and 1-methyl-5-(4,4,5,5-tetramethyl-1,3,2-dioxaborolan-2-yl)pyridin-2(1H)-one (Step 1 of Example 42, 158 mg, 0.672 mmol). The reaction mixture was stirred for 20 min at 110° C. DCM was used instead of EtOAc in the workup. The crude was loaded onto a Varian PL-Thiol MP SPE cartridge (to remove metals traces) and eluted with MeOH. After concentration, the residue was purified by silica gel column chromatography (1% ammonia/5% MeOH/DCM) to afford a beige foam. This foam was purified by preparative achiral SFC (column: 4-EP, 250×30 mm, 5 μm, 60 A, Princeton; eluent: MeOH/scCO$_2$; gradient: 1 min 10% MeOH, 10% to 15% MeOH in 6 min, 15% to 50% MeOH in 1 min, 1.5 min 50% MeOH; flow: 100 mL/min). Trituration of the resulting material in Et$_2$O afforded the title compound (27 mg) as a colorless solid. Rf=0.17 (1% ammonia/5% MeOH/DCM); Rt: 0.76 min (LC-MS 1); MS m/z: 475.1 [M+H]$^+$ (LC-MS 1); $^1$H NMR (400 MHz, DMSO-d6) δ 1.90 (s, 3H) 3.24 (s, 3H) 3.33 (s, 3H) 3.42 (s, 3H) 6.18 (s, 1H) 6.30-6.45 (m, 2H) 7.21-7.46 (m, 5H) 7.46-7.57 (m, 1H) 7.60 (d, J=2.74 Hz, 1H) 7.85 (d, J=2.35 Hz, 1H).

Example 47

6-(4-chlorophenyl)-5-(1,5-dimethyl-6-oxo-1,6-dihydropyridin-3-yl)-1-methyl-2-(1-methyl-2-oxo-1,2-dihydropyridin-3-yl)-5,6-dihydropyrrolo[3,4-b]pyrrol-4(1H)-one

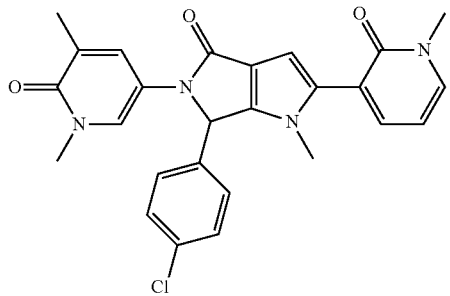 [SMILES: Cc1cc(N2C(=O)c3cc(-c4cccn(C)c4=O)n(C)c3C2c2ccc(Cl)cc2)cn(C)c1=O]

The title compound was prepared using an analogous procedure to that described in Step 4 of Example 25 using 2-bromo-6-(4-chlorophenyl)-5-(1,5-dimethyl-6-oxo-1,6-dihydropyridin-3-yl)-1-methyl-5,6-dihydropyrrolo[3,4-b]pyrrol-4(1H)-one (Step 3 of Example 45, 150 mg, 0.336 mmol) and 1-methyl-3-(4,4,5,5-tetramethyl-1,3,2-dioxaborolan-2-yl)pyridin-2(1H)-one (Step 2 of Example 43, 395 mg, 0.672 mmol). DCM was used instead of EtOAc in the workup. The crude was loaded onto a Varian PL-Thiol MP SPE cartridge (to remove metals traces) and eluted with MeOH. After concentration, the residue was purified by silica gel column chromatography (1% ammonia/5% MeOH/DCM) to afford a beige foam. This foam was purified by preparative achiral SFC (column: 4-EP, 250×30 mm, 5 µm, 60 A, Princeton; eluent: MeOH/scCO$_2$; gradient: 1 min 19% MeOH, 19% to 24% MeOH in 6 min, 24% to 50% MeOH in 1 min, 1.5 min 50% MeOH; flow: 100 mL/min). Trituration of the resulting material in Et$_2$O afforded the title compound (90 mg) as a colorless solid. Rf=0.23 (1% ammonia/5% MeOH/DCM); Rt: 0.81 min (LC-MS 1); MS m/z: 475.2 [M+H]$^+$ (LC-MS 1); $^1$H NMR (400 MHz, DMSO-d6) δ 1.90 (s, 3H) 3.13 (s, 3H) 3.33 (s, 3H) 3.45 (s, 3H) 6.18 (s, 1H) 6.22-6.33 (m, 2H) 7.22-7.44 (m, 5H) 7.49 (dd, J=6.84, 2.15 Hz, 1H) 7.60 (d, J=2.74 Hz, 1H) 7.78 (dd, J=6.84, 2.15 Hz, 1H).

Example 48

6-(4-chlorophenyl)-5-(1,5-dimethyl-6-oxo-1,6-dihydropyridin-3-yl)-1-methyl-2-(1-methyl-6-oxo-1,6-dihydropyridin-2-yl)-5,6-dihydropyrrolo[3,4-b]pyrrol-4(1H)-one

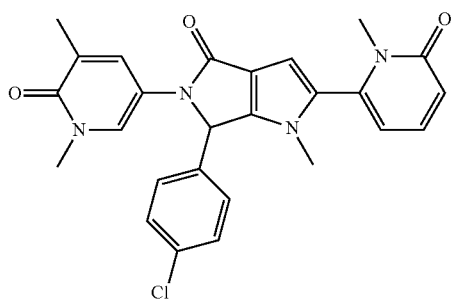 [SMILES: Cc1cc(N2C(=O)c3cc(-c4cccc(=O)n4C)n(C)c3C2c2ccc(Cl)cc2)cn(C)c1=O]

The title compound was prepared using an analogous procedure to that described in Step 4 of Example 25 using 2-bromo-6-(4-chlorophenyl)-5-(1,5-dimethyl-6-oxo-1,6-dihydropyridin-3-yl)-1-methyl-5,6-dihydropyrrolo[3,4-b]pyrrol-4(1H)-one (Step 3 of Example 45, 150 mg, 0.336 mmol) and 1-methyl-6-(4,4,5,5-tetramethyl-1,3,2-dioxaborolan-2-yl)pyridin-2(1H)-one, 1-methyl-6-(4,4,5,5-tetramethyl-1,3,2-dioxaborolan-2-yl)pyridin-2(1H)-one (Step 2 of Example 44, 395 mg, 0.672 mmol). The reaction mixture was stirred 20 min at 110° C. DCM was used instead of EtOAc in the workup. The crude was loaded onto a Varian PL-Thiol MP SPE cartridge (to remove metals traces) and eluted with MeOH. After concentration, the residue was purified by chromatography (1% ammonia/5% MeOH/DCM) to afford a beige foam. This foam was purified by preparative achiral SFC (column: 4-EP, 250×30 mm, 5 µm, 60 A, Princeton; eluent: MeOH/scCO$_2$; gradient: 1 min 14% MeOH, 14% to 19% MeOH in 6 min, 19% to 50% MeOH in 1 min, 1.5 min 50% MeOH; flow: 100 mL/min). Trituration of the resulting material in Et$_2$O afforded the title compound (41 mg) as a colorless solid. Rf=0.21 (1% ammonia/5% MeOH/DCM); Rt: 0.77 min (LC-MS 1); MS m/z: 475.2 [M+H]$^+$ (LC-MS 1); $^1$H NMR (400 MHz, DMSO-d6) δ 1.90 (s, 3H) 3.14 (s, 3H) 3.11 (s, 3H) 3.34 (s, 3H) 6.20 (s, 1H) 6.28 (d, J=6.65 Hz, 1H) 6.48 (d, J=8.60 Hz, 1H) 6.58 (s, 1H) 7.21-7.35 (m, 3H) 7.35-7.48 (m, 3H) 7.58 (s, 1H).

Example 49

6-(4-chlorophenyl)-5-(1,5-dimethyl-6-oxo-1,6-dihydropyridin-3-yl)-1-methyl-2-(2-(trifluoromethyl)pyrimidin-4-yl)-5,6-dihydropyrrolo[3,4-b]pyrrol-4(1H)-one

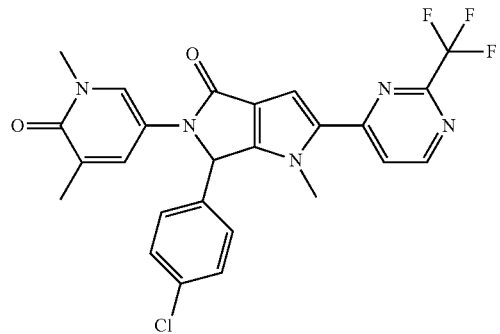 [SMILES: Cc1cc(N2C(=O)c3cc(-c4ccnc(C(F)(F)F)n4)n(C)c3C2c2ccc(Cl)cc2)cn(C)c1=O]

Step 1: 4-(4,4,5,5-tetramethyl-1,3,2-dioxaborolan-2-yl)-2-(trifluoromethyl)pyrimidine The title compound was prepared using an analogous procedure to that described in Step 2 of Example 25 using 4-chloro-2-(trifluoromethyl)pyrimidine (Fluorochem, 1.1 g, 6.03 mmol) and stirring the reaction mixture for 3 h at 110° C. The title compound (3 g, purity 30%) was used without purification and could not be characterized due to the low level of purity.

Step 2: 6-(4-chlorophenyl)-5-(1,5-dimethyl-6-oxo-1,6-dihydropyridin-3-yl)-1-methyl-2-(2-(trifluoromethyl)pyrimidin-4-yl)-5,6-dihydropyrrolo[3,4-b]pyrrol-4(1H)-one The title compound was prepared using an analogous procedure to that described in Step 4 of Example 25 using 2-bromo-6-(4-chlorophenyl)-5-(1,5-dimethyl-6-oxo-1,6-dihydropyridin-3-yl)-1-methyl-5,6-dihydropyrrolo[3,4-b]pyrrol-4(1H)-one (Step 3 of Example 45, 300 mg, 0.672 mmol), 1-methyl-6-(4,4,5,5-tetramethyl-1,3,2-dioxaborolan-2-yl)pyridin-2(1H)-one, 4-(4,4,5,5-tetramethyl-1,3,2-dioxaborolan-2-yl)-2-(trifluoromethyl)pyrimidine (Step 1 of Example 49, 1277 mg, 1.343 mmol) and 0.15 eq of 1,1'-bis(diphenylphosphino)ferrocene-palladium(II)dichloride dichloromethane complex. The reaction mixture was stirred for 1 h at 100° C. DCM was used instead of EtOAc in the workup. The crude material was purified by silica gel column chromatography (1% MeOH/DCM) followed by preparative HPLC (Gilson gx-281. Column: Sunfire C18, 30×100 mm, 5 mm. Flow: 30 mL/min. Gradient: 20% to 50% B in 30 min; A=0.1% TFA in H2O, B=CH3CN. Detection: UV). The resulting material was triturated in Et$_2$O to provide the title compound (91 mg) as a colorless solid. Rf=0.11 (1% MeOH/DCM); Rt: 1.10 min (LC-MS 1); MS m/z: 514.2 [M+H]$^+$ (LC-MS 1); $^1$H NMR (400 MHz, DMSO-d6) δ 1.92 (s, 3H) 3.35 (s, 3H) 3.71 (s, 3H) 6.33 (s, 1H) 7.30 (d, J=8.21 Hz, 2H) 7.35 (s, 1H) 7.41 (d, J=8.21 Hz, 2H) 7.55 (s, 1H) 7.64 (d, J=2.74 Hz, 1H) 8.16 (d, J=5.47 Hz, 1H) 8.92 (d, J=5.47 Hz, 1H).

Example 50

6-(4-chlorophenyl)-5-(1,5-dimethyl-6-oxo-1,6-dihydropyridin-3-yl)-2-(6-(dimethylamino)pyridin-3-yl)-1-methyl-5,6-dihydropyrrolo[3,4-b]pyrrol-4(1H)-one

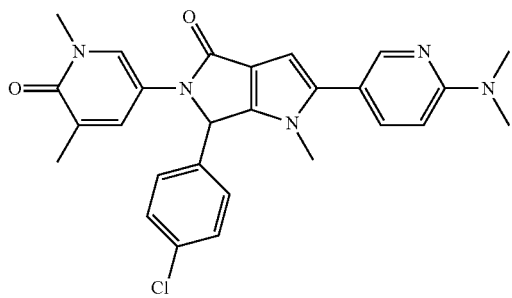 [SMILES: Cc1cc(N2C(=O)c3cc(-c4ccc(N(C)C)nc4)n(C)c3C2c2ccc(Cl)cc2)cn(C)c1=O]

Tripotassium phosphate (190 mg, 0.895 mmol) was added to a stirred solution of 2-bromo-6-(4-chlorophenyl)-5-(1,5-dimethyl-6-oxo-1,6-dihydropyridin-3-yl)-1-methyl-5,6-dihydropyrrolo[3,4-b]pyrrol-4(1H)-one (Step 3 of Example 45, 100 mg, 0.224 mmol) in dioxane (6 mL) and water (2 mL) at rt, under Ar. 1,1'-Bis(diphenylphosphino)ferrocene-palladium(II)dichloride dichloromethane complex (27.4 mg, 0.034 mmol) and (6-(dimethylamino)pyridin-3-yl)boronic acid (Combi-Blocks, 149 mg, 0.895 mmol) were added. The reaction mixture was stirred under MW irradiation for 1 h at 100° C., diluted in DCM/water, and extracted twice with DCM. The combined organic extracts were washed with water and brine, dried (Na$_2$SO$_4$), filtered and the filtrate was concentrated. The residue was purified by silica gel column chromatography (1% MeOH/DCM) to afford a yellow oil. This oil was further purified by preparative HPLC (Gilson gx-281. Column: Sunfire C18, 30×100 mm, 5 mm. Flow: 30 mL/min. Gradient: 20% to 50% B in 30 min; A=0.1% TFA in H2O, B=CH3CN. Detection: UV). The resulting material was triturated in Et$_2$O to afford the title compound (20 mg) as a colorless solid. Rf=0.25 (5% MeOH/DCM); Rt: 0.84 min (LC-MS 1); MS m/z: 488.2 [M+H]$^+$ (LC-MS 1); $^1$H NMR (400 MHz, DMSO-d6) δ 1.92 (s, 3H) 3.03 (s, 6H) 3.25 (s, 3H) 3.35 (s, 3H) 6.19 (s, 1H) 6.34 (s, 1H) 6.66 (d, J=8.60 Hz, 1H) 7.28-7.43 (m, 5H) 7.56-7.63 (m, 2H) 8.15 (d, J=2.35 Hz, 1H).

Example 51

6-(4-chlorophenyl)-5-(1,5-dimethyl-6-oxo-1,6-dihydropyridin-3-yl)-2-(6-(dimethylamino)pyridin-2-yl)-1-methyl-5,6-dihydropyrrolo[3,4-b]pyrrol-4(1H)-one

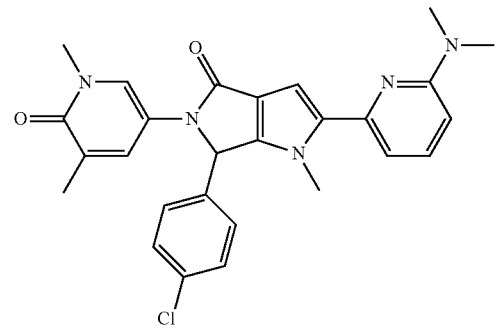 [SMILES: Cc1cc(N2C(=O)c3cc(-c4cccc(N(C)C)n4)n(C)c3C2c2ccc(Cl)cc2)cn(C)c1=O]

Step 1: 6-bromo-N,N-dimethylpyridin-2-amine

A solution of 2,6-dibromopyridine (3 g, 12.66 mmol) and dimethylamine (5.6M in MeOH, 50 mL, 280 mmol) in DMF (40 mL) was stirred for 3 h at 120° C. in a pressure vessel. The reaction mixture was partitioned between water and ethyl acetate. The organic phase was washed with brine, dried over magnesium sulfate, filtered, and concentrated in vacuo. The crude product was purified by silica gel column chromatography (10% EtOAc/hexane) to provide the title compound (1.58 g, purity 85%). Rf=0.60 (20% EtOAc/hexane); Rt: 1.07 min (LC-MS 1); MS m/z: 201.1/203.1 [M+H]$^+$ (LC-MS 1).

Step 2: N,N-dimethyl-6-(4,4,5,5-tetramethyl-1,3,2-dioxaborolan-2-yl)pyridin-2-amine The title compound was prepared using an analogous procedure to that described in Step 2 of Example 25 using 6-bromo-N,N-dimethylpyridin-2-amine (Step 1 of example 51, 1.58 g, 7.86 mmol) and stirring the reaction mixture for 3 h at 110° C. The title compound (4 g, purity 25%) could not be characterized due to the low level of purity and was used without purification.

Step 3: 6-(4-chlorophenyl)-5-(1,5-dimethyl-6-oxo-1,6-dihydropyridin-3-yl)-2-(6-(dimethylamino)pyridin-2-yl)-1-methyl-5,6-dihydropyrrolo[3,4-b]pyrrol-4(1H)-one The title compound was prepared using an analogous procedure to that described in Example using N,N-dimethyl-6-(4,4,5,5-tetramethyl-1,3,2-dioxaborolan-2-yl)pyridin-2-amine (Step 2 of Example 51). Rf=0.25 (5% MeOH/DCM); Rt: 1.15 min (LC-MS 1); MS m/z: 488.2 [M+H]$^+$ (LC-MS 1); $^1$H NMR (600 MHz, DMSO-d6) δ 1.94 (br. s, 3H) 3.01 (br. s, 6H) 3.38 (br. s, 3H) 3.67 (br. s, 3H) 6.27 (br. s, 1H) 6.52 (d, J=8.28 Hz, 1H) 6.85 (s, 1H) 6.99 (d, J=7.15 Hz, 1H) 7.33 (d, J=7.65 Hz, 2H) 7.38 (br. s, 1H) 7.43 (d, J=7.53 Hz, 2H) 7.54 (t, J=7.72 Hz, 1H) 7.66 (br. s, 1H).

Example 52

6-(4-chlorophenyl)-5-(1,5-dimethyl-6-oxo-1,6-dihydropyridin-3-yl)-1-methyl-2-(pyridin-2-yl)-5,6-dihydropyrrolo[3,4-b]pyrrol-4(1H)-one

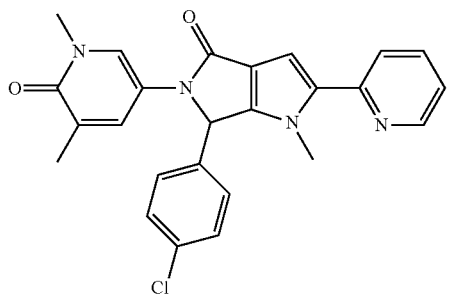 [SMILES: Cc1cc(N2C(=O)c3cc(-c4ccccn4)n(C)c3C2c2ccc(Cl)cc2)cn(C)c1=O]

To a sealed tube was added 2-bromo-6-(4-chlorophenyl)-5-(1,5-dimethyl-6-oxo-1,6-dihydropyridin-3-yl)-1-methyl-5,6-dihydropyrrolo[3,4-b]pyrrol-4(1H)-one (Step 3 of Example 45, 100 mg, 0.224 mmol), DMA (3 mL) and CsF (68.0 mg, 0.448 mmol). The mixture was degassed with argon during 15 minutes at 65° C. 2-(Tributylstannyl)pyridine (Sigma-Aldrich, 0.224 mL, 0.560 mmol) and bis(tri-tert-butyl-phosphine)palladium(0) (17.2 mg, 0.034 mmol) were added. The reaction mixture was stirred for 4 h at 100° C., diluted with brine and extracted with DCM. The combined organic layers were washed with water, dried ($Na_2SO_4$), filtered and the filtrate was concentrated. The residue was purified by silica gel column chromatography (1% MeOH/DCM) to afford a black oil. This oil was further purified by preparative HPLC (Gilson gx-281. Column: Sunfire C18, 30×100 mm, 5 mm. Flow: 30 mL/min. Gradient: 20% to 50% B in 30 min; A=0.1% TFA in H2O, B=CH3CN. Detection: UV). The resulting material was triturated in $Et_2O$ to afford the title compound (18 mg) as a colorless solid. Rf=0.29 (5% MeOH/DCM); Rt: 0.98 min (LC-MS 1); MS m/z: 445.2 [M+H]$^+$ (LC-MS 1); $^1$H NMR (600 MHz, DMSO-d6) δ 1.95 (s, 3H) 3.38 (s, 3H) 3.63 (s, 3H) 6.29 (s, 1H) 6.97 (s, 1H) 7.28 (t, J=5.90 Hz, 1H) 7.32 (d, J=7.91 Hz, 2H) 7.38 (br. s, 1H) 7.44 (d, J=8.03 Hz, 2H) 7.66 (br. s, 1H) 7.78-7.82 (m, 1H) 7.84 (d, J=7.53 Hz, 1H) 8.57 (d, J=3.51 Hz, 1H).

Example 53

6-(4-chlorophenyl)-2-(2,4-dimethoxypyrimidin-5-yl)-5-(1,5-dimethyl-6-oxo-1,6-dihydropyridin-3-yl)-1-methyl-5,6-dihydropyrrolo[3,4-b]pyrrol-4(1H)-one

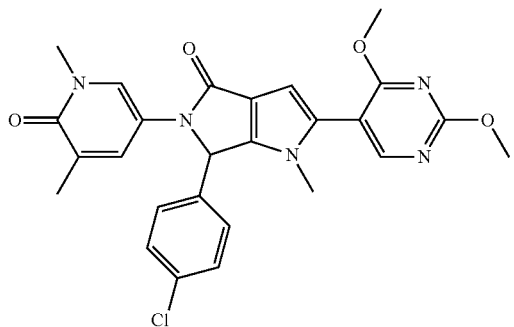 [SMILES: COc1ncc(-c2cc3c(n2C)C(c2ccc(Cl)cc2)N(c2cc(C)c(=O)n(C)c2)C3=O)c(OC)n1]

The title compound was prepared using an analogous procedure to that described in Example 50 using 2,4-dimethoxypyrimidin-5-ylboronic acid (Frontier Scientific, 2.5 eq). Rf=0.31 (5% MeOH/DCM); Rt: 0.94 min (LC-MS 1); MS m/z: 506.3 [M+H]$^+$ (LC-MS 1); $^1$H NMR (400 MHz, DMSO-d6) δ 1.91 (s, 3H) 3.10 (s, 3H) 3.35 (s, 3H) 3.89 (s, 3H) 3.92 (s, 3H) 6.20 (s, 1H) 6.38 (s, 1H) 7.29 (d, J=8.21 Hz, 2H) 7.33 (d, J=1.56 Hz, 1H) 7.41 (d, J=8.60 Hz, 2H) 7.60 (d, J=2.74 Hz, 1H) 8.29 (s, 1H).

Example 54

(R)-6-(4-chlorophenyl)-2-(2,4-dimethoxypyrimidin-5-yl)-5-(1,5-dimethyl-6-oxo-1,6-dihydropyridin-3-yl)-1-methyl-5,6-dihydropyrrolo[3,4-b]pyrrol-4(1H)-one

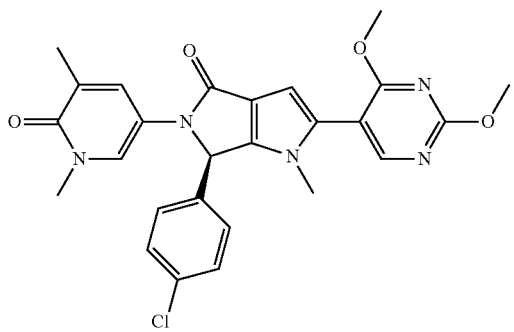 [SMILES: COc1ncc(-c2cc3c(n2C)[C@@H](c2ccc(Cl)cc2)N(c2cc(C)c(=O)n(C)c2)C3=O)c(OC)n1]

The title compound (25 mg, 29.4% yield) was obtained enantiomerically pure (>99% ee) after chiral preparative SFC (system: Gilson Thar SFC 200; column: Chiralpak AD-H, 30×250 mm; mobile phase: scCO$_2$/MeOH 50:50; flow: 100 mL/min; detection UV: 220 nm) of the racemic mixture of 6-(4-chlorophenyl)-2-(2,4-dimethoxypyrimidin-5-yl)-5-(1,5-dimethyl-6-oxo-1,6-dihydropyridin-3-yl)-1-methyl-5,6-dihydropyrrolo[3,4-b]pyrrol-4(1H)-one (Example 53).

(R)-6-(4-chlorophenyl)-2-(2,4-dimethoxypyrimidin-5-yl)-5-(1,5-dimethyl-6-oxo-1,6-dihydropyridin-3-yl)-1-methyl-5,6-dihydropyrrolo[3,4-b]pyrrol-4(1H)-one. Rt: 4.78 min (system: Berger SFC; column: Chiralpak AD-H, 4.6×250 mm; mobile phase: scCO$_2$/MeOH 50:50; flow: 3 mL/min; detection UV: 215 nm).

(S)-6-(4-chlorophenyl)-2-(2,4-dimethoxypyrimidin-5-yl)-5-(1,5-dimethyl-6-oxo-1,6-dihydropyridin-3-yl)-1-methyl-5,6-dihydropyrrolo[3,4-b]pyrrol-4(1H)-one. Rt: 2.35 min (system: Berger SFC; column: Chiralpak AD-H, 4.6×250 mm; mobile phase: scCO$_2$/MeOH 50:50; flow: 3 mL/min; detection UV: 215 nm).

Example 55

6-(4-chlorophenyl)-5-(1,5-dimethyl-6-oxo-1,6-dihydropyridin-3-yl)-2-(2-methoxypyrimidin-5-yl)-1-methyl-5,6-dihydropyrrolo[3,4-b]pyrrol-4(1H)-one

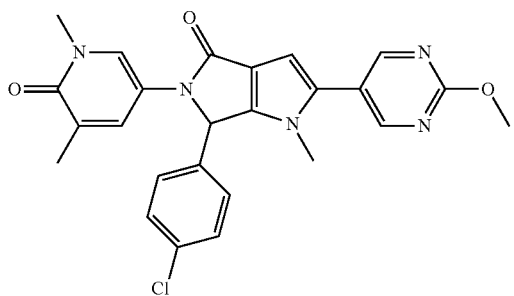 [SMILES: COc1ncc(-c2cc3c(n2C)C(c2ccc(Cl)cc2)N(c2cc(C)c(=O)n(C)c2)C3=O)cn1]

The title compound was prepared using an analogous procedure to that described in Example 50 using (2-methoxypyrimidin-5-yl)boronic acid (Frontier Scientific, 138 mg, 0.895 mmol, 2 eq). The crude product was purified by chromatography (1% MeOH/DCM) followed by trituration of the resulting material in Et₂O to afford the title compound (35 mg) as a colorless solid. Rf=0.25 (1% MeOH/DCM); Rt: 0.86 min (LC-MS 1); MS m/z: 476.2 [M+H]⁺ (LC-MS 1); ¹H NMR (400 MHz, DMSO-d6) δ 1.92 (s, 3H) 3.33 (s, 3H) 3.35 (s, 3H) 3.94 (s, 3H) 6.24 (s, 1H) 6.60 (s, 1H) 7.29-7.45 (m, 5H) 7.62 (d, J=1.96 Hz, 1H) 8.74 (s, 2H).

Example 56

(R)-6-(4-chlorophenyl)-5-(1,5-dimethyl-6-oxo-1,6-dihydropyridin-3-yl)-2-(2-methoxypyrimidin-5-yl)-1-methyl-5,6-dihydropyrrolo[3,4-b]pyrrol-4(1H)-one

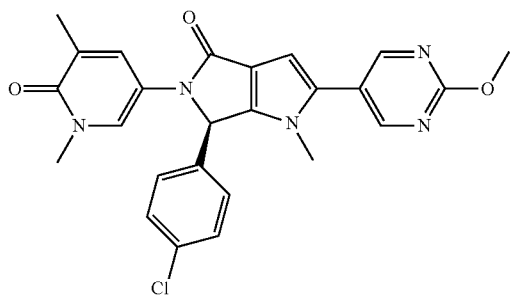 [SMILES: COc1ncc(-c2cc3c(n2C)[C@@H](c2ccc(Cl)cc2)N(c2cc(C)c(=O)n(C)c2)C3=O)cn1]

The title compound (65 mg, 43.3% yield) was obtained enantiomerically pure (>99% ee) after chiral preparative SFC (system: Mg II preparative SFC; column: ChiralPak AS-H, 30×250 mm; mobile phase: scCO₂/IPA 60:40; flow: 40 mL/min; detection UV: 220 nm) of the racemic mixture of 6-(4-chlorophenyl)-5-(1,5-dimethyl-6-oxo-1,6-dihydropyridin-3-yl)-2-(2-methoxypyrimidin-5-yl)-1-methyl-5,6-dihydropyrrolo[3,4-b]pyrrol-4(1H)-one (Example 55).

(R)-6-(4-chlorophenyl)-5-(1,5-dimethyl-6-oxo-1,6-dihydropyridin-3-yl)-2-(2-methoxypyrimidin-5-yl)-1-methyl-5,6-dihydropyrrolo[3,4-b]pyrrol-4(1H)-one. Rt: 9.95 min (system: Thar SFC; column: ChiralPak AS-H, 4.6×250 mm; mobile phase: scCO₂/IPA (0.05% DEA); gradient: 5-40% IPA (0.05% DEA); flow: 2.4 mL/min; detection UV: 220 nm).

(S)-6-(4-chlorophenyl)-5-(1,5-dimethyl-6-oxo-1,6-dihydropyridin-3-yl)-2-(2-methoxypyrimidin-5-yl)-1-methyl-5,6-dihydropyrrolo[3,4-b]pyrrol-4(1H)-one. Rt: 8.92 min (system: Thar SFC; column: ChiralPak AS-H, 4.6×250 mm; mobile phase: scCO₂/IPA (0.05% DEA); gradient: 5-40% IPA (0.05% DEA); flow: 2.4 mL/min; detection UV: 220 nm).

Example 57

6-(4-chlorophenyl)-5-(1,5-dimethyl-6-oxo-1,6-dihydropyridin-3-yl)-2-(2-(dimethylamino)pyrimidin-5-yl)-1-methyl-5,6-dihydropyrrolo[3,4-b]pyrrol-4(1H)-one

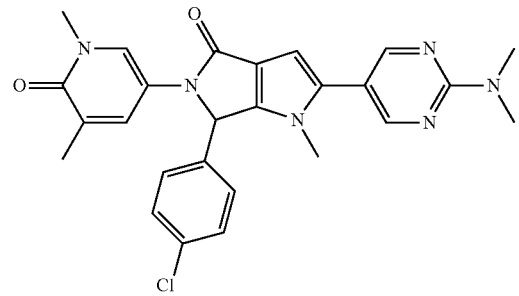 [SMILES: Cc1cc(N2C(=O)c3cc(-c4cnc(N(C)C)nc4)n(C)c3C2c2ccc(Cl)cc2)cn(C)c1=O]

Step 8: 6-(4-chlorophenyl)-5-(1,5-dimethyl-6-oxo-1,6-dihydropyridin-3-yl)-2-(2-(dimethylamino)pyrimidin-5-yl)-1-methyl-5,6-dihydropyrrolo[3,4-b]pyrrol-4(1H)-one The title compound was prepared using an analogous procedure to that described in Example 50 using N,N-dimethyl-5-(4,4,5,5-tetramethyl-1,3,2-dioxaborolan-2-yl)pyrimidin-2-amine (Sigma-Aldrich, 223 mg, 0.895 mmol, 2 eq). The crude product was purified by chromatography (1% MeOH/DCM) followed by trituration of the resulting material in Et₂O to afford the title compound (71 mg) as a colorless solid. Rf=0.27 (1% MeOH/DCM); Rt: 0.97 min (LC-MS 1); MS m/z: 489.3 [M+H]⁺ (LC-MS 1); ¹H NMR (400 MHz, DMSO-d6) δ 1.92 (s, 3H) 3.14 (s, 6H) 3.27 (s, 3H) 3.35 (s, 3H) 6.20 (s, 1H) 6.44 (s, 1H) 7.28-7.37 (m, 3H) 7.38-7.44 (m, 2H) 7.61 (d, J=2.35 Hz, 1H) 8.45 (s, 2H).

Example 58

6-(4-chlorophenyl)-5-(1,5-dimethyl-6-oxo-1,6-dihydropyridin-3-yl)-2-(6-methoxypyridin-3-yl)-1-methyl-5,6-dihydropyrrolo[3,4-b]pyrrol-4(1H)-one

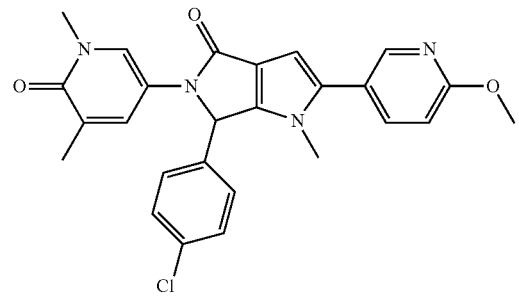 [SMILES: COc1ccc(-c2cc3c(n2C)C(c2ccc(Cl)cc2)N(c2cc(C)c(=O)n(C)c2)C3=O)cn1]

The title compound was prepared using an analogous procedure to that described in Example 50 using (6-methoxypyridin-3-yl)boronic acid (Sigma-Aldrich, 137 mg, 0.895 mmol, 2 eq). The crude product was purified by chromatography (1% MeOH/DCM) followed by trituration of the resulting material in Et₂O to afford the title compound (12 mg) as a colorless solid. Rf=0.28 (1% MeOH/DCM); Rt: 0.98 min (LC-MS 1); MS m/z: 475.2 [M+H]+ (LC-MS 1); 1H NMR (400 MHz, DMSO-d6) δ 1.92 (s, 3H) 3.28 (s, 3H) 3.35 (s, 3H) 3.87 (s, 3H) 6.22 (s, 1H) 6.47 (s, 1H) 6.87 (d, J=8.60 Hz, 1H) 7.28-7.45 (m, 5H) 7.62 (d, J=2.35 Hz, 1H) 7.82 (dd, J=8.60, 2.35 Hz, 1H) 8.27 (d, J=2.35 Hz, 1H).

Example 59

6-(4-chlorophenyl)-5-(1,5-dimethyl-6-oxo-1,6-dihydropyridin-3-yl)-2-(6-methoxypyridin-2-yl)-1-methyl-5,6-dihydropyrrolo[3,4-b]pyrrol-4(1H)-one

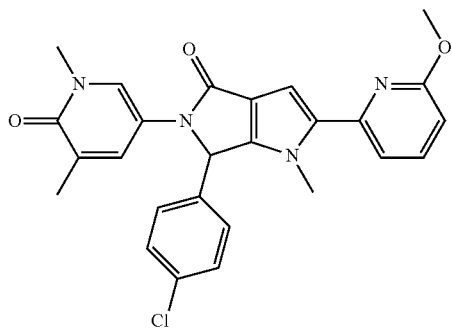 [SMILES: COc1cccc(-c2cc3c(n2C)C(c2ccc(Cl)cc2)N(c2cc(C)c(=O)n(C)c2)C3=O)n1]

The title compound was prepared using an analogous procedure to that described in Example 50 using 2-methoxy-6-(4,4,5,5-tetramethyl-1,3,2-dioxaborolan-2-yl)pyridine (ABCR, 210 mg, 0.895 mmol, 2 eq). The crude product was purified by chromatography (1% MeOH/DCM) followed by trituration of the resulting material in Et2O to afford the title compound (102 mg) as a colorless solid. Rf=0.27 (1% MeOH/DCM); Rt: 1.08 min (LC-MS 1); MS m/z: 475.2 [M+H]+ (LC-MS 1); 1H NMR (400 MHz, DMSO-d6) δ 1.92 (s, 3H) 3.35 (s, 3H) 3.67 (s, 3H) 3.81 (s, 3H) 6.26 (s, 1H) 6.67 (d, J=8.21 Hz, 1H) 6.95 (s, 1H) 7.28-7.45 (m, 6H) 7.62 (d, J=2.74 Hz, 1H) 7.71 (t, J=7.82 Hz, 1H).

Reference Example 60

5-(5-chloro-1-methyl-6-oxo-1,6-dihydropyridin-3-yl)-6-(4-chlorophenyl)-1-cyclopropyl-5,6-dihydropyrrolo[3,4-b]pyrrol-4(1H)-one

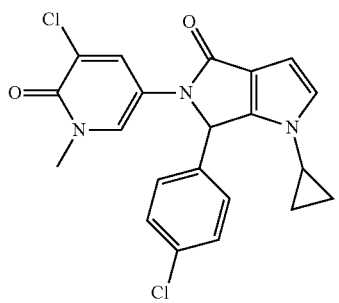 [SMILES: Cn1cc(N2C(=O)c3ccn(C4CC4)c3C2c2ccc(Cl)cc2)cc(Cl)c1=O]

Step 1: Methyl 1-cyclopropyl-1H-pyrrole-3-carboxylate

A mixture of methyl 1H-pyrrole-3-carboxylate (5 g, 40 mmol), cyclopropylboronic acid (6.86 g, 80 mmol), copper (II) acetate (8.71 g, 48 mmol), 2,2'-bipyridyl (6.24 g, 40 mmol), and sodium carbonate (8.47 g, 80 mmol) was stirred for 3 days at 70° C. The reaction mixture was concentrated, diluted in EtOAc/water, and filtered through celite. The filtrate was extracted twice with EtOAc. The combined organic extracts were washed with brine, dried (Na2SO4), filtered and the filtrate was concentrated. The residue was purified by silica gel column chromatography (20% EtOAc/hexane) to afford the title compound (3.26 g) as a yellow oil. Rf=0.26 (20% EtOAc/hexane); Rt: 0.86 min (LC-MS 1); MS m/z: 166.1 [M+H]+ (LC-MS 1).

Step 2: Methyl 2-((4-chlorophenyl)(hydroxy)methyl)-1-cyclopropyl-1H-pyrrole-3-carboxylate LDA (2M in THF/heptane/ethylbenzene, 18.97 mL, 34.2 mmol) was added to a stirred solution of methyl 1-cyclopropyl-1H-pyrrole-3-carboxylate (Step 1 of Example 60, 4.03 g, 24.40 mmol) in THF (80 mL) at −78° C. The reaction mixture was stirred at −78° C. for 30 min. A solution of 4-chlorobenzaldehyde (3.77 g, 26.8 mmol) in THF (20 mL) was added at −78° C. The mixture was allowed to warm to −50° C. over 2 h, quenched with saturated aqueous solution of ammonium chloride, and taken up in EtOAc/saturated ammonium chloride solution. The aqueous layer was extracted twice with EtOAc. The combined organic extracts were washed with brine, dried (Na2SO4), filtered and the filtrate was concentrated. The residue was purified by silica gel column chromatography (20% EtOAc/hexane) to afford the title compound (6.1 g) as a yellow solid. Rf=0.21 (20% EtOAc/hexane); Rt: 1.19 min (LC-MS 1); MS m/z: 288.1 [M-17]+ (LC-MS 1).

Step 3: Methyl 2-(((5-chloro-1-methyl-6-oxo-1,6-dihydropyridin-3-yl)amino)(4-chlorophenyl)methyl)-1-cyclopropyl-1H-pyrrole-3-carboxylate Methanesulfonic anhydride (3.42 g, 19.62 mmol) was added to a stirred solution of methyl 2-((4-chlorophenyl)(hydroxy)methyl)-1-cyclopropyl-1H-pyrrole-3-carboxylate (Step 2 of Example 60, 3 g, 9.81 mmol) and triethylamine (6.84 mL, 49.1 mmol) in DCM (60 mL) at −40° C. The reaction mixture was stirred for 15 min at −40° C. 5-Amino-3-chloro-1-methylpyridin-2(1H)-one (Step 2 of Example 38, 2.02 g, 12.76 mmol) was added. The reaction mixture was allowed to warm from −40° C. to rt over 18 h under stirring, diluted in DCM/water, and extracted twice with DCM. The combined organic extracts were dried (Na2SO4) filtered and the filtrate was concentrated. The residue was purified by silica gel column chromatography (2.5% MeOH/DCM) to afford the title compound (3.04 g) as a green foam. Rf=0.38 (2.5% MeOH/DCM); Rt: 1.16 min (LC-MS 1); MS m/z: 446.1 [M+H]+ (LC-MS 1).

Step 4: 2-(((5-chloro-1-methyl-6-oxo-1,6-dihydropyridin-3-yl)amino)(4-chlorophenyl)methyl)-1-cyclopropyl-1H-pyrrole-3-carboxylic acid A mixture of methyl 2-(((5-chloro-1-methyl-6-oxo-1,6-dihydropyridin-3-yl)amino)(4-chlorophenyl)methyl)-1-cyclopropyl-1H-pyrrole-3-carboxylate (Step 3 of Example 60, 3.04 g, 6.81 mmol) and aqueous NaOH (2N, 25 mL, 50 mmol) in THF (25 mL) and MeOH (25 mL) was stirred for 2 at 70° C. THF and MeOH were evaporated. The resulting aqueous was acidified with 2N HCl to pH 5 and extracted twice with EtOAc. The combined organic extracts were washed with brine, dried (Na2SO4), filtered and the filtrate was concentrated to afford the title compound (3 g, purity 90%) as a purple foam. Rt: 0.98 min (LC-MS 1); MS m/z: 432.1 [M+H]+ (LC-MS 1).

Step 5: 5-(5-chloro-1-methyl-6-oxo-1,6-dihydro-pyridin-3-yl)-6-(4-chlorophenyl)-1-cyclopropyl-5,6-dihydropyrrolo[3,4-b]pyrrol-4(1H)-one 1-Chloro-N,N,2-trimethyl-1-propenyl-amine (1.16 mL, 8.74 mmol) was added to a solution of 2-(((5-chloro-1-methyl-6-oxo-1,6-dihydropyridin-3-yl)amino)(4-chlorophenyl)methyl)-1-cyclopropyl-1H-pyrrole-3-carboxylic acid (Step 4 of Example 60, 3 g, 6.25 mmol) in DCM (40 mL) at 5° C. The reaction mixture was stirred for 2 h at rt, diluted with DCM/saturated aqueous solution of sodium bicarbonate, and extracted twice with DCM. The combined organic extracts were washed with water and brine, dried (Na$_2$SO$_4$), filtered and the filtrate was concentrated. The residue was purified by silica gel column chromatography (5% MeOH/DCM) to afford a red foam. This foam was refluxed in Et$_2$O for 3 h. The resulting precipitate was collected by filtration to provide the title compound (2.12 g) as an off-white solid. Rf=0.32 (5% MeOH/DCM); Rt: 0.99 min (LC-MS 1); MS m/z: 414.1 [M+H]+ (LC-MS 1); $^1$H NMR (400 MHz, DMSO-d6) δ 0.42-0.60 (m, 1H) 0.65-0.75 (m, 2H) 0.89-1.02 (m, 1H) 2.80-2.90 (m, 1H) 3.41 (s, 3H) 6.18-6.34 (m, 2H) 6.91 (d, J=3.13 Hz, 1H) 7.26 (m, J=8.60 Hz, 2H) 7.38 (m, J=8.60 Hz, 2H) 7.87 (d, J=2.74 Hz, 1H) 7.84 (d, J=2.35 Hz, 1H).

Reference Example 61

6-(4-chlorophenyl)-1-cyclopropyl-5-(1,5-dimethyl-6-oxo-1,6-dihydropyridin-3-yl)-5,6-dihydropyrrolo[3,4-b]pyrrol-4(1H)-one

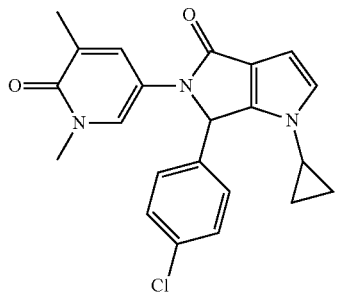 [SMILES: Cc1cc(N2C(=O)c3ccn(C4CC4)c3C2c2ccc(Cl)cc2)cn(C)c1=O]

Step 1: Methyl 2-((4-chlorophenyl)((1,5-dimethyl-6-oxo-1,6-dihydropyridin-3-yl)amino)methyl)-1-cyclopropyl-1H-pyrrole-3-carboxylate The title compound was prepared using an analogous procedure to that described in Step 3 of Example 60 using 5-amino-1,3-dimethylpyridin-2(1H)-one (Step 2 of Example 34, 1.76 g, 12.76 mmol, 1.3 eq). The title compound (2.2 g) was obtained as a brown foam. Rf=0.29 (2.5% MeOH/DCM); Rt: 1.13 min (LC-MS 1); MS m/z: 426.2 [M+H]+ (LC-MS 1).

Step 2: 2-((4-chlorophenyl)((1,5-dimethyl-6-oxo-1,6-dihydropyridin-3-yl)amino)methyl)-1-cyclopropyl-1H-pyrrole-3-carboxylic acid The title compound was prepared using an analogous procedure to that described in Step 4 of Example 60 using methyl 2-((4-chlorophenyl)((1,5-dimethyl-6-oxo-1,6-dihydropyridin-3-yl)amino)methyl)-1-cyclopropyl-1H-pyrrole-3-carboxylate (Step 1 of Example 61, 2.2 g, 5.17 mmol). The title compound (2 g) was obtained as a red foam. Rt: 0.94 min (LC-MS 1); MS m/z: 412.2 [M+H]+ (LC-MS 1).

Step 3: 6-(4-chlorophenyl)-1-cyclopropyl-5-(1,5-dimethyl-6-oxo-1,6-dihydropyridin-3-yl)-5,6-dihydropyrrolo[3,4-b]pyrrol-4(1H)-one The title compound was prepared using an analogous procedure to that described in Step 5 of Example 60 using 2-((4-chlorophenyl)((1,5-dimethyl-6-oxo-1,6-dihydropyridin-3-yl)amino)methyl)-1-cyclopropyl-1H-pyrrole-3-carboxylic acid (Step 2 of Example 61, 2 g, 4.86 mmol) and stirring the reaction mixture for 30 min at rt. The title compound (1.35 g) was obtained as an off-white solid. Rf=0.30 (5% MeOH/DCM); Rt: 0.95 min (LC-MS 1); MS m/z: 394.2 [M+H]+ (LC-MS 1); $^1$H NMR (400 MHz, DMSO-d6) δ 0.42-0.58 (m, 1H) 0.58-0.80 (m, 2H) 0.95-1.04 (m, 1H) 1.90 (s, 3H) 2.77-2.93 (m, 1H) 3.33 (s, 3H) 6.18 (s, 1H) 6.24 (d, J=2.74 Hz, 1H) 6.90 (d, J=2.74 Hz, 1H) 7.24 (d, J=8.60 Hz, 2H) 7.30-7.44 (m, 3H) 7.61 (d, J=2.74 Hz, 1H).

Example 62

5-(5-chloro-1-methyl-6-oxo-1,6-dihydropyridin-3-yl)-6-(4-chlorophenyl)-1-cyclopropyl-2-(1-methyl-6-oxo-1,6-dihydropyridin-2-yl)-5,6-dihydropyrrolo[3,4-b]pyrrol-4(1H)-one

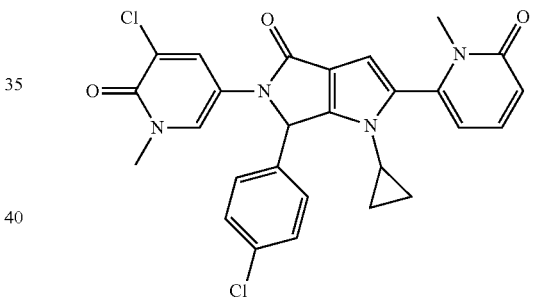

Step 1: 2-bromo-5-(5-chloro-1-methyl-6-oxo-1,6-dihydropyridin-3-yl)-6-(4-chlorophenyl)-1-cyclopropyl-5,6-dihydropyrrolo[3,4-b]pyrrol-4(1H)-one NBS (0.767 g, 4.31 mmol) was added to stirred suspension of 5-(5-chloro-1-methyl-6-oxo-1,6-dihydropyridin-3-yl)-6-(4-chlorophenyl)-1-cyclopropyl-5,6-dihydropyrrolo[3,4-b]pyrrol-4(1H)-one (Step 5 of Example 60, 1.7 g, 4.10 mmol) in carbon tetrachloride (70 mL) at 0° C. The reaction mixture was stirred for 40 h at rt, concentrated, and diluted with EtOAc/water. The resulting precipitate was collected by filtration to provide the title compound (1.58 g) as a colorless solid. Rt: 1.11 min (LC-MS 1); MS m/z: 492/494 [M+H]+ (LC-MS 1).

Step 2: 5-(5-chloro-1-methyl-6-oxo-1,6-dihydropyridin-3-yl)-6-(4-chlorophenyl)-1-cyclopropyl-2-(1-methyl-6-oxo-1,6-dihydropyridin-2-yl)-5,6-dihydropyrrolo[3,4-b]pyrrol-4(1H)-one The title compound was prepared using an analogous procedure to that described in Step 4 of Example 25 using 2-bromo-5-(5-chloro-1-methyl-6-oxo-1,6-dihydropyridin-3-yl)-6-(4-chlorophenyl)-1-cyclopropyl-5,6-dihydropyrrolo[3,4-b]pyrrol-4(1H)-one (Step 1 of Example 62, 150 mg, 0.304 mmol) and 1-methyl-6-(4,4,5,5-tetramethyl-1,3,2-dioxaborolan-2-yl)pyridin-2(1H)-one, 1-methyl-6-(4,4,5,5-tetramethyl-1,3,2-dioxaborolan-2-yl)pyridin-2(1H)-one (Step 2 of Example 44, 358 mg, 0.608 mmol). The reaction mixture was stirred for 5 min at 110° C. DCM was used instead of EtOAc in the workup. The crude was loaded onto a Varian PL-Thiol MP SPE cartridge (to remove metals traces) and eluted with MeOH. After concentration, the residue was purified by silica gel column chromatography (1% ammonia/5% MeOH/DCM) to afford a beige foam. This foam was purified by preparative achiral SFC (column: 4-EP, 250×30 mm, 6 μm, 60 A, Princeton; eluent: MeOH/scCO$_2$; gradient: 1 min 19% MeOH, 19% to 24% MeOH in 6 min, 24% to 50% MeOH in 1 min, 1.5 min 50% MeOH; flow: 100 mL/min). Trituration of the resulting material in Et$_2$O afforded the title compound (32 mg) as a colorless solid. Rf=0.29 (1% ammonia/5% MeOH/DCM); Rt: 0.90 min (LC-MS 1); MS m/z: 521.1 [M+H]$^+$ (LC-MS 1); $^1$H NMR (400 MHz, DMSO-d6) δ 0.28-0.42 (m, 1H) 0.45-0.70 (m, 2H) 0.98-1.05 (m, 1H) 2.76-2.88 (m, 1H) 3.19 (s, 3H) 3.43 (s, 3H) 6.26-6.39 (m, 2H) 6.46 (dd, J=9.38, 1.17 Hz, 1H) 6.58 (s, 1H) 7.32 (d, J=8.60 Hz, 2H) 7.36-7.47 (m, 3H) 7.88 (d, J=2.74 Hz, 1H) 7.84 (d, J=2.74 Hz, 1H).

Example 63

6-(4-chlorophenyl)-1-cyclopropyl-5-(1,5-dimethyl-6-oxo-1,6-dihydropyridin-3-yl)-2-(1-methyl-6-oxo-1,6-dihydropyridin-2-yl)-5,6-dihydropyrrolo[3,4-b]pyrrol-4(1H)-one

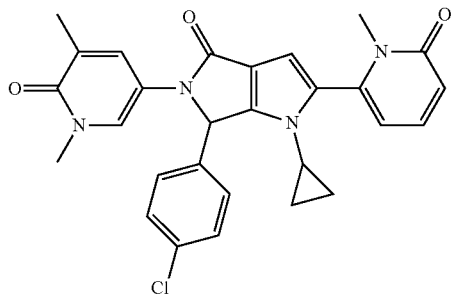 [SMILES: Cc1cc(N2C(=O)c3cc(-c4cccc(=O)n4C)n(C4CC4)c3C2c2ccc(Cl)cc2)cn(C)c1=O]

Step 1: 2-bromo-6-(4-chlorophenyl)-1-cyclopropyl-5-(1,5-dimethyl-6-oxo-1,6-dihydropyridin-3-yl)-5,6-dihydropyrrolo[3,4-b]pyrrol-4(1H)-one The title compound was prepared using an analogous procedure to that described in Step 1 of Example 62 using 6-(4-chlorophenyl)-1-cyclopropyl-5-(1,5-dimethyl-6-oxo-1,6-dihydropyridin-3-yl)-5,6-dihydropyrrolo[3,4-b]pyrrol-4(1H)-one (Step 1 of Example 61, 1.1 g, 2.79 mmol). The reaction mixture was concentrated, diluted in EtOAc/water, and extracted twice with EtOAc. The combined organic extracts were washed with brine, dried (Na$_2$SO$_4$), filtered and the filtrate was concentrated. The residue was purified by silica gel column chromatography (5% MeOH/DCM) to provide a pure batch (batch 1) of the title compound and an impure batch. The latter was purified by preparative achiral SFC (column: 4-EP, 250×30 mm, 6 μm, 60 A, Princeton; eluent: MeOH/scCO$_2$; gradient: 25 min 5% MeOH; flow: 100 mL/min) to provide an additional pure batch (batch 2) of the title compound. The two batches (1 and 2) were combined to afford the title compound (935 mg) as a colorless solid. Rf=0.29 (1% ammonia/5% MeOH/DCM); Rt: 1.07 min (LC-MS 1); MS m/z: 472.1/474.1 [M+H]$^+$ (LC-MS 1).

Step 2: 6-(4-chlorophenyl)-1-cyclopropyl-5-(1,5-dimethyl-6-oxo-1,6-dihydropyridin-3-yl)-2-(1-methyl-6-oxo-1,6-dihydropyridin-2-yl)-5,6-dihydropyrrolo[3,4-b]pyrrol-4(1H)-one The title compound was prepared using an analogous procedure to that described in Step 4 of Example 25 using 2-bromo-6-(4-chlorophenyl)-1-cyclopropyl-5-(1,5-dimethyl-6-oxo-1,6-dihydropyridin-3-yl)-5,6-dihydropyrrolo[3,4-b]pyrrol-4(1H)-one (Step 1 of Example 63, 150 mg, 0.317 mmol) and 1-methyl-6-(4,4,5,5-tetramethyl-1,3,2-dioxaborolan-2-yl)pyridin-2(1H)-one, 1-methyl-6-(4,4,5,5-tetramethyl-1,3,2-dioxaborolan-2-yl)pyridin-2(1H)-one (Step 2 of Example 44, 373 mg, 0.635 mmol). The reaction mixture was stirred for 20 min at 110° C. DCM was used instead of EtOAc in the workup. The crude was loaded onto a Varian PL-Thiol MP SPE cartridge (to remove metals traces) and eluted with MeOH. After concentration, the residue was purified by silica gel column chromatography (1% ammonia/5% MeOH/DCM) to afford a beige foam. This foam was purified by preparative achiral SFC (column: 4-EP, 250×30 mm, 6 μm, 60 A, Princeton; eluent: MeOH/scCO$_2$; gradient: 1 min 14% MeOH, 14% to 19% MeOH in 6 min, 19% to 50% MeOH in 1 min, 1.5 min 50% MeOH; flow: 100 mL/min). Trituration of the resulting material in Et$_2$O afforded the title compound (38 mg) as a colorless solid. Rf=0.23 (1% ammonia/5% MeOH/DCM); Rt: 0.82 min (LC-MS 1); MS m/z: 501.2 [M+H]$^+$ (LC-MS 1); $^1$H NMR (400 MHz, DMSO-d6) δ 0.26 0.40 (m, 1H) 0.43-0.68 (m, 2H) 0.97-1.11 (m, 1H) 1.91 (s, 3H) 2.75-2.87 (m, 1H) 3.19 (s, 3H) 3.34 (s, 3H) 6.25 (s, 1H) 6.31 (d, J=6.65 Hz, 1H) 6.46 (d, J=8.99 Hz, 1H) 6.56 (s, 1H) 7.29 (d, J=8.60 Hz, 2H) 7.33-7.47 (m, 4H) 7.61 (d, J=2.74 Hz, 1H).

Example 64

5-(5-chloro-1-methyl-6-oxo-1,6-dihydropyridin-3-yl)-6-(4-chlorophenyl)-1-cyclopropyl-2-(1-methyl-2-oxo-1,2-dihydropyridin-3-yl)-5,6-dihydropyrrolo[3,4-b]pyrrol-4(1H)-one

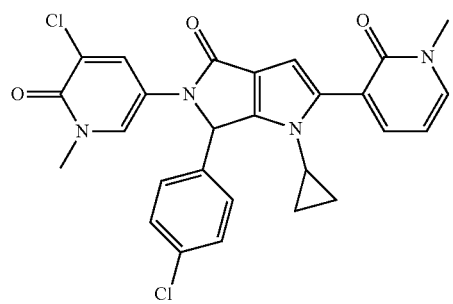 [SMILES: Cn1cc(N2C(=O)c3cc(-c4cccn(C)c4=O)n(C4CC4)c3C2c2ccc(Cl)cc2)cc(Cl)c1=O]

The title compound was prepared using an analogous procedure to that described in Step 4 of Example 25 using 2-bromo-5-(5-chloro-1-methyl-6-oxo-1,6-dihydropyridin-3-yl)-6-(4-chlorophenyl)-1-cyclopropyl-5,6-dihydropyrrolo[3,4-b]pyrrol-4(1H)-one (Step 1 of Example 62, 150 mg, 0.304 mmol) and 1-methyl-3-(4,4,5,5-tetramethyl-1,3,2-dioxaborolan-2-yl)pyridin-2(1H)-one (Step 2 of Example 43, 358 mg, 0.608 mmol). The reaction mixture was stirred for 5 min at 110° C. DCM was used instead of EtOAc in the workup. The crude was loaded onto a Varian PL-Thiol MP SPE cartridge (to remove metals traces) and eluted with MeOH. After concentration, the residue was purified by silica gel column chromatography (1% ammonia/5% MeOH/DCM) to afford a beige foam. This foam was purified by preparative achiral SFC (column: 4-EP, 250×30 mm, 6 μm, 60 A, Princeton; eluent: MeOH/scCO$_2$; gradient: 1 min 19% MeOH, 19% to 24% MeOH in 6 min, 24% to 50% MeOH in 1 min, 1.5 min 50% MeOH; flow: 100 mL/min). Trituration of the resulting material in Et$_2$O afforded the title compound (57 mg) as a colorless solid. Rf=0.28 (1% ammonia/5% MeOH/DCM); Rt: 0.90 min (LC-MS 1); MS m/z: 521.1 [M+H]$^+$ (LC-MS 1); $^1$H NMR (400 MHz, DMSO-d6) δ 0.13-0.32 (m, 1H) 0.42-0.57 (m, 1H) 0.57-0.74 (m, 1H) 0.94-1.07 (m, 1H) 2.86-2.98 (m, 1H) 3.42 (s, 3H) 3.44 (s, 3H) 6.14-6.39 (m, 3H) 7.30 (m, J=8.60 Hz, 2H) 7.40 (m, J=8.21 Hz, 2H) 7.49 (dd, J=6.84, 2.15 Hz, 1H) 7.75 (dd, J=6.84, 1.76 Hz, 1H) 7.86 (d, J=2.74 Hz, 1H) 7.92 (d, J=2.74 Hz, 1H).

Example 65

6-(4-chlorophenyl)-1-cyclopropyl-5-(1,5-dimethyl-6-oxo-1,6-dihydropyridin-3-yl)-2-(1-methyl-2-oxo-1,2-dihydropyridin-3-yl)-5,6-dihydropyrrolo[3,4-b]pyrrol-4(1H)-one

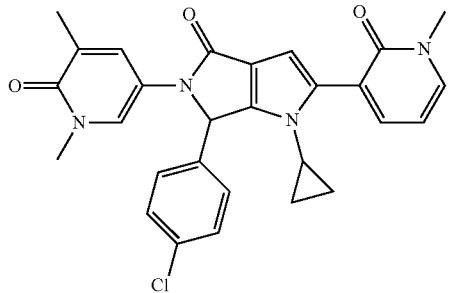 [SMILES: Cc1cc(N2C(=O)c3cc(-c4cccn(C)c4=O)n(C4CC4)c3C2c2ccc(Cl)cc2)cn(C)c1=O]

The title compound was prepared using an analogous procedure to that described in Step 4 of Example 25 using 2-bromo-6-(4-chlorophenyl)-1-cyclopropyl-5-(1,5-dimethyl-6-oxo-1,6-dihydropyridin-3-yl)-5,6-dihydropyrrolo[3,4-b]pyrrol-4(1H)-one (Step 1 of Example 63, 150 mg, 0.317 mmol) and 1-methyl-3-(4,4,5,5-tetramethyl-1,3,2-dioxaborolan-2-yl)pyridin-2(1H)-one (Step 2 of Example 43, 373 mg, 0.635 mmol). The reaction mixture was stirred for 5 min at 110° C. DCM was used instead of EtOAc in the workup. The crude was loaded onto a Varian PL-Thiol MP SPE cartridge (to remove metals traces) and eluted with MeOH. After concentration, the residue was purified by silica gel column chromatography (1% ammonia/5% MeOH/DCM) to afford a beige foam. This foam was purified by preparative achiral SFC (column: PPU, 250×30 mm, 6 μm, 60 A, Princeton; eluent: MeOH/scCO$_2$; gradient: 1 min 16% MeOH, 16% to 21% MeOH in 6 min, 21% to 50% MeOH in 1 min, 1.5 min 50% MeOH; flow: 100 mL/min). Trituration of the resulting material in Et$_2$O afforded the title compound (86 mg) as a colorless solid. Rf=0.23 (1% ammonia/5% MeOH/DCM); Rt: 0.86 min (LC-MS 1); MS m/z: 501.2 [M+H]$^+$ (LC-MS 1); $^1$H NMR (400 MHz, DMSO-d6) δ 0.16-0.27 (m, 1H) 0.41-0.56 (m, 1H) 0.56-0.70 (m, 1H) 0.95-1.10 (m, 1H) 1.91 (s, 3H) 2.83-2.99 (m, 1H) 3.33 (s, 3H) 3.43 (s, 3H) 6.17-6.29 (m, 2H) 6.32 (s, 1H) 7.27 (d, J=8.60 Hz, 2H) 7.33-7.44 (m, 3H) 7.49 (dd, J=7.04, 1.96 Hz, 1H) 7.63 (d, J=2.74 Hz, 1H) 7.74 (dd, J=6.65, 1.96 Hz, 1H).

Example 66

5-(5-chloro-1-methyl-6-oxo-1,6-dihydropyridin-3-yl)-6-(4-chlorophenyl)-1-cyclopropyl-2-(1-methyl-6-oxo-1,6-dihydropyridin-3-yl)-5,6-dihydropyrrolo[3,4-b]pyrrol-4(1H)-one

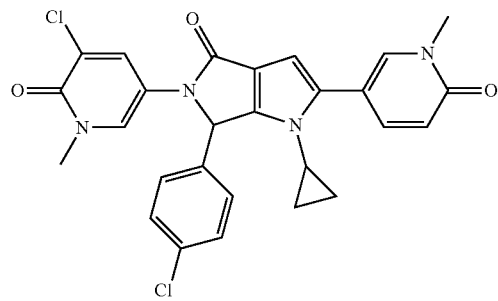 [SMILES: Cn1cc(-c2cc3c(n2C2CC2)C(c2ccc(Cl)cc2)N(c2cc(Cl)c(=O)n(C)c2)C3=O)ccc1=O]

The title compound was prepared using an analogous procedure to that described in Step 4 of Example 25 using 2-bromo-5-(5-chloro-1-methyl-6-oxo-1,6-dihydropyridin-3-yl)-6-(4-chlorophenyl)-1-cyclopropyl-5,6-dihydropyrrolo[3,4-b]pyrrol-4(1H)-one (Step 1 of Example 62, 150 mg, 0.304 mmol) and 1-methyl-5-(4,4,5,5-tetramethyl-1,3,2-dioxaborolan-2-yl)pyridin-2(1H)-one (Step 1 of Example 42, 477 mg, 0.608 mmol). DCM was used instead of EtOAc in the workup. The crude was loaded onto a Varian PL-Thiol MP SPE cartridge (to remove metals traces) and eluted with MeOH. After concentration, the residue was purified by silica gel column chromatography (1% ammonia/5% MeOH/DCM). The resulting material was triturated in Et$_2$O to afford the title compound (59 mg) as a colorless solid. Rf=0.24 (1% ammonia/5% MeOH/DCM); Rt: 0.84 min (LC-MS 1); MS m/z: 521.1 [M+H]$^+$ (LC-MS 1); $^1$H NMR (400 MHz, DMSO-d6) δ 0.24-0.39 (m, 1H) 0.69-0.79 (m, 2H) 1.08-1.19 (m, 1H) 2.95-3.05 (m, 1H) 3.41 (s, 6H) 6.29 (s, 1H) 6.32-6.42 (m, 2H) 7.29 (m, J=8.60 Hz, 2H) 7.39 (m, J=8.60 Hz, 2H) 7.63 (dd, J=9.38, 2.74 Hz, 1H) 7.81-7.95 (m, 3H).

Example 67

6-(4-chlorophenyl)-1-cyclopropyl-5-(1,5-dimethyl-6-oxo-1,6-dihydropyridin-3-yl)-2-(1-methyl-6-oxo-1,6-dihydropyridin-3-yl)-5,6-dihydropyrrolo[3,4-b]pyrrol-4(1H)-one

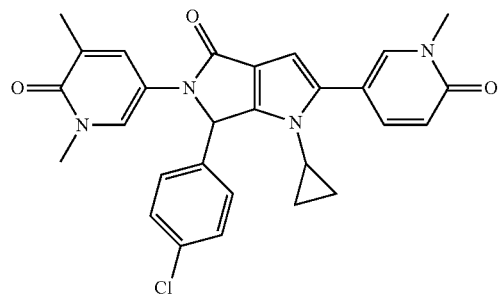 [SMILES: Cc1cc(N2C(=O)c3cc(-c4ccc(=O)n(C)c4)n(C4CC4)c3C2c2ccc(Cl)cc2)cn(C)c1=O]

The title compound was prepared using an analogous procedure to that described in Step 4 of Example 25 using 2-bromo-6-(4-chlorophenyl)-1-cyclopropyl-5-(1,5-dimethyl-6-oxo-1,6-dihydropyridin-3-yl)-5,6-dihydropyrrolo[3,4-b]pyrrol-4(1H)-one (Step 1 of Example 63, 150 mg, 0.317 mmol) and 1-methyl-5-(4,4,5,5-tetramethyl-1,3,2-dioxaborolan-2-yl)pyridin-2(1H)-one (Step 1 of Example 42, 497 mg, 0.635 mmol). The reaction mixture was stirred for 15 min at 110° C. DCM was used instead of EtOAc in the workup. The crude was loaded onto a Varian PL-Thiol MP SPE cartridge (to remove metals traces) and eluted with MeOH. After concentration, the residue was purified by silica gel column chromatography (1% ammonia/5% MeOH/DCM). The resulting material was purified by preparative achiral SFC (column: 4-Ethyl pyridine, 250×30 mm, 5 μm, 60 A, Princeton; eluent: MeOH/scCO$_2$; gradient: 1 min 17% MeOH, 17% to 22% MeOH in 6 min, 22% to 50% MeOH in 1 min, 1.5 min 50% MeOH; flow: 100 mL/min). Trituration of the resulting material in Et$_2$O afforded the title compound (70 mg) as a colorless solid. Rf=0.20 (1% ammonia/5% MeOH/DCM); Rt: 0.81 min (LC-MS 1); MS m/z: 501.2 [M+H]$^+$ (LC-MS 1); $^1$H NMR (400 MHz, DMSO-d6) δ 0.25-0.44 (m, 1H) 0.67-0.85 (m, 2H) 1.11-1.21 (m, 1H) 1.92 (s, 3H) 2.96-3.06 (m, 1H) 3.35 (s, 3H) 3.44 (s, 3H) 6.24 (s, 1H) 6.30-6.44 (m, 2H) 7.23-7.34 (m, 2H) 7.34-7.47 (m, 3H) 7.60-7.73 (m, 2H) 7.91 (d, J=2.73 Hz, 1H).

Example 68

6-(4-chlorophenyl)-2-cyclopropyl-5-(1,5-dimethyl-6-oxo-1,6-dihydropyridin-3-yl)-1-methyl-5,6-dihydropyrrolo[3,4-b]pyrrol-4(1H)-one

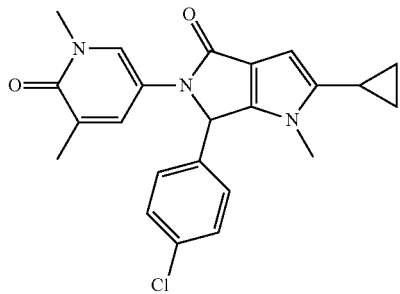 [SMILES: Cc1cc(N2C(=O)c3cc(C4CC4)n(C)c3C2c2ccc(Cl)cc2)cn(C)c1=O]

Palladium (II) acetate (30.2 mg, 0.134 mmol) was added to a stirred solution of 2-bromo-6-(4-chlorophenyl)-5-(1,5-dimethyl-6-oxo-1,6-dihydropyridin-3-yl)-1-methyl-5,6-dihydropyrrolo[3,4-b]pyrrol-4(1H)-one (Step 3 of Example 45, 300 mg, 0.672 mmol), potassium cyclopropyltrifluoroborate (183 mg, 1.679 mmol), cesium carbonate (656 mg, 2.015 mmol) and nBuPAd$_2$ (72.2 mg, 0.201 mmol) in toluene (3 mL) and water (0.3 mL) at 80° C. The reaction mixture was stirred for 6 h at reflux, taken up in DCM/water, and extracted twice with DCM. The combined organic extracts were washed with brine, dried (Na$_2$SO$_4$), filtered and the filtrate was concentrated. The residue was purified by silica gel column chromatography (1% MeOH/DCM) to afford a brown oil. This oil was further purified by preparative HPLC (Gilson gx-281. Column: Sunfire C18, 30×100 mm, 5 mm. Flow: 30 mL/min. Gradient: 20% to 50% B in 30 min; A=0.1% TFA in H$_2$O, B=CH$_3$CN. Detection: UV) to afford the title compound (25 mg). Rf: 0.20 (1% MeOH/DCM); Rt: 1.00 min (LC-MS 1); MS m/z: 408.1 [M+H]$^+$ (LC-MS 1); $^1$H NMR (400 MHz, DMSO-d6) δ 0.46-0.55 (m, 1H) 0.56-0.66 (m, 1H) 0.77-0.90 (m, 2H) 1.68-1.80 (m, 1H) 1.90 (s, 3H) 3.28 (s, 3H) 3.33 (s, 3H) 5.96 (s, 1H) 6.07 (s, 1H) 7.23 (d, J=8.21 Hz, 2H) 7.31 (d, J=3.13 Hz, 1H) 7.38 (d, J=8.21 Hz, 2H) 7.56 (d, J=2.35 Hz, 1H).

Example 69

6-(4-chlorophenyl)-5-(1,5-dimethyl-6-oxo-1,6-dihydropyridin-3-yl)-1,2-dimethyl-5,6-dihydropyrrolo[3,4-b]pyrrol-4(1H)-one

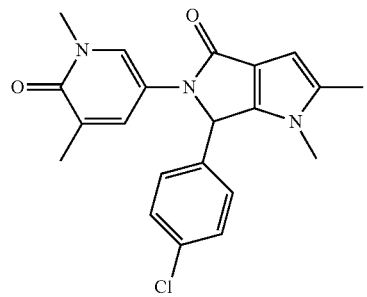 [SMILES: Cc1cc(N2C(=O)c3cc(C)n(C)c3C2c2ccc(Cl)cc2)cn(C)c1=O]

Pd(Ph$_3$)$_4$ (74 mg, 0.064 mmol) was added to a stirred solution of 2-bromo-6-(4-chlorophenyl)-5-(1,5-dimethyl-6-oxo-1,6-dihydropyridin-3-yl)-1-methyl-5,6-dihydropyrrolo[3,4-b]pyrrol-4(1H)-one (Step 3 of Example 45, 286 mg, 0.640 mmol), trimethylboroxine (0.134 mL, 0.960 mmol) and potassium carbonate (133 mg, 0.960 mmol) in dioxane (20 mL). The reaction mixture was heated to 110° C., stirred for 1 h, and concentrated. The residue was diluted in DCM/water, and extracted twice with DCM. The combined organic extracts were washed with brine, dried (Na$_2$SO$_4$), filtered and the filtrate was concentrated. The residue was purified by silica gel column chromatography (1% MeOH/DCM) to afford the title product (147 mg) as a colorless solid. Rf: 0.49 (10% MeOH/DCM); Rt: 0.90 min (LC-MS 1); MS m/z: 382.2 [M+H]$^+$ (LC-MS 1); $^1$H NMR (400 MHz, DMSO-d6) δ 1.90 (s, 3H) 2.17 (s, 3H) 3.16 (s, 3H) 3.33 (s, 3H) 6.03 (d, J=0.78 Hz, 1H) 6.07 (s, 1H) 7.19-7.26 (m, 2H) 7.28-7.34 (m, 1H) 7.34-7.42 (m, 2H) 7.57 (d, J=2.74 Hz, 1H).

Example 70

Blank

Example 71

Blank

Example 72

6-(4-chlorophenyl)-5-(1,5-dimethyl-6-oxo-1,6-dihydropyridin-3-yl)-1-methyl-5,6-dihydropyrrolo[3,4-b]pyrrol-4(1H)-one

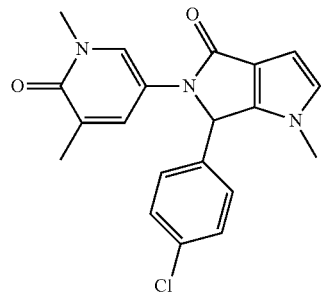 [SMILES: Cc1cc(N2C(=O)c3ccn(C)c3C2c2ccc(Cl)cc2)cn(C)c1=O]

Step 1: Methyl 2-((4-chlorophenyl)(1,5-dimethyl-6-oxo-1,6-dihydropyridin-3-ylamino)methyl)-1-methyl-1H-pyrrole-3-carboxylate The title compound was prepared in a similar manner as described in Step 2 of Example 60 and in Step 1 of Example 61 using methyl 1-methyl-1H-pyrrole-3-carboxylate (Step 1 of Example 29) in Step 2 of Example 60. Rt: 1.04 min (LC-MS 1); MS m/z: 400.2 [M+H]+ (LC-MS 1).

Step 2: 6-(4-chlorophenyl)-5-(1,5-dimethyl-6-oxo-1,6-dihydropyridin-3-yl)-1-methyl-5,6-dihydropyrrolo[3,4-b]pyrrol-4(1H)-one The title compound was prepared in a similar manner as described in Step 10 of Example 1 using methyl 2-((4-chlorophenyl)(1,5-dimethyl-6-oxo-1,6-dihydropyridin-3-ylamino)methyl)-1-methyl-1H-pyrrole-3-carboxylate (Step 1 of Example 72). The reaction mixture was stirred for 2 h at 85° C. Rt: 0.83 min (LC-MS 1); MS m/z: 368.2 [M+H]+ (LC-MS 1); $^1$H NMR (400 MHz, DMSO-d6) δ 1.90 (s, 3H) 3.29 (s, 3H) 3.33 (s, 3H) 6.11 (s, 1H) 6.25 (d, J=2.74 Hz, 1H) 6.88 (d, J=2.74 Hz, 1H) 7.23 (d, J=8.21 Hz, 2H) 7.32 (br. s, 1H) 7.38 (d, J=8.21 Hz, 2H) 7.59 (d, J=2.35 Hz, 1H).

Example 73

Blank

Example 74

5-(5-chloro-1-methyl-6-oxo-1,6-dihydropyridin-3-yl)-6-(4-chlorophenyl)-1,2-dimethyl-5,6-dihydropyrrolo[3,4-b]pyrrol-4(1H)-one

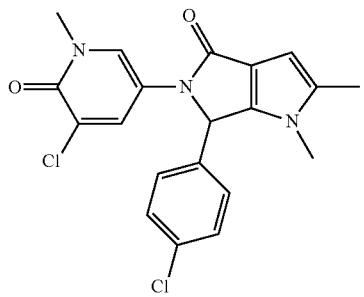 [SMILES: Cc1cc2c(n1C)C(c1ccc(Cl)cc1)N(c1cc(Cl)c(=O)n(C)c1)C2=O]

Step 1: Methyl 1,5-dimethyl-1H-pyrrole-3-carboxylate

The title compound was prepared using an analogous procedure to that described in Example 69 using methyl 5-bromo-1-methyl-1H-pyrrole-3-carboxylate (Step 2 of Example 31, 3 g, 13.76 mmol). Rt: 0.77 min (LC-MS 1); MS m/z: 154.1 [M+H]+ (LC-MS 1).

Step 2: Methyl 2-((4-chlorophenyl)(hydroxy)methyl)-1,5-dimethyl-1H-pyrrole-3-carboxylate The title compound was prepared using an analogous procedure to that described in Step 8 of Example 1 using methyl 1,5-dimethyl-1H-pyrrole-3-carboxylate (Step 1 of Example 74). Rt: 1.10 min (LC-MS 1); MS m/z: 276.1 [M-17]+ (LC-MS 1).

Step 3: Methyl 2-((5-chloro-1-methyl-6-oxo-1,6-dihydropyridin-3-ylamino)(4-chlorophenyl)methyl)-1,5-dimethyl-1H-pyrrole-3-carboxylate The title compound was prepared using an analogous procedure to that described in Step 9 of Example 1 using methyl 2-((4-chlorophenyl)(hydroxy)methyl)-1,5-dimethyl-1H-pyrrole-3-carboxylate (Step 2 of Example 74) and 5-amino-3-chloro-1-methylpyridin-2(1H)-one (Step 2 of Example 38). Rt: 1.11 min (LC-MS 1); MS m/z: 434.1 [M+H]+ (LC-MS 1).

Step 4: 5-(5-chloro-1-methyl-6-oxo-1,6-dihydropyridin-3-yl)-6-(4-chlorophenyl)-1,2-dimethyl-5,6-dihydropyrrolo[3,4-b]pyrrol-4(1H)-one The title compound was prepared using an analogous procedure to that described in Step 10 of Example 1 using methyl 2-((5-chloro-1-methyl-6-oxo-1,6-dihydropyridin-3-ylamino)(4-chlorophenyl)methyl)-1,5-dimethyl-1H-pyrrole-3-carboxylate (Step 3 of Example 74). The reaction mixture was stirred for 2 h at 100° C. Rt: 0.92 min (LC-MS 1); MS m/z: 402.1 [M+H]+ (LC-MS 1); $^1$H NMR (400 MHz, DMSO-d6) δ 2.17 (br. s, 3H) 3.17 (br. s, 3H) 3.42 (br. s, 3H) 5.99-6.20 (m, 2H) 7.19-7.48 (m, 4H) 7.81 (br. s, 2H).

Example 75

(R)-5-(5-chloro-1-methyl-6-oxo-1,6-dihydropyridin-3-yl)-6-(4-chlorophenyl)-1,2-dimethyl-5,6-dihydropyrrolo[3,4-b]pyrrol-4(1H)-one

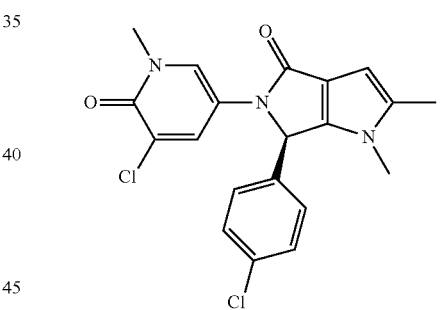

The title compound (18 mg, 34% yield) was obtained enantiomerically pure (>99% ee) after chiral preparative chromatography (system: Gilson 215; column: ChiralPak AD-H, 20×250 mm, 5 μm; mobile phase: EtOH/MeOH 50:50; flow: 12 mL/min; detection UV: 215 nm) of the racemic mixture of 5-(5-chloro-1-methyl-6-oxo-1,6-dihydropyridin-3-yl)-6-(4-chlorophenyl)-1,2-dimethyl-5,6-dihydropyrrolo[3,4-b]pyrrol-4(1H)-one (Step 4 of Example 74).

(R)-5-(5-chloro-1-methyl-6-oxo-1,6-dihydropyridin-3-yl)-6-(4-chlorophenyl)-1,2-dimethyl-5,6-dihydropyrrolo[3,4-b]pyrrol-4(1H)-one. Rt: 11.78 min (system: Gilson 215; column: ChiralPak AD-H, 4.6×250 mm; mobile phase: EtOH/MeOH 40:60; flow: 0.8 mL/min; detection UV: 215 nm).

(S)-5-(5-chloro-1-methyl-6-oxo-1,6-dihydropyridin-3-yl)-6-(4-chlorophenyl)-1,2-dimethyl-5,6-dihydropyrrolo[3,4-b]pyrrol-4(1H)-one. Rt: 7.18 min (system: Gilson 215; column: ChiralPak AD-H, 4.6×250 mm; mobile phase: EtOH/MeOH 40:60; flow: 0.8 mL/min; detection UV: 215 nm).

Example 76

5-(5-chloro-1-methyl-6-oxo-1,6-dihydropyridin-3-yl)-6-(4-chlorophenyl)-1-methyl-5,6-dihydropyrrolo[3,4-b]pyrrol-4(1H)-one

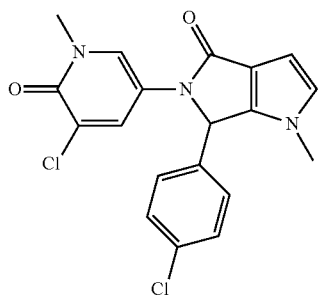 [SMILES: Cn1ccc2c1C(c1ccc(Cl)cc1)N(c1cc(Cl)c(=O)n(C)c1)C2=O]

Step 1: Methyl 2-((5-chloro-1-methyl-6-oxo-1,6-dihydropyridin-3-ylamino)(4-chlorophenyl)methyl)-1-methyl-1H-pyrrole-3-carboxylate The title compound was prepared using an analogous procedure to that described in Step 2 of Example 60 and Step 9 of Example 1 using methyl 1-methyl-1H-pyrrole-3-carboxylate (Step 1 of Example 29) in Step 2 of Example 60 and the resulting product and 5-amino-3-chloro-1-methylpyridin-2(1H)-one (Step 2 of Example 38) in Step 9 of Example 1. Rt: 1.04 min (LC-MS 1); MS m/z: 420.1 [M+H]$^+$ (LC-MS 1).

Step 2: 5-(5-chloro-1-methyl-6-oxo-1,6-dihydropyridin-3-yl)-6-(4-chlorophenyl)-1-methyl-5,6-dihydropyrrolo[3,4-b]pyrrol-4(1H)-one The title compound was prepared using an analogous procedure to that described in Step 10 of Example 1 using methyl 2-((5-chloro-1-methyl-6-oxo-1,6-dihydropyridin-3-ylamino)(4-chlorophenyl)methyl)-1-methyl-1H-pyrrole-3-carboxylate (Step 1 of Example 76). The reaction mixture was stirred for 1 h at 80° C. Rt: 0.86 min (LC-MS 1); MS m/z: 388.1 [M+H]$^+$ (LC-MS 1); $^1$H NMR (400 MHz, DMSO-d6) δ 3.29 (s, 3H) 3.42 (s, 3H) 6.17 (s, 1H) 6.28 (d, J=2.74 Hz, 1H) 6.90 (d, J=2.74 Hz, 1H) 7.26 (d, J=8.60 Hz, 2H) 7.40 (d, J=8.21 Hz, 2H) 7.83 (s, 2H).

Example 77

(R)-5-(5-chloro-1-methyl-6-oxo-1,6-dihydropyridin-3-yl)-6-(4-chlorophenyl)-1-methyl-5,6-dihydropyrrolo[3,4-b]pyrrol-4(1H)-one

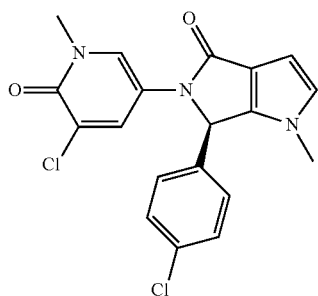 [SMILES: Cn1ccc2c1[C@@H](c1ccc(Cl)cc1)N(c1cc(Cl)c(=O)n(C)c1)C2=O]

The title compound (49 mg, 44.4% yield) was obtained enantiomerically pure (>98% ee) after chiral preparative chromatography (column: ChiralPak AD-H, 50×500 mm, 5 μm; mobile phase: heptane/EtOH 70:30; flow: 70 mL/min; detection UV: 240 nm) of the racemic mixture of 5-(5-chloro-1-methyl-6-oxo-1,6-dihydropyridin-3-yl)-6-(4-chlorophenyl)-1-methyl-5,6-dihydropyrrolo[3,4-b]pyrrol-4(1H)-one (Example 76).

(R)-5-(5-chloro-1-methyl-6-oxo-1,6-dihydropyridin-3-yl)-6-(4-chlorophenyl)-1-methyl-5,6-dihydropyrrolo[3,4-b]pyrrol-4(1H)-one. Rt: 16.56 min (system: Agilent 1200; column: ChiralPak AD-H, 4.6×250 mm; mobile phase: heptane/EtOH 70:30; flow: 1 mL/min; detection UV: 240 nm).

(S)-5-(5-chloro-1-methyl-6-oxo-1,6-dihydropyridin-3-yl)-6-(4-chlorophenyl)-1-methyl-5,6-dihydropyrrolo[3,4-b]pyrrol-4(1H)-one. Rt: 11.38 min (system: Agilent 1200; column: ChiralPak AD-H, 4.6×250 mm; mobile phase: heptane/EtOH 70:30; flow: 1 mL/min; detection UV: 240 nm).

Example 78

6-(4-chlorophenyl)-1-methyl-5-(1-methyl-6-oxo-1,6-dihydropyridin-3-yl)-5,6-dihydropyrrolo[3,4-b]pyrrol-4(1H)-one

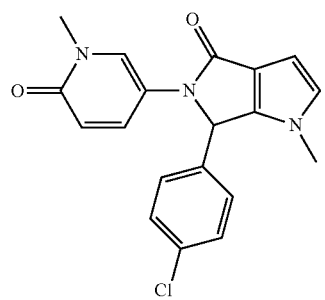 [SMILES: Cn1ccc2c1C(c1ccc(Cl)cc1)N(c1ccc(=O)n(C)c1)C2=O]

Step 1: Methyl 2-((4-chlorophenyl)(1-methyl-6-oxo-1,6-dihydropyridin-3-ylamino)methyl)-1-methyl-1H-pyrrole-3-carboxylate The title compound was prepared using an analogous procedure to that described in Step 2 of Example 60 and Step 9 of Example 1 using methyl 1-methyl-1H-pyrrole-3-carboxylate (Step 1 of Example 29) in Step 2 of Example 60 and the resulting product and 5-amino-1-methylpyridin-2(1H)-one in Step 9 of Example 1. Rt: 0.98 min (LC-MS 2); MS m/z: 386.3 [M+H]$^+$ (LC-MS 2).

Step 2: 6-(4-chlorophenyl)-1-methyl-5-(1-methyl-6-oxo-1,6-dihydropyridin-3-yl)-5,6-dihydropyrrolo[3,4-b]pyrrol-4(1H)-one The title compound was prepared using an analogous procedure to that described in Step 10 of Example 1 using methyl 2-((4-chlorophenyl)(1-methyl-6-oxo-1,6-dihydropyridin-3-ylamino)methyl)-1-methyl-1H-pyrrole-3-carboxylate (Step 1 of Example 78). The reaction mixture was stirred for 1 h at 80° C. Rt: 0.76 min (LC-MS 1); MS m/z: 354.1 [M+H]$^+$ (LC-MS 1); $^1$H NMR (400 MHz, DMSO-d6) δ 3.29 (s, 3H) 3.33 (s, 3H) 6.12 (s, 1H) 6.25-6.30 (m, 2H)

6.89 (d, J=2.74 Hz, 1H) 7.23 (d, J=8.60 Hz, 2H) 7.35-7.41 (m, 3H) 7.76 (d, J=2.74 Hz, 1H).

Example 79

5-(1,5-dimethyl-6-oxo-1,6-dihydropyridin-3-yl)-1-methyl-6-phenyl-5,6-dihydropyrrolo[3,4-b]pyrrol-4(1H)-one

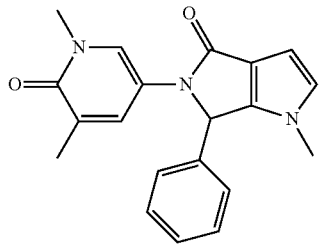 [SMILES: Cc1cc(N2C(=O)c3ccn(C)c3C2c2ccccc2)cn(C)c1=O]

Step 1: Methyl 2-(((1,5-dimethyl-6-oxo-1,6-dihydropyridin-3-yl)amino)(phenyl)methyl)-1-methyl-1H-pyrrole-3-carboxylate The title compound was prepared using an analogous procedure to that described in Step 2 of Example 60 and in Step 1 of Example 61 using methyl 1-methyl-1H-pyrrole-3-carboxylate (Step 1 of Example 29) and benzaldehyde in Step 2 of Example 60. Rf: 0.58 (10% MeOH/DCM); Rt: 0.94 min (LC-MS 1); MS m/z: 366.3 [M+H]$^+$ (LC-MS 1).

Step 2: 5-(1,5-dimethyl-6-oxo-1,6-dihydropyridin-3-yl)-1-methyl-6-phenyl-5,6-dihydropyrrolo[3,4-b]pyrrol-4(1H)-one The title compound was prepared using an analogous procedure to that described in Step 10 of Example 1 using methyl 2-(((1,5-dimethyl-6-oxo-1,6-dihydropyridin-3-yl)amino)(phenyl)methyl)-1-methyl-1H-pyrrole-3-carboxylate (Step 1 of Example 79). The reaction mixture was stirred for 2 h at 85° C. Rt: 0.75 min (LC-MS 1); MS m/z: 334.2 [M+H]$^+$ (LC-MS 1); $^1$H NMR (400 MHz, DMSO-d6) δ 1.92 (s, 3H) 3.29 (s, 3H) 3.35 (s, 3H) 6.10 (s, 1H) 6.27 (d, J=2.74 Hz, 1H) 6.89 (d, J=2.74 Hz, 1H) 7.20-7.25 (m, 2H) 7.27-7.38 (m, 4H) 7.61 (d, J=2.74 Hz, 1H).

Example 80

6-(4-chloro-3-fluorophenyl)-5-(1,5-dimethyl-6-oxo-1,6-dihydropyridin-3-yl)-1-methyl-5,6-dihydropyrrolo[3,4-b]pyrrol-4(1H)-one

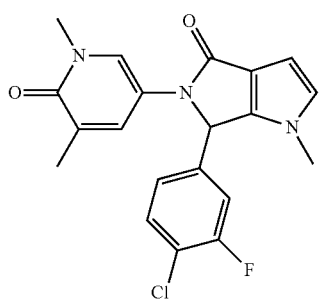 [SMILES: Cc1cc(N2C(=O)c3ccn(C)c3C2c2ccc(Cl)c(F)c2)cn(C)c1=O]

Step 1: methyl 2-((4-chloro-3-fluorophenyl)((1,5-dimethyl-6-oxo-1,6-dihydropyridin-3-yl)amino)methyl)-1-methyl-1H-pyrrole-3-carboxylate The title compound was prepared using an analogous procedure to that described in Step 2 of Example 60 and in Step 1 of Example 61 using methyl 1-methyl-1H-pyrrole-3-carboxylate (Step 1 of Example 29) and 4-chloro-3-fluorobenzaldehyde in Step 2 of Example 60. Rf: 0.61 (10% MeOH/DCM); Rt: 1.06 min (LC-MS 1); MS m/z: 418.2 [M+H]$^+$ (LC-MS 1).

Step 2: 6-(4-chloro-3-fluorophenyl)-5-(1,5-dimethyl-6-oxo-1,6-dihydropyridin-3-yl)-1-methyl-5,6-dihydropyrrolo[3,4-b]pyrrol-4(1H)-one The title compound was prepared using an analogous procedure to that described in Step 10 of Example 1 using methyl 2-((4-chloro-3-fluorophenyl)((1,5-dimethyl-6-oxo-1,6-dihydropyridin-3-yl)amino)methyl)-1-methyl-1H-pyrrole-3-carboxylate (Step 1 of Example 80). The reaction mixture was stirred for 2 h at 85° C. Rf: 0.51 (10% MeOH/DCM); Rt: 0.86 min (LC-MS 1); MS m/z: 386.2 [M+H]$^+$ (LC-MS 1); $^1$H NMR (400 MHz, DMSO-d6) δ 1.94 (s, 3H) 3.36 (d, J=9.77 Hz, 6H) 6.16 (s, 1H) 6.29 (d, J=2.35 Hz, 1H) 6.92 (d, J=2.74 Hz, 1H) 7.12 (d, J=7.43 Hz, 1H) 7.31 (d, J=10.17 Hz, 1H) 7.37 (br. s, 1H) 7.57 (t, J=8.02 Hz, 1H) 7.64 (d, J=2.35 Hz, 1H).

Example 81

5-(1,5-dimethyl-6-oxo-1,6-dihydropyridin-3-yl)-1-methyl-6-(p-tolyl)-5,6-dihydropyrrolo[3,4-b]pyrrol-4(1H)-one

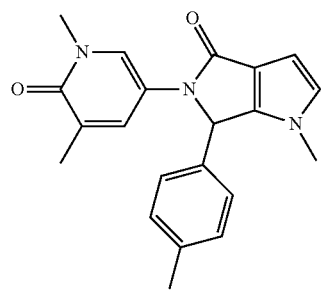 [SMILES: Cc1ccc(C2c3c(ccn3C)C(=O)N2c2cc(C)c(=O)n(C)c2)cc1]

Step 1: Methyl 2-(((1,5-dimethyl-6-oxo-1,6-dihydropyridin-3-yl)amino)(p-tolyl)methyl)-1-methyl-1H-pyrrole-3-carboxylate The title compound was prepared using an analogous procedure to that described in Step 2 of Example 60 and in Step 1 of Example 61 using methyl 1-methyl-1H-pyrrole-3-carboxylate (Step 1 of Example 29) and 4-methylbenzaldehyde in Step 2 of Example 60. Rf: 0.61 (10% MeOH/DCM); Rt: 1.01 min (LC-MS 1); MS m/z: 380.3 [M+H]$^+$ (LC-MS 1).

Step 2: 5-(1,5-dimethyl-6-oxo-1,6-dihydropyridin-3-yl)-1-methyl-6-(p-tolyl)-5,6-dihydropyrrolo[3,4-b]pyrrol-4(1H)-one The title compound was prepared using an analogous procedure to that described in Step 10 of Example 1 using methyl 2-(((1,5-dimethyl-6-oxo-1,6-dihydropyridin-3-yl) amino)(p-tolyl)methyl)-1-methyl-1H-pyrrole-3-carboxylate (Step 1 of Example 81). The reaction mixture was stirred for 2 h at 85° C. Rt: 0.82 min (LC-MS 1); MS m/z: 348.3 [M+H]+ (LC-MS 1); $^1$H NMR (400 MHz, DMSO-d6) δ 1.92 (s, 3H) 2.25 (s, 3H) 3.29 (s, 3H) 3.33-3.37 (m, 3H) 6.06 (s, 1H) 6.26 (d, J=2.74 Hz, 1H) 6.88 (d, J=2.74 Hz, 1H) 7.07-7.17 (m, 4H) 7.35 (d, J=1.56 Hz, 1H) 7.60 (d, J=2.74 Hz, 1H).

Example 82

5-(1,5-dimethyl-6-oxo-1,6-dihydropyridin-3-yl)-6-(4-fluorophenyl)-1-methyl-5,6-dihydropyrrolo[3,4-b]pyrrol-4(1H)-one

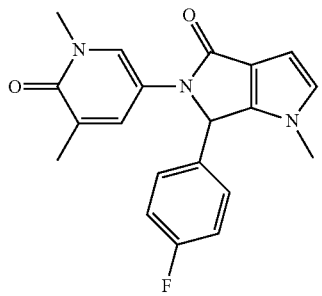 [SMILES: Cc1cc(N2C(=O)c3ccn(C)c3C2c2ccc(F)cc2)cn(C)c1=O]

Step 1: Methyl 2-(((1,5-dimethyl-6-oxo-1,6-dihydropyridin-3-yl)amino)(4-fluorophenyl)methyl)-1-methyl-1H-pyrrole-3-carboxylate The title compound was prepared using an analogous procedure to that described in Step 2 of Example 60 and in Step 1 of Example 61 using methyl 1-methyl-1H-pyrrole-3-carboxylate (Step 1 of Example 29) and 4-fluorobenzaldehyde in Step 2 of Example 60. Rf: 0.55 (10% MeOH/DCM); Rt: 0.96 min (LC-MS 1); MS m/z: 384.3 [M+H]+ (LC-MS 1).

Step 2: 5-(1,5-dimethyl-6-oxo-1,6-dihydropyridin-3-yl)-6-(4-fluorophenyl)-1-methyl-5,6-dihydropyrrolo[3,4-b]pyrrol-4(1H)-one The title compound was prepared using an analogous procedure to that described in Step 10 of Example 1 using methyl 2-(((1,5-dimethyl-6-oxo-1,6-dihydropyridin-3-yl)amino)(4-fluorophenyl)methyl)-1-methyl-1H-pyrrole-3-carboxylate (Step 1 of Example 82). The reaction mixture was stirred for 2 h at 85° C. Rt: 0.77 min (LC-MS 1); MS m/z: 352.3 [M+H]+ (LC-MS 1); $^1$H NMR (400 MHz, DMSO-d6) δ 1.93 (s, 3H) 3.31 (s, 3H) 3.36 (s, 3H) 6.13 (s, 1H) 6.28 (d, J=2.35 Hz, 1H) 6.91 (d, J=2.35 Hz, 1H) 7.14-7.21 (m, 2H) 7.27 (dd, J=8.41, 5.67 Hz, 2H) 7.34 (br. s, 1H) 7.61 (d, J=2.35 Hz, 1H).

Example 83

4-(5-(1,5-dimethyl-6-oxo-1,6-dihydropyridin-3-yl)-1-methyl-4-oxo-1,4,5,6-tetrahydropyrrolo[3,4-b]pyrrol-6-yl)benzonitrile

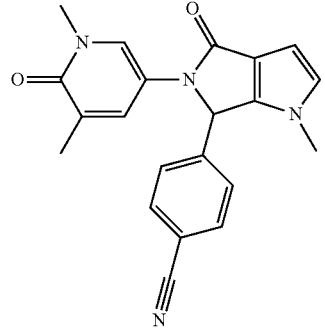 [SMILES: Cc1cc(N2C(=O)c3ccn(C)c3C2c2ccc(C#N)cc2)cn(C)c1=O]

Step 1: Methyl 2-((4-cyanophenyl)((1,5-dimethyl-6-oxo-1,6-dihydropyridin-3-yl)amino)methyl)-1-methyl-1H-pyrrole-3-carboxylate The title compound was prepared using an analogous procedure to that described in Step 2 of Example 60 and in Step 1 of Example 61 using methyl 1-methyl-1H-pyrrole-3-carboxylate (Step 1 of Example 29) and 4-formylbenzonitrile in Step 2 of Example 60. Rf: 0.55 (10% MeOH/DCM); Rt: 0.88 min (LC-MS 1); MS m/z: 391.2 [M+H]+ (LC-MS 1).

Step 2: 4-(5-(1,5-dimethyl-6-oxo-1,6-dihydropyridin-3-yl)-1-methyl-4-oxo-1,4,5,6-tetrahydropyrrolo[3,4-b]pyrrol-6-yl)benzonitrile The title compound was prepared using an analogous procedure to that described in Step 10 of Example 1 using methyl 2-((4-cyanophenyl)((1,5-dimethyl-6-oxo-1,6-dihydropyridin-3-yl)amino)methyl)-1-methyl-1H-pyrrole-3-carboxylate (Step 1 of Example 83). The reaction mixture was stirred for 2 h at 85° C. Rf: 0.50 (10% MeOH/DCM); Rt: 0.70 min (LC-MS 1); MS m/z: 359.2 [M+H]+ (LC-MS 1); $^1$H NMR (400 MHz, DMSO-d6) δ 1.93 (s, 3H) 3.32 (s, 3H) 3.36 (s, 3H) 6.24 (s, 1H) 6.30 (d, J=2.74 Hz, 1H) 6.92 (d, J=2.74 Hz, 1H) 7.36 (s, 1H) 7.45 (d, J=8.21 Hz, 2H) 7.63 (d, J=2.74 Hz, 1H) 7.82 (d, J=8.21 Hz, 2H).

Example 84

5-(1,5-di methyl-6-oxo-1,6-dihydropyridin-3-yl)-6-(4-methoxyphenyl)-1-methyl-5,6-dihydropyrrolo[3,4-b]pyrrol-4(1H)-one

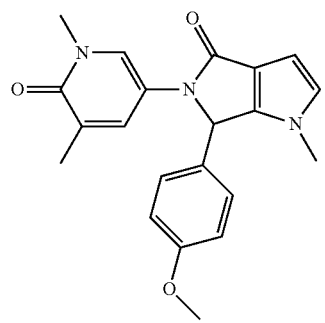 [SMILES: COc1ccc(C2c3c(ccn3C)C(=O)N2c2cc(C)c(=O)n(C)c2)cc1]

Step 1: Methyl 2-(((1,5-dimethyl-6-oxo-1,6-dihydropyridin-3-yl)amino)(4-methoxyphenyl)methyl)-1-methyl-1H-pyrrole-3-carboxylate The title compound was prepared using an analogous procedure to that described in Step 2 of Example 60 and in Step 1 of Example 61 using methyl 1-methyl-1H-pyrrole-3-carboxylate (Step 1 of Example 29) and 4-methoxybenzaldehyde in Step 2 of Example 60. Rf: 0.48 (10% MeOH/DCM); Rt: 0.93 min (LC-MS 1); MS m/z: 396.3 [M+H]+ (LC-MS 1).

Step 2: 5-(1,5-dimethyl-6-oxo-1,6-dihydropyridin-3-yl)-6-(4-methoxyphenyl)-1-methyl-5,6-dihydropyrrolo[3,4-b]pyrrol-4(1H)-one The title compound was prepared using an analogous procedure to that described in Step 10 of Example 1 using methyl 2-(((1,5-dimethyl-6-oxo-1,6-dihydropyridin-3-yl)amino)(4-methoxyphenyl)methyl)-1-methyl-1H-pyrrole-3-carboxylate (Step 1 of Example 84). The reaction mixture was stirred for 2 h at 85° C. Rf: 0.50 (10% MeOH/DCM); Rt: 0.75 min (LC-MS 1); MS m/z: 364.2 [M+H]+ (LC-MS 1); $^1$H NMR (400 MHz, DMSO-d6) δ 1.93 (s, 3H) 3.29 (s, 3H) 3.36 (s, 3H) 3.72 (s, 3H) 6.05 (s, 1H) 6.26 (d, J=3.13 Hz, 1H) 6.87-6.92 (m, 3H) 7.13 (d, J=8.60 Hz, 2H) 7.35 (d, J=1.56 Hz, 1H) 7.60 (d, J=2.74 Hz, 1H).

Example 85

5-(1,5-dimethyl-6-oxo-1,6-dihydropyridin-3-yl)-6-(3-methoxyphenyl)-1-methyl-5,6-dihydropyrrolo[3,4-b]pyrrol-4(1H)-one

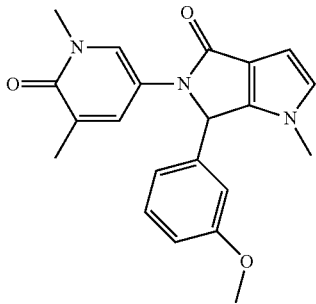 [SMILES: COc1cccc(C2c3c(ccn3C)C(=O)N2c2cc(C)c(=O)n(C)c2)c1]

Step 1: Methyl 2-(((1,5-dimethyl-6-oxo-1,6-dihydropyridin-3-yl)amino)(3-methoxyphenyl)methyl)-1-methyl-1H-pyrrole-3-carboxylate The title compound was prepared using an analogous procedure to that described in Step 2 of Example 60 and in Step 1 of Example 61 using methyl 1-methyl-1H-pyrrole-3-carboxylate (Step 1 of Example 29) and 3-methoxybenzaldehyde in Step 2 of Example 60. Rf: 0.49 (10% MeOH/DCM); Rt: 0.94 min (LC-MS 1); MS m/z: 396.3 [M+H]+ (LC-MS 1).

Step 2: 5-(1,5-dimethyl-6-oxo-1,6-dihydropyridin-3-yl)-6-(3-methoxyphenyl)-1-methyl-5,6-dihydropyrrolo[3,4-b]pyrrol-4(1H)-one The title compound was prepared using an analogous procedure to that described in Step 10 of Example 1 using methyl 2-(((1,5-dimethyl-6-oxo-1,6-dihydropyridin-3-yl)amino)(3-methoxyphenyl)methyl)-1-methyl-1H-pyrrole-3-carboxylate (Step 1 of Example 85). The reaction mixture was stirred for 2 h at 85° C. Rf: 0.53 (10% MeOH/DCM); Rt: 0.76 min (LC-MS 1); MS m/z: 364.3 [M+H]+ (LC-MS 1); $^1$H NMR (400 MHz, DMSO-d6) δ 1.94 (s, 3H) 3.32 (s, 3H) 3.37 (s, 3H) 3.71 (s, 3H) 6.09 (s, 1H) 6.28 (d, J=2.74 Hz, 1H) 6.75-6.83 (m, 2H) 6.85-6.93 (m, 2H) 7.27 (t, J=7.82 Hz, 1H) 7.38 (br. s, 1H) 7.64 (s, 1H).

Example 86

5-(5-chloro-1-methyl-6-oxo-1,6-dihydropyridin-3-yl)-1-methyl-6-phenyl-5,6-dihydropyrrolo[3,4-b]pyrrol-4(1H)-one

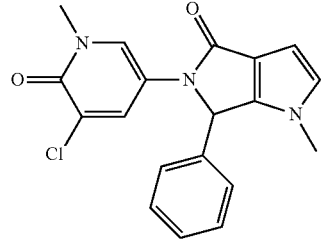 [SMILES: Cn1ccc2c1C(c1ccccc1)N(c1cc(Cl)c(=O)n(C)c1)C2=O]

Step 1: Methyl 2-(((5-chloro-1-methyl-6-oxo-1,6-dihydropyridin-3-yl)amino)(phenyl)methyl)-1-methyl-1H-pyrrole-3-carboxylate The title compound was prepared using an analogous procedure to that described in Steps 2 and 3 of Example 60 using methyl 1-methyl-1H-pyrrole-3-carboxylate (Step 1 of Example 29) and benzaldehyde in Step 2 of Example 60. Rf: 0.51 (10% MeOH/DCM); Rt: 0.98 min (LC-MS 1); MS m/z: 386.2 [M+H]+ (LC-MS 1).

Step 2: 5-(5-chloro-1-methyl-6-oxo-1,6-dihydropyridin-3-yl)-1-methyl-6-phenyl-5,6-dihydropyrrolo[3,4-b]pyrrol-4(1H)-one The title compound was prepared using an analogous procedure to that described in Step 10 of Example 1 using methyl 2-(((5-chloro-1-methyl-6-oxo-1,6-dihydropyridin-3-yl)amino)(phenyl)methyl)-1-methyl-1H-pyrrole-3-carboxylate (Step 1 of Example 86). The reaction mixture was stirred for 2 h at 85° C. Rf: 0.42 (10% MeOH/DCM); Rt: 0.78 min (LC-MS 1); MS m/z: 354.2 [M+H]+ (LC-MS 1); $^1$H NMR (400 MHz, DMSO-d6) δ 3.30 (s, 3H) 3.44 (s, 3H) 6.16 (s, 1H) 6.30 (d, J=2.74 Hz, 1H) 6.91 (d, J=2.74 Hz, 1H) 7.21-7.41 (m, 5H) 7.85 (dd, J=11.93, 2.54 Hz, 2H).

Example 87

5-(5-chloro-1-methyl-6-oxo-1,6-dihydropyridin-3-yl)-1-methyl-6-(p-tolyl)-5,6-dihydropyrrolo[3,4-b]pyrrol-4(1H)-one

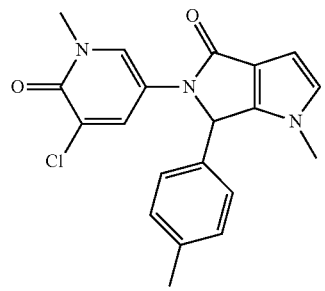 [SMILES: Cc1ccc(C2c3c(ccn3C)C(=O)N2c2cc(Cl)c(=O)n(C)c2)cc1]

Step 1: Methyl 2-(((5-chloro-1-methyl-6-oxo-1,6-dihydropyridin-3-yl)amino)(p-tolyl)methyl)-1-methyl-1H-pyrrole-3-carboxylate The title compound was prepared using an analogous procedure to that described in Steps 2 and 3 of Example 60 using methyl 1-methyl-1H-pyrrole-3-carboxylate (Step 1 of Example 29) and 4-methylbenzaldehyde in Step 2 of Example 60. Rf: 0.55 (10% MeOH/DCM); Rt: 1.04 min (LC-MS 1); MS m/z: 400.3 [M+H]⁺ (LC-MS 1).

Step 2: 5-(5-chloro-1-methyl-6-oxo-1,6-dihydropyridin-3-yl)-1-methyl-6-(p-tolyl)-5,6-dihydropyrrolo[3,4-b]pyrrol-4(1H)-one The title compound was prepared using an analogous procedure to that described in Step 10 of Example 1 using methyl 2-(((5-chloro-1-methyl-6-oxo-1,6-dihydropyridin-3-yl)amino)(p-tolyl)methyl)-1-methyl-1H-pyrrole-3-carboxylate (Step 1 of Example 87). The reaction mixture was stirred for 2 h at 85° C. Rf: 0.51 (10% MeOH/DCM); Rt: 0.86 min (LC-MS 1); MS m/z: 368.2 [M+H]⁺ (LC-MS 1); ¹H NMR (400 MHz, DMSO-d6) δ 2.26 (s, 3H) 3.30 (s, 3H) 3.44 (s, 3H) 6.13 (s, 1H) 6.29 (d, J=2.74 Hz, 1H) 6.90 (d, J=2.74 Hz, 1H) 7.14 (q, J=8.21 Hz, 4H) 7.82-7.87 (m, 2H).

Example 88

5-(5-chloro-1-methyl-6-oxo-1,6-dihydropyridin-3-yl)-6-(4-fluorophenyl)-1-methyl-5,6-dihydropyrrolo[3,4-b]pyrrol-4(1H)-one

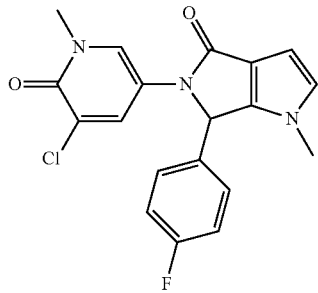

Step 1: Methyl 2-(((5-chloro-1-methyl-6-oxo-1,6-dihydropyridin-3-yl)amino)(4-fluorophenyl)methyl)-1-methyl-1H-pyrrole-3-carboxylate The title compound was prepared using an analogous procedure to that described in Steps 2 and 3 of Example 60 using methyl 1-methyl-1H-pyrrole-3-carboxylate (Step 1 of Example 29) and 4-fluorobenzaldehyde in Step 2 of Example 60. Rf: 0.52 (10% MeOH/DCM); Rt: 0.99 min (LC-MS 1); MS m/z: 404.2 [M+H]⁺ (LC-MS 1).

Step 2: 5-(5-chloro-1-methyl-6-oxo-1,6-dihydropyridin-3-yl)-6-(4-fluorophenyl)-1-methyl-5,6-dihydropyrrolo[3,4-b]pyrrol-4(1H)-one The title compound was prepared using an analogous procedure to that described in Step 10 of Example 1 using methyl 2-(((5-chloro-1-methyl-6-oxo-1,6-dihydropyridin-3-yl)amino)(4-fluorophenyl)methyl)-1-methyl-1H-pyrrole-3-carboxylate (Step 1 of Example 88). The reaction mixture was stirred for 2 h at 85° C. Rf: 0.48 (10% MeOH/DCM); Rt: 0.80 min (LC-MS 1); MS m/z: 372.1 [M+H]⁺ (LC-MS 1); ¹H NMR (400 MHz, DMSO-d6) δ 3.31 (s, 3H) 3.45 (s, 3H) 6.18 (s, 1H) 6.30 (d, J=3.13 Hz, 1H) 6.92 (d, J=3.13 Hz, 1H) 7.15-7.23 (m, 2H) 7.30 (dd, J=8.60, 5.47 Hz, 2H) 7.84 (s, 2H).

Example 89

4-(5-(5-chloro-1-methyl-6-oxo-1,6-dihydropyridin-3-yl)-1-methyl-4-oxo-1,4,5,6-tetrahydropyrrolo[3,4-b]pyrrol-6-yl)benzonitrile

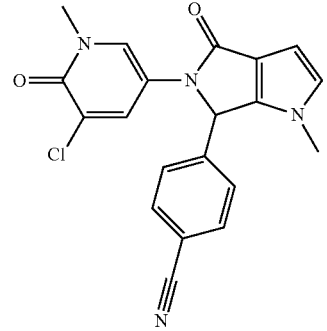 [SMILES: Cn1ccc2c1C(c1ccc(C#N)cc1)N(c1cc(Cl)c(=O)n(C)c1)C2=O]

Step 1: Methyl 2-(((5-chloro-1-methyl-6-oxo-1,6-dihydropyridin-3-yl)amino)(4-cyanophenyl)methyl)-1-methyl-1H-pyrrole-3-carboxylate The title compound was prepared using an analogous procedure to that described in Steps 2 and 3 of Example 60 using methyl 1-methyl-1H-pyrrole-3-carboxylate (Step 1 of Example 29) and 4-formylbenzonitrile in Step 2 of Example 60. Rf: 0.49 (10% MeOH/DCM); Rt: 0.91 min (LC-MS 1); MS m/z: 411.2 [M+H]⁺ (LC-MS 1).

Step 2: 4-(5-(5-chloro-1-methyl-6-oxo-1,6-dihydropyridin-3-yl)-1-methyl-4-oxo-1,4,5,6-tetrahydropyrrolo[3,4-b]pyrrol-6-yl)benzonitrile The title compound was prepared using an analogous procedure to that described in Step 10 of Example 1 using methyl 2-(((5-chloro-1-methyl-6-oxo-1,6-dihydropyridin-3-yl)amino)(4-cyanophenyl)methyl)-1-methyl-1H-pyrrole-3-carboxylate (Step 1 of Example 89). The reaction mixture was stirred for 2 h at 85° C. Rf: 0.50 (10% MeOH/DCM); Rt: 0.73 min (LC-MS 1); MS m/z: 379.2 [M+H]⁺ (LC-MS 1); ¹H NMR (400 MHz, DMSO-d6) δ 3.31 (s, 3H) 3.44 (s, 3H) 6.29 (s, 1H) 6.31 (d, J=2.74 Hz, 1H) 6.93 (d, J=2.74 Hz, 1H) 7.48 (d, J=8.21 Hz, 2H) 7.81-7.89 (m, 4H).

Example 90

5-(5-chloro-1-methyl-6-oxo-1,6-dihydropyridin-3-yl)-6-(4-chloro-3-fluorophenyl)-1-methyl-5,6-dihydropyrrolo[3,4-b]pyrrol-4(1H)-one

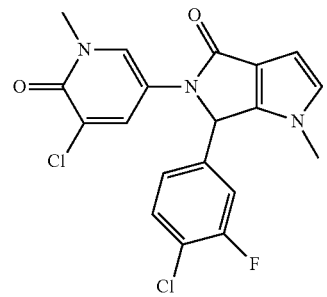 [SMILES: Cn1ccc2c1C(c1ccc(Cl)c(F)c1)N(c1cc(Cl)c(=O)n(C)c1)C2=O]

Step 1: Methyl 2-(((5-chloro-1-methyl-6-oxo-1,6-dihydropyridin-3-yl)amino)(4-chloro-3-fluorophenyl)methyl)-1-methyl-1H-pyrrole-3-carboxylate The title compound was prepared using an analogous procedure to that described in Steps 2 and 3 of Example 60 using methyl 1-methyl-1H-pyrrole-3-carboxylate (Step 1 of Example 29) and 4-chloro-3-fluorobenzaldehyde in Step 2 of Example 60. Rf: 0.55 (10% MeOH/DCM); Rt: 1.08 min (LC-MS 1); MS m/z: 438.1 [M+H]$^+$ (LC-MS 1).

Step 2: 5-(5-chloro-1-methyl-6-oxo-1,6-dihydropyridin-3-yl)-6-(4-chloro-3-fluorophenyl)-1-methyl-5,6-dihydropyrrolo[3,4-b]pyrrol-4(1H)-one The title compound was prepared using an analogous procedure to that described in Step 10 of Example 1 using methyl 2-(((5-chloro-1-methyl-6-oxo-1,6-dihydropyridin-3-yl)amino)(4-chloro-3-fluorophenyl)methyl)-1-methyl-1H-pyrrole-3-carboxylate (Step 1 of Example 90). The reaction mixture was stirred for 2 h at 85° C. Rf: 0.52 (10% MeOH/DCM); Rt: 0.89 min (LC-MS 1); MS m/z: 406.2 [M+H]$^+$ (LC-MS 1); $^1$H NMR (400 MHz, DMSO-d6) δ 3.34 (s, 3H) 3.45 (s, 3H) 6.19 (s, 1H) 6.30 (d, J=2.74 Hz, 1H) 6.93 (d, J=3.13 Hz, 1H) 7.16 (dd, J=8.41, 1.76 Hz, 1H) 7.34 (dd, J=9.97, 1.76 Hz, 1H) 7.58 (t, J=7.82 Hz, 1H) 7.86 (d, J=2.74 Hz, 1H) 7.89 (d, J=2.74 Hz, 1H).

Example 91

5-(5-chloro-1-methyl-6-oxo-1,6-dihydropyridin-3-yl)-6-(3-methoxyphenyl)-1-methyl-5,6-dihydropyrrolo[3,4-b]pyrrol-4(1H)-one

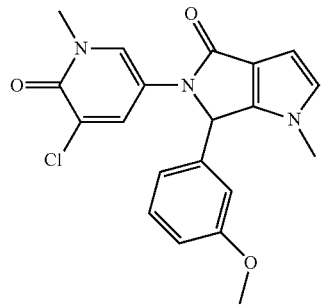 [SMILES: COc1cccc(C2c3c(ccn3C)C(=O)N2c2cc(Cl)c(=O)n(C)c2)c1]

Step 1: Methyl 2-(((5-chloro-1-methyl-6-oxo-1,6-dihydropyridin-3-yl)amino)(3-methoxyphenyl)methyl)-1-methyl-1H-pyrrole-3-carboxylate The title compound was prepared using an analogous procedure to that described in Steps 2 and 3 of Example 60 using methyl 1-methyl-1H-pyrrole-3-carboxylate (Step 1 of Example 29) and 3-methoxybenzaldehyde in Step 2 of Example 60. Rf: 0.53 (10% MeOH/DCM); Rt: 0.96 min (LC-MS 1); MS m/z: 416.2 [M+H]$^+$ (LC-MS 1).

Step 2: 5-(5-chloro-1-methyl-6-oxo-1,6-dihydropyridin-3-yl)-6-(3-methoxyphenyl)-1-methyl-5,6-dihydropyrrolo[3,4-b]pyrrol-4(1H)-one The title compound was prepared using an analogous procedure to that described in Step 10 of Example 1 using methyl 2-(((5-chloro-1-methyl-6-oxo-1,6-dihydropyridin-3-yl)amino)(3-methoxyphenyl)methyl)-1-methyl-1H-pyrrole-3-carboxylate (Step 1 of Example 91). The reaction mixture was stirred for 2 h at 85° C. Rf: 0.51 (10% MeOH/DCM); Rt: 0.81 min (LC-MS 1); MS m/z: 384.1 [M+H]$^+$ (LC-MS 1); $^1$H NMR (400 MHz, DMSO-d6) δ 3.33 (br. s, 3H) 3.46 (br. s, 3H) 3.72 (br. s, 3H) 6.14 (br. s, 1H) 6.30 (br. s, 1H) 6.74-7.01 (m, 4H) 7.29 (br. s, 1H) 7.89 (br. s, 2H).

Example 92

5-(5-chloro-1-methyl-6-oxo-1,6-dihydropyridin-3-yl)-6-(4-methoxyphenyl)-1-methyl-5,6-dihydropyrrolo[3,4-b]pyrrol-4(1H)-one

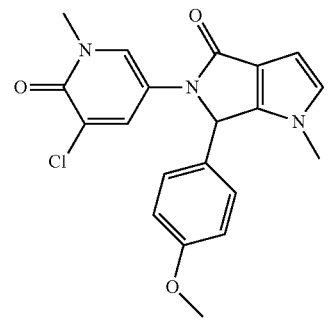 [SMILES: COc1ccc(C2c3c(ccn3C)C(=O)N2c2cc(Cl)c(=O)n(C)c2)cc1]

Step 1: Methyl 2-(((5-chloro-1-methyl-6-oxo-1,6-dihydropyridin-3-yl)amino)(4-methoxyphenyl)methyl)-1-methyl-1H-pyrrole-3-carboxylate The title compound was prepared using an analogous procedure to that described in Steps 2 and 3 of Example 60 using methyl 1-methyl-1H-pyrrole-3-carboxylate (Step 1 of Example 29) and 4-methoxybenzaldehyde in Step 2 of Example 60. Rt: 0.95 min (LC-MS 1); MS m/z: 416.2 [M+H]$^+$ (LC-MS 1).

Step 2: 5-(5-chloro-1-methyl-6-oxo-1,6-dihydropyridin-3-yl)-6-(4-methoxyphenyl)-1-methyl-5,6-dihydropyrrolo[3,4-b]pyrrol-4(1H)-one The title compound was prepared using an analogous procedure to that described in Step 10 of Example 1 using methyl 2-(((5-chloro-1-methyl-6-oxo-1,6-dihydropyridin-3-yl)amino)(4-methoxyphenyl)methyl)-1-methyl-1H-pyrrole-3-carboxylate (Step 1 of Example 92). The reaction mixture was stirred for 2 h at 85° C. Rt: 0.79 min (LC-MS 1); MS m/z: 384.1 [M+H]$^+$ (LC-MS 1); $^1$H NMR (400 MHz, DMSO-d6) δ 3.32 (s, 3H) 3.48 (s, 3H) 3.74 (s, 3H) 6.21 (s, 1H) 6.30 (d, J=2.74 Hz, 1H) 6.89-6.97 (m, 3H) 7.19 (d, J=8.60 Hz, 2H) 7.86 (d, J=2.74 Hz, 1H) 7.94 (d, J=2.74 Hz, 1H).

Example 93

6-(4-chlorophenyl)-5-(3,7-dimethyl-3H-[1,2,3]triazolo[4,5-b]pyridin-5-yl)-N,1-dimethyl-4-oxo-1,4,5,6-tetrahydropyrrolo[3,4-b]pyrrole-3-carboxamide

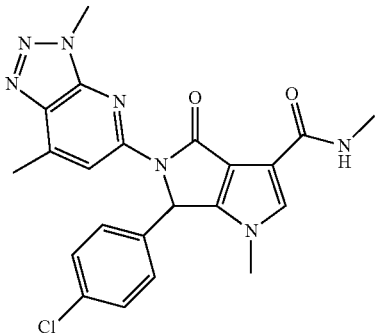 [SMILES: CNC(=O)c1cn(C)c2c1C(=O)N(c1cc(C)c3nnn(C)c3n1)C2c1ccc(Cl)cc1]

Step 1: Diethyl 1-methyl-1H-pyrrole-3,4-dicarboxylate

Potassium hydroxide (4.01 g, 71.4 mmol) and iodomethane (3.28 mL, 52.4 mmol) were added sequentially to a solution of diethyl 1H-pyrrole-3,4-dicarboxylate (Sigma-Aldrich, 10.06 g, 47.6 mmol) in DMSO (80 mL). The reaction mixture was stirred for 18 h at rt, diluted in EtOAc/water, and extracted three times with EtOAc. The combined organic extracts were washed with brine, dried ($Na_2SO_4$), filtered and the filtrate was concentrated. The residue was purified by silica gel chromatography on Combiflash Isco (eluent: EtOAc/Hexane; gradient: 0-57.3% EtOAc in 34.5 min; flow: 85 mL/min) to afford the title compound (9.63 g) as a colorless solid. Rt: 0.83 min (LC-MS 1); MS m/z: 226.1 [M+H]$^+$ (LC-MS 1); $^1$H NMR (400 MHz, DMSO-d6) δ 7.35 (s, 2H), 4.12 (q, J=7.1 Hz, 4H), 3.63 (s, 3H), 1.21 (t, J=7.1 Hz, 6H).

Step 2: Diethyl 2-((4-chlorophenyl)(hydroxy)methyl)-1-methyl-1H-pyrrole-3,4-dicarboxylate LDA (2M in THF/heptane/ethylbenzene, 27.8 mL, 55.6 mmol) was added to a stirred solution of diethyl 1-methyl-1H-pyrrole-3,4-dicarboxylate (Step 1 of Example 93, 9.63 g, 42.8 mmol) in THF (450 mL) at −78° C. The mixture was stirred for 40 min at −78° C. A solution of 4-chlorobenzaldehyde (6.01 g, 42.8 mmol) in THF (50 mL) was added drop-wise. The reaction mixture was stirred for 1 h, quenched by addition of a saturated solution of ammonium chloride, diluted in EtOAc/saturated ammonium chloride solution, and extracted twice with EtOAc. The combined organic extracts were washed with water and brine, dried ($Na_2SO_4$), filtered and the filtrate was concentrated. The residue was purified by silica gel chromatography on Combiflash Isco (eluent: EtOAc/hexane; gradient: 0-40% EtOAc in 36.1 min; flow: 85 mL/min) to afford the title compound (7.2 g) as a yellow solid. Rf=0.40 (40% EtOAc/hexane); Rt: 1.13 min (LC-MS 1); MS m/z: 366.1 [M+H]$^+$ (LC-MS 1); $^1$H NMR (400 MHz, DMSO-d6) δ 7.48-7.21 (m, 5H), 6.35 (d, J=4.4 Hz, 1H), 6.13 (d, J=4.6 Hz, 1H), 4.26-4.00 (m, 4H), 3.36 (s, 3H), 1.28-1.11 (m, 6H).

Step 3: Diethyl 2-((4-chlorophenyl)((3,7-dimethyl-3H-[1,2,3]triazolo[4,5-b]pyridin-5-yl)amino)methyl)-1-methyl-1H-pyrrole-3,4-dicarboxylate 1-Chloro-N,N,2-trimethyl-1-propenylamine (0.613 mL, 4.64 mmol) was added to a stirred solution of diethyl 2-((4-chlorophenyl)(hydroxy)methyl)-1-methyl-1H-pyrrole-3,4-dicarboxylate (Step 2 of Example 93, 1.19 g, 3.09 mmol) in DCM (25 mL) at rt. The reaction mixture was stirred for 3 h and then cooled to 0° C. Triethylamine (1.29 mL, 9.27 mmol) and 3,7-dimethyl-3H-[1,2,3]triazolo[4,5-b]pyridin-5-amine (Step 5 of Example 1, 0.504 g, 3.09 mmol) were added in sequence. The reaction mixture was stirred for 2 h at rt, diluted in DCM/water, and extracted twice with DCM. The combined organic extracts were washed with water and brine, dried ($Na_2SO_4$), filtered and the filtrate was concentrated. The residue was purified by by silica gel chromatography on Combiflash Isco (eluent: MeOH/DCM; gradient: 2.2 min 0% MeOH, 0% to 5% MeOH in 29.6 min; flow: 60 mL/min) to afford the title compound (1.9 g, purity 83%) as an orange foam. Rf=0.43 (5% MeOH/DCM); Rt: 1.05 min (LC-MS 1); MS m/z: 510.2 [M+H]$^+$ (LC-MS 1); $^1$H NMR (400 MHz, DMSO-d6) δ 7.97 (d, J=7.2 Hz, 1H), 7.50-7.22 (m, 5H), 6.75 (d, J=7.1 Hz, 1H), 6.65 (d, J=1.4 Hz, 1H), 4.21-3.98 (m, 4H), 3.92 (s, 3H), 3.54 (s, 3H), 2.78 (s, 3H), 1.18 (t, J=7.0 Hz, 3H), 1.07 (t, J=7.1 Hz, 3H).

Step 4: 2-((4-chlorophenyl)((3,7-dimethyl-3H-[1,2,3]triazolo[4,5-b]pyridin-5-yl)amino)methyl)-1-methyl-1H-pyrrole-3,4-dicarboxylic acid Aqueous sodium hydroxide (2N, 30 mL, 60.0 mmol) was added to a stirred solution of diethyl 2-((4-chlorophenyl)((3,7-dimethyl-3H-[1,2,3]triazolo[4,5-b]pyridin-5-yl)amino)methyl)-1-methyl-1H-pyrrole-3,4-dicarboxylate (Step 3 of Example 93, 1.9 g, 3.09 mmol) in THF (30 mL) and MeOH (30 mL). The reaction mixture was heated to 100° C. and stirred for 2 h. THF and MeOH were evaporated. The resulting aqueous residue was washed with EtOAc and then acidified to pH 3 with 6N HCl, diluted with DCM, and stirred 30 min. The resulting precipitate was collected by filtration to afford the title compound (1.05 g) as an off-white solid. Rt: 0.77 min (LC-MS 1); MS m/z: 455.2 [M+H]$^+$ (LC-MS 1); $^1$H NMR (400 MHz, DMSO-d6) δ 8.13 (d, J=8.1 Hz, 1H), 7.62 (s, 1H), 7.49-7.32 (m, 3H), 7.22 (d, J=8.5 Hz, 2H), 6.68 (s, 1H), 3.96 (s, 3H), 3.65 (s, 3H), 2.48-2.52 (m, 3H).

Step 5: 6-(4-chlorophenyl)-5-(3,7-dimethyl-3H-[1,2,3]triazolo[4,5-b]pyridin-5-yl)-1-methyl-4-oxo-1,4,5,6-tetrahydropyrrolo[3,4-b]pyrrole-3-carboxylic acid 1-Chloro-N,N,2-trimethyl-1-propenylamine (0.419 mL, 3.17 mmol) was added to a stirred suspension of 2-((4-chlorophenyl)((3,7-dimethyl-3H-[1,2,3]triazolo[4,5-b]pyridin-5-yl)amino)methyl)-1-methyl-1H-pyrrole-3,4-dicarboxylic acid (Step 4 of Example 93, 1.05 g, 2.262 mmol) in DCM (25 mL) at rt under argon. The reaction mixture was stirred for 1 h at rt. The resulting precipitate was collected by filtration to afford the title compound (983 mg) as a colorless solid. Rt: 0.94 min (LC-MS 1); MS m/z: 437.2 [M+H]$^+$ (LC-MS 1); $^1$H NMR (400 MHz, DMSO-d6) δ 8.26 (s, 1H), 7.60 (s, 1H), 7.51-7.24 (m, 4H), 6.74 (s, 1H), 4.10 (s, 3H), 3.35 (s, 3H), 2.65 (s, 3H).

Step 6: 6-(4-chlorophenyl)-5-(3,7-dimethyl-3H-[1,2,3]triazolo[4,5-b]pyridin-5-yl)-N,1-dimethyl-4-oxo-1,4,5,6-tetrahydropyrrolo[3,4-b]pyrrole-3-carboxamide DIEA (0.096 mL, 0.549 mmol) was added to 6-(4-chlorophenyl)-5-(3,7-dimethyl-3H-[1,2,3]triazolo[4,5-b]pyridin-5-yl)-1-methyl-4-oxo-1,4,5,6-tetrahydropyrrolo[3,4-b]pyrrole-3-carboxylic acid (Step 5 of Example 93, 80 mg, 0.183 mmol), TBTU (70.6 mg, 0.220 mmol) and methylamine hydrochloride (37.1 mg, 0.549 mmol) in DMF (2 mL) at rt under argon. The reaction mixture was stirred for 1 h at rt, diluted in EtOAc/water, and extracted twice with EtOAc. The combined organic extracts were washed with water and brine, dried (Na₂SO₄), filtered and the filtrate was concentrated. The residue was purified by silica gel chromatography on Combiflash Isco (eluent: MeOH/DCM; gradient: 1 min 0% MeOH, 0% to 5% MeOH in 12 min, 8.9 min 5% MeOH; flow: 30 mL/min) followed by trituration of the resulting material in Et₂O to afford the title compound (14 mg) as a colorless solid. Rf=0.60 (5% MeOH/DCM); Rt: 1.03 min (LC-MS 1); MS m/z: 450.2 [M+H]⁺ (LC-MS 1); ¹H NMR (400 MHz, DMSO-d6) δ 8.25 (q, J=0.7 Hz, 1H), 8.08 (q, J=4.7 Hz, 1H), 7.58-7.27 (m, 5H), 6.85 (s, 1H), 4.11 (s, 3H), 3.36 (s, 3H), 2.86 (d, J=4.6 Hz, 3H), 2.67 (d, J=0.8 Hz, 3H).

Example 94

6-(4-chlorophenyl)-5-(3,7-dimethyl-3H-[1,2,3]tri-azolo[4,5-b]pyridin-5-yl)-N,N,1-trimethyl-4-oxo-1, 4,5,6-tetrahydropyrrolo[3,4-b]pyrrole-3-carboxamide

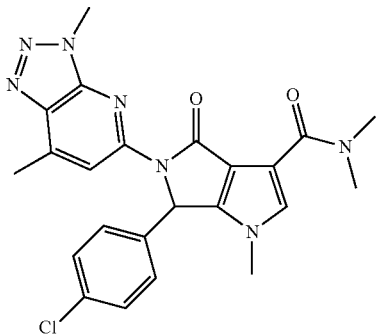 [SMILES: Cc1cc(N2C(=O)c3c(C(=O)N(C)C)cn(C)c3C2c2ccc(Cl)cc2)nc2c1nnn2C]

The title compound was prepared using an analogous procedure to that described in Step 6 of Example 93 using dimethylamine hydrochloride (5 eq) and stirring the reaction mixture for 14 h at rt. Rf=0.42 (5% MeOH/DCM); Rt: 0.98 min (LC-MS 1); MS m/z: 464.2 [M+H]⁺ (LC-MS 1); ¹H NMR (400 MHz, DMSO-d6) δ 8.26 (d, J=1.4 Hz, 1H), 7.45 (d, J=8.4 Hz, 2H), 7.37 (d, J=8.4 Hz, 2H), 7.26 (s, 1H), 6.76 (s, 1H), 4.10 (s, 3H), 3.34 (s, 3H), 3.23-2.86 (m, 6H), 2.65 (s, 3H).

Example 95

Tert-butyl (6-(4-chlorophenyl)-5-(3,7-dimethyl-3H-[1,2,3]triazolo[4,5-b]pyridin-5-yl)-1-methyl-4-oxo-1, 4,5,6-tetrahydropyrrolo[3,4-b]pyrrol-3-yl)carbamate

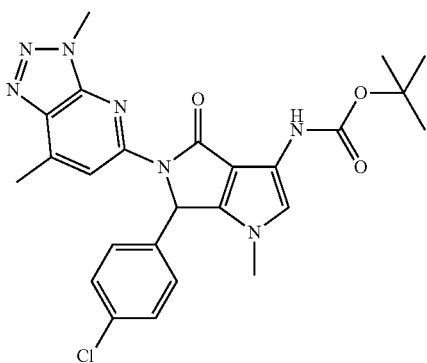 [SMILES: Cc1cc(N2C(=O)c3c(NC(=O)OC(C)(C)C)cn(C)c3C2c2ccc(Cl)cc2)nc2c1nnn2C]

Step 1: 6-(4-chlorophenyl)-5-(3,7-dimethyl-3H-[1,2, 3]triazolo[4,5-b]pyridin-5-yl)-1-methyl-4-oxo-1,4,5, 6-tetrahydropyrrolo[3,4-b]pyrrole-3-carbonyl azide A mixture of DIEA (0.879 mL, 5.03 mmol) was added to 6-(4-chlorophenyl)-5-(3,7-dimethyl-3H-[1,2,3]triazolo[4,5-b]pyridin-5-yl)-1-methyl-4-oxo-1,4,5,6-tetrahydropyrrolo[3,4-b]pyrrole-3-carboxylic acid (Step 5 of Example 93, 733 mg, 1.678 mmol), TBTU (646 mg, 2.014 mmol) and sodium azide (120 mg, 1.846 mmol) in DMF (15 mL) was stirred for 1 h at rt under Ar and then diluted with EtOAc/water. The resulting precipitate was collected by filtration to afford the title compound (581 mg) as a colorless solid. Rt: 1.11 min (LC-MS 1); MS m/z: 462.2 [M+H]⁺ (LC-MS 1); ¹H NMR (400 MHz, DMSO-d6) δ 8.26 (d, J=0.7 Hz, 1H), 7.83 (s, 1H), 7.44 (d, J=8.5 Hz, 2H), 7.36 (d, J=8.5 Hz, 2H), 6.79 (s, 1H), 4.11 (s, 3H), 3.38 (s, 3H), 2.70-2.61 (m, 3H).

Step 2: Tert-butyl (6-(4-chlorophenyl)-5-(3,7-dim-ethyl-3H-[1,2,3]triazolo[4,5-b]pyridin-5-yl)-1-methyl-4-oxo-1,4,5,6-tetrahydropyrrolo[3,4-b]pyr-rol-3-yl)carbamate A mixture of 6-(4-chlorophenyl)-5-(3,7-dimethyl-3H-[1, 2,3]triazolo[4,5-b]pyridin-5-yl)-1-methyl-4-oxo-1,4,5,6-tetrahydropyrrolo[3,4-b]pyrrole-3-carbonyl azide (Step 1 of Example 95, 578 mg, 1.251 mmol), toluene (20 mL) and tert-butanol (2 mL) was stirred for 3 h at 100° C. and concentrated. The residue was purified by silica gel column chromatography (50% EtOAc/hexane) to afford the title compound (479 mg) as a colorless solid. Rt: 1.26 min (LC-MS 1); MS m/z: 508.3 [M+H]⁺ (LC-MS 1); ¹H NMR (400 MHz, DMSO-d6) δ 8.63 (s, 1H), 8.25 (d, J=1.3 Hz, 1H), 7.20-7.55 (m, 4H), 6.91 (s, 1H), 6.67 (s, 1H), 4.09 (s, 3H), 3.25 (s, 3H), 2.64 (s, 3H), 1.45 (s, 9H).

Example 96

N-(6-(4-chlorophenyl)-5-(3,7-dimethyl-3H-[1,2,3] triazolo[4,5-b]pyridin-5-yl)-1-methyl-4-oxo-1,4,5,6-tetrahydropyrrolo[3,4-b]pyrrol-3-yl)acetamide

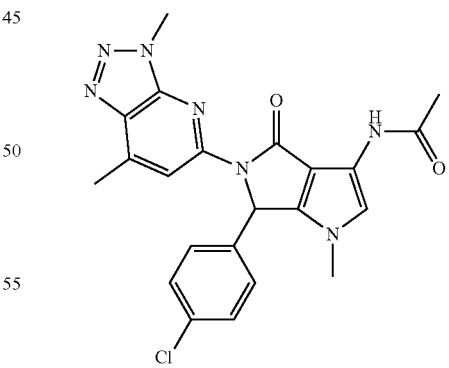

Step 1: 3-amino-6-(4-chlorophenyl)-5-(3,7-dim-ethyl-3H-[1,2,3]triazolo[4,5-b]pyridin-5-yl)-1-methyl-5,6-dihydropyrrolo[3,4-b]pyrrol-4(1H)-one A mixture of HCl (4N in dioxane, 2 mL, 8.00 mmol) and tert-butyl (6-(4-chlorophenyl)-5-(3,7-dimethyl-3H-[1,2,3] triazolo[4,5-b]pyridin-5-yl)-1- methyl-4-oxo-1,4,5,6-tetrahydropyrrolo[3,4-b]pyrrol-3-yl)carbamate (Step 2 of Example 95, 186 mg, 0.366 mmol) was stirred for 1.5 h at rt and then concentrated to afford the title compound (218 mg, purity 93%) as a colorless solid. Rt: 1.26 min (LC-MS 1); MS m/z: 408.2 [M+H]$^+$ (LC-MS 1).

Step 2: N-(6-(4-chlorophenyl)-5-(3,7-dimethyl-3H-[1,2,3]triazolo[4,5-b]pyridin-5-yl)-1-methyl-4-oxo-1, 4,5,6-tetrahydropyrrolo[3,4-b]pyrrol-3-yl)acetamide Acetic anhydride (0.024 mL, 0.252 mmol) was added to a stirred suspension of 3-amino-6-(4-chlorophenyl)-5-(3,7-dimethyl-3H-[1,2,3]triazolo[4,5-b]pyridin-5-yl)-1-methyl-5,6-dihydropyrrolo[3,4-b]pyrrol-4(1H)-one (Step 1 of Example 96, 100 mg, 0.168 mmol) and triethylamine (0.117 mL, 0.840 mmol) in DCM (4 mL) at rt. The reaction mixture was stirred for 5 min at rt, diluted in DCM/water, and extracted twice with DCM. The combined organic extracts were washed with brine, dried (Na$_2$SO$_4$), filtered and the filtrate was concentrated. The residue was purified by silica gel chromatography on Combiflash Isco (eluent: MeOH/DCM; gradient: 1 min 0% MeOH, 0% to 3% MeOH in 10 min; flow: 30 mL/min) followed by trituration of the resulting material in Et$_2$O to afford the title compound (54 mg) as a colorless solid. Rf=0.44 (5% MeOH/DCM); Rt: 0.99 min (LC-MS 1); MS m/z: 450.2 [M+H]$^+$ (LC-MS 1); $^1$H NMR (400 MHz, DMSO-d6) δ 9.80 (s, 1H), 8.26 (s, 1H), 7.55-7.08 (m, 5H), 6.69 (s, 1H), 4.10 (s, 3H), 3.27 (s, 3H), 2.65 (s, 3H), 2.06 (s, 3H).

Example 97

Ethyl (6-(4-chlorophenyl)-5-(3,7-dimethyl-3H-[1,2,3]triazolo[4,5-b]pyridin-5-yl)-1-methyl-4-oxo-1,4,5,6-tetrahydropyrrolo[3,4-b]pyrrol-3-yl)carbamate

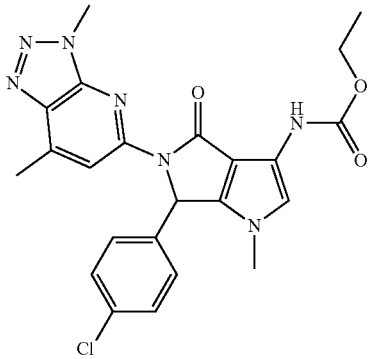 [SMILES: CCOC(=O)Nc1cn(C)c2c1C(=O)N(c1cc(C)c3nnn(C)c3n1)C2c1ccc(Cl)cc1]

Ethyl chloroformate (0.022 mL, 0.234 mmol) was added to a stirred solution of 3-amino-6-(4-chlorophenyl)-5-(3,7-dimethyl-3H-[1,2,3]triazolo[4,5-b]pyridin-5-yl)-1-methyl-5,6-dihydropyrrolo[3,4-b]pyrrol-4(1H)-one (Step 1 of Example 96, 116 mg, 0.195 mmol) and triethylamine (0.136 mL, 0.974 mmol) in DCM (5 mL) at rt. The reaction mixture was stirred for 30 min at rt, diluted in DCM/water, and extracted twice with DCM. The combined organic extracts were washed with brine, dried (Na$_2$SO$_4$), filtered and the filtrate was concentrated. The residue was purified by silica gel chromatography on Combiflash Isco (eluent: EtOAc/hexane; gradient: 1 min 40% EtOAc, 40% to 80% EtOAc in 11 min; flow: 30 mL/min) followed by trituration of the resulting material in Et$_2$O to afford the title compound (49 mg) as a colorless solid. Rf=0.30 (75% EtOAc/hexane); Rt: 1.13 min (LC-MS 1); MS m/z: 480.2 [M+H]$^+$ (LC-MS 1); $^1$H NMR (400 MHz, DMSO-d6) δ 8.98 (s, 1H), 8.25 (d, J=1.1 Hz, 1H), 7.51-7.27 (m, 4H), 6.90 (s, 1H), 6.68 (s, 1H), 4.22-3.93 (m, 5H), 3.27 (s, 3H), 2.64 (s, 3H), 1.21 (t, J=7.1 Hz, 3H).

Example 98

6-(4-chlorophenyl)-5-(1,4-dimethyl-1H-benzo[d][1,2,3]triazol-6-yl)-N,1-dimethyl-4-oxo-1,4,5,6-tetrahydropyrrolo[3,4-b]pyrrole-3-carboxamide

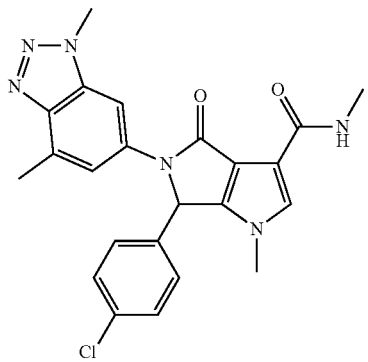 [SMILES: CNC(=O)c1cn(C)c2c1C(=O)N(c1cc(C)c3nnn(C)c3c1)C2c1ccc(Cl)cc1]

Step 1:
1,4-dimethyl-1H-benzo[d][1,2,3]triazol-6-amine

A mixture of 6-bromo-1,4-dimethyl-1H-benzo[d][1,2,3]triazole (Step 3 of Example 28, 5 g, 19.68 mmol), ammonium hydroxide (50 mL, 424 mmol), copper(I) iodide (0.187 g, 0.984 mmol), and THF (5 mL) were stirred in a pressure vessel for 14 h at 120° C. The reaction mixture was diluted in DCM/water, and extracted three times with DCM. The combined organic extracts were dried (Na$_2$SO$_4$), filtered and the filtrate was concentrated. The residue was purified by silica gel chromatography on Combiflash Isco (eluent: MeOH/DCM; gradient: 2.1 min 0% MeOH, 0% to 1% MeOH in 4.9 min, 9 min 1% MeOH, 15 to 5% in 15.2 min; flow: 60 mL/min) to afford the title compound (49 mg) as a brown solid. Rf=0.37 (5% MeOH/DCM); Rt: 0.47 min (LC-MS 1); MS m/z: 163.0 [M+H]$^+$ (LC-MS 1).

Step 2: Diethyl 2-((4-chlorophenyl)((1,4-dimethyl-1H-benzo[d][1,2,3]triazol-6-yl)amino)methyl)-1-methyl-1H-pyrrole-3,4-dicarboxylate 1-Chloro-N,N,2-trimethyl-1-propenylamine (1.443 mL, 10.91 mmol) was added to a stirred solution of diethyl 2-((4-chlorophenyl)(hydroxy)methyl)-1-methyl-1H-pyrrole-3,4-dicarboxylate (Step 2 of Example 93, 2.8 g, 7.27 mmol) in DCM (75 mL) at rt. The mixture was stirred for 3 h at rt and then cooled to 0° C. Triethylamine (3.04 mL, 21.81 mmol) and 1,4-dimethyl-1H-benzo[d][1,2,3]triazol-6-amine (Step 1 of Example 98, 1.25 g, 7.71 mmol) were added in sequence. The reaction mixture was allowed to warm to rt and was stirred for 17 h. 1,4-Dimethyl-1H-benzo[d][1,2,3]triazol-6-amine (Step 1 of Example 98, 500 mg, 3.08 mmol) was added and stirring was continued for 1 h and 45 min. 1,4-Dimethyl-1H-benzo[d][1,2,3]triazol-6-amine (Step 1 of Example 98, 200 mg, 1.23 mmol) was added. The reaction mixture was stirred for 1 h, diluted in DCM/water, and extracted twice with DCM. The combined organic extracts were washed with water and brine, dried (Na₂SO₄), filtered and the filtrate was concentrated. The residue was purified by silica gel chromatography on Combiflash Isco (eluent: EtOAc/hexane, gradient: 50% EtOAc for 2 min, 50% to 90% EtOAc in 25 min; flow: 60 mL/min) to afford the title compound (3.17 g, purity 87%) as an orange foam. Rf=0.19 (75% EtOAc/hexane); Rt: 1.18 min (LC-MS 1); MS m/z: 510.2 [M+H]⁺ (LC-MS 1).

Step 3: 2-((4-chlorophenyl)((1,4-dimethyl-1H-benzo [d][1,2,3]triazol-6-yl)amino)methyl)-1-methyl-1H-pyrrole-3,4-dicarboxylic acid Diethyl 2-((4-chlorophenyl)((1,4-dimethyl-1H-benzo[d][1,2,3]triazol-6-yl)amino)methyl)-1-methyl-1H-pyrrole-3,4-dicarboxylate (Step 2 of Example 98, 3.17 g, 5.41 mmol) was dissolved in THF (50 mL) and MeOH (50 mL) and aqueous NaOH (2N, 50 mL, 100 mmol) was added. The reaction mixture was heated to 100° C. for 1 h. THF and MeOH were evaporated. The resulting aqueous residue was washed with EtOAc, acidified to pH 3 with 6N HCl, and extracted twice with DCM. The combined organic extracts were dried (Na₂SO₄), filtered and the filtrate concentrated to afford a 1:1 mixture (2.59 g) of the title compound and 6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrole-3-carboxylic acid (Step 4, of Example 98) as a reddish solid. The title compound. Rt: 0.75 min (LC-MS 1); MS m/z: 454.2 [M+H]⁺ (LC-MS 1).

Step 4: 6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrole-3-carboxylic acid 1-Chloro-N,N,2-trimethyl-1-propenylamine (1.057 mL, 7.99 mmol) was added to a stirred suspension of 2-((4-chlorophenyl)((1,4-dimethyl-1H-benzo[d][1,2,3]triazol-6-yl)amino)methyl)-1-methyl-1H-pyrrole-3,4-dicarboxylic acid (Step 3 of Example 98, 2.59 g, 5.71 mmol, mixture of two compounds) in DCM at rt under Ar. The reaction mixture was stirred for 1 h at rt and concentrated. The residue was triturated in Et₂O to afford the title compound (2.18 g, purity 85%) as a yellow solid. Rt: 0.88 min (LC-MS 1); MS m/z: 436.2 [M+H]⁺ (LC-MS 1)

Step 5: 6-(4-chlorophenyl)-5-(1,4-dimethyl-1H-benzo[d][1,2,3]triazol-6-yl)-N,1-dimethyl-4-oxo-1,4,5,6-tetrahydropyrrolo[3,4-b]pyrrole-3-carboxamide DIEA (0.163 mL, 0.936 mmol) was added to a stirred suspension of 6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrole-3-carboxylic acid (Step 4 of Example 98, 120 mg, 0.234 mmol), TBTU (98 mg, 0.304 mmol) and methylamine hydrochloride (79 mg, 1.170 mmol) in DMF (2 mL) at rt. The reaction mixture was stirred for 2 h, diluted in EtOAc/water, and extracted twice with EtOAc. The combined organic extracts were washed with brine, dried (Na₂SO₄), filtered and the filtrate was concentrated. The residue was purified by silica gel chromatography on Combiflash Isco (eluent: MeOH/DCM; gradient: 0% to 6.2% MeOH in 17.8 min; flow: 30 mL/min) followed by trituration of the resulting material in Et₂O to afford the title compound (47 mg) as a colorless solid. Rf=0.17 (5% MeOH/DCM); Rt: 0.92 min (LC-MS 1); MS m/z: 449.3 [M+H]⁺ (LC-MS 1); ¹H NMR (400 MHz, DMSO-d6) δ 8.22 (q, J=4.5 Hz, 1H), 7.77 (d, J=1.7 Hz, 1H), 7.46 (s, 1H), 7.42-7.30 (m, 5H), 6.75 (s, 1H), 4.19 (s, 3H), 3.37 (s, 3H), 2.83 (d, J=4.5 Hz, 3H), 2.59 (s, 3H).

Example 99

6-(4-chlorophenyl)-5-(3,8-dimethyl-[1,2,4]triazolo[4,3-a]pyridin-6-yl)-N,1-dimethyl-4-oxo-1,4,5,6-tetrahydropyrrolo[3,4-b]pyrrole-3-carboxamide

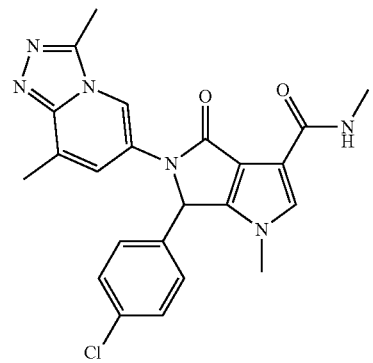 [SMILES: CNC(=O)c1cn(C)c2c1C(=O)N(c1cc(C)c3nnc(C)n3c1)C2c1ccc(Cl)cc1]

The title compound was prepared using an analogous procedure to that described in Steps 2-5 of Example 98 using 3,8-dimethyl-[1,2,4]triazolo[4,3-a]pyridin-6-amine (Step 4 of Example 3) in Step 2 of Example 98. Rf: 0.16 (1% ammonia/5% MeOH/DCM); Rt: 0.77 min (LC-MS 1); MS m/z: 449.3 [M+H]⁺ (LC-MS 1); ¹H NMR (400 MHz, DMSO-d6) δ 2.43 (s, 3H) 2.61 (s, 3H) 2.82 (d, J=4.69 Hz, 3H) 3.37 (s, 3H) 6.62 (s, 1H) 7.28-7.43 (m, 5H) 7.48 (s, 1H) 8.13 (q, J=4.56 Hz, 1H) 8.39 (s, 1H).

Example 100

6-(4-chlorophenyl)-5-(3,8-dimethyl-[1,2,4]triazolo[4,3-a]pyridin-6-yl)-N,N,1-trimethyl-4-oxo-1,4,5,6-tetrahydropyrrolo[3,4-b]pyrrole-3-carboxamide

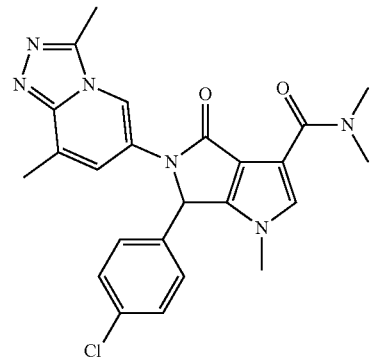 [SMILES: Cc1cc(N2C(=O)c3c(C(=O)N(C)C)cn(C)c3C2c2ccc(Cl)cc2)cn2c(C)nnc12]

The title compound was prepared using an analogous procedure to that described in Steps 2-5 of Example 98 using 3,8-dimethyl-[1,2,4]triazolo[4,3-a]pyridin-6-amine (Step 4 of Example 3) in Step 2 of Example 98 and dimethylamine hydrochloride in Step 5 of Example 98. Rf: 0.18 (1% ammonia/5% MeOH/DCM); Rt: 0.75 min (LC-MS 1); MS m/z: 463.3 [M+H]$^+$ (LC-MS 1); $^1$H NMR (400 MHz, DMSO-d6) δ 2.42 (s, 3H) 2.60 (s, 3H) 2.94 (br. s, 3H) 3.14 (br. s, 3H) 3.34 (s, 3H) 6.54 (s, 1H) 7.25 (s, 1H) 7.28-7.46 (m, 5H) 8.34 (s, 1H).

Example 101

6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrole-3-carboxamide

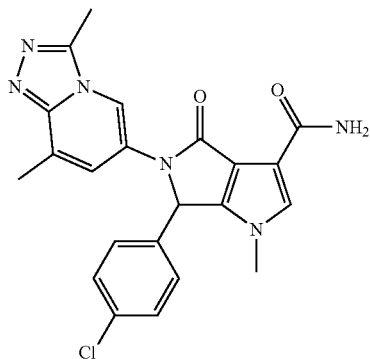 [SMILES: Cc1cc(N2C(=O)c3c(C(N)=O)cn(C)c3C2c2ccc(Cl)cc2)cn2c(C)nnc12]

Step 1: 6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrole-3-carboxylic acid The title compound was prepared using an analogous procedure to that described in Steps 2-4 of Example 98 using 3,8-dimethyl-[1,2,4]triazolo[4,3-a]pyridin-6-amine (Step 4 of Example 3) in Step 2 of Example 98. Rt: 0.73 min (LC-MS 1); MS m/z: 436.3 [M+H]$^+$ (LC-MS 1).

Step 2: 6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrole-3-carbonyl chloride Oxalyl chloride (0.202 mL, 2.313 mmol) was added to 6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrole-3-carboxylic acid (Step 1 of Example 101, 672 mg, 1.542 mmol) in toluene (10 mL) and pyridine (0.1 mL). The reaction mixture was heated to 100° C., stirred for 2 h, and concentrated to afford the title compound (1.14 g, purity 46%) as a brown solid. Rt: 0.80 min (LC-MS 1); MS m/z: 450.3 [M+H]$^+$ (methyl ester) (LC-MS 1).

Step 3: 6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrole-3-carboxamide A mixture of 6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrole-3-carbonyl chloride (Step 2 of Example 101, 300 mg, 0.660 mmol) and ammonium hydroxide (3 mL, 23.11 mmol) was stirred for 5 h at rt, diluted in DCM/water, and extracted twice with DCM. The combined organic extracts were dried (Na$_2$SO$_4$), filtered and the filtrate was concentrated. The residue was purified by silica gel chromatography on Combiflash Isco (eluent: MeOH/DCM; gradient: 1.6 min 0% MeOH, 0% to 9.9% MeOH in 18.4 min, 7.5 min 9.9% MeOH; flow: 35 mL/min) followed by trituration of the resulting material in acetonitrile to afford the title compound (14 mg) as a colorless solid. Rf=0.37 (10% MeOH/DCM); Rt: 0.72 min (LC-MS 1); MS m/z: 435.3 [M+H]$^+$ (LC-MS 1); $^1$H NMR (400 MHz, DMSO-d6) δ 2.43 (s, 3H) 2.61 (s, 3H) 3.37 (s, 3H) 6.60 (s, 1H) 7.24-7.41 (m, 6H) 7.45 (s, 1H) 7.70 (br. s, 1H) 8.38 (s, 1H).

Example 102

Tert-butyl (6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)carbamate

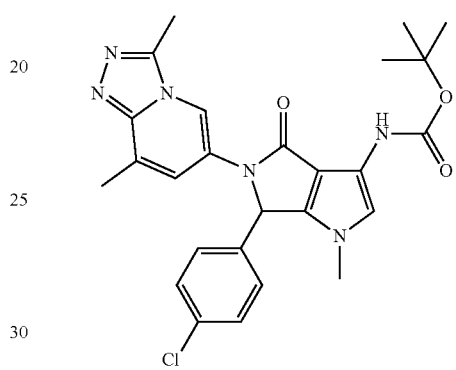

Step 1: 6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrole-3-carbonyl azide A mixture of 6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrole-3-carboxylic acid (Step 1 of Example 101, 100 mg, 0.184 mmol), sodium azide (14.32 mg, 0.220 mmol), TBTU (64.8 mg, 0.202 mmol) and DIEA (0.096 mL, 0.551 mmol) in DMF (2 mL) was stirred for 2 h at rt under Ar, diluted in EtOAc/water, and extracted once with EtOAc. The combined organic extracts were washed with brine, dried (Na$_2$SO$_4$), filtered and the filtrate was concentrated to afford the title compound (62 mg, purity 88%) as a beige solid. Rt: 0.88 min (LC-MS 1); MS m/z: 461.2 [M+H]$^+$ (LC-MS 1).

Step 2: Tert-butyl (6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)carbamate A mixture of 6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrole-3-carbonyl azide (Step 1 of Example 102, 62 mg, 0.118 mmol) in toluene (2 mL) and tert-butanol (0.2 mL) was heated to 100° C., stirred for 1 h, and concentrated. The residue was purified by silica gel chromatography on Combiflash Isco (eluent: MeOH/DCM; gradient: 0% to 7% MeOH in 15.9 min; flow: 30 mL/min) to afford the title compound (40 mg) as a colorless solid. Rf=0.22 (5% MeOH/DCM); Rt: 1.04 min (LC-MS 1); MS m/z: 507.3 [M+H]$^+$ (LC-MS 1); $^1$H NMR (400 MHz, DMSO-d6) δ ppm 1.43 (s, 9H) 2.42 (s, 3H) 2.59 (s, 3H) 3.25 (s, 3H) 6.45 (s, 1H) 6.90 (br. s, 1H) 7.23-7.43 (m, 5H) 8.29 (s, 1H) 8.55 (br. s, 1H).

Example 103

N-(6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)acetamide

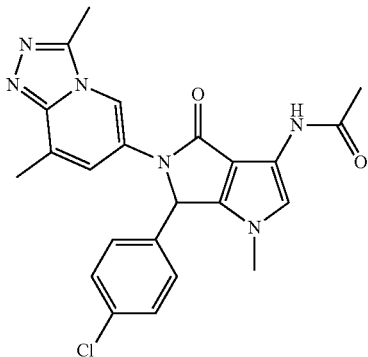 [SMILES: CC(=O)Nc1cn(C)c2c1C(=O)N(c1cc(C)c3nnc(C)n3c1)C2c1ccc(Cl)cc1]

Step 1: 3-amino-6-(4-chlorophenyl)-5-(3,8-dimethyl-[1,2,4]triazolo[4,3-a]pyridin-6-yl)-1-methyl-5,6-dihydropyrrolo[3,4-b]pyrrol-4(1H)-one TFA (1 mL) was added to a stirred solution of tert-butyl (6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)carbamate (Step 2 of Example 102, 228 mg, 0.427 mmol) in DCM (2 mL) at 0° C. The reaction mixture was allowed to warm to rt, stirred for 30 min, diluted in DCM, poured into a cold, saturated aqueous solution of sodium bicarbonate, and extracted twice with DCM. The combined organic extracts were dried ($Na_2SO_4$), filtered and the filtrate was concentrated to afford the title compound (177 mg) as a yellow solid (the free base is prone to decomposition). Rt: 0.66 min (LC-MS 1); MS m/z: 407.3 $[M+H]^+$ (LC-MS 1).

Step 2: N-(6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)acetamide Acetyl chloride (0.013 mL, 0.177 mmol) was added to a stirred solution of 3-amino-6-(4-chlorophenyl)-5-(3,8-dimethyl-[1,2,4]triazolo[4,3-a]pyridin-6-yl)-1-methyl-5,6-dihydropyrrolo[3,4-b]pyrrol-4(1H)-one (Step 1 of Example 103, 60 mg, 0.147 mmol) and triethylamine (0.062 mL, 0.442 mmol) in DCM (2 mL) at 0° C. The reaction mixture was stirred for 5 min at 0° C., diluted in DCM/water, and extracted twice with DCM. The combined organic extracts were washed with brine, dried ($Na_2SO_4$), filtered and the filtrate was concentrated. The residue was purified by preparative achiral SFC (column: 4-EP 250×30 mm, 5 μm, 100 A, Princeton; eluent: MeOH/scCO$_2$; gradient: 1 min 13% MeOH, 13% to 18% MeOH in 6 min, 18% to 50% MeOH, in 1 min, 1.5 min 50% MeOH; flow: 100 mL/min). The resulting material was triturated in $Et_2O$ to afford the title compound (27 mg) as a yellow solid. Rf=0.39 (10% MeOH/DCM); Rt: 0.77 min (LC-MS 1); MS m/z: 449.3 $[M+H]^+$ (LC-MS 1); $^1$H NMR (400 MHz, DMSO-d6) δ 9.77 (s, 1H), 8.32 (d, J=1.6 Hz, 1H), 7.45-7.20 (m, 6H), 6.47 (s, 1H), 3.26 (s, 3H), 2.60 (s, 3H), 2.42 (s, 3H), 2.04 (s, 3H).

Example 104

6-(4-chlorophenyl)-3-cyclopropyl-5-(3,7-dimethyl-3H-[1,2,3]triazolo[4,5-b]pyridin-5-yl)-1-(oxetan-3-yl)-5,6-dihydropyrrolo[3,4-b]pyrrol-4(1H)-one

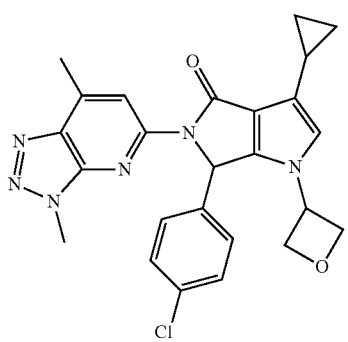 [SMILES: Cc1cc(N2C(=O)c3c(C4CC4)cn(C4COC4)c3C2c2ccc(Cl)cc2)nc2c1nnn2C]

Step 1: 6-(4-chlorophenyl)-3-cyclopropyl-5-(3,7-dimethyl-3H-[1,2,3]triazolo[4,5-b]pyridin-5-yl)-5,6-dihydropyrrolo[3,4-b]pyrrol-4(1H)-one To a stirred solution of 6-(4-chlorophenyl)-3-cyclopropyl-5-(3,7-dimethyl-3H-[1,2,3]triazolo[4,5-b]pyridin-5-yl)-1-(hydroxymethyl)-5,6-dihydropyrrolo[3,4-b]pyrrol-4(1H)-one (Step 10 of Example 1, 490 mg, 1.092 mmol) in THF (10 mL) was added aqueous NaOH (1N in water, 10.92 mL, 10.92 mmol). The reaction mixture was stirred for 1 h at rt, diluted with aqueous NaOH (0.1N, 75 mL), and extracted with EtOAc (2×100 mL). The combined organic extracts were dried ($Na_2SO_4$), filtered and the filtrate was concentrated. The residue was triturated in DCM to afford the title compound (346 mg, purity 92%) as a colorless solid. Rt: 1.17 min (LC-MS 1); MS m/z: 419.3 $[M+H]^+$ (LC-MS 1).

Step 2: 6-(4-chlorophenyl)-3-cyclopropyl-5-(3,7-dimethyl-3H-[1,2,3]triazolo[4,5-b]pyridin-5-yl)-1-(oxetan-3-yl)-5,6-dihydropyrrolo[3,4-b]pyrrol-4(1H)-one The title compound was prepared using an analogous procedure to that described in Example 6 using 6-(4-chlorophenyl)-3-cyclopropyl-5-(3,7-dimethyl-3H-[1,2,3]triazolo[4,5-b]pyridin-5-yl)-5,6-dihydropyrrolo[3,4-b]pyrrol-4(1H)-one (Step 1 of Example 104). Rf=0.33 (50% EtOAc/hexane); Rt: 1.21 min (LC-MS 1); MS m/z: 475.3 $[M+H]^+$ (LC-MS 1); $^1$H NMR (400 MHz, DMSO-d6) δ 8.26 (s, 1H), 7.49-7.17 (m, 5H), 6.67 (s, 1H), 5.00 (p, J=7.0 Hz, 1H), 4.84-4.55 (m, 2H), 4.30 (t, J=6.6 Hz, 1H), 4.11 (s, 3H), 4.06-3.94 (m, 1H), 2.63 (s, 3H), 1.95-1.72 (m, 1H), 1.01-0.71 (m, 4H).

Example 105

1-(1-acetylazetidin-3-yl)-6-(4-chlorophenyl)-3-cyclopropyl-5-(3,7-dimethyl-3H-[1,2,3]triazolo[4,5-b]pyridin-5-yl)-5,6-dihydropyrrolo[3,4-b]pyrrol-4(1H)-one

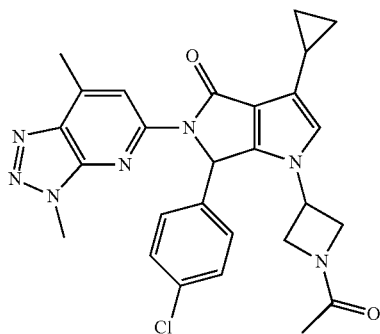 [SMILES: CC(=O)N1CC(n2cc(C3CC3)c3c2C(c2ccc(Cl)cc2)N(c2cc(C)c4nnn(C)c4n2)C3=O)C1]

Step 1: Tert-butyl 3-(6-(4-chlorophenyl)-3-cyclopropyl-5-(3,7-dimethyl-3H-[1,2,3]triazolo[4,5-b]pyridin-5-yl)-4-oxo-5,6-dihydropyrrolo[3,4-b]pyrrol-1(4H)-yl)azetidine-1-carboxylate The title compound was prepared using an analogous procedure to that described in Step 3 of Example 4 using 6-(4-chlorophenyl)-3-cyclopropyl-5-(3,7-dimethyl-3H-[1,2,3]triazolo[4,5-b]pyridin-5-yl)-5,6-dihydropyrrolo[3,4-b]pyrrol-4(1H)-one (Step 1 of Example 104) and stirring the reaction mixture for 2 h at 80° C. Rf=0.53 (50% EtOAc/hexane); Rt: 1.38 min (LC-MS 1); MS m/z: 574.4 [M+H]$^+$ (LC-MS 1).

Step 2: 1-(azetidin-3-yl)-6-(4-chlorophenyl)-3-cyclopropyl-5-(3,7-dimethyl-3H-[1,2,3]triazolo[4,5-b]pyridin-5-yl)-5,6-dihydropyrrolo[3,4-b]pyrrol-4(1H)-one The title compound was prepared using an analogous procedure to that described in Step 4 of Example 4 using tert-butyl 3-(6-(4-chlorophenyl)-3-cyclopropyl-5-(3,7-dimethyl-3H-[1,2,3]triazolo[4,5-b]pyridin-5-yl)-4-oxo-5,6-dihydropyrrolo[3,4-b]pyrrol-1(4H)-yl)azetidine-1-carboxylate (Step 1 of Example 105) and stirring the reaction mixture for 1 h at rt. Rf=0.35 (10% MeOH/DCM); Rt: 0.85 min (LC-MS 1); MS m/z: 474.3 [M+H]$^+$ (LC-MS 1).

Step 3: 1-(1-acetylazetidin-3-yl)-6-(4-chlorophenyl)-3-cyclopropyl-5-(3,7-dimethyl-3H-[1,2,3]triazolo[4,5-b]pyridin-5-yl)-5,6-dihydropyrrolo[3,4-b]pyrrol-4(1H)-one The title compound was prepared using an analogous procedure to that described in Example 7 using 1-(azetidin-3-yl)-6-(4-chlorophenyl)-3-cyclopropyl-5-(3,7-dimethyl-3H-[1,2,3]triazolo[4,5-b]pyridin-5-yl)-5,6-dihydropyrrolo[3,4-b]pyrrol-4(1H)-one (Step 2 of Example 105). Rf=0.58 (10% MeOH/DCM); Rt: 1.09 min (LC-MS 1); MS m/z: 516.3 [M+H]$^+$ (LC-MS 1); $^1$H NMR (400 MHz, DMSO-d6) δ 8.26 (s, 1H), 7.51-7.26 (m, 4H), 7.18 (s, 1H), 6.70 (s, 1H), 4.77-4.58 (m, 1H), 4.39-3.79 (m, 6H), 3.65-3.43 (m, 1H), 2.63 (s, 3H), 1.95-1.78 (m, 1H), 1.69 (s, 3H), 1.01-0.77 (m, 4H).

Example 106

6-(4-chlorophenyl)-3-cyclopropyl-5-(3,7-dimethyl-3H-[1,2,3]triazolo[4,5-b]pyridin-5-yl)-1-(1-methylazetidin-3-yl)-5,6-dihydropyrrolo[3,4-b]pyrrol-4(1H)-one

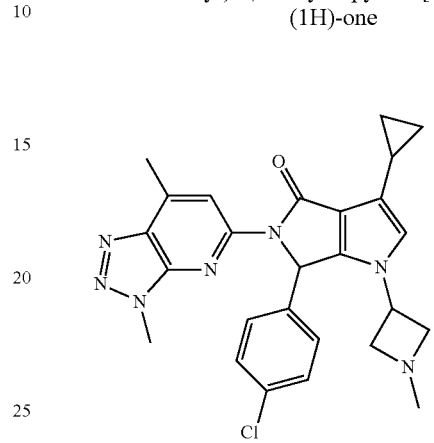

The title compound was prepared using an analogous procedure to that described in Example 5 using 1-(azetidin-3-yl)-6-(4-chlorophenyl)-3-cyclopropyl-5-(3,7-dimethyl-3H-[1,2,3]triazolo[4,5-b]pyridin-5-yl)-5,6-dihydropyrrolo[3,4-b]pyrrol-4(1H)-one (Step 2 of Example 105) and stirring the reaction mixture for 16 h at rt. Rf=0.49 (10% MeOH/DCM); Rt: 0.89 min (LC-MS 1); MS m/z: 488.3 [M+H]$^+$ (LC-MS 1); $^1$H NMR (400 MHz, DMSO-d6) δ 8.26 (q, J=0.8 Hz, 1H), 7.43-7.29 (m, 4H), 7.14 (s, 1H), 6.64 (s, 1H), 4.38-4.24 (m, 1H), 4.11 (s, 3H), 3.57-3.43 (m, 1H), 3.25-3.20 (m, 1H), 2.83-2.72 (m, 1H), 2.72-2.59 (m, 4H), 2.16 (s, 3H), 1.92-1.78 (m, 1H), 0.99-0.77 (m, 4H).

Example 107

6-(4-chlorophenyl)-5-(3-(difluoromethyl)-8-methyl-[1,2,4]triazolo[4,3-a]pyridin-6-yl)-1,3-dimethyl-5,6-dihydropyrrolo[3,4-b]pyrrol-4(1H)-one

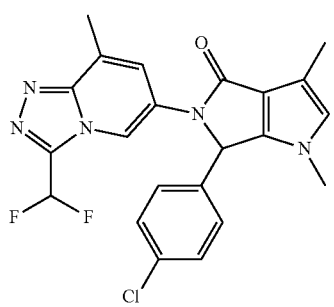 [SMILES: Cc1cn(C)c2c1C(=O)N(c1cc(C)c3nnc(C(F)F)n3c1)C2c1ccc(Cl)cc1]

Step 1: 2-hydrazinyl-3-methyl-5-nitropyridine

At rt 2-chloro-3-methyl-5-nitropyridine (250 g, 1449 mmol) and ethanol (2800 mL) were placed in a 4.5 L 4-neck flask equipped with stirrer, internal thermometer and bubble counter to give a yellow suspension. Hydrazine hydrate (352 mL, 7243 mmol) was added via a dropping funnel within 15 min. The reaction was slightly exothermic with the reaction temperature raising to 50° C. after 1 hour. After additional 2 hours the reaction was complete. It was cooled to 10° C. in an ice/acetone bath and stirred for 30 min. The resulting suspension was filtered and the collected solid washed with cold water (200 mL) and TBME (200 mL) and dried under vacuum at 50° C. for 5 h to give the title compound (238 g) as a yellow solid. Rt: 0.46 min (LC-MS 1); MS m/z: 169.1 [M+H]$^+$ (LC-MS 1).

Step 2: 2,2-difluoro-N'-(3-methyl-5-nitropyridin-2-yl)acetohydrazide, 3-(difluoromethyl)-8-methyl-6-nitro-[1,2,4]triazolo[4,3-a]pyridine To a solution of 2-hydrazinyl-3-methyl-5-nitropyridine (Step 1 of Example 107, 14 g, 83 mmol) in dioxane (114 mL) was added 2,2-difluoroacetic anhydride (11.78 mL, 92 mmol) diluted with THF (2 mL) over a period of 30 min at 0° C. The reaction mixture was stirred for 0.5 h at 0° C. and then heated to 140° C. with MW irradiation for 1.5 h. It was allowed to cool to rt and concentrated to give a brown solid, which was washed with cold EtOAc to give a beige solid. Combined washing solvents were concentrated and submitted to silica gel column chromatography (hexanes/EtOAc; gradient 9:1-1:1; then EtOAc with 10% MeOH) to give a second batch of the title compound as beige solid (combined: 16.3 g). Rt: 0.70 min (LC-MS 1); MS m/z: 229.1 [M]$^+$ (LC-MS 1).

Step 3: 3-(difluoromethyl)-8-methyl-[1,2,4]triazolo[4,3-a]pyridin-6-amine 3-(Difluoromethyl)-8-methyl-6-nitro-[1,2,4]triazolo[4,3-a]pyridine (Step 2 of Example 107, 15 g, 90% purity; 59.2 mol) was dissolved in MeOH (300 mL). Pd—C (10%; 4.09 g) was added and the reaction mixture exposed to hydrogen atmosphere in a shaker for 3 h at 55° C. The reaction mixture was then allowed to cool to rt and the catalyst removed by filtration. The filter cake was washed with MeOH. Combined filtrates and washing solvents were concentrated under reduced pressure. The remaining crude material was purified by silica gel column chromatography (hexanes/EtOAc, gradient 7:3→1:4; then (9:1 CH$_2$Cl$_2$/MeOH+0.1% NH$_3$ conc) to give the title compound (8.6 g) as a beige solid. Rt: 0.48 min (LC-MS 1); MS m/z: 199.1 [M]$^+$ (LC-MS 1).

Step 4: Ethyl 2-((4-chlorophenyl)((3-(difluoromethyl)-8-methyl-[1,2,4]triazolo[4,3-a]pyridin-6-yl)amino)methyl)-1,4-dimethyl-1H-pyrrole-3-carboxylate To a solution of ethyl 2-((4-chlorophenyl)(hydroxy)methyl)-1,4-dimethyl-1H-pyrrole-3-carboxylate (Step 1 of Example 32, 250 mg, 0.812 mmol) in DCM (6 mL) was added 1-chloro-N,N,2-trimethyl-1-propenylamine (Aldrich; 0.168 mL, 1.218 mmol) under Argon. The colorless solution was stirred for 2 h at rt. Triethylamine (0.340 mL, 2.437 mmol) and 3-(difluoromethyl)-8-methyl-[1,2,4]triazolo[4,3-a]pyridin-6-amine (Step 3 of Example 107, 177 mg, 0.894 mmol) were then then added at 0° C. and then the reaction mixture slowly allowed to warm to rt and stirred for 12 h at rt. Brine and EtOAc were added and the phases separated. The aqueous phase was repeatedly extracted with EtOAc and combined extracts were dried over sodium sulfate and concentrated. The residue was purified by silica gel chromatography on Combiflash Isco (eluent: EtOAc/hexane; 3 min 0% EtOAc, 0% to 50% EtOAc in 17 min, 20 min 50% EtOAc, 50% to 100% EtOAc in 20 min; flow 35 mL/min) to afford the title compound (264 mg; purity 96%) as a pale yellow solid. Rt: 1.23 min (LC-MS 1); MS m/z: 488 [M+H]$^+$ (LC-MS 1); $^1$H NMR (400 MHz, CD$_3$OD) δ 7.50 (s, 1H), 7.41-7.32 (m, 2H), 7.22 (dd, J=14.3, 8.7 Hz, 3H),6.87 (d, J=5.7 Hz, 1H), 6.44 (s, 1H), 4.57 (s, 1H), 4.37-4.18 (m, 2H), 3.42 (s, 3H), 3.35 (s, 1H), 2.57 (s, 3H), 2.20 (s, 3H), 1.34 (t, J=7.1 Hz, 3H).

Step 5: 2-((4-chlorophenyl)((3-(difluoromethyl)-8-methyl-[1,2,4]triazolo[4,3-a]pyridin-6-yl)amino)methyl)-1,4-dimethyl-1H-pyrrole-3-carboxylic acid To a cooled solution of ethyl 2-((4-chlorophenyl)((3-(difluoromethyl)-8-methyl-[1,2,4]triazolo[4,3-a]pyridin-6-yl)amino)methyl)-1,4-dimethyl-1H-pyrrole-3-carboxylate (Step 4 of Example 107, 50 mg, 0.102 mmol) in THF (1 mL) and MeOH (1 mL) was added drop wise aqueous NaOH (2M, 1.025 mL, 2.049 mmol). The reaction mixture was allowed to warm to rt, stirred for 1 h and successively heated to 100° C. and stirred for additional 5 h. It was then allowed to cool to rt and concentrated. The residue was further cooled to 0° C. and treated with 1 mL of 2M HCl, the pH was adjusted to 6 and the aqueous layers were extracted with EtOAc containing 5% MeOH. Combined extracts were dried over sodium sulfate, filtered and concentrated to give the title compound (32 mg; purity 75%) as a yellow solid. Rt: 1.00 min (LC-MS 1); MS m/z: 460.1 [M+H]$^+$ (LC-MS 1).

Step 6: 6-(4-chlorophenyl)-5-(3-(difluoromethyl)-8-methyl-[1,2,4]triazolo[4,3-a]pyridin-6-yl)-1,3-dimethyl-5,6-dihydropyrrolo[3,4-b]pyrrol-4(1H)-one 2-((4-Chlorophenyl)((3-(difluoromethyl)-8-methyl-[1,2,4]triazolo[4,3-a]pyridin-6-yl)amino)methyl)-1,4-dimethyl-1H-pyrrole-3-carboxylic acid (Step 5 of Example 107, 32 mg, 0.052 mmol) was suspended in DCM (2 mL) and cooled to 0° C. under Ar. 1-Chloro-N,N,2-trimethylprop-1-en-1-amine (Aldrich, 0.014 mL, 0.104 mmol) was added drop wise while the solids gradually dissolved resulting in a yellow solution, which was allowed to stir at rt for 30 min. Water and DCM were added to the reaction mixture. The biphasic mixture was separated and the organic phase was dried over sodium sulfate, filtered and concentrated. The crude product was purified by preparative achiral SFC (column: 4-EP, 250×30 mm, 5 μm, 60 A, Princeton; eluent: MeOH/scCO$_2$; gradient: 1 min 10% MeOH, 10% to 15% MeOH in 6 min, 15% to 50% MeOH in 1 min, 1.5 min 50% MeOH; flow: 100 mL/min). The fractions containing product were collected, concentrated and dried under vacuum to give the title compound (9 mg) as a white solid. Rt: 1.04 min (LC-MS 1); MS m/z: 442.2 [M+H]$^+$ (LC-MS 1); $^1$H NMR (400 MHz, CD$_3$OD) δ 8.63 (s, 1H), 7.63 (s, 1H), 7.58-7.22 (m, 5H), 6.60 (s, 1H), 6.31 (s, 1H), 3.33 (s, 3H), 2.60 (s, 3H), 2.25 (s, 3H).

Example 108

6-(4-chlorophenyl)-5-(3-(difluoromethyl)-8-methyl-[1,2,4]triazolo[4,3-b]pyridazin-6-yl)-N,1-dimethyl-4-oxo-1,4,5,6-tetrahydropyrrolo[3,4-b]pyrrole-3-carboxamide

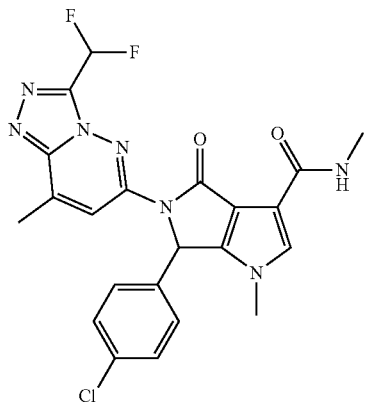 [SMILES: CNC(=O)c1cn(C)c2c1C(=O)N(c1cc(C)c3nnc(C(F)F)n3n1)C2c1ccc(Cl)cc1]

Step 1: 6-chloro-3-hydrazinyl-4-methylpyridazine 3,6-Dichloro-4-methylpyridazine (Combi-Blocks) (60 g, 361 mmol) was dissolved in hydrazine monohydrate (Aldrich) (335 mL, 5411 mmol) and the solution was stirred at 80° C. for 1 h, forming a white precipitate. The reaction mixture was diluted with water and the precipitated products isolated by filtration. The solid crude product was suspended in EtOH and left in an ultra sound bath for 1 h. The desired product (22.4 g, 90% purity) was obtained after filtration and drying under vacuum as a beige solid. $t_R$: 0.31 min (LC-MS 1); ESI-MS: 160.0 [M+H]$^+$ (LC-MS 1). $^1$H NMR (400 MHz; DMSO-d6) δ ppm 7.83 (br.s, 1H) 7.32 (s, 1H) 4.49 (br.s, 2H) 2.05 (s, 3H).

Step 2: 6-chloro-3-(difluoromethyl)-8-methyl-[1,2,4]triazolo[4,3-b]pyridazine To a beige suspension of 6-chloro-3-hydrazinyl-4-methylpyridazine (Step 1) (22.44 g, 127 mmol) in dioxane (250 mL) was added difluoroacetic acid (Aldrich) (9.40 mL, 146 mmol) and the reaction mixture was stirred at rt for 5 min, then heated-up to 120° C. for 2.5 hr. With heating the suspension turned into a red-orange solution. The reaction mixture was cooled to rt. Et$_2$O (80 mL) was added and the suspension was stirred for 2 h at 0° C. Precipitated solids were isolated by filtration, suspended in hexanes and filtered again. After repeated washings with hexanes the title compound (18.14 g, 80% purity) was obtained as an orange solid.

$t_R$: 0.72 min (LC-MS 2); ESI-MS: 219.2 [M+H]$^+$ (LC-MS 2). $^1$H NMR (400 MHz; DMSO-d6) δ ppm 7.68 (t, 1H) 7.60 (s, 1H) 2.68 (s, 3H).

Step 3: 3-(difluoromethyl)-8-methyl-[1,2,4]triazolo[4,3-b]pyridazin-6-amine 6-chloro-3-(difluoromethyl)-8-methyl-[1,2,4]triazolo[4,3-b]pyridazine (Step 2) (3.0 g, 13.7 mmol) was suspended in aqueous NH$_3$ solution (24% wt; 41 mL) and copper iodide (135 mg, 0.709 mmol) was added. The reaction was heated at 100° C. for 18 h and allowed to cool to ambient temperature. The precipitated product was isolated by filtration and dried under vacuum to give the title compound (1.725 g) as an orange powder. $t_R$: 0.45 min (LC-MS 2); ESI-MS: 200.2 [M+H]$^+$/198.2 [M−H]$^−$ (LC-MS 2).

Step 4: Diethyl 2-((4-chlorophenyl)((3-(difluoromethyl)-8-methyl-[1,2,4]triazolo[4,3-b]pyridazin-6-yl)amino)methyl)-1-methyl-1H-pyrrole-3,4-dicarboxylate The title compound was prepared using an analogous procedure to that described in Step 3 of Example 93 but with the following modifications. After addition of 1-chloro-N,N,2-trimethyl-1-propenylamine (1.288 mL, 9.74 mmol, 1.5 eq), the reaction mixture was stirred for 16 h at rt. After addition of 3-(difluoromethyl)-8-methyl-[1,2,4]triazolo[4,3-b]pyridazin-6-amine (Step 3, 1.422 g, 7.14 mmol, 1.1 eq), the reaction mixture was stirred for 5 days at rt. The crude material was purified by silica gel chromatography on Combiflash Isco (eluent: MeOH/DCM, 0-3% MeOH in 25 min; flow: 60 mL/min) to afford the title compound (1.728 g) as a beige foam. Rt: 1.13 min (LC-MS 1); ESI-MS m/z: 200.1 [M+H]$^+$ (LC-MS 1).

Step 5: 2-((4-chlorophenyl)((3-(difluoromethyl)-8-methyl-[1,2,4]triazolo[4,3-b]pyridazin-6-yl)amino)methyl)-1-methyl-1H-pyrrole-3,4-dicarboxylic acid The title compound was prepared using an analogous procedure to that described in Step 4 of Example 93 but using diethyl 2-((4-chlorophenyl)((3-(difluoromethyl)-8-methyl-[1,2,4]triazolo[4,3-b]pyridazin-6-yl)amino)methyl)-1-methyl-1H-pyrrole-3,4-dicarboxylate (Step 4, 1.728 g, 3.16 mmol). The title compound (1.377 g) was obtained as a beige solid. Rt: 0.76 min (LC-MS 1); ESI-MS m/z: 491.2 [M+H]$^+$ (LC-MS 1).

Step 6: 6-(4-chlorophenyl)-5-(3-(difluoromethyl)-8-methyl-[1,2,4]triazolo[4,3-b]pyridazin-6-yl)-1-methyl-4-oxo-1,4,5,6-tetrahydropyrrolo[3,4-b]pyrrole-3-carboxylic acid The title compound was prepared using an analogous procedure to that described in Step 5 of Example 93 but using 2-((4-chlorophenyl)((3-(difluoromethyl)-8-methyl-[1,2,4]triazolo[4,3-b]pyridazin-6-yl)amino)methyl)-1-methyl-1H-pyrrole-3,4-dicarboxylic acid (Step 5, 1.375 g, 2.80 mmol). The reaction mixture was stirred for 3 h at rt. The title compound (1.165 g) was obtained as a colorless solid. Rt: 0.89 min (LC-MS 1); ESI-MS m/z: 473.3 [M+H]$^+$ (LC-MS 1).

Step 7: 6-(4-chlorophenyl)-5-(3-(difluoromethyl)-8-methyl-[1,2,4]triazolo[4,3-b]pyridazin-6-yl)-N,1-dimethyl-4-oxo-1,4,5,6-tetrahydropyrrolo[3,4-b]pyrrole-3-carboxamide The title compound was prepared using an analogous procedure to that described in Step 6 of Example 93 but using 6-(4-chlorophenyl)-5-(3-(difluoromethyl)-8-methyl-[1,2,4]triazolo[4,3-b]pyridazin-6-yl)-1-methyl-4-oxo-1,4,5,6-tetrahydropyrrolo[3,4-b]pyrrole-3-carboxylic acid (Step 6, 120 mg, 0.254 mmol), 4 eq of DIEA and 5 eq of methylamine hydrochloride. The crude material was triturated in EtOAc to afford the title compound (97 mg) as a colorless solid. Rt: 0.95 min (LC-MS 1); ESI-MS m/z: 486.2 [M+H]⁺ (LC-MS 1); ¹H NMR (400 MHz, DMSO-d6) δ 8.36 (s, 1H), 7.92 (d, J=5.0 Hz, 1H), 7.73-7.17 (m, 6H), 6.65 (s, 1H), 3.34 (s, 3H), 2.85 (d, J=4.6 Hz, 3H), 2.63 (s, 3H).

Example 109

N-(6-(4-chlorophenyl)-5-(3-(difluoromethyl)-8-methyl-[1,2,4]triazolo[4,3-b]pyridazin-6-yl)-1-methyl-4-oxo-1,4,5,6-tetrahydropyrrolo[3,4-b]pyrrol-3-yl)acetamide

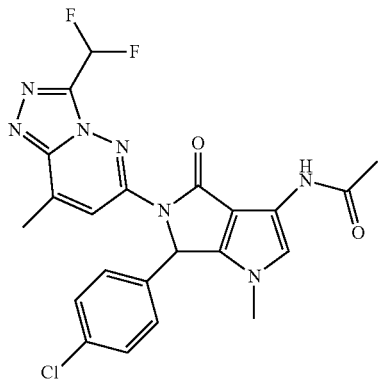 [SMILES: CC(=O)Nc1cn(C)c2c1C(=O)N(c1cc(C)c3nnc(C(F)F)n3n1)C2c1ccc(Cl)cc1]

Step 1: 6-(4-chlorophenyl)-5-(3-(difluoromethyl)-8-methyl-[1,2,4]triazolo[4,3-b]pyridazin-6-yl)-1-methyl-4-oxo-1,4,5,6-tetrahydropyrrolo[3,4-b]pyrrole-3-carbonyl azide The title compound was prepared using an analogous procedure to that described in Step 1 of Example 95 but using 6-(4-chlorophenyl)-5-(3-(difluoromethyl)-8-methyl-[1,2,4]triazolo[4,3-b]pyridazin-6-yl)-1-methyl-4-oxo-1,4,5,6-tetrahydropyrrolo[3,4-b]pyrrole-3-carboxylic acid (Step 6 of Example 108, 797 mg, 1.686 mmol) and 4 eq of DIEA. The reaction mixture was stirred for 1 h at rt, diluted in EtOAc/water, and extracted twice with EtOAc. The combined organic extracts were washed with brine, dried (Na₂SO₄) and concentrated. The crude material was triturated in EtOAc to afford the title compound (771 mg) as a colorless solid. Rt: 1.07 min (LC-MS 1); ESI-MS m/z: 498.1 (LC-MS 1).

Step 2: Tert-butyl (6-(4-chlorophenyl)-5-(3-(difluoromethyl)-8-methyl-[1,2,4]triazolo[4,3-b]pyridazin-6-yl)-1-methyl-4-oxo-1,4,5,6-tetrahydropyrrolo[3,4-b]pyrrol-3-yl)carbamate The title compound was prepared using an analogous procedure to that described in Step 2 of Example 95 but using 6-(4-chlorophenyl)-5-(3-(difluoromethyl)-8-methyl-[1,2,4]triazolo[4,3-b]pyridazin-6-yl)-1-methyl-4-oxo-1,4,5,6-tetrahydropyrrolo[3,4-b]pyrrole-3-carbonyl azide (Step 1, 768 mg, 1.466 mmol). The reaction mixture was stirred for 3 h at reflux. The crude material was purified by silica gel chromatography on Combiflash Isco (eluent: EtOAc/Hexane; gradient: 40-62.2% EtOAc in 10.6 min; flow: 40 mL/min) to afford the title compound (550 mg) as a colorless solid. Rt: 1.21 min (LC-MS 1); ESI-MS m/z: 544.2 (LC-MS 1).

Step 3: 3-amino-6-(4-chlorophenyl)-5-(3-(difluoromethyl)-8-methyl-[1,2,4]triazolo[4,3-b]pyridazin-6-yl)-1-methyl-5,6-dihydropyrrolo[3,4-b]pyrrol-4 (1H)-one HCl (4N in dioxane, 10 mL, 40.0 mmol) was added to tert-butyl (6-(4-chlorophenyl)-5-(3-(difluoromethyl)-8-methyl-[1,2,4]triazolo[4,3-b]pyridazin-6-yl)-1-methyl-4-oxo-1,4,5,6-tetrahydropyrrolo[3,4-b]pyrrol-3-yl)carbamate (Step 2, 547 mg, 1.006 mmol) at 0° C. The reaction mixture was stirred for 4.5 h at rt and concentrated to afford the title compound (578 mg, 89% purity) as a yellow solid. Rt: 0.87 min (LC-MS 1); ESI-MS m/z: 444.2 (LC-MS 1).

Step 4: N-(6-(4-chlorophenyl)-5-(3-(difluoromethyl)-8-methyl-[1,2,4]triazolo[4,3-b]pyridazin-6-yl)-1-methyl-4-oxo-1,4,5,6-tetrahydropyrrolo[3,4-b] pyrrol-3-yl)acetamide The title compound was prepared using an analogous procedure to that described in Step 2 of Example 96 but using 3-amino-6-(4-chlorophenyl)-5-(3-(difluoromethyl)-8-methyl-[1,2,4]triazolo[4,3-b]pyridazin-6-yl)-1-methyl-5,6-dihydropyrrolo[3,4-b]pyrrol-4(1H)-one (Step 3, 100 mg, 0.161 mmol). The reaction mixture was stirred for 1 h at rt. The crude material was purified by silica gel chromatography on Combiflash Isco (eluent: MeOH/DCM; gradient: 0-5.6% MeOH in 14.7 min; flow: 30 mL/min) and subsequent trituration of the resulting material in diethyl ether to afford the title compound (63 mg) as a colorless solid. Rt: 0.95 min (LC-MS 1); ESI-MS m/z: 486.2 [M+H]⁺ (LC-MS 1); ¹H NMR (400 MHz, DMSO-d6) δ 9.84 (s, 1H), 8.36 (d, J=1.8 Hz, 1H), 7.72-7.18 (m, 6H), 6.50 (s, 1H), 3.24 (s, 3H), 2.60 (d, J=1.1 Hz, 3H), 2.05 (s, 3H).

Example 110

N-(6-(4-chlorophenyl)-5-(3-(difluoromethyl)-8-methyl-[1,2,4]triazolo[4,3-b]pyridazin-6-yl)-1-methyl-4-oxo-1,4,5,6-tetrahydropyrrolo[3,4-b]pyrrol-3-yl)-3-(dimethylamino)propanamide

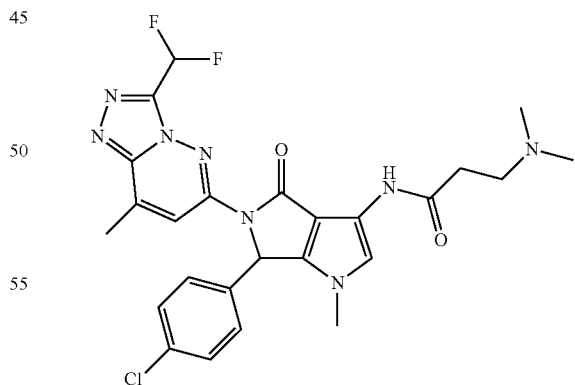

A mixture of 3-amino-6-(4-chlorophenyl)-5-(3-(difluoromethyl)-8-methyl-[1,2,4]triazolo[4,3-b]pyridazin-6-yl)-1-methyl-5,6-dihydropyrrolo[3,4-b]pyrrol-4(1H)-one (Step 3 of Example 109, 120 mg, 0.193 mmol),3-(dimethylamino) propanoic acid (24.88 mg, 0.212 mmol, 1.1 eq), TBTU (81 mg, 0.25 mmol, 1.3 eq), and DIEA (0.135 mL, 0.772 mmol, 4 eq) in DMF (3 mL) was stirred for 2 h at rt. The reaction mixture was diluted in DCM/water and extracted twice with DCM. The combined organic extracts were washed with brine, dried (Na₂SO₄) and concentrated. The residue was purified by preparative achiral SFC (column: Reprosil 70 NH2 (250×30 mm, 5 μm, 70 A, Dr Maisch; eluent: MeOH/scCO₂; gradient: 1 min 32% MeOH, 32-37% MeOH in 6 min, 37-50% MeOH in 1 min, 1.5 min 50% MeOH; flow: 100 mL/min) and subsequent trituration of the resulting material in diethyl ether to afford the title compound (11 mg) as a colorless solid. Rt: 0.77 min (LC-MS 1); ESI-MS m/z: 543.2 [M+H]⁺ (LC-MS 1); ¹H NMR (400 MHz, DMSO-d6) δ 10.73 (s, 1H), 8.37 (s, 1H), 7.72-7.17 (m, 6H), 6.50 (s, 1H), 3.24 (s, 3H), 2.60 (s, 3H), 2.57-2.40 (m, 4H), 2.24 (s, 6H).

Example 111

1-(6-(4-chlorophenyl)-5-(3-(difluoromethyl)-8-methyl-[1,2,4]triazolo[4,3-b]pyridazin-6-yl)-1-methyl-4-oxo-1,4,5,6-tetrahydropyrrolo[3,4-b]pyrrol-3-yl)-3-methylurea

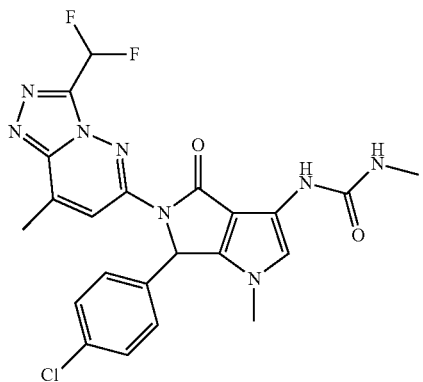 [SMILES: CNC(=O)Nc1cn(C)c2c1C(=O)N(c1cc(C)c3nnc(C(F)F)n3n1)C2c1ccc(Cl)cc1]

A mixture of 3-amino-6-(4-chlorophenyl)-5-(3-(difluoromethyl)-8-methyl-[1,2,4]triazolo[4,3-b]pyridazin-6-yl)-1-methyl-5,6-dihydropyrrolo[3,4-b]pyrrol-4(1H)-one (Step 3 of Example 109, 100 mg, 0.161 mmol), N-methyl-1H-imidazole-1-carboxamide (Step 1 of Example 9, 30.2 mg, 0.241 mmol) and triethylamine (0.090 mL, 0.644 mmol) in DCM (3 mL) were stirred for 20 h at rt. The reaction mixture was stirred for 8 h at reflux. N-methyl-1H-imidazole-1-carboxamide (Step 1 of Example 9, 210 mg, 1.678 mmol) and DCM (3 mL) were added. The reaction mixture was stirred for 16 h at reflux, diluted in DCM/water and extracted twice with DCM. The combined organic extracts were washed with brine, dried (Na₂SO₄) and concentrated. The residue was purified by silica gel chromatography on Combiflash Isco (eluent: MeOH/DCM; gradient: 0-6% MeOH in 20 min; flow: 30 mL/min) and subsequent trituration of the resulting material in diethyl ether to afford the title compound (34 mg) as a colorless solid. Rt: 0.93 min (LC-MS 1); ESI-MS m/z: 501.2 [M+H]⁺ (LC-MS 1); ¹H NMR (400 MHz, DMSO-d6) δ 8.37 (d, J=1.7 Hz, 1H), 8.20 (s, 1H), 7.68-7.27 (m, 5H), 7.05 (s, 1H), 6.53-6.38 (m, 2H), 3.21 (s, 3H), 2.69-2.55 (m, 6H).

Example 112

6-(4-chlorophenyl)-5-(1,4-dimethyl-1H-benzo[d][1,2,3]triazol-6-yl)-N-(2-(dimethylamino)ethyl)-1-methyl-4-oxo-1,4,5,6-tetrahydropyrrolo[3,4-b]pyrrole-3-carboxamide

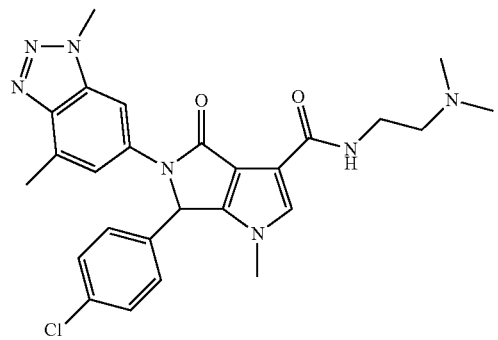 [SMILES: Cc1cc(N2C(=O)c3c(C(=O)NCCN(C)C)cn(C)c3C2c2ccc(Cl)cc2)cc2c1nnn2C]

Step 1:
1,4-dimethyl-1H-benzo[d][1,2,3]triazol-6-amine

A mixture of 6-bromo-1,4-dimethyl-1H-benzo[d][1,2,3]triazole (Step 3 of Example 28, 5 g, 19.68 mmol), NH₄OH (50 mL, 424 mmol) and copper(I) iodide (0.187 g, 0.984 mmol) was stirred in a pressure vessel for 14 h at 120° C., diluted in DCM/water, and extracted three times with DCM. The combined organic extracts were dried (Na₂SO₄) and concentrated. The residue was purified by silica gel chromatography on Combiflash Isco (eluent: MeOH/DCM; gradient: 0% MeOH 2.1 min, 0-1% MeOH in 4.9 min, 1% MeOH 9 min, 1-5% MeOH in 15.2 min; flow: 60 mL/min) to afford the title compound (1.256 g) as a brown solid. Rt: 0.47 min (LC-MS 1); ESI-MS m/z: 163.0 [M+H]⁺ (LC-MS 1).

Step 2: Diethyl 2-((4-chlorophenyl)((1,4-dimethyl-1H-benzo[d][1,2,3]triazol-6-yl)amino)methyl)-1-methyl-1H-pyrrole-3,4-dicarboxylate The title compound was prepared using an analogous procedure to that described in Step 3 of Example 93 but with the following modifications. After addition of 1,4-dimethyl-1H-benzo[d][1,2,3]triazol-6-amine (Step 1, 1.25 g, 7.71 mmol), the reaction mixture was stirred for 16 h at rt. Further 1,4-dimethyl-1H-benzo[d][1,2,3]triazol-6-amine (Step 1, 500 mg, 3.08 mmol) was added, followed after 2 h by additional 200 mg (1.23 mmol). The crude material was purified by silica gel chromatography on Combiflash Isco (eluent: EtOAc/Hexane, 50% EtOAc 2 min, 50-90% EtOAc in 25 min; flow: 60 mL/min) to afford the title compound (3.17 g, 87% purity) as an orange foam. Rt: 1.18 min (LC-MS 1); ESI-MS m/z: 510.1 [M+H]⁺ (LC-MS 1).

Step 3: 2-((4-chlorophenyl)((1,4-dimethyl-1H-benzo[d][1,2,3]triazol-6-yl)amino)methyl)-1-methyl-1H-pyrrole-3,4-dicarboxylic acid The title compound was prepared using an analogous procedure to that described in Step 4 of Example 93 but using diethyl 2-((4-chlorophenyl)((1,4-dimethyl-1H-benzo[d][1,2,3]triazol-6-yl)amino)methyl)-1-methyl-1H-pyrrole-3,4-dicarboxylate (Step 2, 3.17 g, 5.41 mmol). The reaction mixture was stirred for 1 h at 110° C. The crude material (2.59 g) contained a 1:1 mixture of the title compound and 6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrole-3-carboxylic acid (Step 4). Title compound: Rt: 0.75 min (LC-MS 1); ESI-MS m/z: 454.2 [M+H]+ (LC-MS 1).

Step 4: 6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrole-3-carboxylic acid The title compound was prepared using an analogous procedure to that described in Step 5 of Example 93 but using 2-((4-chlorophenyl)((1,4-dimethyl-1H-benzo[d][1,2,3]triazol-6-yl)amino)methyl)-1-methyl-1H-pyrrole-3,4-dicarboxylic acid (Step 3, 2.59 g, 5.71 mmol). The reaction mixture was concentrated. The residue was triturated in diethyl ether to provide the title compound (2.18 g, 85% purity) as a yellow solid. Rt: 0.88 min (LC-MS 1); ESI-MS m/z: 436.2 [M+H]+ (LC-MS 1).

Step 5: 6-(4-chlorophenyl)-5-(1,4-dimethyl-1H-benzo[d][1,2,3]triazol-6-yl)-N-(2-(dimethylamino)ethyl)-1-methyl-4-oxo-1,4,5,6-tetrahydropyrrolo[3,4-b]pyrrole-3-carboxamide The title compound was prepared using an analogous procedure to that described in Step 6 of Example 93 but using 6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrole-3-carboxylic acid (Step 4, 170 mg, 0.332 mmol), 4 eq of DIEA, 1.3 eq of TBTU and 1.2 eq of 2-dimethylaminoethylamine. The reaction mixture was stirred for 2 h at rt. The crude material was purified by silica gel chromatography on Combiflash Isco (eluent: MeOH/DCM; gradient: 0% to 7.7% MeOH in 13.8 min, 7.7% to 8.4% in 8.2 min; flow: 30 mL/min). The resulting material was further purified by preparative HPLC (Gilson gx-281. Column: Sunfire C18, 30×100 mm, 5 mm. Flow: 30 mL/min. Gradient: 5-50% B in 18 min; A=0.1% TFA in H$_2$O, B=CH$_3$CN. Detection: UV) and subsequent trituration in diethyl ether to afford the title compound (97 mg) as a colorless solid. Rt: 0.75 min (LC-MS 1); ESI-MS m/z: 506.3 [M+H]+ (LC-MS 1); $^1$H NMR (400 MHz, DMSO-d6) δ 8.27 (t, J=5.7 Hz, 1H), 7.74 (d, J=1.7 Hz, 1H), 7.45 (s, 1H), 7.41-7.26 (m, 5H), 6.72 (s, 1H), 4.19 (s, 3H), 3.48-3.31 (m, 5H), 2.58 (s, 3H), 2.38 (t, J=6.7 Hz, 2H), 2.16 (s, 6H).

Example 113

N-(6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrol-3-yl)acetamide

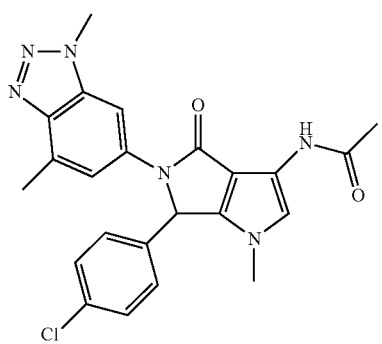 [SMILES: CC(=O)Nc1cn(C)c2c1C(=O)N(c1cc(C)c3nnn(C)c3c1)C2c1ccc(Cl)cc1]

Step 1: 6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrole-3-carbonyl azide The title compound was prepared using an analogous procedure to that described in Step 1 of Example 95 but using 6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrole-3-carboxylic acid (Step 4 of Example 112, 1.56 g, 3.04 mmol), 1.3 eq of TBTU and 4 eq of DIEA. The reaction mixture was stirred for 3 h at rt, diluted in EtOAc/water, and extracted twice with EtOAc. The combined organic extracts were washed with brine, dried (Na$_2$SO$_4$) and concentrated. The crude material was triturated in diethyl ether to afford the title compound (1.2 g) as a beige solid. Rt: 1.03 min (LC-MS 1); ESI-MS m/z: 461.1 (LC-MS 1).

Step 2: Tert-butyl (6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrol-3-yl)carbamate The title compound was prepared using an analogous procedure to that described in Step 2 of Example 95 but using. 6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrole-3-carbonyl azide (Step 1, 1.2 g, 2.448 mmol). The reaction mixture was stirred for 1 h at reflux. The crude material was purified by silica gel chromatography on Combiflash Isco (eluent: EtOAc/Hexane; gradient: 49.9% to 72.4% EtOAc in 8.5 min; flow: 40 mL/min) to afford the title compound (735 mg, 92% purity) as a colorless solid. Rt: 1.19 min (LC-MS 1); ESI-MS m/z: 507.2 [M+H]+ (LC-MS 1).

Step 3: 3-amino-6-(4-chlorophenyl)-5-(1,4-dimethyl-1H-benzo[d][1,2,3]triazol-6-yl)-1-methyl-5,6-dihydropyrrolo[3,4-b]pyrrol-4(1H)-one HCl (4N in dioxane, 10 mL, 40.0 mmol) was added to tert-butyl (6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrol-3-yl)carbamate (Step 2, 735 mg, 1.334 mmol) at 0° C. The reaction mixture was stirred for 4.5 h at rt and concentrated to afford the title compound (730 mg, 88% purity) as a beige solid. Rt: 0.79 min (LC-MS 1); ESI-MS m/z: 407.12 [M+H]+ (LC-MS 1).

Step 4: N-(6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrol-3-yl)acetamide The title compound was prepared using an analogous procedure to that described in Step 2 of Example 96 but using 3-amino-6-(4-chlorophenyl)-5-(1,4-dimethyl-1H-benzo[d][1,2,3]triazol-6-yl)-1-methyl-5,6-dihydropyrrolo[3,4-b]pyrrol-4(1H)-one (Step 3, 100 mg, 0.183 mmol), 2 eq of acetic anhydride and 4 eq of triethylamine. The reaction mixture was stirred for 15 min at rt. The crude material was purified by silica gel chromatography on Combiflash Isco (eluent: MeOH/DCM; gradient: 0-3.8% MeOH in 15.4 min; flow: 30 mL/min) and subsequent trituration of the resulting material in diethyl ether to afford the title compound (70 mg) as a colorless solid. Rt: 0.90 min (LC-MS 1); ESI-MS m/z: 449.3 [M+H]+ (LC-MS 1); $^1$H NMR (400 MHz, DMSO-d6) δ 9.73 (s, 1H), 7.69 (d, J=1.8 Hz, 1H), 7.45-7.15 (m, 6H), 6.58 (s, 1H), 4.17 (s, 3H), 3.26 (s, 3H), 2.57 (s, 3H), 2.04 (s, 3H).

Example 114

1-(6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrol-3-yl)-3-methylurea

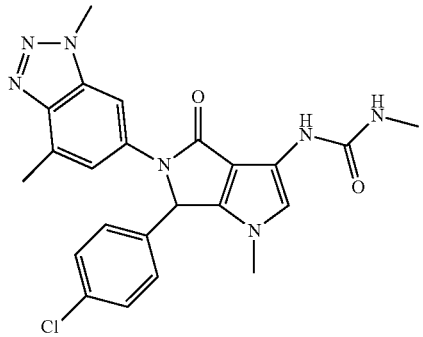 [SMILES: CNC(=O)Nc1cn(C)c2c1C(=O)N(c1cc(C)c3nnn(C)c3c1)C2c1ccc(Cl)cc1]

Step 1: 1-(6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrol-3-yl)-3-methylurea The title compound was prepared using an analogous procedure to that described in Example 111 but using 3-amino-6-(4-chlorophenyl)-5-(1,4-dimethyl-1H-benzo[d][1,2,3]triazol-6-yl)-1-methyl-5,6-dihydropyrrolo[3,4-b]pyrrol-4(1H)-one (Step 3 of Example 113, 100 mg, 0.183 mmol) and 4 eq of N-methyl-1H-imidazole-1-carboxamide (Step 1 of Example 9). The crude material was purified by silica gel chromatography on Combiflash Isco (eluent: MeOH/DCM; gradient: 0-7% MeOH in 20 min; flow: 35 mL/min). The resulting material was further purified by SFC (column: Reprosil 70 NH2 250×30 mm, 5 µm, 70 A, Dr Maisch; eluent: MeOH/scCO$_2$; gradient: 1 min 25% MeOH, 25-30% MeOH in 6 min, 30-50% MeOH in 1 min, 1.5 min 50% MeOH; flow: 100 mL/min) and subsequent trituration in diethyl ether to afford the title compound (19 mg) as a colorless solid. Rt: 0.90 min (LC-MS 1); ESI-MS m/z: 464.2 [M+H]$^+$ (LC-MS 1); $^1$H NMR (400 MHz, DMSO-d6) δ 8.11 (s, 1H), 7.68 (d, J=1.6 Hz, 1H), 7.43-7.24 (m, 5H), 7.00 (s, 1H), 6.55 (s, 1H), 6.45 (d, J=4.8 Hz, 1H), 4.16 (s, 3H), 3.24 (s, 3H), 2.61 (d, J=4.4 Hz, 3H), 2.56 (s, 3H).

Example 115

N-(6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrol-3-yl)-3-(dimethylamino)propanamide

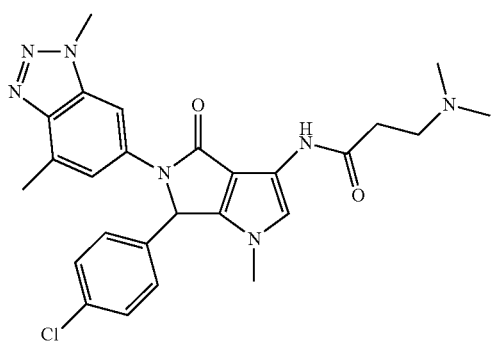 [SMILES: Cc1cc(N2C(=O)c3c(NC(=O)CCN(C)C)cn(C)c3C2c2ccc(Cl)cc2)cc2c1nnn2C]

The title compound was prepared using an analogous procedure to that described in Example 110 but using 3-amino-6-(4-chlorophenyl)-5-(1,4-dimethyl-1H-benzo[d][1,2,3]triazol-6-yl)-1-methyl-5,6-dihydropyrrolo[3,4-b]pyrrol-4(1H)-one (Step 3 of Example 113, 128 mg, 0.235 mmol). The crude material was purified by silica gel chromatography on Combiflash Isco (eluent: (20% ammonia/MeOH)/DCM; gradient: 0-8.0%(20% ammonia/MeOH) in 16 min, then 10%(20% ammonia/MeOH) in 3.8 min; flow: 30 mL/min) and subsequent trituration of the resulting material in diethyl ether to afford the title compound (13 mg) as a beige solid. Rt: 0.75 min (LC-MS 1); ESI-MS m/z: 506.3 [M+H]$^+$ (LC-MS 1); $^1$H NMR (400 MHz, DMSO-d6) δ 10.54 (s, 1H), 7.69 (s, 1H), 7.44-7.19 (m, 6H), 6.58 (s, 1H), 4.17 (s, 3H), 3.27 (s, 3H), 2.60-2.42 (m, 7H), 2.22 (s, 6H).

Example 116

N-(6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)-2-(dimethylamino)acetamide

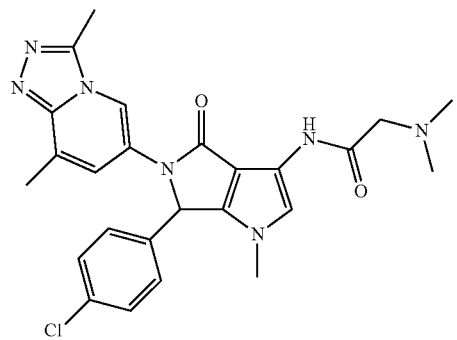 [SMILES: Cc1cc(N2C(=O)c3c(NC(=O)CN(C)C)cn(C)c3C2c2ccc(Cl)cc2)cn2c(C)nnc12]

DIEA (0.136 mL, 0.778 mmol) was added to a stirred solution of 3-amino-6-(4-chlorophenyl)-5-(3,8-dimethyl-[1,2,4]triazolo[4,3-a]pyridin-6-yl)-1-methyl-5,6-dihydropyrrolo[3,4-b]pyrrol-4(1H)-one (Step 1 of Example 103, 86 mg, 0.156 mmol) and 2-(dimethylamino)acetic acid (20.86 mg, 0.202 mmol) in DMF (3 mL). The reaction mixture was stirred for 1 h at rt, diluted in EtOAc/water and extracted twice with EtOAc. The combined organic extracts were washed with brine, dried (Na$_2$SO$_4$) and concentrated. The residue was purified by silica gel chromatography on Combiflash Isco (eluent: MeOH/DCM; gradient: 0-10% MeOH in 20 min; flow: 30 mL/min) and subsequent trituration of the resulting material in diethyl ether to afford the title compound (60 mg) as a colorless solid. Rt: 0.67 min (LC-MS 1); ESI-MS m/z: 492.2 [M+H]$^+$ (LC-MS 1); $^1$H NMR (400 MHz, DMSO-d6) δ 9.30 (s, 1H), 8.34 (d, J=1.6 Hz, 1H), 7.43-7.26 (m, 6H), 6.52 (s, 1H), 3.29 (s, 3H), 3.14-2.98 (m, 2H), 2.60 (s, 3H), 2.42 (s, 3H), 2.29 (s, 6H).

Example 117

3-(1-acetylazetidin-3-yl)-6-(4-chlorophenyl)-5-(3,8-dimethyl-[1,2,4]triazolo[4,3-a]pyridin-6-yl)-1-methyl-5,6-dihydropyrrolo[3,4-b]pyrrol-4(1H)-one

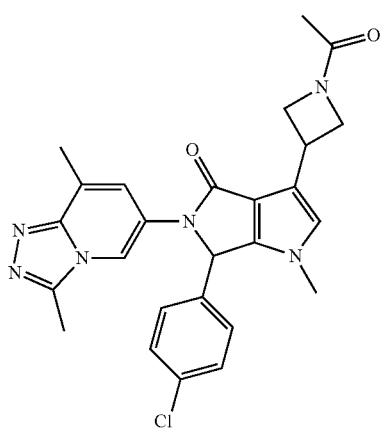 [SMILES: CC(=O)N1CC(c2cn(C)c3c2C(=O)N(c2cc(C)c4nnc(C)n4c2)C3c2ccc(Cl)cc2)C1]

Step 1: (E)-tert-butyl 3-(3-ethoxy-3-oxoprop-1-en-1-yl)azetidine-1-carboxylate To a stirred solution of triethyl phosphonacetate (8.87 mL, 44.7 mmol) in THF (100 mL) was added KOtBu (5.02 g, 44.7 mmol) portionwise under argon. Then, azetidine-3-carboxaldehyde, N-Boc protected (4.60 g, 24.84 mmol) in THF (30 mL) was added. The reaction mixture was stirred for 1 h at rt, quenched with aqueous 1N HCl (100 mL), and extracted with EtOAc (2×100 mL). The organic layers were combined and washed with a saturated aqueous solution of $NaHCO_3$ (175 mL), dried on $Na_2SO_4$ and evaporated. The residue was purified by silica gel chromatography on Combiflash Isco (eluent: EtOAc/Hexane; gradient: 0-31% EtOAc in 16.7 min; flow: 60 mL/min) to afford the title compound (4.04 g, 90% purity) as a colorless oil. Rt: 0.75 min (LC-MS 1); Rf: 0.75 (Hexane/EtOAc 1:1).

Step 2: Ethyl 4-(1-(tert-butoxycarbonyl)azetidin-3-yl)-1H-pyrrole-3-carboxylate To a stirred solution of (E)-tert-butyl 3-(3-ethoxy-3-oxoprop-1-en-1-yl)azetidine-1-carboxylate (Step 1, 4 g, 15.67 mmol) and p-toluenesulphonylmethyl isocyanide (3.73 g, 19.11 mmol) in $Et_2O$ (50 mL) and DMSO (25 mL) was added NaH (0.846 g, 21.15 mmol) portionwise under argon. The reaction mixture was stirred for 1 h at rt, quenched with brine (100 mL) and extracted with $Et_2O$ (2×100 mL). The organic layers were combined and washed with brine (100 mL), dried on $Na_2SO_4$ and evaporated. The residue was purified by silica gel chromatography on Combiflash Isco (eluent: EtOAc/Hexane; gradient: 0-67.4% EtOAc in 18.9 min; flow: 60 mL/min) to afford the title compound (3.38 g) as a colorless solid. Rt: 0.98 min (LC-MS 1); ESI-MS m/z: 295.2 [M+H]+ (LC-MS 1).

Step 3: Ethyl 4-(1-(tert-butoxycarbonyl)azetidin-3-yl)-1-methyl-1H-pyrrole-3-carboxylate To a stirred solution of ethyl 4-(1-(tert-butoxycarbonyl)azetidin-3-yl)-1H-pyrrole-3-carboxylate (Step 2, 3.38 g, 11.48 mmol) in DMF (50 mL) was added NaH (0.551 g, 13.78 mmol) at 0° C. under argon. The reaction mixture was stirred for 30 min at rt. Methyl iodide (0.862 mL, 13.78 mmol) was added. The reaction mixture was stirred for 30 min at rt, quenched with a saturated aqueous solution of $NaHCO_3$ (75 mL), dried on $Na_2SO_4$ and evaporated. The residue was purified by silica gel chromatography on Combiflash Isco (eluent: EtOAc/Hexane; gradient: 0-60.1% EtOAc in 16.3 min; flow: 60 mL/min) to afford the title compound (3.49 g) as a colorless oil. Rt: 1.09 min (LC-MS 1); ESI-MS m/z: 309.2 [M+H]+ (LC-MS 1).

Step 4: Ethyl 4-(1-(tert-butoxycarbonyl)azetidin-3-yl)-2-((4-chlorophenyl)(hydroxy)methyl)-1-methyl-1H-pyrrole-3-carboxylate The title compound was prepared using an analogous procedure to that described in Step 8 of Example 1 but using ethyl 4-(1-(tert-butoxycarbonyl)azetidin-3-yl)-1-methyl-1H-pyrrole-3-carboxylate (Step 3, 1 g, 3.24 mmol). The reaction mixture was quenched with a saturated aqueous solution of $NH_4Cl$. The crude material was purified by silica gel chromatography on Combiflash Isco (eluent: EtOAc/Hexane; gradient: 0-50% EtOAc in 13.1 min; flow: 35 mL/min) to afford the title compound (1.24 g, 80% purity) as a colorless solid. Rt: 1.29 min (LC-MS 1); ESI-MS m/z: 449.3 [M+H]+ (LC-MS 1).

Step 5: Ethyl 4-(1-(tert-butoxycarbonyl)azetidin-3-yl)-2-((4-chlorophenyl)((3,8-dimethyl-[1,2,4]triazolo[4,3-a]pyridin-6-yl)amino)methyl)-1-methyl-1H-pyrrole-3-carboxylate The title compound was prepared using an analogous procedure to that described in Step 9 of Example 1 but using ethyl 4-(1-(tert-butoxycarbonyl)azetidin-3-yl)-2-((4-chlorophenyl)(hydroxy)methyl)-1-methyl-1H-pyrrole-3-carboxylate (Step 4, 400 mg, 0.891 mmol) and 3,8-dimethyl-[1,2,4]triazolo[4,3-a]pyridin-6-amine (Step 4 of Example 3, 159 mg, 0.980 mmol). The crude material was purified by silica gel chromatography on Combiflash Isco (eluent: MeOH/DCM; gradient: 0-50% EtOAc in 13.1 min; flow: 35 mL/min) to afford the title compound (360 mg, 85% purity) as a yellow solid. Rt: 1.22 min (LC-MS 1); ESI-MS m/z: 593.4 [M+H]+ (LC-MS 1).

Step 6: 4-(1-(tert-butoxycarbonyl)azetidin-3-yl)-2-((4-chlorophenyl)((3,8-dimethyl-[1,2,4]triazolo[4,3-a]pyridin-6-yl)amino)methyl)-1-methyl-1H-pyrrole-3-carboxylic acid To a stirred solution of ethyl 4-(1-(tert-butoxycarbonyl)azetidin-3-yl)-2-((4-chlorophenyl)((3,8-dimethyl-[1,2,4]triazolo[4,3-a]pyridin-6-yl)amino)methyl)-1-methyl-1H-pyrrole-3-carboxylate (Step 5, 360 mg, 0.607 mmol) in THF (5 mL) and MeOH (5 mL) was added aqueous 2N NaOH (3.03 mL, 6.07 mmol). The reaction mixture was stirred for 20 h at 100° C., concentrated, quenched with of aqueous 1N HCl (100 mL) and extracted with EtOAc (2×100 mL). The organic layers were combined, dried on $Na_2SO_4$ and evaporated to afford the title compound (324 mg, 85% purity) as a colorless solid.

Step 7: Tert-butyl 3-(6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)azetidine-1-carboxylate To a stirred solution of 4-(1-(tert-butoxycarbonyl)azetidin-3-yl)-2-((4-chlorophenyl)((3,8-dimethyl-[1,2,4]triazolo

[4,3-a]pyridin-6-yl)amino)methyl)-1-methyl-1H-pyrrole-3-carboxylic acid (Step 6, 324 mg, 0.573 mmol) in DCM (5 mL) was added 1-chloro-N,N,2-trimethyl-1-propenylamine (0.106 mL, 0.803 mmol) at rt under argon. The reaction mixture was stirred for 3 days at rt, quenched with a saturated aqueous solution of NaHCO$_3$ (100 mL) and extracted with DCM (2×100 mL). The organic layers were combined, washed with a saturated aqueous solution of NaHCO$_3$ (100 mL), dried on Na$_2$SO$_4$ and evaporated. The crude material was purified by silica gel chromatography on Combiflash Isco (eluent: MeOH/DCM; gradient: 0-9.5% EtOAc in 13.4 min; flow: 30 mL/min) to afford the title compound (181 mg) as a yellow solid. Rt: 1.08 min (LC-MS 1); ESI-MS m/z: 547.3 [M+H]$^+$ (LC-MS 1).

Step 8: 3-(azetidin-3-yl)-6-(4-chlorophenyl)-5-(3,8-dimethyl-[1,2,4]triazolo[4,3-a]pyridin-6-yl)-1-methyl-5,6-dihydropyrrolo[3,4-b]pyrrol-4(1H)-one To a stirred solution of tert-butyl 3-(6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)azetidine-1-carboxylate (Step 7, 180 mg, 0.329 mmol) in DCM (2 mL) was added TFA (254 µL, 3.29 mmol). The reaction mixture was stirred for 60 min at rt, quenched with a saturated aqueous solution of NaHCO$_3$ and extracted with DCM (2×100 mL). The organic layers were combined, dried on Na$_2$SO$_4$ and evaporated. The residue was purified by silica gel chromatography on Combiflash Isco (eluent: DCM/(MeOH/NH$_4$OH:80/20); gradient: 5-10% (MeOH/NH$_4$OH:80/20) in 11 min, 7.9 min 10% (MeOH/NH$_4$OH:80/20); flow: 18 mL/min) to afford the title compound (79 mg) as a yellow solid. Rt: 0.65 min (LC-MS 1); ESI-MS m/z: 447.2 [M+H]$^+$ (LC-MS 1).

Step 9: 3-(1-acetylazetidin-3-yl)-6-(4-chlorophenyl)-5-(3,8-dimethyl-[1,2,4]triazolo[4,3-a]pyridin-6-yl)-1-methyl-5,6-dihydropyrrolo[3,4-b]pyrrol-4(1H)-one To a stirred solution of 3-(azetidin-3-yl)-6-(4-chlorophenyl)-5-(3,8-dimethyl-[1,2,4]triazolo[4,3-a]pyridin-6-yl)-1-methyl-5,6-dihydropyrrolo[3,4-b]pyrrol-4(1H)-one (Step 8, 38 mg, 0.085 mmol) in DCM (1 mL) were added NEt$_3$ (0.047 mL, 0.340 mmol) and Ac$_2$O (0.016 mL, 0.170 mmol) under argon. The reaction mixture was stirred for 1 h at rt, diluted with water (75 mL) and extracted with EtOAc (2×100 mL). The organic layers were combined and washed with water (100 mL), dried on Na$_2$SO$_4$ and evaporated. The residue was purified by silica gel chromatography on Combiflash Isco (eluent: MeOH/DCM; gradient: 5-10% MeOH in 10 min, 4.8 min 10% MeOH; flow: 18 mL/min) to afford the title compound (28 mg) as a colorless solid. Rt: 0.81 min (LC-MS 1); ESI-MS m/z: 489.2 [M+H]$^+$ (LC-MS 1); $^1$H NMR (400 MHz, DMSO-d6) δ 8.33 (s, 1H), 7.42-7.26 (m, 5H), 6.87 (d, J=1.5 Hz, 1H), 6.50 (s, 1H), 4.52-4.35 (m, 1H), 4.34-4.05 (m, 2H), 4.01-3.65 (m, 2H), 3.27 (s, 3H), 2.60 (s, 3H), 2.42 (s, 3H), 1.82-1.67 (m, 3H).

Example 118

6-(4-chlorophenyl)-5-(3,8-di methyl-[1,2,4]triazolo[4,3-a]pyridin-6-yl)-1-methyl-3-(1-methylazetidin-3-yl)-5,6-dihydropyrrolo[3,4-b]pyrrol-4(1H)-one

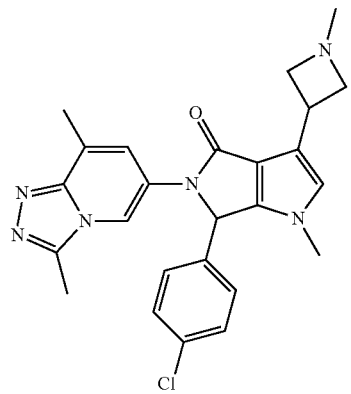 [SMILES: Cc1cc(N2C(=O)c3c(C4CN(C)C4)cn(C)c3C2c2ccc(Cl)cc2)cn2c(C)nnc12]

To a stirred solution of 3-(azetidin-3-yl)-6-(4-chlorophenyl)-5-(3,8-dimethyl-[1,2,4]triazolo[4,3-a]pyridin-6-yl)-1-methyl-5,6-dihydropyrrolo[3,4-b]pyrrol-4(1H)-one (Step 8 of Example 117, 38 mg, 0.085 mmol) in MeOH (2 mL) was added formaldehyde (0.023 mL, 0.255 mmol). After 5 min at rt, NaB(OAc)$_3$H (90 mg, 0.425 mmol) was added. The reaction mixture was stirred for 1 h at rt, quenched with a saturated aqueous solution of NaHCO$_3$ (50 mL) and extracted with EtOAc (2×100 mL). The organic layers were combined, washed with a saturated aqueous solution of NaHCO$_3$ (75 mL), dried on Na$_2$SO$_4$ and evaporated. The residue was purified by silica gel chromatography on Combiflash Isco (eluent: DCM/(MeOH/NH$_4$OH:80/20); gradient: 0-10% (MeOH/NH$_4$OH:80/20) in 12 min, 7.3 min 10% (MeOH/NH$_4$OH:80/20); flow: 18 mL/min). The resulting material was triturated in Et$_2$O to afford the title compound (20 mg) as a colorless solid. Rt: 0.67 min (LC-MS 1); ESI-MS m/z: 461.2 [M+H]$^+$ (LC-MS 1); $^1$H NMR (400 MHz, DMSO-d6) δ 8.33 (s, 1H), 7.48-7.23 (m, 5H), 6.77 (s, 1H), 6.46 (s, 1H), 3.68-3.44 (m, 3H), 3.28-3.17 (m, 5H), 2.60 (s, 3H), 2.42 (s, 3H), 2.30 (s, 3H).

Example 119

6-(4-chlorophenyl)-3-cyclopropyl-2-(3,6-dihydro-2H-pyran-4-yl)-5-(3,8-di methyl-[1,2,4]triazolo[4,3-a]pyridin-6-yl)-1-methyl-5,6-dihydropyrrolo[3,4-b]pyrrol-4(1H)-one

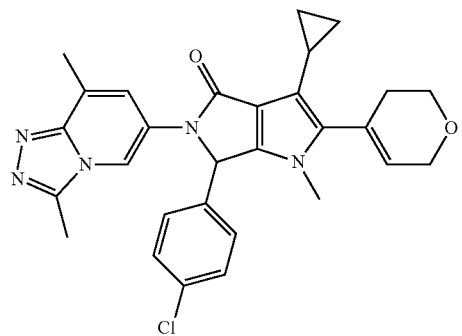 [SMILES: Cc1cc(N2C(=O)c3c(C4CC4)c(C4=CCOCC4)n(C)c3C2c2ccc(Cl)cc2)cn2c(C)nnc12]

Step 1: 2-bromo-6-(4-chlorophenyl)-3-cyclopropyl-5-(3,8-dimethyl-[1,2,4]triazolo[4,3-a]pyridin-6-yl)-1-methyl-5,6-dihydropyrrolo[3,4-b]pyrrol-4(1H)-one To a stirred solution of 6-(4-chlorophenyl)-3-cyclopropyl-5-(3,8-dimethyl-[1,2,4]triazolo[4,3-a]pyridin-6-yl)-1-methyl-5,6-dihydropyrrolo[3,4-b]pyrrol-4(1H)-one (Step 4 of Example 35, 460 mg, 1.065 mmol) in CHCl$_3$ (15 mL) was added NBS (190 mg, 1.065 mmol) under argon. The reaction mixture was stirred for 16 h at rt, quenched with brine (50 mL) and extracted with DCM (2×75 mL). The organic layers were combined, washed with brine (50 mL), dried on Na$_2$SO$_4$ and evaporated. The residue was purified by silica gel chromatography on Combiflash Isco (eluent: DCM/MeOH; gradient: 0-7.4% MeOH in 10.4 min; flow: 30 mL/min). The resulting material was triturated in Et$_2$O to afford the title compound (489 mg, 85% purity) as a yellow solid. Rt: 1.15 min (LC-MS 1); ESI-MS m/z: 512.2 [M+H]$^+$ (LC-MS 1).

Step 2: 6-(4-chlorophenyl)-3-cyclopropyl-2-(3,6-dihydro-2H-pyran-4-yl)-5-(3,8-dimethyl-[1,2,4]triazolo[4,3-a]pyridin-6-yl)-1-methyl-5,6-dihydropyrrolo[3,4-b]pyrrol-4(1H)-one A mixture of 2-bromo-6-(4-chlorophenyl)-3-cyclopropyl-5-(3,8-dimethyl-[1,2,4]triazolo[4,3-a]pyridin-6-yl)-1-methyl-5,6-dihydropyrrolo[3,4-b]pyrrol-4(1H)-one (Step 1, 200 mg, 0.392 mmol), 3,6-dihydro-2H-pyran-4-boronic acid pinacol (165 mg, 0.783 mmol), K$_3$PO$_4$ (332 mg, 1.566 mmol) and PdCl$_2$(dppf).CH$_2$Cl$_2$ adduct (63.9 mg, 0.078 mmol) in 1,4-dioxane (2 mL) and water (2 mL) was stirred for 1 h at 100° C., quenched with a saturated aqueous solution of NaHCO$_3$ (75 mL) and extracted with EtOAc (2×75 mL). The organic layers were combined, washed with a saturated aqueous solution of NaHCO$_3$ (75 mL), dried on Na$_2$SO$_4$ and evaporated. The residue was purified by silica gel chromatography on Combiflash Isco (eluent: DCM/MeOH; gradient: 0-8.5% MeOH in 10.2 min; flow: 18 mL/min). The resulting material was purified by SFC (column: Reprosil 70 NH2 250×30 mm, 5 μm, 70 A, Dr Maisch; eluent: MeOH/scCO$_2$; gradient: 1 min 23% MeOH, 25-28% MeOH in 6 min, 28-50% MeOH in 1 min, 1.5 min 50% MeOH; flow: 100 mL/min) to afford the title compound (95 mg) as a colorless solid. Rt: 1.05 min (LC-MS 1); ESI-MS m/z: 514.2 [M+H]$^+$ (LC-MS 1); $^1$H NMR (400 MHz, DMSO-d6) δ 8.28 (d, J=1.7 Hz, 1H), 7.42-7.11 (m, 5H), 6.43 (s, 1H), 5.89 (t, J=2.4 Hz, 1H), 4.29-4.02 (m, 2H), 3.78 (t, J=5.3 Hz, 2H), 3.15 (s, 3H), 2.59 (s, 3H), 2.41 (s, 3H), 2.35-2.15 (m, 2H), 1.81-1.61 (m, 1H), 1.16-1.05 (m, 1H), 1.04-0.89 (m, 1H), 0.88-0.73 (m, 2H).

Example 120

6-(4-chlorophenyl)-3-cyclopropyl-5-(3,8-dimethyl-[1,2,4]triazolo[4,3-a]pyridin-6-yl)-2-(2-methoxypyridin-3-yl)-1-methyl-5,6-dihydropyrrolo[3,4-b]pyrrol-4(1H)-one

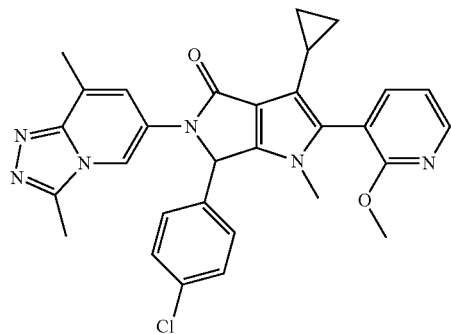 [SMILES: COc1ncccc1-c1c(C2CC2)c2c(n1C)C(c1ccc(Cl)cc1)N(c1cc(C)c3nnc(C)n3c1)C2=O]

The title compound was prepared using an analogous procedure to that described in Step 2 of Example 119 but using 2-methoxy-3-pyridineboronic acid (64.7 mg, 0.423 mmol, 1.5 eq). The reaction mixture was stirred for 3 h at 100° C. The crude product was purified by silica gel chromatography on Combiflash Isco (eluent: DCM/MeOH; gradient: 0-6.8% MeOH in 10.2 min; flow: 18 mL/min). The resulting material was further purified by preparative HPLC (Gilson gx-281. Column: Sunfire C18, 30×100 mm, 5 mm. Flow: 30 mL/min. Gradient: 5-50% B in 20 min; A=0.1% TFA in H$_2$O, B=CH$_3$CN. Detection: UV) to afford the title compound (42 mg) as a colorless solid. Rt: 1.12 min (LC-MS 1); ESI-MS m/z: 539.2 [M+H]$^+$ (LC-MS 1); $^1$H NMR (400 MHz, DMSO-d6) δ 8.33-8.29 (m, 1H), 8.25 (d, J=5.1 Hz, 1H), 7.73 (d, J=7.2 Hz, 1H), 7.42-7.35 (m, 4H), 7.31 (s, 1H), 7.19-7.01 (m, 1H), 6.55-6.48 (m, 1H), 3.92-3.74 (m, 3H), 3.05-2.95 (m, 3H), 2.60 (s, 3H), 2.42 (s, 3H), 1.47-1.33 (m, 1H), 1.19-0.65 (m, 4H).

Example 121

6-(4-chlorophenyl)-5-(3,8-dimethyl-[1,2,4]triazolo[4,3-a]pyridin-6-yl)-1-methyl-2-(tetrahydro-2H-pyran-4-yl)-5,6-dihydropyrrolo[3,4-b]pyrrol-4(1H)-one

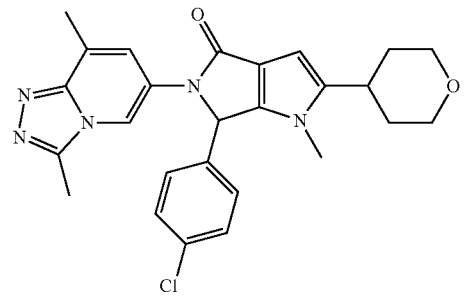 [SMILES: Cc1cc(N2C(=O)c3cc(C4CCOCC4)n(C)c3C2c2ccc(Cl)cc2)cn2c(C)nnc12]

A mixture of 6-(4-chlorophenyl)-2-(3,6-dihydro-2H-pyran-4-yl)-5-(3,8-dimethyl-[1,2,4]triazolo[4,3-a]pyridin-6-yl)-1-methyl-5,6-dihydropyrrolo[3,4-b]pyrrol-4(1H)-one (Step 6 of Example 31, 150 mg, 0.316 mmol) and Pd(OH)$_2$/C20% wet 50% (44.4 mg) in EtOH (5 mL) was shaken for 18.5 h at rt under a hydrogen atmosphere (0.1 bar), filtered over celite and concentrated. The residue was purified by silica gel chromatography on Combiflash Isco (eluent: DCM/MeOH; gradient: 0-10% MeOH in 12 min; 0.6 min 10% MeOH; flow: 18 mL/min). The resulting material was further purified by SFC (column: PPU 250×30 mm, 5 μm, 101 A, Princeton; eluent: MeOH/scCO$_2$; gradient: 1 min 19% MeOH, 19-24% MeOH in 6 min, 24-50% MeOH in 1 min, 1.5 min 50% MeOH; flow: 100 mL/min) and subsequent trituration in diethyl ether to afford the title compound (51 mg) as a colorless solid. Rt: 0.90 min (LC-MS 1); ESI-MS m/z: 476.2 [M+H]$^+$ (LC-MS 1); $^1$H NMR (400 MHz, DMSO-d6) δ 8.27 (s, 1H), 7.51-7.11 (m, 5H), 6.46 (s, 1H), 6.14 (s, 1H), 3.96-3.75 (m, 2H), 3.27 (s, 3H), 2.82 (dq, J=11.3, 6.1, 4.0 Hz, 1H), 2.58 (s, 3H), 2.41 (s, 3H), 1.82-1.46 (m, 4H).

Example 122

6-(4-chlorophenyl)-3-cyclopropyl-5-(3,8-dimethyl-[1,2,4]triazolo[4,3-a]pyridin-6-yl)-1,2-dimethyl-5,6-dihydropyrrolo[3,4-b]pyrrol-4(1H)-one

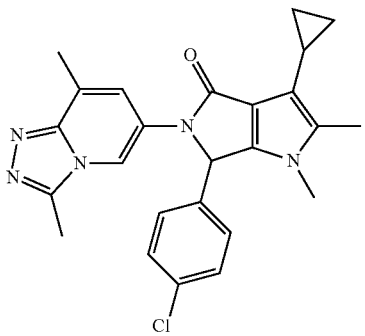 [SMILES: Cc1cc(N2C(=O)c3c(C4CC4)c(C)n(C)c3C2c2ccc(Cl)cc2)cn2c(C)nnc12]

The title compound was prepared using an analogous procedure to that described in Step 2 of Example 119 but using trimethylboroxine (0.137 mL, 0.979 mmol, 5 eq) and stirring the reaction mixture for 2 h at 100° C. The crude product was purified by silica gel chromatography on Combiflash Isco (eluent: DCM/MeOH; gradient: 0-7% MeOH in 11.2 min; flow: 18 mL/min). The resulting material was further purified by SFC (column: PFP 250×30 mm, 5 μm, 120 A, ES Industries; eluent: MeOH/scCO$_2$; gradient: 1 min 15% MeOH, 15-20% MeOH in 6 min, 20-50% MeOH in 1 min, 1.5 min 50% MeOH; flow: 100 mL/min) and subsequent preparative HPLC (Gilson gx-281. Column: Sunfire C18, 30×100 mm, 5 mm. Flow: 30 mL/min. Gradient: 5-100% B in 20 min; A=0.1% TFA in H$_2$O, B=CH$_3$CN. Detection: UV) to afford the title compound (17 mg) as a colorless solid. Rt: 1.06 min (LC-MS 1); ESI-MS m/z: 446.2 [M+H]$^+$ (LC-MS 1); $^1$H NMR (400 MHz, DMSO-d6) δ 8.40-8.18 (m, 1H), 7.44-7.15 (m, 5H), 6.40 (s, 1H), 3.16 (s, 3H), 2.59 (s, 3H), 2.40 (s, 3H), 2.18 (s, 3H), 1.80-1.59 (m, 1H), 1.10-0.64 (m, 4H).

Example 123

Ethyl 6-(4-chlorophenyl)-2-(3,6-dihydro-2H-pyran-4-yl)-5-(3,8-dimethyl-[1,2,4]triazolo[4,3-a]pyridin-6-yl)-3-methyl-4-oxo-5,6-dihydropyrrolo[3,4-b]pyrrole-1(4H)-carboxylate

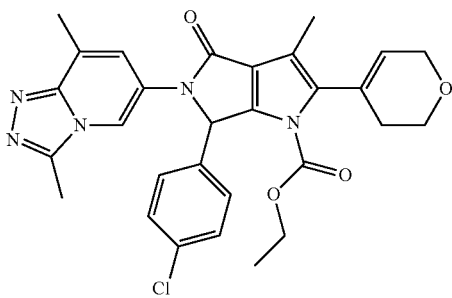 [SMILES: CCOC(=O)n1c(C2=CCOCC2)c(C)c2c1C(c1ccc(Cl)cc1)N(c1cc(C)c3nnc(C)n3c1)C2=O]

Step 1: 2-bromo-6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one The title compound was prepared using an analogous procedure to that described in Step 1 of Example 119 but using 6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one (Step 10 of Example 3, 341 mg, 0.870 mmol). The reaction mixture was concentrated. The residue was purified by silica gel chromatography on Combiflash Isco (eluent: DCM/MeOH; gradient: 2 min 0% MeOH, 0-10% MeOH in 11 min; 2 min 10% MeOH; flow: 30 mL/min) to afford the title compound (247 mg, 92% purity) as a yellow solid. Rt: 0.95 min (LC-MS 1); ESI-MS m/z: 472.1 [M+H]$^+$ (LC-MS 1).

Step 2: Ethyl 2-bromo-6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrole-1(4H)-carboxylate To a stirred solution of 2-bromo-6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one (Step 1, 245 mg, 0.520 mmol) in DCM (5 mL) was added NEt$_3$ (0.218 mL, 1.561 mmol) and ethyl chloroformate (0.075 mL, 0.781 mmol) under argon. The reaction mixture was stirred for 16 h at rt, diluted with water (75 mL) and extracted with EtOAc (2×100 mL). The organic layers were combined, washed with water (100 mL), dried on Na$_2$SO$_4$ and evaporated. The residue was purified by silica gel chromatography on Combiflash Isco (eluent: DCM/MeOH; gradient: 0-5% MeOH in 13 min; 0.8 min 5% MeOH; flow: 18 mL/min) to afford the title compound (201 mg) as a yellow solid. Rt: 1.13 min (LC-MS 1); ESI-MS m/z: 544.1 [M+H]$^+$ (LC-MS 1).

Step 3: Ethyl 6-(4-chlorophenyl)-2-(3,6-dihydro-2H-pyran-4-yl)-5-(3,8-dimethyl-[1,2,4]triazolo[4,3-a]pyridin-6-yl)-3-methyl-4-oxo-5,6-dihydropyrrolo[3,4-b]pyrrole-1(4H)-carboxylate The title compound was prepared using an analogous procedure to that described in Step 2 of Example 119 but using ethyl 2-bromo-6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrole-1(4H)-carboxylate (Step 2, 100 mg, 0.184 mmol) and stirring the reaction mixture for 2 h at 100° C. The crude product was purified by silica gel chromatography on Combiflash Isco (eluent: DCM/MeOH; gradient: 0-10% MeOH in 15 min, 3 min 10% MeOH; flow: 18 mL/min). The resulting material was further purified by SFC (column: PFP 250×30 mm, 5 μm, 120 A, ES Industries; eluent: MeOH/scCO$_2$; gradient: 1 min 15% MeOH, 15-20% MeOH in 6 min, 20-50% MeOH in 1 min, 1.5 min 50% MeOH; flow: 100 mL/min) to afford the title compound (10 mg) as a colorless solid. Rt: 1.06 min (LC-MS 1); ESI-MS m/z: 546.2 [M+H]$^+$ (LC-MS 1); $^1$H NMR (400 MHz, DMSO-d6) δ 8.37 (s, 1H), 7.39-7.06 (m, 5H), 6.54 (s, 1H), 5.79 (s, 1H), 4.26-3.99 (m, 5H), 3.80-3.63 (m, 2H), 2.61 (s, 3H), 2.41 (s, 3H), 2.14 (s, 3H), 1.15-0.92 (m, 4H).

Example 124

Ethyl 6-(4-chlorophenyl)-5-(3,8-dimethyl-[1,2,4]triazolo[4,3-a]pyridin-6-yl)-2-(2-methoxypyridin-3-yl)-3-methyl-4-oxo-5,6-dihydropyrrolo[3,4-b]pyrrole-1(4H)-carboxylate

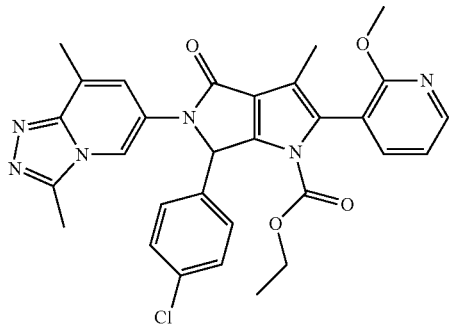 [SMILES: CCOC(=O)n1c(-c2cccnc2OC)c(C)c2c1C(c1ccc(Cl)cc1)N(c1cc(C)c3nnc(C)n3c1)C2=O]

The title compound was prepared using an analogous procedure to that described in Step 2 of Example 119 but using ethyl 2-bromo-6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrole-1(4H)-carboxylate (Step 2 of Example 123, 100 mg, 0.184 mmol), 2-methoxy-3-pyridineboronic acid (56.4 mg, 0.368 mmol), K$_3$PO$_4$ (156 mg, 0.737 mmol) and stirring the reaction mixture for 2 h at 100° C. The crude product was purified by silica gel chromatography on Combiflash Isco (eluent: DCM/MeOH; gradient: 0-10% MeOH in 15 min, 0.3 min 10% MeOH; flow: 18 mL/min). The resulting material was further purified by preparative HPLC (Gilson gx-281. Column: Sunfire C18, 30×100 mm, 5 µm. Flow: 30 mL/min. Gradient: 5-100% B in 20 min; A=0.1% TFA in H$_2$O, B=CH$_3$CN. Detection: UV) and subsequent SFC (column: PPU 250×30 mm, 5 µm, 101 A, Princeton; eluent: MeOH/scCO$_2$; gradient: 1 min 20% MeOH, 20-25% MeOH in 6 min, 25-50% MeOH in 1 min, 1.5 min 50% MeOH; flow: 100 mL/min) to afford the title compound (20 mg) as a colorless solid. Rt: 1.10 min (LC-MS 1); ESI-MS m/z: 571.2 [M+H]$^+$ (LC-MS 1); $^1$H NMR (400 MHz, DMSO-d6) δ 8.50-8.33 (m, 1H), 8.26-8.08 (m, 1H), 7.80-7.56 (m, 1H), 7.43-7.18 (m, 5H), 7.12-7.01 (m, 1H), 6.77-6.50 (m, 1H), 4.08-3.83 (m, 2H), 3.82-3.65 (m, 3H), 2.62 (s, 3H), 2.42 (s, 3H), 2.12-1.94 (m, 3H), 0.93-0.67 (m, 3H).

Example 125

Ethyl 6-(4-chlorophenyl)-3-cyclopropyl-5-(3,8-dimethyl-[1,2,4]triazolo[4,3-a]pyridin-6-yl)-4-oxo-5,6-dihydropyrrolo[3,4-b]pyrrole-1(4H)-carboxylate

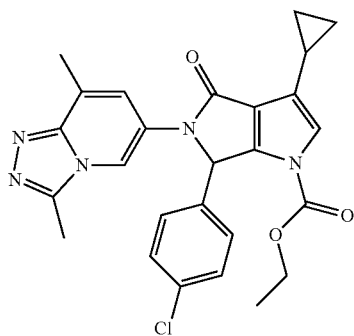 [SMILES: CCOC(=O)n1cc(C2CC2)c2c1C(c1ccc(Cl)cc1)N(c1cc(C)c3nnc(C)n3c1)C2=O]

Step 1: 6-(4-chlorophenyl)-3-cyclopropyl-5-(3,8-dimethyl-[1,2,4]triazolo[4,3-a]pyridin-6-yl)-1-(hydroxymethyl)-5,6-dihydropyrrolo[3,4-b]pyrrol-4(1H)-one To a stirred solution of ethyl 2-((4-chlorophenyl)((3,8-dimethyl-[1,2,4]triazolo[4,3-a]pyridin-6-yl)amino)methyl)-4-cyclopropyl-1-((2-(trimethylsilyl)ethoxy)methyl)-1H-pyrrole-3-carboxylate (Step 1 of Example 15, 380 mg, 0.639 mmol) in toluene (10 mL) was added dimethylaluminium chloride in hexane (3.84 mL, 3.84 mmol) at rt under argon. The reaction mixture was stirred for 16 h at 120° C., diluted with a saturated aqueous solution of Rochelle salt (100 mL) and extracted with EtOAc (2×100 mL). The organic layers were combined, washed with water (100 mL), dried on Na$_2$SO$_4$ and evaporated. The residue was purified by silica gel chromatography on Combiflash Isco (eluent: DCM/MeOH; gradient: 0-10% MeOH in 15 min, 4.7 min 10% MeOH; flow: 18 mL/min) to afford the title compound (206 mg, 80% purity). Rt: 0.89 min (LC-MS 1); ESI-MS m/z: 448.2 [M+H]$^+$ (LC-MS 1).

Step 2: 6-(4-chlorophenyl)-3-cyclopropyl-5-(3,8-dimethyl-[1,2,4]triazolo[4,3-a]pyridin-6-yl)-5,6-dihydropyrrolo[3,4-b]pyrrol-4(1H)-one To a stirred solution of 6-(4-chlorophenyl)-3-cyclopropyl-5-(3,8-dimethyl-[1,2,4]triazolo[4,3-a]pyridin-6-yl)-1-(hydroxymethyl)-5,6-dihydropyrrolo[3,4-b]pyrrol-4(1H)-one (Step 1, 205 mg, 0.458 mmol) in THF (10 mL) was added aqueous 1N NaOH (4.58 mL, 4.58 mmol). The reaction mixture was stirred for 1 h at rt, diluted with aqueous 1N NaOH (75 mL) and extracted with EtOAc (2×100 mL). The organic layers were combined, dried on Na$_2$SO$_4$ and evaporated. The residue was purified by silica gel chromatography on Combiflash Isco (eluent: DCM/MeOH; gradient: 0-10% MeOH in 12 min, 0.1 min 10% MeOH; flow: 18 mL/min) to afford the title compound (110 mg, 80% purity) as a brown solid. Rt: 0.93 min (LC-MS 1); ESI-MS m/z: 418.2 [M+H]$^+$ (LC-MS 1).

Step 3: Ethyl 6-(4-chlorophenyl)-3-cyclopropyl-5-(3,8-dimethyl-[1,2,4]triazolo[4,3-a]pyridin-6-yl)-4-oxo-5,6-dihydropyrrolo[3,4-b]pyrrole-1(4H)-carboxylate The title compound was prepared using an analogous procedure to that described in Step 2 of Example 123 but using 6-(4-chlorophenyl)-3-cyclopropyl-5-(3,8-dimethyl-[1,2,4]triazolo[4,3-a]pyridin-6-yl)-5,6-dihydropyrrolo[3,4-b]pyrrol-4(1H)-one (Step 2, 110 mg, 0.263 mmol). The crude product was purified by silica gel chromatography on Combiflash Isco (eluent: DCM/MeOH; gradient: 0-9% MeOH in 11.6 min; flow: 18 mL/min). The resulting material was further purified by SFC (column: Reprosil 70 NH2 250×30 mm, 5 µm, 70 A, Dr Maisch; eluent: MeOH/scCO$_2$; gradient: 1 min 16% MeOH, 16-21% MeOH in 6 min, 21-50% MeOH in 1 min, 1.5 min 50% MeOH; flow: 100 mL/min) and subsequent preparative HPLC (Gilson gx-281. Column: Sunfire C18, 30×100 mm, 5 µm. Flow: 30 mL/min. Gradient: 5-100% B in 20 min; A=0.1% TFA in H$_2$O, B=CH$_3$CN. Detection: UV) to afford the title compound (26 mg) as a colorless solid. Rt: 1.14 min (LC-MS 1); ESI-MS m/z: 490.2 [M+H]$^+$ (LC-MS 1); $^1$H NMR (400 MHz, DMSO-d6) δ 8.38 (d, J=1.8 Hz, 1H), 7.36-7.13 (m, 6H), 6.55 (s, 1H), 4.17 (q, J=7.1 Hz, 2H), 2.61 (s, 3H), 2.41 (s, 3H), 1.99-1.82 (m, 1H), 1.07 (t, J=7.1 Hz, 3H), 1.02-0.78 (m, 4H).

Example 126

6-(4-chlorophenyl)-5-(3,8-di methyl-[1,2,4]triazolo[4,3-a]pyridin-6-yl)-3-methyl-1-(1-methyl-2-oxopyrrolidin-3-yl)-5,6-dihydropyrrolo[3,4-b]pyrrol-4(1H)-one

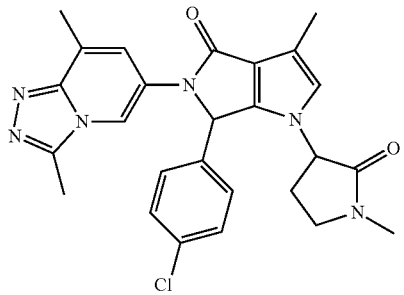 [SMILES: Cc1cn(C2CCN(C)C2=O)c2c1C(=O)N(c1cc(C)c3nnc(C)n3c1)C2c1ccc(Cl)cc1]

To a stirred solution of 6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one (Step 10 of Example 3, 100 mg, 0.255 mmol) in DMF (4 mL) was added NaH (13.27 mg, 0.332 mmol) under Ar. After 30 min at rt, 3-bromo-1-methylpyrrolidin-2-one (54.5 mg, 0.306 mmol) was added. The reaction mixture stirred for 1 h at rt, quenched with a saturated aqueous solution of NaHCO$_3$ (75 mL) and extracted with EtOAc (2×75 mL). The organic layers were combined, washed with a saturated aqueous solution of NaHCO$_3$ (75 mL), dried on Na$_2$SO$_4$ and evaporated. The residue was purified by silica gel chromatography on Combiflash Isco (eluent: DCM/MeOH; gradient: 0-10% MeOH in 12 min, 2 min 10% MeOH; flow: 18 mL/min) and subsequent SFC to afford 12 mg of diastereomer A and 25 mg of diastereomer B.

Diastereomer A. Rt: 0.84 min (LC-MS 1); ESI-MS m/z: 489.2 [M+H]$^+$ (LC-MS 1); Rf: 0.29 (DCM/MeOH 9:1); $^1$H NMR (400 MHz, DMSO-d6) δ 8.36 (s, 1H), 7.41-7.30 (m, 3H), 7.25-7.10 (m, 2H), 6.73 (s, 1H), 6.13 (s, 1H), 4.81 (t, J=9.7 Hz, 1H), 3.22-3.08 (m, 1H), 2.78 (s, 3H), 2.69-2.55 (m, 4H), 2.39 (s, 3H), 2.33-2.20 (m, 1H), 2.15 (s, 3H), 0.95-0.78 (m, 1H). Diastereomer B. Rt: 0.83 min (LC-MS 1); ESI-MS m/z: 489.2 [M+H]$^+$ (LC-MS 1); Rf: 0.36 (DCM/MeOH 9:1); $^1$H NMR (400 MHz, DMSO-d6) δ 8.32 (d, J=1.6 Hz, 1H), 7.43-7.19 (m, 5H), 6.68 (d, J=1.3 Hz, 1H), 6.51 (s, 1H), 4.56 (t, J=9.5 Hz, 1H), 3.24-3.08 (m, 2H), 2.59 (s, 3H), 2.51 (s, 3H), 2.40 (s, 3H), 2.15 (s, 3H), 2.11-1.95 (m, 2H).

Example 127

2-(6-(4-chlorophenyl)-5-(3,8-di methyl-[1,2,4]triazolo[4,3-a]pyridin-6-yl)-3-methyl-4-oxo-5,6-dihydropyrrolo[3,4-b]pyrrol-1(4H)-yl)-N-methylacetamide

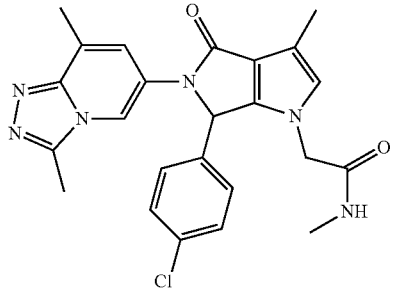 [SMILES: CNC(=O)Cn1cc(C)c2c1C(c1ccc(Cl)cc1)N(c1cc(C)c3nnc(C)n3c1)C2=O]

The title compound was prepared using an analogous procedure to that described in Example 126 but using bromo-N-methylacetamide (42.7 mg, 0.281 mmol, 1.1 eq). The crude product was purified by silica gel chromatography on Combiflash Isco (eluent: DCM/MeOH; gradient: 0-10% MeOH in 12 min, 3.9 min 10% MeOH; flow: 18 mL/min). The resulting material was further purified by SFC (column: PPU 250×30 mm, 5 μm, 100 A, Princeton; eluent: MeOH/scCO$_2$; gradient: 1 min 21% MeOH, 21-26% MeOH in 6 min, 26-50% MeOH in 1 min, 1.5 min 50% MeOH; flow: 100 mL/min) and subsequent trituration in diethyl ether to afford (14 mg) of the title compound as a colorless solid. Rt: 0.75 min (LC-MS 1); ESI-MS m/z: 463.3 [M+H]$^+$ (LC-MS 1); $^1$H NMR (400 MHz, DMSO-d6) δ 8.35 (d, J=1.6 Hz, 1H), 7.79-7.66 (m, 1H), 7.36 (d, J=1.6 Hz, 1H), 7.33-7.22 (m, 4H), 6.64 (s, 1H), 6.32 (s, 1H), 4.36 (d, J=16.5 Hz, 1H), 3.89 (d, J=16.5 Hz, 1H), 2.59 (s, 3H), 2.52-2.49 (m, 3H), 2.40 (s, 3H), 2.15 (s, 3H).

Example 128

6-(4-chlorophenyl)-5-(3,8-di methyl-[1,2,4]triazolo[4,3-a]pyridin-6-yl)-1-(2-(dimethylamino)ethyl)-3-methyl-5,6-dihydropyrrolo[3,4-b]pyrrol-4(1H)-one

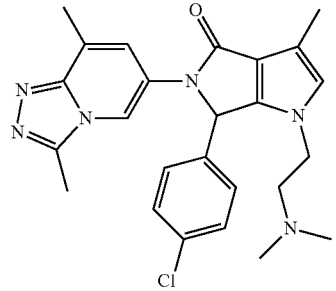 [SMILES: Cc1cn(CCN(C)C)c2c1C(=O)N(c1cc(C)c3nnc(C)n3c1)C2c1ccc(Cl)cc1]

The title compound was prepared using an analogous procedure to that described in Example 126 but using dimethylaminoethyl bromide hydrobromide (71.3 mg, 0.306 mmol, 1.2 eq) and 3 eq of NaH. The crude product was purified by silica gel chromatography on Combiflash Isco (eluent: DCM/MeOH; gradient: 0-10% MeOH in 12 min, 3.6 min 10% MeOH; flow: 18 mL/min) and subsequent trituration of the resulting material in diethyl ether to afford (65 mg) of the title compound as a colorless solid. Rt: 0.62 min (LC-MS 1); ESI-MS m/z: 463.2 [M+H]$^+$ (LC-MS 1); $^1$H NMR (400 MHz, DMSO-d6) δ 8.31 (d, J=1.7 Hz, 1H), 7.42-7.26 (m, 5H), 6.71 (s, 1H), 6.42 (s, 1H), 3.72-3.57 (m, 1H), 3.57-3.44 (m, 1H), 2.59 (s, 3H), 2.41 (s, 3H), 2.29-2.18 (m, 1H), 2.14 (s, 3H), 2.08-1.91 (m, 7H).

Example 129

2-(6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrol-1(4H)-yl)-N,N-dimethylacetamide

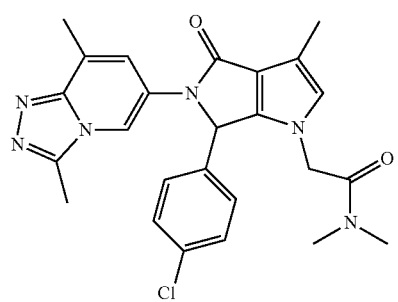 [SMILES: Cc1cn(CC(=O)N(C)C)c2c1C(=O)N(c1cc(C)c3nnc(C)n3c1)C2c1ccc(Cl)cc1]

Step 1: Ethyl 2-(6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrol-1(4H)-yl)acetate The title compound was prepared using an analogous procedure to that described in Example 126 but using ethyl bromoacetate (0.056 mL, 0.505 mmol, 1.1 eq). The crude product was purified by silica gel chromatography on Combiflash Isco (eluent: DCM/MeOH; gradient: 0-9.1% MeOH in 12.3 min; flow: 18 mL/min) to afford (182 mg, 93% purity) of the title compound as a yellow solid. Rt: 0.97 min (LC-MS 1); ESI-MS m/z: 478.3 [M+H]$^+$ (LC-MS 1).

Step 2: 2-(6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrol-1(4H)-yl)-N,N-dimethylacetamide In a 2-ml MW flask were introduced ethyl 2-(6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrol-1(4H)-yl)acetate (Step 1, 180 mg, 0.377 mmol) and 5.6 M dimethylamine in ethanol (3363 μL, 18.83 mmol). The reaction mixture was stirred for 30 min at 100° C. under MW and concentrated. The residue was purified by silica gel chromatography on Combiflash Isco (eluent: DCM/MeOH; gradient: 0-8.7% MeOH in 11.5 min; flow: 18 mL/min). The resulting material was further purified by SFC (column: PPU 250×30 mm, 5 μm, 100 A, Princeton; eluent: MeOH/scCO$_2$; gradient: 1 min 21% MeOH, 201-25% MeOH in 6 min, 25-50% MeOH in 1 min, 1.5 min 50% MeOH; flow: 100 mL/min) and subsequent trituration in diethyl ether to afford (48 mg) of the title compound as a colorless solid. Rt: 0.83 min (LC-MS 1); ESI-MS m/z: 477.3 [M+H]$^+$ (LC-MS 1); $^1$H NMR (400 MHz, DMSO-d6) δ 8.35 (d, J=1.7 Hz, 1H), 7.37-7.29 (m, 3H), 7.24 (d, J=8.2 Hz, 2H), 6.60 (s, 1H), 6.27 (s, 1H), 4.77 (d, J=17.0 Hz, 1H), 4.08 (d, J=17.0 Hz, 1H), 2.79 (s, 3H), 2.73 (s, 3H), 2.58 (s, 3H), 2.40 (s, 3H), 2.14 (s, 3H).

Example 130

3-(azetidin-3-yl)-6-(4-chlorophenyl)-5-(3,7-dimethyl-3H-[1,2,3]triazolo[4,5-b]pyridin-5-yl)-1-methyl-5,6-dihydropyrrolo[3,4-b]pyrrol-4(1H)-one

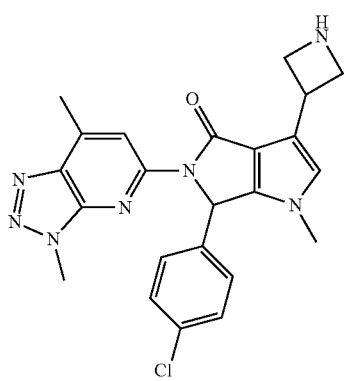 [SMILES: Cc1cc(N2C(=O)c3c(C4CNC4)cn(C)c3C2c2ccc(Cl)cc2)nc2c1nnn2C]

Step 1: Ethyl 4-(1-(tert-butoxycarbonyl)azetidin-3-yl)-2-((4-chlorophenyl)((3,7-dimethyl-3H-[1,2,3]triazolo[4,5-b]pyridin-5-yl)amino)methyl)-1-methyl-1H-pyrrole-3-carboxylate The title compound was prepared using an analogous procedure to that described in Step 9 of Example 1 but using ethyl 4-(1-(tert-butoxycarbonyl)azetidin-3-yl)-2-((4-chlorophenyl)(hydroxy)methyl)-1-methyl-1H-pyrrole-3-carboxylate (Step 4 of Example 117, 400 mg, 0.891 mmol) and 3,7-dimethyl-3H-[1,2,3]triazolo[4,5-b]pyridin-5-amine (Step 5 of Example 1, 160 mg, 0.980 mmol). The residue was purified by silica gel chromatography on Combiflash Isco (eluent: MeOH/EtOAc; gradient: 0-6.2% MeOH in 15.6 min; flow: 30 mL/min). The resulting material was further purified by preparative HPLC (Gilson gx-281. Column: Sunfire C18, 30×100 mm, 5 μm. Flow: 30 mL/min. Gradient: 5-100% B in 20 min; A=0.1% TFA in H$_2$O, B=CH$_3$CN. Detection: UV) to afford the title compound (163 mg) as a colorless solid. Rt: 1.35 min (LC-MS 1); ESI-MS m/z: 594.4 [M+H]$^+$ (LC-MS 1).

Step 2: 4-(1-(tert-butoxycarbonyl)azetidin-3-yl)-2-((4-chlorophenyl)((3,7-dimethyl-3H-[1,2,3]triazolo[4,5-b]pyridin-5-yl)amino)methyl)-1-methyl-1H-pyrrole-3-carboxylic The title compound was prepared using an analogous procedure to that described in Step 6 of Example 117 but using ethyl 4-(1-(tert-butoxycarbonyl)azetidin-3-yl)-2-((4-chlorophenyl)((3,7-dimethyl-3H-[1,2,3]triazolo[4,5-b]pyridin-5-yl)amino)methyl)-1-methyl-1H-pyrrole-3-carboxylate (Step 1, 160 mg, 0.269 mmol). Rt: 1.16 min (LC-MS 1); ESI-MS m/z: 566.3 [M+H]$^+$ (LC-MS 1).

Step 3: Tert-butyl 3-(6-(4-chlorophenyl)-5-(3,7-dimethyl-3H-[1,2,3]triazolo[4,5-b]pyridin-5-yl)-1-methyl-4-oxo-1,4,5,6-tetrahydropyrrolo[3,4-b]pyrrol-3-yl)azetidine-1-carboxylate The title compound was prepared using an analogous procedure to that described in Step 7 of Example 117 but using 4-(1-(tert-butoxycarbonyl)azetidin-3-yl)-2-((4-chlorophenyl)((3,7-dimethyl-3H-[1,2,3]triazolo[4,5-b]pyridin-5-yl)amino)methyl)-1-methyl-1H-pyrrole-3-carboxylic acid (Step 2, 150 mg, 0.265 mmol) and stirring the reaction mixture for 20 h at rt. The crude product was purified by silica gel chromatography on Combiflash Isco (eluent: EtOAc/Hexane; gradient: 0-100% EtOAc in 13 min, 1 min 100% EtOAc; flow: 30 mL/min) to afford the title compound (110 mg) as a colorless solid. Rt: 1.30 min (LC-MS 1); ESI-MS m/z: 548.2 [M+H]$^+$ (LC-MS 1).

Step 4: 3-(azetidin-3-yl)-6-(4-chlorophenyl)-5-(3,7-dimethyl-3H-[1,2,3]triazolo[4,5-b]pyridin-5-yl)-1-methyl-5,6-dihydropyrrolo[3,4-b]pyrrol-4(1H)-one The title compound was prepared using an analogous procedure to that described in Step 8 of Example 117 but using tert-butyl 3-(6-(4-chlorophenyl)-5-(3,7-dimethyl-3H-[1,2,3]triazolo[4,5-b]pyridin-5-yl)-1-methyl-4-oxo-1,4,5,6-tetrahydropyrrolo[3,4-b]pyrrol-3-yl)azetidine-1-carboxylate (Step 3, 110 mg, 0.201 mmol). The crude product was purified by silica gel chromatography on Combiflash Isco (eluent: DCM/MeOH; gradient: 0-10% MeOH in 12 min, 1.9 min 10% MeOH; flow: 18 mL/min) and subsequent trituration of the resulting material in diethyl ether to afford the title compound (62 mg) as a colorless solid. Rt: 0.82 min (LC-MS 1); ESI-MS m/z: 448.2 [M+H]+ (LC-MS 1); $^1$H NMR (400 MHz, DMSO-d6) δ 8.41-8.20 (m, 1H), 7.51-7.27 (m, 4H), 6.97-6.58 (m, 2H), 4.18-4.00 (m, 5H), 3.98-3.88 (m, 2H), 3.76-3.42 (m, 1H), 3.27 (s, 3H), 2.65 (s, 3H).

Example 131

6-(4-chlorophenyl)-5-(3,8-di methyl-[1,2,4]triazolo[4,3-b]pyridazin-6-yl)-1-methyl-5,6-dihydropyrrolo[3,4-b]pyrrol-4(1H)-one

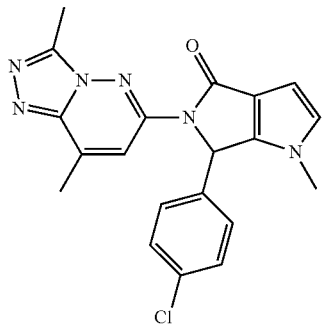 [SMILES: Cc1cc(N2C(=O)c3ccn(C)c3C2c2ccc(Cl)cc2)nn2c(C)nnc12]

Step 1: 6-chloro-3-hydrazinyl-4-methylpyridazine

A mixture of 3,6-dichloro-4-methylpyridazine (24.8 g, 152 mmol) and hydrazine hydrate (113 mL, 2282 mmol) was stirred at 80° C. for 1 h. The reaction mixture was diluted in EtOH and mechanically stirred for 6 h. The resulting solid was collected by vacuum filtration to afford the title compound (6.96 g) as a colorless solid. Rt: 0.32 min (LC-MS 1); ESI-MS m/z: 159.0 [M+H]+ (LC-MS 1).

Step 2: 6-chloro-3,8-dimethyl-[1,2,4]triazolo[4,3-b]pyridazine

6-Chloro-3-hydrazinyl-4-methylpyridazine (Step 1, 6.96 g, 41.3 mmol) in AcOH (50 mL) was stirred for 1 h at 100° C., cooled to rt, diluted with DCM and a saturated aqueous NaHCO$_3$ solution, and extracted twice with DCM. The combined organic extracts were washed with brine, dried (Na$_2$SO$_4$) and concentrated. The residue was purified by silica gel chromatography on Combiflash Isco (eluent: DCM/MeOH; gradient: 0-6% MeOH in 33.3 min; flow: 60 mL/min) to afford the title compound (7.214 g) as a pale pink solid. Rt: 0.59 min (LC-MS 1); ESI-MS m/z: 183.0 [M+H]+ (LC-MS 1).

Step 3: Methyl 1-methyl-1H-pyrrole-3-carboxylate

To a stirred solution of methyl pyrrole-3-carboxylate (2.5 g, 19.98 mmol) in DMSO (20 mL) was added under argon KOH (1.681 g, 30.0 mmol). After 10 min, methyl iodide (1.874 mL, 30.0 mmol) was added. The reaction mixture was stirred for 1 h at rt, quenched with aqueous 1N HCl (200 mL), and extracted with EtOAc (2×200 mL). The combined organic layers were washed brine (1×200 mL), dried (Na$_2$SO$_4$) and concentrated. The residue was purified by silica gel chromatography on Combiflash Isco (eluent: EtOAc/Hexane; gradient: 0-3% EtOAc in 5.6 min, 3-16% EtOAc in 16 min, 16% EtOAc 5 min; flow: 85 mL/min) and subsequent trituration of the resulting material in diethyl ether to afford the title compound (2.74 g) as a colorless oil. Rt: 0.65 min (LC-MS 1); ESI-MS m/z: 140.1 [M+H]+ (LC-MS 1).

Step 4: Methyl 2-((4-chlorophenyl)(hydroxy)methyl)-1-methyl-1H-pyrrole-3-carboxylate The title compound was prepared using an analogous procedure to that described in Step 8 of Example 1 but using methyl 1-methyl-1H-pyrrole-3-carboxylate (Step 3, 2.74 g, 19.69 mmol). The crude material was purified by silica gel chromatography on Combiflash Isco (eluent: EtOAc/Hexane; gradient: 0-2% EtOAc in 2 min, 2-9.4% EtOAc in 9.8 min, 9.4-20.8% EtOAc in 6 min, 20.8% EtOAc 0.5 min, 20.8-25% EtOAc in 2.2 min, 25% EtOAc 2.2 min; flow: 85 mL/min) to afford the title compound (4.95 g, 92% purity) as a colorless solid. Rt: 1.06 min (LC-MS 1); ESI-MS m/z: 262.1 [M-17]+ (LC-MS 1).

Step 5: Methyl 2-(azido(4-chlorophenyl)methyl)-1-methyl-1H-pyrrole-3-carboxylate 1-Chloro-N,N,2-trimethyl-1-propenylamine (2.020 mL, 15.27 mmol) was added to a stirred solution of methyl 2-((4-chlorophenyl)(hydroxy)methyl)-1-methyl-1H-pyrrole-3-carboxylate (Step 4, 2.847 g, 10.18 mmol) in DCM (60 mL) at rt. The mixture was stirred for 5 h and cooled to 0° C. After addition of triethylamine (4.26 mL, 30.5 mmol) and tetrabutylammonium azide (3.47 g, 12.21 mmol), the reaction mixture was allowed to warm to rt, stirred for 15 h, diluted in DCM/water, and extracted once with DCM. The combined organic extracts were washed with brine, dried (Na$_2$SO$_4$) and concentrated. The residue was purified by silica gel chromatography on Combiflash Isco (eluent: EtOAc/Hexane; gradient: 0% to 7.3% EtOAc in 12.2 min; flow: 60 mL/min) to afford the title compound (2.561 g) as a colorless solid. Rt: 1.27 min (LC-MS 1); ESI-MS m/z: 277.1 [M-27]+ (LC-MS 1).

Step 6: Methyl 2-(amino(4-chlorophenyl)methyl)-1-methyl-1H-pyrrole-3-carboxylate A mixture of methyl 2-(azido(4-chlorophenyl)methyl)-1-methyl-1H-pyrrole-3-carboxylate (Step 5, 2.56 g, 8.40 mmol) and Ra—Ni (Degussa, 0.72 g) in MeOH (50 mL) was stirred for 5 h at rt under a hydrogen atmosphere (0.1 bar). Further Ra—Ni (Degussa, 0.5 g) was added. The reaction mixture was stirred for additional 5 h at rt, filtered over celite and concentrated to afford the title compound (2.26 g) as a reddish oil. Rf=0.19 (50% EtOAc/hexane); Rt: 0.72 min (LC-MS 1); MS m/z: 279.1 [M+H]+ (LC-MS 1).

Step 7: 6-(4-chlorophenyl)-1-methyl-5,6-dihydropyrrolo[3,4-b]pyrrol-4(1H)-one

The title compound was prepared using an analogous procedure to that described in Step 10 of Example 1 but using methyl 2-(amino(4-chlorophenyl)methyl)-1-methyl-1H-pyrrole-3-carboxylate (Step 6, 2.26 g, 7.86 mmol). The reaction mixture was stirred for 16 h at 110° C., diluted with a saturated aqueous solution of Rochelle's salt, stirred for 2 h at rt, and extracted with DCM. The Crude material was triturated in EtOAc to afford the title compound (1.768 g) as a colorless solid. Rt: 0.79 min (LC-MS 1); ESI-MS m/z: 247.1 [M+H]+ (LC-MS 1).

Step 8: 6-(4-chlorophenyl)-5-(3,8-dimethyl-[1,2,4]triazolo[4,3-b]pyridazin-6-yl)-1-methyl-5,6-dihydropyrrolo[3,4-b]pyrrol-4(1H)-one A mixture of 6-(4-chlorophenyl)-1-methyl-5,6-dihydropyrrolo[3,4-b]pyrrol-4(1H)-one (Step 7, 100 mg, 0.405 mmol), 6-chloro-3,8-dimethyl-[1,2,4]triazolo[4,3-b]pyridazine (Step 2, 148 mg, 0.811 mmol), Pd$_2$dba$_3$ (37.1 mg, 0.041 mmol), Xantphos (46.9 mg, 0.081 mmol) and cesium carbonate (264 mg, 0.811 mmol) in dioxane (3 mL) was stirred under argon in a microwave vial for 16 h at 100° C. The reaction mixture was diluted in DCM/water, and extracted twice with DCM. The combined organic extracts were dried (Na$_2$SO$_4$) and concentrated. The residue was filtered through a Varian PL-Thiol MP SPE cartridge (to remove metals traces) eluting with MeOH. After concentration, the resulting material was purified by silica gel chromatography on Combiflash Isco (eluent: MeOH/DCM; gradient: 0-5.5% MeOH in 12.6 min; flow: 30 mL/min). The resulting material was further purified by preparative achiral SFC (column: Reprosil 70 NH2 (250×30 mm, 5 μm, 70 A, Dr Maisch; eluent: MeOH/scCO$_2$; gradient: 1 min 13% MeOH, 13-18% MeOH in 6 min, 18-50% MeOH in 1 min, 1.5 min 50% MeOH; flow: 100 mL/min) and subsequent trituration in diethyl ether to afford the title compound (55 mg) as a colorless solid. Rt: 0.95 min (LC-MS 1); ESI-MS m/z: 393.1 [M+H]$^+$ (LC-MS 1); $^1$H NMR (400 MHz, DMSO-d6) δ 8.24 (q, J=1.2 Hz, 1H), 7.39-7.46 (m, 4H), 7.01 (d, J=2.9 Hz, 1H), 6.64 (s, 1H), 6.42 (d, J=2.9 Hz, 1H), 3.36 (s, 3H), 2.61-2.53 (m, 6H).

Example 132

6-(4-chlorophenyl)-5-(3-(difluoromethyl)-8-methyl-[1,2,4]triazolo[4,3-a]pyridin-6-yl)-N,1-dimethyl-4-oxo-1,4,5,6-tetrahydropyrrolo[3,4-b]pyrrole-3-carboxamide

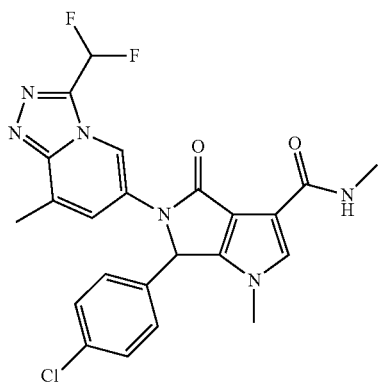 [SMILES: CNC(=O)c1cn(C)c2c1C(=O)N(c1cc(C)c3nnc(C(F)F)n3c1)C2c1ccc(Cl)cc1]

Step 1: Diethyl 2-((4-chlorophenyl)((3-(difluoromethyl)-8-methyl-[1,2,4]triazolo[4,3-a]pyridin-6-yl)amino)methyl)-1-methyl-1H-pyrrole-3,4-dicarboxylate The title compound was prepared using an analogous procedure to that described in Step 3 of Example 93 but using diethyl 2-((4-chlorophenyl)(hydroxy)methyl)-1-methyl-1H-pyrrole-3,4-dicarboxylate (Step 2 of Example 93, 3.96 g, 10.28 mmol) and 3-(difluoromethyl)-8-methyl-[1,2,4]triazolo[4,3-a]pyridin-6-amine (Step 3 of Example 107, 2.038 g, 10.28 mmol). After addition of 1-chloro-N,N,2-trimethyl-1-propenylamine, the reaction mixture was stirred for 6 h at rt. After addition of 3-(difluoromethyl)-8-methyl-[1,2,4]triazolo[4,3-a]pyridin-6-amine, the reaction mixture was stirred for 16 h at rt. The crude product was purified by silica gel chromatography on Combiflash Isco (eluent: MeOH/DCM; gradient: 0-4.4% MeOH in 22.7 min; flow: 85 mL/min) and subsequent trituration of the resulting material in diethyl ether to afford the title compound (3.5 g) as a colorless solid. Rt: 1.16 min (LC-MS 1); ESI-MS m/z: 546.2 [M+H]$^+$ (LC-MS 1).

Step 2: 2-((4-chlorophenyl)((3-(difluoromethyl)-8-methyl-[1,2,4]triazolo[4,3-a]pyridin-6-yl)amino)methyl)-1-methyl-1H-pyrrole-3,4-dicarboxylic acid and 6-(4-chlorophenyl)-5-(3-(difluoromethyl)-8-methyl-[1,2,4]triazolo[4,3-a]pyridin-6-yl)-1-methyl-4-oxo-1,4,5,6-tetrahydropyrrolo[3,4-b]pyrrole-3-carboxylic acid The title compounds were obtained using an analogous procedure to that described in Step 4 of Example 93 but using diethyl 2-((4-chlorophenyl)((3-(difluoromethyl)-8-methyl-[1,2,4]triazolo[4,3-a]pyridin-6-yl)amino)methyl)-1-methyl-1H-pyrrole-3,4-dicarboxylate (Step 1, 3.5 g, 6.41 mmol). The reaction mixture was stirred for 2 h at 100° C. After acidification, the resulting precipitate was collected by filtration to afford 6-(4-chlorophenyl)-5-(3-(difluoromethyl)-8-methyl-[1,2,4]triazolo[4,3-a]pyridin-6-yl)-1-methyl-4-oxo-1,4,5,6-tetrahydropyrrolo[3,4-b]pyrrole-3-carboxylic acid (467 mg, 76% purity). Rt: 0.87 min (LC-MS 1); ESI-MS m/z: 472.2 [M+H]$^+$ (LC-MS 1). The filtrate was extracted twice with DCM. The combined organic extracts were dried (Na$_2$SO$_4$) and concentrated. The residue triturated in diethyl ether to afford 2-((4-chlorophenyl)((3-(difluoromethyl)-8-methyl-[1,2,4]triazolo[4,3-a]pyridin-6-yl)amino)methyl)-1-methyl-1H-pyrrole-3,4-dicarboxylic acid (2.235 g) as a beige solid. Rt: 0.75 min (LC-MS 1); ESI-MS m/z: 490.2 [M+H]$^+$ (LC-MS 1).

Step 3: 6-(4-chlorophenyl)-5-(3-(difluoromethyl)-8-methyl-[1,2,4]triazolo[4,3-a]pyridin-6-yl)-N,1-dimethyl-4-oxo-1,4,5,6-tetrahydropyrrolo[3,4-b]pyrrole-3-carboxamide A mixture of 6-(4-chlorophenyl)-5-(3-(difluoromethyl)-8-methyl-[1,2,4]triazolo[4,3-a]pyridin-6-yl)-1-methyl-4-oxo-1,4,5,6-tetrahydropyrrolo[3,4-b]pyrrole-3-carboxylic acid (Step 2, 200 mg, 0.322 mmol), methylamine hydrochloride (109 mg, 1.611 mmol), TBTU (134 mg, 0.419 mmol) and DIEA (0.281 mL, 1.611 mmol) in DMF (3 mL) was stirred for 15 min at rt under argon, diluted in EtOAc/water and extracted twice with EtOAc. The combined organic extract were washed with brine, dried (Na$_2$SO$_4$) and concentrated. The residue was purified by silica gel chromatography on Combiflash Isco (eluent: (20% ammonia/MeOH)/DCM; gradient: 0-7% (20% ammonia/MeOH) in 16 min; flow: 30 mL/min) to afford the title compound (122 mg). Rt: 0.92 min (LC-MS 1); ESI-MS m/z: 485.2 [M+H]$^+$ (LC-MS 1).

Example 133

N-(6-(4-chlorophenyl)-5-(3-(difluoromethyl)-8-methyl-[1,2,4]triazolo[4,3-a]pyridin-6-yl)-1-methyl-4-oxo-1,4,5,6-tetrahydropyrrolo[3,4-b]pyrrol-3-yl)acetamide

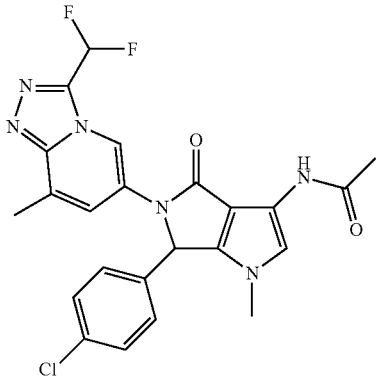 [SMILES: CC(=O)Nc1cn(C)c2c1C(=O)N(c1cc(C)c3nnc(C(F)F)n3c1)C2c1ccc(Cl)cc1]

Step 1: 6-(4-chlorophenyl)-5-(3-(difluoromethyl)-8-methyl-[1,2,4]triazolo[4,3-a]pyridin-6-yl)-1-methyl-4-oxo-1,4,5,6-tetrahydropyrrolo[3,4-b]pyrrole-3-carboxylic acid 1-Chloro-N,N,2-trimethyl-1-propenylamine (0.894 mL, 6.76 mmol) was added to a stirred suspension of 2-((4-chlorophenyl)((3-(difluoromethyl)-8-methyl-[1,2,4]triazolo[4,3-a]pyridin-6-yl)amino)methyl)-1-methyl-1H-pyrrole-3,4-dicarboxylic acid (Step 2 of Example 132, 2.23 g, 4.51 mmol) in DCM at rt under argon. The reaction mixture was stirred for 3 h at rt and concentrated. The residue was triturated in diethyl ether to afford the title compound (2.35 g, 90% purity) as a colorless solid. Rt: 0.87 min (LC-MS 1); ESI-MS m/z: 472.2 [M+H]$^+$ (LC-MS 1).

Step 2: 6-(4-chlorophenyl)-5-(3-(difluoromethyl)-8-methyl-[1,2,4]triazolo[4,3-a]pyridin-6-yl)-1-methyl-4-oxo-1,4,5,6-tetrahydropyrrolo[3,4-b]pyrrole-3-carbonyl azide Sodium azide (0.350 g, 5.38 mmol) and DIEA (3.13 mL, 17.93 mmol) were added sequentially to a stirred suspension of 6-(4-chlorophenyl)-5-(3-(difluoromethyl)-8-methyl-[1,2,4]triazolo[4,3-a]pyridin-6-yl)-1-methyl-4-oxo-1,4,5,6-tetrahydropyrrolo[3,4-b]pyrrole-3-carboxylic acid (Step 1, 2.35 g, 4.48 mmol) and TBTU (2.015 g, 6.28 mmol) in DMF (30 mL) at 0° C. The reaction mixture was stirred for 4 h at rt. Sodium azide (0.350 g, 5.38 mmol) was added. The reaction mixture was stirred for 2 h at rt, diluted in EtOAc/water and extracted twice with EtOAc. The combined organic extracts were washed with brine, dried (Na$_2$SO$_4$) and concentrated. The residue was triturated in Et$_2$O to afford the title compound (2 g) as a colorless solid. Rt: 1.02 min (LC-MS 1); ESI-MS m/z: 497.2 [M+H]$^+$ (LC-MS 1).

Step 3: Tert-butyl (6-(4-chlorophenyl)-5-(3-(difluoromethyl)-8-methyl-[1,2,4]triazolo[4,3-a]pyridin-6-yl)-1-methyl-4-oxo-1,4,5,6-tetrahydropyrrolo[3,4-b]pyrrol-3-yl)carbamate Tert-Butanol (4 mL) was added to a stirred suspension of 6-(4-chlorophenyl)-5-(3-(difluoromethyl)-8-methyl-[1,2,4]triazolo[4,3-a]pyridin-6-yl)-1-methyl-4-oxo-1,4,5,6-tetrahydropyrrolo[3,4-b]pyrrole-3-carbonyl azide (Step 2, 2 g, 3.82 mmol) in toluene (40 mL). The reaction mixture was stirred for 2 h at 100° C. and concentrated. The residue was purified by silica gel chromatography on Combiflash Isco (eluent: MeOH/DCM; gradient: 0-5% MeOH in 20 min; flow: 40 mL/min) to afford the title compound (983 mg) as a pale pink solid. Rt: 1.18 min (LC-MS 1); ESI-MS m/z: 543.3 [M+H]$^+$ (LC-MS 1).

Step 4: 3-amino-6-(4-chlorophenyl)-5-(3-(difluoromethyl)-8-methyl-[1,2,4]triazolo[4,3-a]pyridin-6-yl)-1-methyl-5,6-dihydropyrrolo[3,4-b]pyrrol-4(1H)-one HCl (4N in dioxane, 15 mL, 60.0 mmol) was added to cooled (0-5° C., by ice bath) tert-butyl (6-(4-chlorophenyl)-5-(3-(difluoromethyl)-8-methyl-[1,2,4]triazolo[4,3-a]pyridin-6-yl)-1-methyl-4-oxo-1,4,5,6-tetrahydropyrrolo[3,4-b]pyrrol-3-yl)carbamate (Step 3, 980 mg, 1.805 mmol) under argon. After 5 min, the ice bath was removed. The reaction mixture was stirred for 2 h at rt and concentrated to afford the title compound (995 mg, 94% purity) as a colorless solid. Rt: 0.81 min (LC-MS 1); ESI-MS m/z: 443.2 [M+H]$^+$ (LC-MS 1).

Step 5: N-(6-(4-chlorophenyl)-5-(3-(difluoromethyl)-8-methyl-[1,2,4]triazolo[4,3-a]pyridin-6-yl)-1-methyl-4-oxo-1,4,5,6-tetrahydropyrrolo[3,4-b]pyrrol-3-yl)acetamide Ac$_2$O (0.048 mL, 0.511 mmol) was added to a stirred solution of 3-amino-6-(4-chlorophenyl)-5-(3-(difluoromethyl)-8-methyl-[1,2,4]triazolo[4,3-a]pyridin-6-yl)-1-methyl-5,6-dihydropyrrolo[3,4-b]pyrrol-4(1H)-one (Step 4, 150 mg, 0.255 mmol) in triethylamine (0.178 mL, 1.277 mmol) and DCM (5 mL). The reaction mixture was stirred for 15 min at rt, diluted in DCM/water and extracted twice with DCM. The combined organic extracts were washed with brine, dried (Na$_2$SO$_4$) and concentrated. The residue was purified by silica gel chromatography on Combiflash Isco (eluent: MeOH/DCM; gradient: 0-5.4% MeOH in 14.5 min; flow: 30 mL/min) and subsequent trituration of the resulting material in Et$_2$O to afford the title compound (96 mg) as a colorless solid. Rt: 0.92 min (LC-MS 1); ESI-MS m/z: 485.2 [M+H]$^+$ (LC-MS 1); $^1$H NMR (400 MHz, DMSO-d6) δ 9.81 (s, 1H), 8.71 (d, J=1.6 Hz, 1H), 7.85-7.53 (m, 2H), 7.43-7.31 (m, 4H), 7.27 (s, 1H), 6.58 (s, 1H), 3.27 (s, 3H), 2.51 (s, 3H), 2.04 (s, 3H).

Example 134

N-(6-(4-chlorophenyl)-5-(3-(difluoromethyl)-8-methyl-[1,2,4]triazolo[4,3-a]pyridin-6-yl)-1-methyl-4-oxo-1,4,5,6-tetrahydropyrrolo[3,4-b]pyrrol-3-yl)-2-(dimethylamino)acetamide

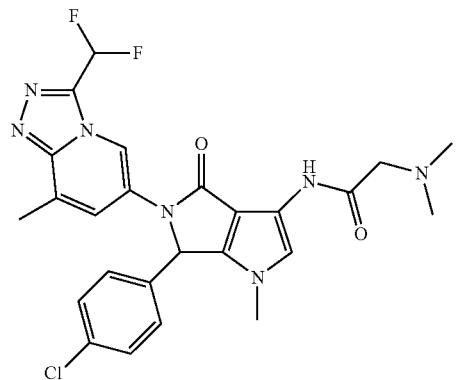 [SMILES: Cc1cc(N2C(=O)c3c(NC(=O)CN(C)C)cn(C)c3C2c2ccc(Cl)cc2)cn2c(C(F)F)nnc12]

DIEA (0.178 mL, 1.021 mmol) was added to a stirred suspension of 3-amino-6-(4-chlorophenyl)-5-(3-(difluoromethyl)-8-methyl-[1,2,4]triazolo[4,3-a]pyridin-6-yl)-1-methyl-5,6-dihydropyrrolo[3,4-b]pyrrol-4(1H)-one (Step 4 of Example 133, 150 mg, 0.255 mmol), TBTU (107 mg, 0.332 mmol) and N,N-dimethylglycine (29.0 mg, 0.281 mmol) in DMF (3 mL). The reaction mixture was stirred for 1.5 h at rt, diluted in EtOAc/water and extracted twice with EtOAc The combined organic extracts were washed with brine, dried (Na$_2$SO$_4$) and concentrated. The residue was purified by silica gel chromatography on Combiflash Isco (eluent: (20% ammonia/MeOH)/DCM; gradient: 0-7% (20% ammonia/MeOH) in 14.5 min; flow: 30 mL/min) and subsequent trituration of the resulting material in Et$_2$O to afford the title compound (76 mg) as a colorless solid. Rt: 0.76 min (LC-MS 1); ESI-MS m/z: 528.3 [M+H]$^+$ (LC-MS 1); $^1$H NMR (400 MHz, DMSO-d6) δ 9.33 (s, 1H), 8.66 (s, 1H), 7.86-7.51 (m, 2H), 7.38 (s, 4H), 7.31 (s, 1H), 6.62 (s, 1H), 3.29 (s, 3H), 3.14-2.99 (m, 2H), 2.51 (s, 3H), 2.29 (s, 6H).

Example 135

(R)-6-(4-chlorophenyl)-5-(3,8-di methyl-[1,2,4]triazolo[4,3-a]pyridin-6-yl)-2-(2-methoxypyridin-3-yl)-1-methyl-5,6-dihydropyrrolo[3,4-b]pyrrol-4(1H)-one

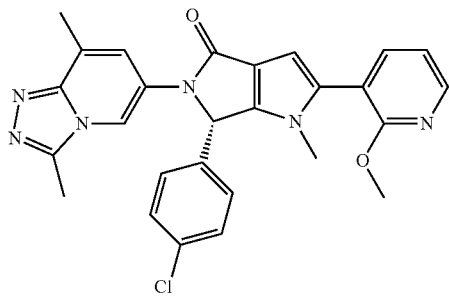 [SMILES: COc1ncccc1-c1cc2c(n1C)[C@H](c1ccc(Cl)cc1)N(c1cc(C)c3nnc(C)n3c1)C2=O]

The title compound was obtained by chiral separation of the compound described in Example 30.

(R)-6-(4-chlorophenyl)-5-(3,8-dimethyl-[1,2,4]triazolo[4,3-a]pyridin-6-yl)-2-(2-methoxypyridin-3-yl)-1-methyl-5,6-dihydropyrrolo[3,4-b]pyrrol-4(1H)-one t$_R$: 23.00 min (system: LaChrome Analytical HPLC; column: Chiralpak AD 5 μm, 4.6×250 mm; mobile phase: MeOH/EtOH 50/50; flow: 0.9 mL/min; detection UV: 210 nm); Rt: 1.00 min (LC-MS 1); ESI-MS m/z: 499.2 [M+H]$^+$ (LC-MS 1).

(S)-6-(4-chlorophenyl)-5-(3,8-dimethyl-[1,2,4]triazolo[4,3-a]pyridin-6-yl)-2-(2-methoxypyridin-3-yl)-1-methyl-5,6-dihydropyrrolo[3,4-b]pyrrol-4(1H)-one t$_R$: 9.99 min (system: LaChrome Analytical H PLC; column: Chiralpak AD 5 μm, 4.6×250 mm; mobile phase: MeOH/EtOH 1:1; flow: 0.9 mL/min; detection UV: 210 nm).

Example 136

(R)—N-(6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)acetamide

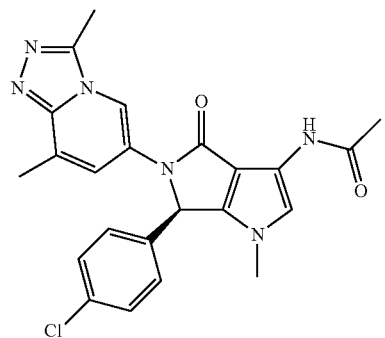 [SMILES: CC(=O)Nc1cn(C)c2c1C(=O)N(c1cc(C)c3nnc(C)n3c1)[C@@H]2c1ccc(Cl)cc1]

The title compound was obtained by chiral separation of the compound described in Example 103.

(R)—N-(6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)acetamide t$_R$: 17.47 min (column: Chiralpak AD-H 5 μm, 4.6×250 mm; mobile phase: heptane/MeOH/EtOH 50/25/25; flow: 0.9 mL/min; detection UV: 220 nm); Rt: 0.79 min (LC-MS 1); ESI-MS m/z: 449.2 [M+H]$^+$ (LC-MS 1).

(S)—N-(6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)acetamide. t$_R$: 4.93 min (column: Chiralpak AD-H 5 μm, 4.6×250 mm; mobile phase: heptane/MeOH/EtOH 50/25/25; flow: 0.9 mL/min; detection UV: 220 nm).

Example 137

(R)-6-(4-chlorophenyl)-2-(3,6-dihydro-2H-pyran-4-yl)-5-(3,8-dimethyl-[1,2,4]triazolo[4,3-a]pyridin-6-yl)-1-methyl-5,6-dihydropyrrolo[3,4-b]pyrrol-4(1H)-one

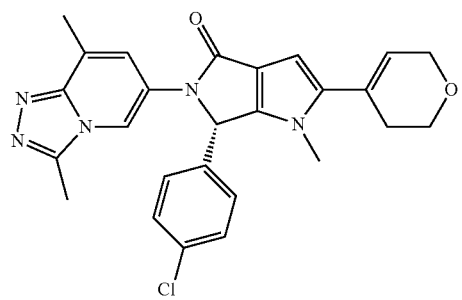 [SMILES: Cc1cc(N2C(=O)c3cc(C4=CCOCC4)n(C)c3[C@@H]2c2ccc(Cl)cc2)cn2c(C)nnc12]

The title compound was obtained by SFC chiral separation of the compound described in Example 31 and subsequent purification of each enantiomer by achiral SFC and trituration in Et$_2$O.

(R)-6-(4-chlorophenyl)-2-(3,6-dihydro-2H-pyran-4-yl)-5-(3,8-dimethyl-[1,2,4]triazolo[4, 3-a]pyridin-6-yl)-1-methyl-5,6-dihydropyrrolo[3,4-b]pyrrol-4(1H)-one t$_R$: 5.41 min (system: Waters Investigator SFC: Chiracel OD-H 5 µm, 4.6×250 mm; mobile phase: scCO$_2$/MeOH 70/30; flow: 4 mL/min; detection DAD: 250-300 nm); Rt: 0.93 min (LC-MS 1); ESI-MS m/z: 474.3 [M+H]$^+$ (LC-MS 1).

(S)-6-(4-chlorophenyl)-2-(3,6-dihydro-2H-pyran-4-yl)-5-(3,8-dimethyl-[1,2,4]triazolo[4,3-a]pyridin-6-yl)-1-methyl-5,6-dihydropyrrolo[3,4-b]pyrrol-4(1H)-one $t_R$: 3.63 min (system: Waters Investigator SFC: Chiracel OD-H 5 µm, 4.6×250 mm; mobile phase: scCO$_2$/MeOH 70/30; flow: 4 mL/min; detection DAD: 250-300 nm).

Assays

The activity of a compound according to the present invention can be assessed by the following methods.

TR-FRET In-Vitro Binding Assays for BRD2, BRD3, and BRD4:

All assays were performed in 384-well microtiter plates. Each assay plate contained 8-point serial dilutions for 40 test compounds, plus 16 high- and 16 low controls. Liquid handling and incubation steps were done on an Innovadyne Nanodrop Express equipped with a robotic arm (Thermo CatX, Perkin Elmer/Caliper Twister II) and an incubator (Liconic STX40, Thermo Cytomat 2C450). The assay plates were prepared by addition of 50 nl per well of compound solution in 90% DMSO HummingBird nanodispenser (Zinsser Analytic). The assay was started by stepwise addition of 4.5 µL per well of bromo domain protein (50 mM HEPES, pH 7.5, 0.005% Tween20, 0.1% BSA, 50 mM NaCl, 45 nM His-Brd2(60-472) or 45 nM His-Brd3(20-477) or 45 nM His-Brd4(44-477) all proteins produced in-house) and 4.5 µL per well of peptide solution (50 mM HEPES, pH 7.5, 0.005% Tween20, 0.1% BSA, 50 mM NaCl, 60 nM acetyl-histone H4 (AcK 5, 8, 12, 16) (Biosyntan GmbH)). Reactions were incubated at 30° C. for 35 minutes. Subsequently 4.5 µL per well detection mix (50 mM HEPES, pH 7.5, 0.005% Tween20, 0.1% BSA, 50 mM NaCl, 3 nM Eu-labeled anti-His6 antibody, 21 nM streptavidin-allophycocyanin) were added. After 35 minutes incubation at 30° C., plates were measured in a Perkin Elmer EnVision multilabel reader. Concentrations causing 50% inhibition (1050 values) were determined from percent inhibition values at different compound concentrations by non-linear regression analysis.

AlphaScreen In-Vitro Binding Assay for CREBBP

In order to assess bromodomain selectivity, we set up a binding assay using the bromodomain encoded by the CREBBP gene. Compounds were tested in the CREBBP assay with a similar protocol, however using AlphaScreen (Amplified Luminescent Proximity Homogeneous Assay, Perkin Elmer) as detection readout instead of TR-FRET. The assay was started by stepwise addition of 4.5 µL per well of bromo domain protein (50 mM HEPES, pH 7.5, 0.005% Tween20, 0.02% BSA, 150 mM NaCl, 324 nM His-CREBBP (1081-1197) (custom production at Viva Biotech Ltd.)) and 4.5 µL per well of peptide solution (50 mM HEPES, pH 7.5, 0.005% Tween20, 0.02% BSA, 150 mM NaCl, 120 nM acetyl-histone H4 (AcK 5, 8, 12) (Biosyntan GmbH)). Reactions were incubated at 30° C. for 35 minutes. Subsequently 4.5 µL per well detection mix (50 mM HEPES, pH 7.5, 0.005% Tween20, 0.02% BSA, 150 mM NaCl, 45 µg/ml Ni-chelate acceptor beads, 45 µg/mL streptavidin-donor beads) (Perkin Elmer)) were added. After 60 minutes incubation at room temperature, plates were measured in a Perkin Elmer EnVision multilabel reader. IC50 values were determined from percent inhibition values at different compound concentrations by non-linear regression analysis.

For further bromodomain selectivity profiling, additional panel assays were performed using analog protocols with minor modifications specific for the individual assay, using either TR-FRET or AlphaScreen for detection.

Preparation of Compound Dilutions

Test compounds were dissolved in DMSO (10 mM) and transferred into 1.4 mL flat bottom or V-shaped Matrix tubes carrying a unique 2D matrix. The stock solutions were stored at +2° C. if not used immediately. For the test procedure the vials were defrosted and identified by a scanner whereby a working sheet was generated that guided the subsequent working steps. Compound dilutions were made in 96 well plates. This format enabled the assay of maximally individual test compounds at 8 concentrations (single points) including 4 reference compounds, if desired (known BET inhibitors from the prior art, for this and other assays of the type disclosed herein). The dilution protocol included the production of "pre-dilution plates", "master plates" and "assay plates".

Pre-Dilution Plates:

Polypropylene 96-well plates were used as pre-dilution plates. A total of 4 pre-dilution plates were prepared including 10 test compounds each on the plate positions A1-A10, one standard compound at A11 and one DMSO control at A2. All dilution steps were done on a HamiltonSTAR robot.

Master Plates:

30 µL of individual compound dilutions including standard compound and controls of the 4 "pre-dilution plates" were transferred into a 384-well "master plate" including the following concentrations 10000, 3003, 1000, 300, 100, 30, 10 and 3 µM, respectively in 90% of DMSO.

Assay Plates:

Identical "assay plates" were then prepared by pipetting 50 nL each of compound dilutions of the "master plates" into 384-well "assay plates" by means of a HummingBird 384-channel dispenser. These plates were used directly for the assay which was performed in a total volume of 13.55 µL. This led to a final compound concentration of 37, 11, 3.7, 1.1, 0.37, 0.11, 0.037 and 0.011 µM and a final DMSO concentration of 0.37% in the assay.

Cell Growth Inhibition Assay

The human leukemia cell lines MV-4-11, THP-1 and K-562 were employed to characterize the effect of BET inhibitors on cellular proliferation and viability. Cells were obtained from the American Type Culture Collection (ATCC) and cultured at 37° C. in a humidified 5% CO$_2$ incubator in the following media: MV-4-11: DMEM high glucose (Animed #1-26F01-I), 10% FCS (Animed #2-01F26-I), 4 mM L-Glutamine (Animed #5-10K50), 1 mM Sodium Pyruvate (Animed # G03625P), 1× Penicillin-Streptomycin (Animed # F12478P); K-562: Iscove's MEM (Animed #1-28F16-I), 10% FCS (Animed #2-01F26-I), 4 mM L-Glutamine (Animed #5-10K50), 1× Penicillin-Streptomycin (Animed # F12478P); THP-1: RPMI-1640 (Animed #1-41F01-I), 10% FCS (Animed #2-01F26-I), 2 mM L-Glutamine (Animed #5-10K50), 10 mM HEPES (Animed #5-31F100), 1 mM Sodium Pyruvate (Animed # G03625P), 1× Penicillin-Streptomycin (Animed # F12478P). The AML lines MV-4-11 and THP-1 are very sensitive to BET inhibitors and show massive cell death upon BET inhibition (Zuber et al., Nature, 478 (2011), 524-8). Compound-mediated suppression of cell proliferation/viability was assessed by quantification of cellular ATP levels using the CellTiter-Glo (CTG) reagent (Promega). Briefly, cells were seeded in 20 µl fresh medium into 384-well plates, followed by addition of 5 µL medium containing compound dilutions at 5-fold their final intended concentration. Dose-response effects were assessed by 3-fold serial dilutions of the test compound, starting at 10 µM. Following incubation of the cells for 4 days at 37° C. and 5% CO$_2$, the effect of inhibitors on cell viability was quantified following addition of 20 µl CTG and luminescence quantification (integration time: 100 ms) as per vendor manual, using a correspondingly equipped Tecan M200 multi-mode platereader (TECAN, Switzerland). For data analysis, the assay background value determined in wells containing medium, but no cells, was subtracted from all data points. To enable differentiation of cytotoxic from cytostatic compounds, the number of viable cells is assessed relative to that observed at the time of compound addition using a separate cell plate (day 0). The effect of a particular test compound concentration on cell proliferation/viability is expressed as percentage of the background- and day 0-corrected luminescence reading obtained for cells treated with vehicle only (DMSO, 0.1% final concentration), which is set as 100%, whereas that luminescence reading for wells containing medium is set as −100%. Compound concentrations leading to half-maximal (IC50) and total growth inhibition (TGI) were determined using standard four parameter curve fitting.

Nut-Foci Formation Assay

HCC2494 NUT midline carcinoma cells (expressing BRD4-NUT-fusion) is obtained from the University of Texas Southwestern and cultured in RPMI-1640 medium containing 10% Foetal Calf Serum at 37° C. in a humidified 5% $CO_2$ incubator.

Compound-mediated inhibition of BRD4 activity can be monitored by quantification of the number and intensity of nuclear BRD4-NUT foci using automated immunofluorescence microscopy. Briefly, 5000 cells in 20 µL fresh medium are seeded into Poly-D-Lysine-precoated 384-well plates and incubated overnight at 37° C. and 5% $CO_2$, followed by addition of 5 µl medium containing compound dilutions at 5-fold their final intended concentration. Dose-response effects are assessed by 3-fold serial dilutions of the test compound, starting at 10 µM. Following incubation of the cells for 24 hours at 37° C. and 5% $CO_2$, the cells are fixed by incubation with 3.7% formaldehyde for 10 min, followed by immunofluorescence staining using rabbit anti-NUT (Cell Signaling Technologies, Cat#3625) as primary, and AlexaFluor488-labeled goat anti-rabbit (Invitrogen, Cat#A11008) as secondary antibody (latter complemented with 1 µg/mL Hoechst33342 as DNA dye). Assay plates can be imaged using the appropriate filter sets on the Cellomics VTi automated fluorescence microscopy platform (Thermo-Fisher Scientific) and the population average of the number of NUT-foci per nucleus is quantified using the Cellomics Spot Detection BioApplication image analysis algorithm (ThermoFisher Scientific). The effect of a particular test compound concentration on NUT-foci number and intensity is expressed as percentage of the value obtained for cells treated with vehicle only (DMSO, 0.1% final concentration), which was set as 100. Compound concentrations leading to half-maximal ($IC_{50}$) inhibition of the aforementioned read-out parameters are determined using standard four parameter curve fitting.

TABLE 1

Biochemical IC50 values

IC50 (µM)

| Example | BRD4 | BRD2 | BRD3 | CREBBP |
|---|---|---|---|---|
| 1 | | | | |
| 2 | 0.012 | 0.023 | 0.016 | >37 |
| 3 | 0.014 | 0.024 | 0.016 | 8.2 |
| 4 | | | | |
| 5 | 0.024 | 0.045 | 0.025 | 6.3 |
| 6 | 0.017 | 0.04 | 0.023 | 6 |
| 7 | 0.017 | 0.032 | 0.016 | 7.6 |
| 8 | 0.018 | 0.041 | 0.034 | 5.1 |
| 9 | 0.024 | 0.028 | 0.015 | 6 |
| 10 | 0.033 | 0.055 | 0.034 | 14.5 |
| 11 | 0.038 | 0.039 | 0.05 | 7.3 |
| 12 | 0.054 | 0.08 | 0.052 | 23.9 |
| 13 | 0.062 | 0.071 | 0.067 | 13.7 |
| 14 | 0.022 | 0.023 | 0.025 | 6.6 |
| 15 | | | | |
| 16 | 0.014 | 0.014 | 0.019 | 5 |
| 17 | <0.011 | <0.011 | <0.011 | 4.1 |
| 18 | 0.012 | 0.014 | 0.014 | |
| 19 | | | | |
| 20 | 0.016 | 0.023 | 0.02 | >37 |
| 21 | 0.047 | 0.082 | 0.053 | 5.1 |
| 22 | 0.025 | 0.038 | 0.026 | 12.5 |
| 23 | 0.052 | 0.085 | 0.039 | 4.2 |
| 24 | 0.08 | 0.22 | 0.087 | 13.3 |
| 25 | 0.017 | 0.038 | 0.023 | 4.4 |
| 26 | 0.06 | 0.078 | 0.052 | 4 |
| 27 | 0.017 | 0.037 | 0.021 | |
| 28 | 0.016 | 0.02 | 0.021 | 1.9 |
| 29 | | | | |
| 30 | 0.04 | 0.05 | 0.047 | 1.3 |
| 31 | 0.036 | 0.062 | 0.047 | 3.1 |
| 32 | 0.11 | 0.16 | 0.1 | >37 |
| 33 | 0.031 | 0.036 | 0.035 | 10.1 |
| 34 | 0.043 | 0.037 | 0.032 | 1.9 |
| 35 | 0.018 | 0.019 | 0.015 | 6.1 |
| 36 | 0.013 | 0.018 | 0.015 | 4.1 |
| 37 | 0.037 | 0.038 | 0.032 | 1.9 |
| 38 | 0.047 | 0.3225 | 0.059 | 0.205 |
| 39 | 0.305 | 0.28 | 0.22 | 1.2 |
| 40 | 0.078 | 0.0725 | 0.054 | 0.365 |
| 41 | 0.085 | 0.083 | 0.0655 | 0.535 |
| 42 | 0.27 | | 0.053 | 0.31 |
| 43 | 0.12 | 0.09 | 0.077 | 0.69 |
| 44 | 0.066 | 0.054 | 0.041 | 0.31 |
| 45 | 0.0245 | 0.022 | 0.0185 | 0.37 |
| 46 | 0.014 | 0.019 | 0.016 | 0.28 |
| 47 | 0.14 | 0.11 | 0.082 | 0.69 |
| 48 | 0.11 | 0.091 | 0.076 | |
| 49 | 0.083 | 0.076 | 0.075 | |
| 50 | 0.046 | 0.037 | 0.042 | |
| 51 | 0.033 | 0.032 | 0.038 | |
| 52 | 0.0553333 | 0.067 | 0.054 | 0.72 |
| 53 | 0.04 | 0.041 | 0.039 | |
| 54 | 0.045 | 0.027 | 0.028 | 0.091 |
| 55 | 0.052 | 0.053 | 0.05 | |
| 56 | 0.0283333 | 0.03 | 0.022 | 0.13 |
| 57 | 0.059 | 0.05 | 0.054 | |
| 58 | 0.042 | 0.04 | 0.034 | |
| 59 | 0.072 | 0.08 | 0.078 | 0.94 |
| 60 | | | | |
| 61 | 0.068 | 0.068 | 0.053 | |
| 62 | 0.17 | 0.14 | 0.13 | 0.27 |
| 63 | 0.12 | 0.1 | 0.085 | 0.18 |
| 64 | 0.085 | 0.05 | 0.082 | 1.5 |
| 65 | 0.22 | 0.12 | 0.2 | |
| 66 | 0.095 | 0.052 | 0.095 | 0.24 |
| 67 | 0.088 | 0.042 | 0.085 | 0.3 |
| 68 | 0.0632 | 0.0672 | 0.0522 | 0.62 |
| 69 | 0.1213333 | 0.159 | 0.087 | 1.2 |
| 72 | 0.0896714 | 0.1705 | 0.09075 | 1.4333333 |
| 74 | 0.023 | | | |
| 75 | 0.0853333 | 0.1353333 | 0.0533333 | 0.79 |
| 76 | 0.037 | | | |
| 77 | 0.1086667 | 0.1985 | 0.0945 | 1.3 |
| 78 | 0.15 | | | |
| 79 | 0.434 | 0.66 | 0.2225 | 26.8 |
| 80 | 0.1535 | 0.2916667 | 0.147 | 1.5 |
| 81 | 0.131 | 0.1263333 | 0.08125 | 4.5 |
| 82 | 0.195 | 0.23 | 0.14 | 4.7 |

TABLE 1-continued

Biochemical IC50 values

| Example | BRD4 IC50 (μM) | BRD2 | BRD3 | CREBBP |
|---|---|---|---|---|
| 83 | 0.3225 | 0.2733333 | 0.2 | 7.15 |
| 84 | 0.23 | 0.196 | 0.161 | 4.7 |
| 85 | 0.695 | 0.74 | 0.56 | |
| 86 | 0.4366667 | 0.4333333 | 0.2766667 | 18.4 |
| 87 | 0.1196667 | 0.1083333 | 0.0763333 | 4.1 |
| 88 | 0.33 | 0.2866667 | 0.19 | 7.6 |
| 89 | 0.3566667 | 0.23 | 0.21 | 10.65 |
| 90 | 0.2666667 | 0.265 | 0.1963333 | 1.45 |
| 91 | 1.0833333 | 0.83 | 0.6666667 | 11.1 |
| 92 | 0.89 | 0.85 | 0.69 | |
| 93 | 0.013 | 0.015 | 0.014 | >37 |
| 94 | 0.012 | 0.017 | 0.013 | >37 |
| 95 | 0.016 | 0.034 | 0.026 | >37 |
| 96 | 0.016 | 0.036 | 0.017 | >37 |
| 97 | 0.035 | 0.015 | <0.011 | >37 |
| 98 | <0.011 | | 0.012 | 6.7 |
| 99 | <0.011 | 0.016 | 0.013 | >37 |
| 100 | 0.03 | 0.04 | 0.047 | >37 |
| 101 | 0.041 | 0.054 | 0.042 | 30.6 |
| 102 | 0.032 | 0.044 | 0.034 | 3.2 |
| 103 | 0.023 | 0.031 | 0.023 | 5.2 |
| 104 | 0.021 | 0.035 | 0.021 | 14.8 |
| 105 | <0.011 | 0.013 | 0.012 | 14.1 |
| 106 | 0.012 | 0.013 | 0.012 | |
| 107 | 0.017 | | 0.021 | 27.9 |
| 108 | 0.016 | | 0.019 | >37 |
| 109 | 0.023 | | 0.02 | >37 |
| 110 | 0.03 | | 0.037 | >37 |
| 111 | <0.011 | | 0.019 | >37 |
| 112 | 0.12 | | 0.064 | 17.3 |
| 113 | 0.013 | | 0.015 | 1.6 |
| 114 | 0.034 | | 0.038 | 1.3 |
| 115 | 0.026 | | 0.036 | 3.9 |
| 116 | 0.026 | | 0.034 | 4.2 |
| 117 | 0.014 | | 0.017 | 13.7 |
| 118 | 0.021 | | 0.022 | 32.3 |
| 119 | <0.011 | | <0.011 | 1.7 |
| 120 | <0.011 | | <0.011 | 1.6 |
| 121 | 0.056 | | 0.044 | 0.64 |
| 122 | 0.012 | | 0.015 | 4.5 |
| 123 | <0.011 | | 0.011 | 2.8 |
| 124 | 0.011 | | 0.014 | 1.5 |
| 125 | 0.015 | | 0.015 | 13.7 |
| 126 | 0.043 | | 0.048 | 12.9 |
| 127 | 0.085 | | 0.081 | 7.5 |
| 128 | 0.045 | | 0.046 | 27.6 |
| 129 | 0.054 | | 0.058 | 8.1 |
| 130 | 0.012 | | 0.013 | 12.8 |
| 131 | 0.033 | | 0.027 | >37 |
| 132 | 0.016 | | 0.023 | 14.1 |
| 133 | 0.029 | | 0.032 | 13.9 |
| 134 | 0.022 | | 0.029 | >37 |
| 135 | 0.014 | | 0.021 | 0.47 |
| 136 | 0.021 | | 0.019 | 1.4 |
| 137 | <0.011 | | 0.013 | 0.59 |

*Values from either single determination or n ≥ 2 independent determinations

TABLE 2

Cellular IC50 values

| Example | MV-4-11 GI50 (μM) | MV-4-11 TGI (μM) | THP-1 GI50 (μM) | THP-1 TGI (μM) | K-562 GI50 (μM) | K-562 TGI (μM) | HCS Brd4-NUT IC50 (μM) |
|---|---|---|---|---|---|---|---|
| 1 | | | | | | | |
| 2 | 0.007655 | 0.0197 | 0.0151 | 0.0347 | 0.06215 | >10 | |
| 3 | 0.00768 | 0.01875 | 0.01565 | 0.0369 | 0.0554 | >10 | |
| 4 | | | | | | | |
| 5 | 0.0063 | 0.01305 | 0.01205 | 0.0362 | 0.0478 | >10 | |
| 6 | 0.00674 | 0.0214 | 0.010615 | 0.02925 | 0.05055 | >10 | |
| 7 | 0.0502 | 0.1358 | 0.1955 | 0.4495 | 2.06 | >10 | |
| 8 | 0.0252 | 0.03775 | 0.04165 | 0.09395 | 0.1321 | >10 | |
| 9 | 0.013 | 0.02675 | 0.01705 | 0.0433 | 0.0787 | >10 | |
| 10 | 0.0194 | 0.03625 | 0.02975 | 0.06985 | 0.10155 | >10 | |
| 11 | 0.0187 | 0.03155 | 0.026 | 0.05895 | 0.11275 | >10 | |
| 12 | 0.07485 | 0.149 | 0.219 | 0.6185 | 1.0475 | >10 | |
| 13 | 0.0127 | 0.02485 | 0.01755 | 0.0389 | 0.0736 | >10 | |
| 14 | 0.01455 | 0.03085 | 0.0356 | 0.08155 | 0.11505 | >10 | |
| 15 | | | | | | | |
| 16 | 0.003815 | 0.0124 | 0.0117 | 0.0355 | 0.0452 | >10 | |
| 17 | 0.01111 | 0.03485 | 0.0433 | 0.168 | 0.2295 | >10 | |
| 18 | 0.002865 | 0.00813 | 0.00463 | 0.01335 | 0.01645 | >10 | |
| 19 | | | | | | | |
| 20 | 0.007895 | 0.02125 | 0.01295 | 0.038 | 0.06335 | >10 | |
| 21 | 0.04525 | 0.08105 | 0.0633 | 0.178 | 0.2465 | >10 | |
| 22 | 0.0468 | 0.08615 | 0.06015 | 0.13 | 0.2255 | >10 | |
| 23 | 0.029 | 0.0547 | 0.0392 | 0.1017 | 0.206 | >10 | |
| 24 | 0.09275 | 0.152 | 0.0964 | 0.2675 | 0.527 | >10 | |
| 25 | 0.0368 | 0.05815 | 0.03925 | 0.0949 | 0.156 | >10 | |
| 26 | 0.06995 | 0.1185 | 0.1355 | 0.34 | 0.839 | >10 | |
| 27 | 0.0225 | 0.0377 | 0.03435 | 0.088 | 0.108 | >10 | |
| 28 | 0.01284 | 0.02635 | 0.01925 | 0.03815 | 0.0556 | >10 | |
| 29 | | | | | | | |
| 30 | 0.01121 | 0.0213 | 0.0198 | 0.03905 | 0.05725 | >10 | |
| 31 | 0.0133 | 0.0237 | 0.0309 | 0.0525 | 0.0572 | >10 | |
| 32 | 0.11065 | 0.2035 | 0.1735 | 0.343 | 0.4295 | >10 | |
| 33 | 0.007705 | 0.02005 | 0.01745 | 0.0356 | 0.09745 | >10 | 0.00955 |
| 34 | 0.0194 | 0.0483 | 0.0438 | 0.0994 | 0.241 | >10 | 0.0268 |

TABLE 2-continued

Cellular IC50 values

| Example | MV-4-11 GI50 (μM) | MV-4-11 TGI (μM) | THP-1 GI50 (μM) | THP-1 TGI (μM) | K-562 GI50 (μM) | K-562 TGI (μM) | HCS Brd4-NUT IC50 (μM) |
|---|---|---|---|---|---|---|---|
| 35 | 0.00408 | 0.00867 | 0.00894 | 0.01785 | 0.04585 | >10 | |
| 36 | 0.002145 | 0.00622 | 0.00336 | 0.010915 | 0.01795 | >10 | |
| 37 | 0.0213 | 0.03855 | 0.0449 | 0.09815 | 0.18 | >10 | |
| 38 | 0.0294 | 0.0515 | 0.0375 | 0.0727 | 0.154 | >10 | 0.07245 |
| 39 | 0.0786 | 0.105 | 0.128 | 0.238 | 0.55 | >10 | |
| 40 | 0.0839 | 0.127 | 0.0919 | 0.137 | 0.326 | >10 | |
| 41 | 0.0787 | 0.128 | 0.167 | 0.307 | 0.517 | >10 | |
| 42 | 0.227 | 0.348 | 0.811 | 1.47 | 3.19 | >10 | 4.97 |
| 43 | 0.183 | 0.31 | 0.276 | 0.492 | 0.934 | >10 | |
| 44 | 0.264 | 0.391 | 1.42 | 2.7 | 2.59 | >10 | |
| 45 | 0.0559 | 0.0967 | 0.109 | 0.213 | 0.345 | >10 | 0.0973 |
| 46 | 0.165 | 0.292 | 0.525 | 1.07 | 1.6 | >10 | |
| 47 | 0.0984 | 0.156 | 0.195 | 0.351 | 0.698 | >10 | |
| 48 | 0.15 | 0.27 | 0.711 | 1.16 | 1.68 | >10 | |
| 49 | 0.0923 | 0.134 | 0.169 | 0.301 | 0.386 | >10 | |
| 50 | 0.0208 | 0.033 | 0.0316 | 0.0649 | 0.105 | >10 | 0.0733 |
| 51 | 0.0881 | 0.116 | 0.104 | 0.165 | 0.449 | >10 | |
| 52 | 0.8715 | 2.355 | 0.7755 | 2.63 | 2.75 | >10 | |
| 53 | | | | | | | |
| 54 | 0.0089 | 0.018 | 0.0233 | 0.0415 | 0.0483 | >10 | 0.0267 |
| 55 | 0.0345 | 0.0542 | 0.0763 | 0.13 | 0.231 | >10 | 0.1456 |
| 56 | 0.0248 | 0.0445 | 0.0303 | 0.0507 | 0.103 | >10 | 0.03915 |
| 57 | 0.0376 | 0.0598 | 0.076 | 0.126 | 0.2 | >10 | |
| 58 | 0.0181 | 0.0338 | 0.0332 | 0.0704 | 0.133 | >10 | |
| 59 | 0.074 | 0.106 | 0.0863 | 0.136 | 0.297 | >10 | |
| 60 | | | | | | | |
| 61 | 0.0616 | 0.106 | 0.102 | 0.224 | 0.421 | >10 | 0.1355 |
| 62 | 0.226 | 0.329 | 0.758 | 1.19 | 1.03 | >10 | |
| 63 | 0.0944 | 0.16 | 0.426 | 0.788 | 0.68 | >10 | |
| 64 | 0.1175 | 0.196 | 0.10945 | 0.2155 | 0.353 | >10 | |
| 65 | 0.08045 | 0.1285 | 0.09625 | 0.1675 | 0.2705 | >10 | |
| 66 | 0.04385 | 0.08745 | 0.0764 | 0.135 | 0.25 | >10 | |
| 67 | 0.0667 | 0.118 | 0.143 | 0.353 | 0.4045 | >10 | |
| 68 | 0.0287 | 0.0517 | 0.0468 | 0.096 | 0.148 | >10 | |
| 69 | 0.0378 | 0.0843 | 0.065 | 0.144 | 0.236 | >10 | |
| 72 | 0.0764 | 0.125 | 0.159 | 0.301 | 0.294 | >10 | |
| 74 | 0.09005 | 0.142 | 0.0927 | 0.1715 | 0.273 | >10 | |
| 75 | 0.0548 | 0.102 | 0.0743 | 0.167 | 0.289 | >10 | 0.0112 |
| 76 | 0.1075 | 0.178 | 0.1185 | 0.238 | 0.3675 | >10 | |
| 77 | 0.0576 | 0.0963 | 0.0889 | 0.146 | 0.342 | >10 | 0.0101 |
| 78 | 0.4865 | 0.7945 | 0.573 | 1.35 | 1.61 | >10 | 0.729 |
| 79 | 0.295 | 0.496 | 0.396 | 0.904 | 1.79 | >10 | |
| 80 | 0.1485 | 0.267 | 0.1465 | 0.3695 | 0.455 | >10 | |
| 81 | 0.0798 | 0.121 | 0.149 | 0.3 | 0.721 | >10 | |
| 82 | 0.104 | 0.189 | 0.206 | 0.397 | 0.618 | >10 | |
| 83 | 0.326 | 0.636 | 0.634 | 1.27 | 1.13 | >10 | |
| 84 | 0.1575 | 0.3385 | 0.167 | 0.4195 | 0.548 | >10 | |
| 85 | | | | | | | |
| 86 | 0.3375 | 0.642 | 0.392 | 0.7955 | 1.105 | >10 | |
| 87 | 0.0753 | 0.151 | 0.0839 | 0.255 | 0.266 | >10 | |
| 88 | 0.21 | 0.359 | 0.321 | 0.683 | 0.715 | >10 | |
| 89 | 0.4025 | 0.785 | 0.598 | 2.015 | 1.91 | >10 | |
| 90 | 0.2215 | 0.4075 | 0.2185 | 0.4465 | 0.618 | >10 | |
| 91 | 0.371 | 0.6415 | 0.466 | 1.0025 | 1.715 | >10 | |
| 92 | 0.655 | 1.495 | 0.68 | 2.405 | 2.87 | >10 | |
| 93 | 0.002545 | 0.01049 | 0.00312 | 0.011245 | 0.02745 | >10 | |
| 94 | 0.008195 | 0.02195 | 0.01245 | 0.02985 | 0.03465 | >10 | |
| 95 | 0.03145 | 0.0631 | 0.03485 | 0.0815 | 0.1229 | >10 | |
| 96 | 0.010945 | 0.0212 | 0.0112 | 0.02125 | 0.0328 | >10 | |
| 97 | 0.01365 | 0.02495 | 0.0179 | 0.03345 | 0.0487 | >10 | |
| 98 | 0.004946 | 0.012532 | 0.0055725 | 0.015972 | 0.03734 | >8.2 | |
| 99 | 0.0136 | 0.0383 | 0.02775 | 0.096 | 0.138 | >10 | |
| 100 | 0.1285 | 0.3685 | 0.5175 | 2.135 | 2.045 | >10 | |
| 101 | 0.05735 | 0.1605 | 0.15 | 0.4505 | 1.295 | >10 | |
| 102 | 0.0373 | 0.0904 | 0.0533 | 0.118 | 0.185 | >10 | |
| 103 | 0.0199 | 0.0526 | 0.045 | 0.119 | 0.241 | >10 | |
| 104 | 0.00298 | 0.011 | 0.00631 | 0.0184 | 0.0365 | >10 | |
| 105 | 0.000341 | 0.00243 | 0.0006745 | 0.00238 | 0.00476 | >10 | |
| 106 | 0.000522 | 0.00223 | 0.001164 | 0.003335 | 0.005675 | >10 | |
| 107 | 0.007205 | 0.02295 | 0.01535 | 0.022 | 0.197 | >10 | |
| 108 | 0.0432 | 0.07835 | 0.03235 | 0.07275 | 0.322 | >10 | |
| 109 | 0.0194 | 0.04075 | 0.0173 | 0.0386 | 0.11395 | >10 | |
| 110 | 0.01 | 0.0255 | 0.257 | 0.2935 | 0.211 | 5.64 | |
| 111 | 0.0132 | 0.0312 | 0.0107 | 0.0301 | 0.113 | >10 | |

TABLE 2-continued

| | Cellular IC50 values | | | | | | |
|---|---|---|---|---|---|---|---|
| Example | MV-4-11 GI50 (μM) | MV-4-11 TGI (μM) | THP-1 GI50 (μM) | THP-1 TGI (μM) | K-562 GI50 (μM) | K-562 TGI (μM) | HCS Brd4-NUT IC50 (μM) |
| 112 | 0.01945 | 0.03475 | 0.0393 | 0.09595 | 0.409 | >10 | |
| 113 | 0.0136 | 0.02725 | 0.0129 | 0.03035 | 0.07205 | >10 | |
| 114 | 0.02675 | 0.066 | 0.02705 | 0.1052 | 0.499 | >10 | |
| 115 | 0.0161 | 0.0257 | 0.0293 | 0.079 | 0.15655 | >10 | |
| 116 | 0.03775 | 0.08745 | 0.05955 | 0.123 | 0.288 | >10 | |
| 117 | 0.124 | 0.2175 | 0.1845 | 0.354 | 1.487 | >10 | |
| 118 | 0.3745 | 0.5915 | 0.9565 | 1.81 | 3.83 | >10 | |
| 119 | 0.00124 | 0.00376 | 0.00157 | 0.003665 | 0.0116633 | | 3.74 |
| 120 | 0.003025 | 0.0050533 | 0.003665 | 0.0055033 | 0.0253667 | >7 | |
| 121 | 0.05495 | 0.0893 | 0.04473 | 0.0862 | 0.1635 | >10 | |
| 122 | 0.00911 | 0.0129667 | 0.00604 | 0.0119333 | 0.0410333 | >7 | |
| 123 | 0.00514 | 0.009695 | 0.00603 | 0.0135 | 0.03755 | >10 | |
| 124 | 0.006575 | 0.0132 | 0.00756 | 0.0158 | 0.0416 | >10 | |
| 125 | 0.01205 | 0.01925 | 0.01505 | 0.0284 | 0.1154 | >10 | |
| 126 | 0.07455 | 0.18 | 0.1128 | 0.3155 | 0.6285 | >10 | |
| 127 | 0.4125 | 0.64 | 0.8235 | 1.129 | 2.32 | >10 | |
| 128 | 0.0395 | 0.0629 | 0.03765 | 0.10515 | 0.203 | >10 | |
| 129 | 0.0963 | 0.143 | 0.1885 | 0.4395 | 0.4915 | >10 | |
| 130 | <0.003 | 0.00621 | 0.012945 | 0.031 | 0.07635 | | 3.5 |
| 131 | 0.00921 | 0.0215 | 0.00976 | 0.03025 | 0.0671 | >10 | |
| 132 | 0.009575 | 0.02315 | 0.010085 | 0.026 | 0.0586 | >10 | |
| 133 | 0.0246 | 0.0497 | 0.02995 | 0.07425 | 0.0927 | >10 | |
| 134 | 0.0315 | 0.065 | 0.0342 | 0.0824 | 0.181 | >10 | |
| 135 | 0.006085 | 0.012445 | 0.0064 | 0.01495 | 0.02135 | >10 | |
| 136 | 0.01985 | 0.0395 | 0.0337 | 0.0792 | 0.119 | >10 | |
| 137 | 0.010035 | 0.01875 | 0.01105 | 0.02275 | 0.03105 | >10 | |

*Values from either single determination or n ≥ 2 independent determinations

The invention claimed is:

1. A compound of formula (I) or a pharmaceutically acceptable salt thereof,

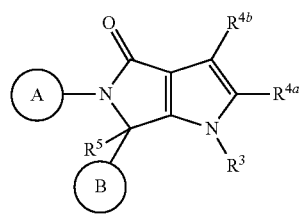

(I)

wherein:
A is selected from

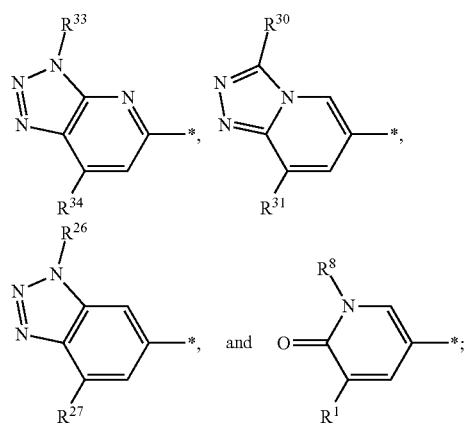

or A is

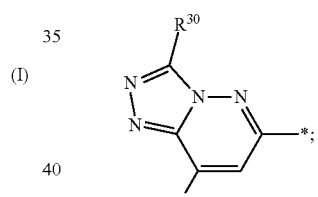

$R^{26}$ is methyl;
$R^{27}$ is methyl;
$R^{30}$ is methyl or $CF_2$;
$R^{31}$ is methyl;
$R^{33}$ is methyl;
$R^{34}$ is methyl;
$R^8$ is $(C_1-C_4)$alkyl;
$R^1$ is selected from H, chloro and methyl;
B is selected from

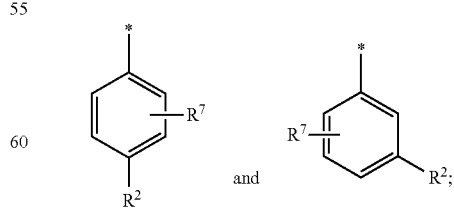

$R^2$ is selected from halo, methoxy, cyano, methyl and H;
$R^5$ is H;
$R^7$ is selected from H and halo;

$R^3$ is selected from H, methyl, ethyl, methoxyethyl, hydroxymethyl, methoxymethyl, hydroxyethyl, —C(O)O—($C_1$-$C_2$)alkyl, —C(O)$NR^9R^{10}$, cyclopropyl, isopropyl,

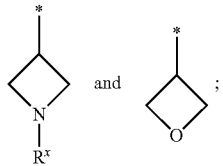

or $R^3$ is selected from —$CH_2$C(O)$NR^9R^{10}$, —($C_1$-$C_2$)alkyl-$NR^9R^{10}$ and

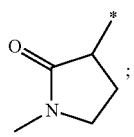 [SMILES: *C1CCN(C)C1=O]

$R^x$ is selected from H, methyl, —C(O)O—($C_1$-$C_2$)alkyl, ethyl, isopropyl and —C(O)—($C_1$-$C_2$)alkyl; wherein said —C(O)—($C_1$-$C_2$)alkyl being optionally substituted by methoxy; or $R^x$ is selected from

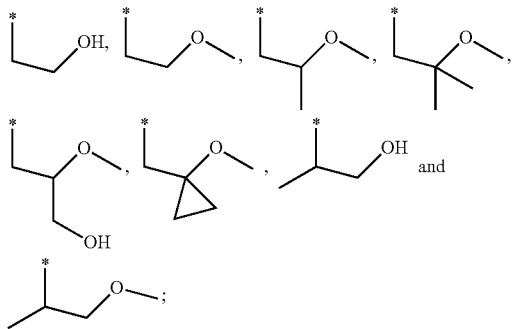

$R^9$ is selected from H and methyl;
$R^{10}$ is selected from H and methyl;
$R^{4a}$ is selected from H, methyl, cyclopropyl,

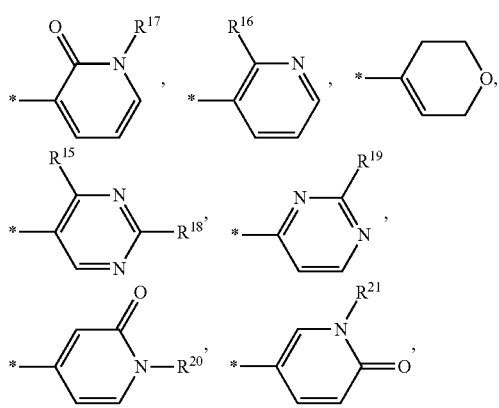

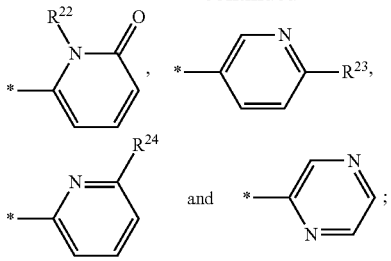

or $R^{4a}$ is

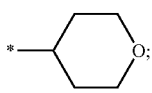

$R^{4b}$ is selected from H, cyclopropyl, methyl, —C(O)$NR^9R^{10}$, —C(O)OH, —NHC(O)—O—($C_1$-$C_4$alkyl), —NHC(O)—($C_1$-$C_4$alkyl) and $NR^9R^{10}$; or $R^{4b}$ is selected from —NHC(O)$NR^9R^{10}$, —C(O)NH($C_1$-$C_2$alkyl)-$NR^9R^{10}$, —NHC(O)—($C_1$-$C_2$alkyl)-$NR^9R^{10}$ and

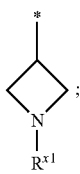

$R^{15}$ is selected from methoxy and H;
$R^{16}$ is selected from methoxy and hydroxy;
$R^{17}$ is methyl;
$R^{18}$ is selected from methoxy and —$NR^9R^{10}$;
$R^{19}$ is selected from methoxy and $CF_3$;
$R^{20}$ is methyl;
$R^{21}$ is methyl;
$R^{22}$ is methyl;
$R^{23}$ is selected from —$NR^9R^{10}$ and methoxy;
$R^{24}$ is selected from —$NR^9R^{10}$, H and methoxy;
$R^{x1}$ is selected from H, methyl and —C(O)—($C_1$-$C_2$)alkyl;
and
* indicates the point of attachment to the remainder of the molecule;
with the proviso that
when A is:

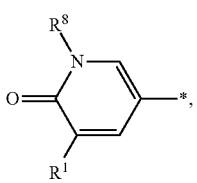

and R³ is selected from ethyl, cyclopropyl and isopropyl; then R⁴ᵃ is selected from

[chemical structures: pyridinone with R¹⁷; tetrahydropyran; pyrimidine with R¹⁹; pyridine with R²¹; pyridinone with R²²; pyrazine]

or R⁴ᵃ is

[chemical structure: tetrahydropyran]

and the remaining substituents are as defined herein.

2. A compound of formula (I) or a pharmaceutically acceptable salt thereof, according to claim 1, wherein:

A is selected from

[chemical structures: triazolopyridine with R³³, R³⁴; triazolopyridine with R³⁰, R³¹; benzotriazole with R²⁶, R²⁷; pyridinone with R⁸, R¹]

R²⁶ is methyl;
R²⁷ is methyl;
R³⁰ is methyl or CF₂;
R³¹ is methyl;
R³³ is methyl;
R³⁴ is methyl;
R⁸ is (C₁-C₄)alkyl;
R¹ is selected from H, chloro and methyl;

B is selected from

[chemical structures: phenyl substituted with R² and R⁷; phenyl substituted with R² and R⁷]

$R^2$ is selected from halo, methoxy, cyano, methyl and H;
$R^5$ is H;
$R^7$ is selected from H and halo;
$R^3$ is selected from H, methyl, ethyl, methoxyethyl, hydroxymethyl, methoxymethyl, hydroxyethyl, —C(O)O—(C₁-C₂)alkyl, —C(O)NR⁹R¹⁰, cyclopropyl, isopropyl,

[chemical structures: azetidine with Rˣ; oxetane]

$R^x$ is selected from H, methyl, —C(O)O—(C₁-C₂)alkyl, ethyl, isopropyl and —C(O)—(C₁-C₂)alkyl; wherein said —C(O)—(C₁-C₂)alkyl being optionally substituted by methoxy; or $R^x$ is selected from

[chemical structures: various hydroxyalkyl and methoxyalkyl groups]

$R^9$ is selected from H and methyl;
$R^{10}$ is selected from H and methyl;
$R^{4a}$ is selected from H, methyl, cyclopropyl,

[chemical structures: pyridinone with R¹⁷; pyridine with R¹⁶; tetrahydropyran; pyrimidine with R¹⁵, R¹⁸; pyrimidine with R¹⁹]

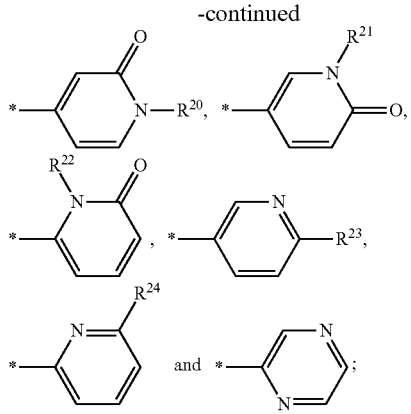

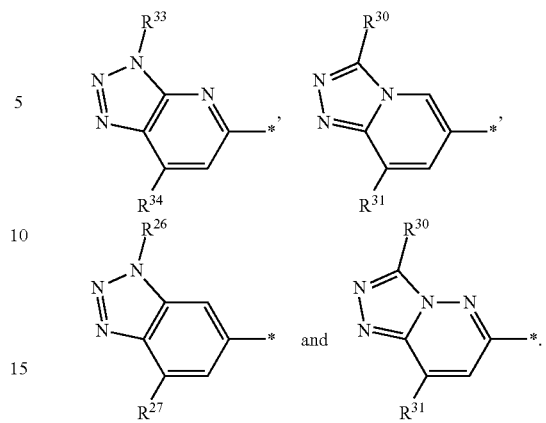

$R^{4b}$ is selected from H, cyclopropyl, methyl, —C(O)NR$^9$R$^{10}$, —C(O)OH, —NHC(O)—O—(C$_1$-C$_4$alkyl), —NHC(O)—(C$_1$-C$_4$alkyl) and NR$^9$R$^{10}$;
$R^{15}$ is selected from methoxy and H;
$R^{16}$ is selected from methoxy and hydroxy;
$R^{17}$ is methyl;
$R^{18}$ is selected from methoxy and —NR$^9$R$^{10}$;
$R^{19}$ is selected from methoxy and CF$_3$;
$R^{20}$ is methyl;
$R^{21}$ is methyl;
$R^{22}$ is methyl;
$R^{23}$ is selected from —NR$^9$R$^{10}$ and methoxy;
$R^{24}$ is selected from —NR$^9$R$^{10}$, H and methoxy;
and
* indicates the point of attachment to the remainder of the molecule;
with the proviso that
when A is:

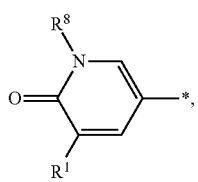

and R$^3$ is selected from ethyl, cyclopropyl and isopropyl; then R$^{4a}$ is selected from

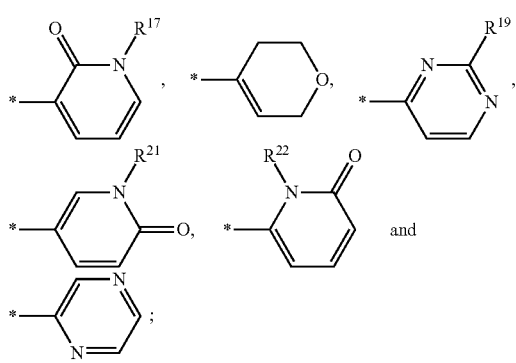

and the remaining substituents are as defined herein.

3. A compound of formula (I) or a pharmaceutically acceptable salt thereof, according to claim 1, wherein A is selected from:

4. A compound of formula (I) or a pharmaceutically acceptable salt thereof, according to claim 1, wherein B is:

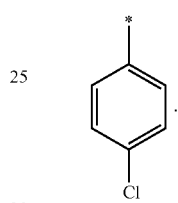

5. A compound of formula (I) or a pharmaceutically acceptable salt thereof, according to claim 1, wherein R$^3$ is methyl, —C(O)O—CH$_2$CH$_3$,

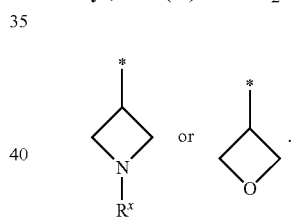

6. A compound of formula (I) or a pharmaceutically acceptable salt thereof, according to claim 1, wherein R$^x$ is selected from methyl, —C(O)—CH$_3$ and —C(O)O—CH$_2$CH$_3$.

7. A compound of formula (I) or a pharmaceutically acceptable salt thereof, according to claim 1, wherein R$^{4a}$ is selected from H,

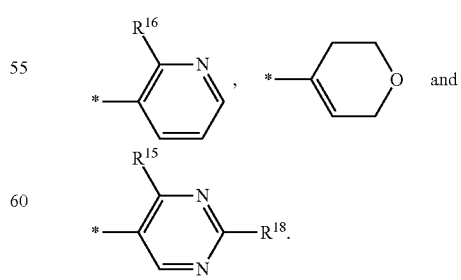

8. A compound of formula (I) or a pharmaceutically acceptable salt thereof, according to claim 1, wherein R$^{4b}$ is selected from —C(O)NR$^9$R$^{10}$, cyclopropyl, methyl, H, —NHC(O)—(C$_1$-C$_4$alkyl), —C(O)NH(C$_1$-C$_2$alkyl)-NR$^9$R$^{10}$ and —NHC(O)—(C$_1$-C$_2$alkyl)-NR$^9$R$^{10}$.

9. A compound of formula (I) or a pharmaceutically acceptable salt thereof, according to claim 1, wherein the compound of formula (I) has the stereochemistry of formula (Ic):

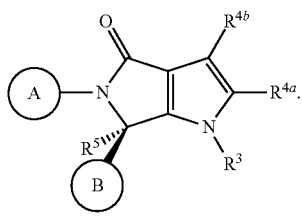

10. A compound of formula (I) or a pharmaceutically acceptable salt thereof, according to claim 1, wherein A is:

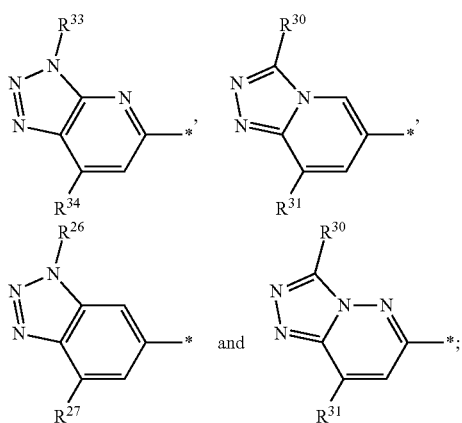

B is:

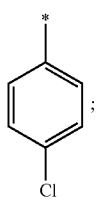

R$^3$ is methyl, —C(O)O—CH$_2$CH$_3$,

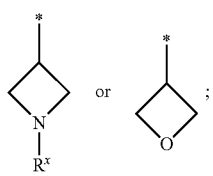

R$^x$ is selected from methyl, —C(O)—CH$_3$ and —C(O)O—CH$_2$CH$_3$;

R$^{4a}$ is selected from H,

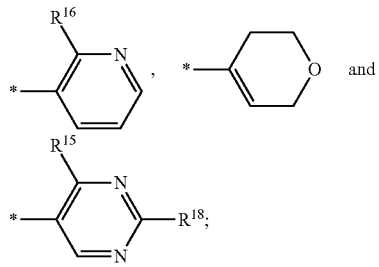

and

R$^{4b}$ is selected from —C(O)NR$^9$R$^{10}$, cyclopropyl, methyl, H, —NHC(O)—(C$_1$-C$_4$alkyl), —C(O)NH(C$_1$-C$_2$alkyl)-NR$^9$R$^{10}$ and —NHC(O)—(C$_1$-C$_2$alkyl)-NR$^9$R$^{10}$.

11. A pharmaceutical composition comprising a therapeutically effective amount of a compound according to claim 1, or a pharmaceutically acceptable salt thereof, and one or more pharmaceutically acceptable carriers.

12. A combination comprising a therapeutically effective amount of a compound according to claim 1, or a pharmaceutically acceptable salt thereof, and one or more therapeutically active agents.

13. A compound of formula (I) or a pharmaceutically acceptable salt thereof, according to claim 1, which is selected from:

Example 1: 6-(4-chlorophenyl)-3-cyclopropyl-5-(3,7-dimethyl-3H-[1,2,3]triazolo[4,5-b]pyridin-5-yl)-1-(hydroxymethyl)-5,6-dihydropyrrolo[3,4-b]pyrrol-4(1H)-one;

Example 2: 6-(4-chlorophenyl)-5-(3,7-dimethyl-3H-[1,2,3]triazolo[4,5-b]pyridin-5-yl)-1-(methoxymethyl)-3-methyl-5,6-dihydropyrrolo[3,4-b]pyrrol-4(1H)-one;

Example 3: 6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one;

Example 4: 1-(azetidin-3-yl)-6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one;

Example 5: 6-(4-chlorophenyl)-5-(3,8-dimethyl-[1,2,4]triazolo[4,3-a]pyridin-6-yl)-3-methyl-1-(1-methylazetidin-3-yl)-5,6-dihydropyrrolo[3,4-b]pyrrol-4(1H)-one;

Example 6: 6-(4-chlorophenyl)-5-(3,8-dimethyl-[1,2,4]triazolo[4,3-a]pyridin-6-yl)-3-methyl-1-(oxetan-3-yl)-5,6-dihydropyrrolo[3,4-b]pyrrol-4(1H)-one;

Example 7: 1-(1-acetylazetidin-3-yl)-6-(4-chlorophenyl)-5-(3,8-dimethyl-[1,2,4]triazolo[4,3-a]pyridin-6-yl)-3-methyl-5,6-dihydropyrrolo[3,4-b]pyrrol-4(1H)-one;

Example 8: Ethyl 3-(6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrol-1(4H)-yl)azetidine-1-carboxylate;

Example 9: 6-(4-chlorophenyl)-5-(3,8-dimethyl-[1,2,4]triazolo[4,3-a]pyridin-6-yl)-N,3-dimethyl-4-oxo-5,6-dihydropyrrolo[3,4-b]pyrrole-1(4H)-carboxamide;

Example 10: 6-(4-chlorophenyl)-5-(3,8-dimethyl-[1,2,4]triazolo[4,3-a]pyridin-6-yl)-N,N,3-trimethyl-4-oxo-5,6-dihydropyrrolo[3,4-b]pyrrole-1(4H)-carboxamide;

Example 11: Ethyl 6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrole-1(4H)-carboxylate;

Example 12: 6-(4-chlorophenyl)-5-(3,8-dimethyl-[1,2,4]triazolo[4,3-a]pyridin-6-yl)-1-(1-(2-methoxyacetyl)azetidin-3-yl)-3-methyl-5,6-dihydropyrrolo[3,4-b]pyrrol-4(1H)-one;

Example 13: 6-(4-chlorophenyl)-5-(3,8-dimethyl-[1,2,4]triazolo[4,3-a]pyridin-6-yl)-1-(2-methoxyethyl)-3-methyl-5,6-dihydropyrrolo[3,4-b]pyrrol-4(1H)-one;

Example 14: 6-(4-chlorophenyl)-5-(3,8-dimethyl-[1,2,4]triazolo[4,3-a]pyridin-6-yl)-1-(2-hydroxyethyl)-3-methyl-5,6-dihydropyrrolo[3,4-b]pyrrol-4(1H)-one;

Example 15: 1-(azetidin-3-yl)-6-(4-chlorophenyl)-3-cyclopropyl-5-(3,8-dimethyl-[1,2,4]triazolo[4,3-a]pyridin-6-yl)-5,6-dihydropyrrolo[3,4-b]pyrrol-4(1H)-one;

Example 16: 6-(4-chlorophenyl)-3-cyclopropyl-5-(3,8-dimethyl-[1,2,4]triazolo[4,3-a]pyridin-6-yl)-1-(1-methylazetidin-3-yl)-5,6-dihydropyrrolo[3,4-b]pyrrol-4(1H)-one;

Example 17: 1-(1-acetylazetidin-3-yl)-6-(4-chlorophenyl)-3-cyclopropyl-5-(3,8-dimethyl-[1,2,4]triazolo[4,3-a]pyridin-6-yl)-5,6-dihydropyrrolo[3,4-b]pyrrol-4(1H)-one;

Example 18: 6-(4-chlorophenyl)-3-cyclopropyl-5-(3,8-dimethyl-[1,2,4]triazolo[4,3-a]pyridin-6-yl)-1-(oxetan-3-yl)-5,6-dihydropyrrolo[3,4-b]pyrrol-4(1H)-one;

Example 19: 1-(azetidin-3-yl)-6-(4-chlorophenyl)-5-(3,7-dimethyl-3H-[1,2,3]triazolo[4,5-b]pyridin-5-yl)-3-methyl-5,6-dihydropyrrolo[3,4-b]pyrrol-4(1H)-one;

Example 20: 6-(4-chlorophenyl)-5-(3,7-dimethyl-3H-[1,2,3]triazolo[4,5-b]pyridin-5-yl)-3-methyl-1-(1-methylazetidin-3-yl)-5,6-dihydropyrrolo[3,4-b]pyrrol-4(1H)-one;

Example 21: 6-(4-chlorophenyl)-5-(3,8-dimethyl-[1,2,4]triazolo[4,3-a]pyridin-6-yl)-5,6-dihydropyrrolo[3,4-b]pyrrol-4(1H)-one;

Example 22: Ethyl 6-(4-chlorophenyl)-5-(3,8-dimethyl-[1,2,4]triazolo[4,3-a]pyridin-6-yl)-4-oxo-5,6-dihydropyrrolo[3,4-b]pyrrole-1(4H)-carboxylate;

Example 23: 6-(4-chlorophenyl)-5-(3,8-dimethyl-[1,2,4]triazolo[4,3-a]pyridin-6-yl)-N-methyl-4-oxo-5,6-dihydropyrrolo[3,4-b]pyrrole-1(4H)-carboxamide;

Example 24: 6-(4-chlorophenyl)-5-(3,8-dimethyl-[1,2,4]triazolo[4,3-a]pyridin-6-yl)-N,N-dimethyl-4-oxo-5,6-dihydropyrrolo[3,4-b]pyrrole-1(4H)-carboxamide;

Example 25: 6-(4-chlorophenyl)-5-(3,8-dimethyl-[1,2,4]triazolo[4,3-a]pyridin-6-yl)-2-(1-methyl-2-oxo-1,2-dihydropyridin-3-yl)-5,6-dihydropyrrolo[3,4-b]pyrrol-4(1H)-one;

Example 26: 6-(4-chlorophenyl)-5-(3,8-dimethyl-[1,2,4]triazolo[4,3-a]pyridin-6-yl)-2-(2-hydroxypyridin-3-yl)-5,6-dihydropyrrolo[3,4-b]pyrrol-4(1H)-one;

Example 27: 6-(4-chlorophenyl)-5-(3,8-dimethyl-[1,2,4]triazolo[4,3-a]pyridin-6-yl)-2-(2-methoxypyridin-3-yl)-5,6-dihydropyrrolo[3,4-b]pyrrol-4(1H)-one;

Example 28: 6-(4-chlorophenyl)-5-(1,4-dimethyl-1H-benzo[d][1,2,3]triazol-6-yl)-1,3-dimethyl-5,6-dihydropyrrolo[3,4-b]pyrrol-4(1H)-one;

Example 29: 6-(4-chlorophenyl)-5-(3,8-dimethyl-[1,2,4]triazolo[4,3-a]pyridin-6-yl)-1-methyl-5,6-dihydropyrrolo[3,4-b]pyrrol-4(1H)-one;

Example 30: 6-(4-chlorophenyl)-5-(3,8-dimethyl-[1,2,4]triazolo[4,3-a]pyridin-6-yl)-2-(2-methoxypyridin-3-yl)-1-methyl-5,6-dihydropyrrolo[3,4-b]pyrrol-4(1H)-one;

Example 31: 6-(4-chlorophenyl)-2-(3,6-dihydro-2H-pyran-4-yl)-5-(3,8-dimethyl-[1,2,4]triazolo[4,3-a]pyridin-6-yl)-1-methyl-5,6-dihydropyrrolo[3,4-b]pyrrol-4(1H)-one;

Example 32: 6-(4-chlorophenyl)-5-(3,7-dimethyl-3H-[1,2,3]triazolo[4,5-b]pyridin-5-yl)-1,3-dimethyl-5,6-dihydropyrrolo[3,4-b]pyrrol-4(1H)-one;

Example 33: 6-(4-chlorophenyl)-5-(3,8-dimethyl-[1,2,4]triazolo[4,3-a]pyridin-6-yl)-1,3-dimethyl-5,6-dihydropyrrolo[3,4-b]pyrrol-4(1H)-one Example 34: 6-(4-chlorophenyl)-5-(1,5-dimethyl-6-oxo-1,6-dihydropyridin-3-yl)-1,3-dimethyl-5,6-dihydropyrrolo[3,4-b]pyrrol-4(1H)-one;

Example 35: 6-(4-chlorophenyl)-3-cyclopropyl-5-(3,8-dimethyl-[1,2,4]triazolo[4,3-a]pyridin-6-yl)-1-methyl-5,6-dihydropyrrolo[3,4-b]pyrrol-4(1H)-one;

Example 36: (R)-6-(4-chlorophenyl)-3-cyclopropyl-5-(3,8-dimethyl-[1,2,4]triazolo[4,3-a]pyridin-6-yl)-1-methyl-5,6-dihydropyrrolo[3,4-b]pyrrol-4(1H)-one;

Example 37: 6-(4-chlorophenyl)-3-cyclopropyl-5-(1,5-dimethyl-6-oxo-1,6-dihydropyridin-3-yl)-1-methyl-5,6-dihydropyrrolo[3,4-b]pyrrol-4(1H)-one;

Example 38: 5-(5-chloro-1-methyl-6-oxo-1,6-dihydropyridin-3-yl)-6-(4-chlorophenyl)-2-(2,4-dimethoxypyrimidin-5-yl)-1-methyl-5,6-dihydropyrrolo[3,4-b]pyrrol-4(1H)-one;

Example 39: 5-(5-chloro-1-methyl-6-oxo-1,6-dihydropyridin-3-yl)-6-(4-chlorophenyl)-2-(2-methoxypyrimidin-4-yl)-1-methyl-5,6-dihydropyrrolo[3,4-b]pyrrol-4(1H)-one;

Example 40: 5-(5-chloro-1-methyl-6-oxo-1,6-dihydropyridin-3-yl)-6-(4-chlorophenyl)-2-(2-methoxypyrimidin-5-yl)-1-methyl-5,6-dihydropyrrolo[3,4-b]pyrrol-4(1H)-one;

Example 41: 5-(5-chloro-1-methyl-6-oxo-1,6-dihydropyridin-3-yl)-6-(4-chlorophenyl)-1-methyl-2-(1-methyl-2-oxo-1,2-dihydropyridin-4-yl)-5,6-dihydropyrrolo[3,4-b]pyrrol-4(1H)-one;

Example 42: 5-(5-chloro-1-methyl-6-oxo-1,6-dihydropyridin-3-yl)-6-(4-chlorophenyl)-1-methyl-2-(1-methyl-6-oxo-1,6-dihydropyridin-3-yl)-5,6-dihydropyrrolo[3,4-b]pyrrol-4(1H)-one;

Example 43: 5-(5-chloro-1-methyl-6-oxo-1,6-dihydropyridin-3-yl)-6-(4-chlorophenyl)-1-methyl-2-(1-methyl-2-oxo-1,2-dihydropyridin-3-yl)-5,6-dihydropyrrolo[3,4-b]pyrrol-4(1H)-one;

Example 44: 5-(5-chloro-1-methyl-6-oxo-1,6-dihydropyridin-3-yl)-6-(4-chlorophenyl)-1-methyl-2-(1-methyl-6-oxo-1,6-dihydropyridin-2-yl)-5,6-dihydropyrrolo[3,4-b]pyrrol-4(1H)-one;

Example 45: 6-(4-chlorophenyl)-5-(1,5-dimethyl-6-oxo-1,6-dihydropyridin-3-yl)-1-methyl-2-(1-methyl-2-oxo-1,2-dihydropyridin-4-yl)-5,6-dihydropyrrolo[3,4-b]pyrrol-4(1H)-one;

Example 46: 6-(4-chlorophenyl)-5-(1,5-dimethyl-6-oxo-1,6-dihydropyridin-3-yl)-1-methyl-2-(1-methyl-6-oxo-1,6-dihydropyridin-3-yl)-5,6-dihydropyrrolo[3,4-b]pyrrol-4(1H)-one;

Example 47: 6-(4-chlorophenyl)-5-(1,5-dimethyl-6-oxo-1,6-dihydropyridin-3-yl)-1-methyl-2-(1-methyl-2-oxo-1,2-dihydropyridin-3-yl)-5,6-dihydropyrrolo[3,4-b]pyrrol-4(1H)-one;

Example 48: 6-(4-chlorophenyl)-5-(1,5-dimethyl-6-oxo-1,6-dihydropyridin-3-yl)-1-methyl-2-(1-methyl-6-oxo-1,6-dihydropyridin-2-yl)-5,6-dihydropyrrolo[3,4-b]pyrrol-4(1H)-one;

Example 49: 6-(4-chlorophenyl)-5-(1,5-dimethyl-6-oxo-1,6-dihydropyridin-3-yl)-1-methyl-2-(2-(trifluoromethyl)pyrimidin-4-yl)-5,6-dihydropyrrolo[3,4-b]pyrrol-4(1H)-one;

Example 50: 6-(4-chlorophenyl)-5-(1,5-dimethyl-6-oxo-1,6-dihydropyridin-3-yl)-2-(6-(dimethylamino)pyridin-3-yl)-1-methyl-5,6-dihydropyrrolo[3,4-b]pyrrol-4(1H)-one;

Example 51: 6-(4-chlorophenyl)-5-(1,5-dimethyl-6-oxo-1,6-dihydropyridin-3-yl)-2-(6-(dimethylamino)pyridin-2-yl)-1-methyl-5,6-dihydropyrrolo[3,4-b]pyrrol-4(1H)-one;

Example 52: 6-(4-chlorophenyl)-5-(1,5-dimethyl-6-oxo-1,6-dihydropyridin-3-yl)-1-methyl-2-(pyridin-2-yl)-5,6-dihydropyrrolo[3,4-b]pyrrol-4(1H)-one;

Example 53: 6-(4-chlorophenyl)-2-(2,4-dimethoxypyrimidin-5-yl)-5-(1,5-dimethyl-6-oxo-1,6-dihydropyridin-3-yl)-1-methyl-5,6-dihydropyrrolo[3,4-b]pyrrol-4(1H)-one;

Example 54: (R)-6-(4-chlorophenyl)-2-(2,4-dimethoxypyrimidin-5-yl)-5-(1,5-dimethyl-6-oxo-1,6-dihydropyridin-3-yl)-1-methyl-5,6-dihydropyrrolo[3,4-b]pyrrol-4(1H)-one;

Example 55: 6-(4-chlorophenyl)-5-(1,5-dimethyl-6-oxo-1,6-dihydropyridin-3-yl)-2-(2-methoxypyrimidin-5-yl)-1-methyl-5,6-dihydropyrrolo[3,4-b]pyrrol-4(1H)-one;

Example 56: (R)-6-(4-chlorophenyl)-5-(1,5-dimethyl-6-oxo-1,6-dihydropyridin-3-yl)-2-(2-methoxypyrimidin-5-yl)-1-methyl-5,6-dihydropyrrolo[3,4-b]pyrrol-4(1H)-one;

Example 57: 6-(4-chlorophenyl)-5-(1,5-dimethyl-6-oxo-1,6-dihydropyridin-3-yl)-2-(2-(dimethylamino)pyrimidin-5-yl)-1-methyl-5,6-dihydropyrrolo[3,4-b]pyrrol-4(1H)-one;

Example 58: 6-(4-chlorophenyl)-5-(1,5-dimethyl-6-oxo-1,6-dihydropyridin-3-yl)-2-(6-methoxypyridin-3-yl)-1-methyl-5,6-dihydropyrrolo[3,4-b]pyrrol-4(1H)-one;

Example 59: 6-(4-chlorophenyl)-5-(1,5-dimethyl-6-oxo-1,6-dihydropyridin-3-yl)-2-(6-methoxypyridin-2-yl)-1-methyl-5,6-dihydropyrrolo[3,4-b]pyrrol-4(1H)-one;

Example 62: 5-(5-chloro-1-methyl-6-oxo-1,6-dihydropyridin-3-yl)-6-(4-chlorophenyl)-1-cyclopropyl-2-(1-methyl-6-oxo-1,6-dihydropyridin-2-yl)-5,6-dihydropyrrolo[3,4-b]pyrrol-4(1H)-one;

Example 63: 6-(4-chlorophenyl)-1-cyclopropyl-5-(1,5-dimethyl-6-oxo-1,6-dihydropyridin-3-yl)-2-(1-methyl-6-oxo-1,6-dihydropyridin-2-yl)-5,6-dihydropyrrolo[3,4-b]pyrrol-4(1H)-one;

Example 64: 5-(5-chloro-1-methyl-6-oxo-1,6-dihydropyridin-3-yl)-6-(4-chlorophenyl)-1-cyclopropyl-2-(1-methyl-2-oxo-1,2-dihydropyridin-3-yl)-5,6-dihydropyrrolo[3,4-b]pyrrol-4(1H)-one;

Example 65: 6-(4-chlorophenyl)-1-cyclopropyl-5-(1,5-dimethyl-6-oxo-1,6-dihydropyridin-3-yl)-2-(1-methyl-2-oxo-1,2-dihydropyridin-3-yl)-5,6-dihydropyrrolo[3,4-b]pyrrol-4(1H)-one;

Example 66: 5-(5-chloro-1-methyl-6-oxo-1,6-dihydropyridin-3-yl)-6-(4-chlorophenyl)-1-cyclopropyl-2-(1-methyl-6-oxo-1,6-dihydropyridin-3-yl)-5,6-dihydropyrrolo[3,4-b]pyrrol-4(1H)-one;

Example 67: 6-(4-chlorophenyl)-1-cyclopropyl-5-(1,5-dimethyl-6-oxo-1,6-dihydropyridin-3-yl)-2-(1-methyl-6-oxo-1,6-dihydropyridin-3-yl)-5,6-dihydropyrrolo[3,4-b]pyrrol-4(1H)-one;

Example 68: 6-(4-chlorophenyl)-2-cyclopropyl-5-(1,5-dimethyl-6-oxo-1,6-dihydropyridin-3-yl)-1-methyl-5,6-dihydropyrrolo[3,4-b]pyrrol-4(1H)-one;

Example 69: 6-(4-chlorophenyl)-5-(1,5-dimethyl-6-oxo-1,6-dihydropyridin-3-yl)-1,2-dimethyl-5,6-dihydropyrrolo[3,4-b]pyrrol-4(1H)-one;

Example 72: 6-(4-chlorophenyl)-5-(1,5-dimethyl-6-oxo-1,6-dihydropyridin-3-yl)-1-methyl-5,6-dihydropyrrolo[3,4-b]pyrrol-4(1H)-one;

Example 74: 5-(5-chloro-1-methyl-6-oxo-1,6-dihydropyridin-3-yl)-6-(4-chlorophenyl)-1,2-dimethyl-5,6-dihydropyrrolo[3,4-b]pyrrol-4(1H)-one;

Example 75: (R)-5-(5-chloro-1-methyl-6-oxo-1,6-dihydropyridin-3-yl)-6-(4-chlorophenyl)-1,2-dimethyl-5,6-dihydropyrrolo[3,4-b]pyrrol-4(1H)-one;

Example 76: 5-(5-chloro-1-methyl-6-oxo-1,6-dihydropyridin-3-yl)-6-(4-chlorophenyl)-1-methyl-5,6-dihydropyrrolo[3,4-b]pyrrol-4(1H)-one;

Example 77: (R)-5-(5-chloro-1-methyl-6-oxo-1,6-dihydropyridin-3-yl)-6-(4-chlorophenyl)-1-methyl-5,6-dihydropyrrolo[3,4-b]pyrrol-4(1H)-one;

Example 78: 6-(4-chlorophenyl)-1-methyl-5-(1-methyl-6-oxo-1,6-dihydropyridin-3-yl)-5,6-dihydropyrrolo[3,4-b]pyrrol-4(1H)-one;

Example 79: 5-(1,5-dimethyl-6-oxo-1,6-dihydropyridin-3-yl)-1-methyl-6-phenyl-5,6-dihydropyrrolo[3,4-b]pyrrol-4(1H)-one;

Example 80: 6-(4-chloro-3-fluorophenyl)-5-(1,5-dimethyl-6-oxo-1,6-dihydropyridin-3-yl)-1-methyl-5,6-dihydropyrrolo[3,4-b]pyrrol-4(1H)-one;

Example 81: 5-(1,5-dimethyl-6-oxo-1,6-dihydropyridin-3-yl)-1-methyl-6-(p-tolyl)-5,6-dihydropyrrolo[3,4-b]pyrrol-4(1H)-one;

Example 82: 5-(1,5-dimethyl-6-oxo-1,6-dihydropyridin-3-yl)-6-(4-fluorophenyl)-1-methyl-5,6-dihydropyrrolo[3,4-b]pyrrol-4(1H)-one;

Example 83: 4-(5-(1,5-dimethyl-6-oxo-1,6-dihydropyridin-3-yl)-1-methyl-4-oxo-1,4,5,6-tetrahydropyrrolo[3,4-b]pyrrol-6-yl)benzonitrile;

Example 84: 5-(1,5-dimethyl-6-oxo-1,6-dihydropyridin-3-yl)-6-(4-methoxyphenyl)-1-methyl-5,6-dihydropyrrolo[3,4-b]pyrrol-4(1H)-one;

Example 85: 5-(1,5-dimethyl-6-oxo-1,6-dihydropyridin-3-yl)-6-(3-methoxyphenyl)-1-methyl-5,6-dihydropyrrolo[3,4-b]pyrrol-4(1H)-one;

Example 86: 5-(5-chloro-1-methyl-6-oxo-1,6-dihydropyridin-3-yl)-1-methyl-6-phenyl-5,6-dihydropyrrolo[3,4-b]pyrrol-4(1H)-one;

Example 87: 5-(5-chloro-1-methyl-6-oxo-1,6-dihydropyridin-3-yl)-1-methyl-6-(p-tolyl)-5,6-dihydropyrrolo[3,4-b]pyrrol-4(1H)-one;

Example 88: 5-(5-chloro-1-methyl-6-oxo-1,6-dihydropyridin-3-yl)-6-(4-fluorophenyl)-1-methyl-5,6-dihydropyrrolo[3,4-b]pyrrol-4(1H)-one;

Example 89: 4-(5-(5-chloro-1-methyl-6-oxo-1,6-dihydropyridin-3-yl)-1-methyl-4-oxo-1,4,5,6-tetrahydropyrrolo[3,4-b]pyrrol-6-yl)benzonitrile;

Example 90: 5-(5-chloro-1-methyl-6-oxo-1,6-dihydropyridin-3-yl)-6-(4-chloro-3-fluorophenyl)-1-methyl-5,6-dihydropyrrolo[3,4-b]pyrrol-4(1H)-one;

Example 91: 5-(5-chloro-1-methyl-6-oxo-1,6-dihydropyridin-3-yl)-6-(3-methoxyphenyl)-1-methyl-5,6-dihydropyrrolo[3,4-b]pyrrol-4(1H)-one;

Example 92: 5-(5-chloro-1-methyl-6-oxo-1,6-dihydropyridin-3-yl)-6-(4-methoxyphenyl)-1-methyl-5,6-dihydropyrrolo[3,4-b]pyrrol-4(1H)-one;

Example 93: 6-(4-chlorophenyl)-5-(3,7-dimethyl-3H-[1,2,3]triazolo[4,5-b]pyridin-5-yl)-N,1-dimethyl-4-oxo-1,4,5,6-tetrahydropyrrolo[3,4-b]pyrrole-3-carboxamide;

Example 94: 6-(4-chlorophenyl)-5-(3,7-dimethyl-3H-[1,2,3]triazolo[4,5-b]pyridin-5-yl)-N,N,1-trimethyl-4-oxo-1,4,5,6-tetrahydropyrrolo[3,4-b]pyrrole-3-carboxamide;

Example 95: Tert-butyl (6-(4-chlorophenyl)-5-(3,7-dimethyl-3H-[1,2,3]triazolo[4,5-b]pyridin-5-yl)-1-methyl-4-oxo-1,4,5,6-tetrahydropyrrolo[3,4-b]pyrrol-3-yl)carbamate;

Example 96: N-(6-(4-chlorophenyl)-5-(3,7-dimethyl-3H-[1,2,3]triazolo[4,5-b]pyridin-5-yl)-1-methyl-4-oxo-1,4,5,6-tetrahydropyrrolo[3,4-b]pyrrol-3-yl)acetamide;

Example 97: Ethyl (6-(4-chlorophenyl)-5-(3,7-dimethyl-3H-[1,2,3]triazolo[4,5-b]pyridin-5-yl)-1-methyl-4-oxo-1,4,5,6-tetrahydropyrrolo[3,4-b]pyrrol-3-yl)carbamate;

Example 98: 6-(4-chlorophenyl)-5-(1,4-dimethyl-1H-benzo[d][1,2,3]triazol-6-yl)-N,1-dimethyl-4-oxo-1,4,5,6-tetrahydropyrrolo[3,4-b]pyrrole-3-carboxamide;

Example 99: 6-(4-chlorophenyl)-5-(3,8-dimethyl-[1,2,4]triazolo[4,3-a]pyridin-6-yl)-N,1-dimethyl-4-oxo-1,4,5,6-tetrahydropyrrolo[3,4-b]pyrrole-3-carboxamide;

Example 100: 6-(4-chlorophenyl)-5-(3,8-dimethyl-[1,2,4]triazolo[4,3-a]pyridin-6-yl)-N,N,1-trimethyl-4-oxo-1,4,5,6-tetrahydropyrrolo[3,4-b]pyrrole-3-carboxamide;

Example 101: 6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrole-3-carboxamide;

Example 102: Tert-butyl (6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)carbamate;

Example 103: N-(6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)acetamide;

Example 104: 6-(4-chlorophenyl)-3-cyclopropyl-5-(3,7-dimethyl-3H-[1,2,3]triazolo[4,5-b]pyridin-5-yl)-1-(oxetan-3-yl)-5,6-dihydropyrrolo[3,4-b]pyrrol-4(1H)-one;

Example 105: 1-(1-acetylazetidin-3-yl)-6-(4-chlorophenyl)-3-cyclopropyl-5-(3,7-dimethyl-3H-[1,2,3]triazolo[4,5-b]pyridin-5-yl)-5,6-dihydropyrrolo[3,4-b]pyrrol-4(1H)-one;

Example 106: 6-(4-chlorophenyl)-3-cyclopropyl-5-(3,7-dimethyl-3H-[1,2,3]triazolo[4,5-b]pyridin-5-yl)-1-(1-methylazetidin-3-yl)-5,6-dihydropyrrolo[3,4-b]pyrrol-4(1H)-one;

Example 107: 6-(4-chlorophenyl)-5-(3-(difluoromethyl)-8-methyl-[1,2,4]triazolo[4,3-a]pyridin-6-yl)-1,3-dimethyl-5,6-dihydropyrrolo[3,4-b]pyrrol-4(1H)-one;

Example 108: 6-(4-chlorophenyl)-5-(3-(difluoromethyl)-8-methyl-[1,2,4]triazolo[4,3-b]pyridazin-6-yl)-N,1-dimethyl-4-oxo-1,4,5,6-tetrahydropyrrolo[3,4-b]pyrrole-3-carboxamide;

Example 109: N-(6-(4-chlorophenyl)-5-(3-(difluoromethyl)-8-methyl-[1,2,4]triazolo[4,3-b]pyridazin-6-yl)-1-methyl-4-oxo-1,4,5,6-tetrahydropyrrolo[3,4-b]pyrrol-3-yl)acetamide;

Example 110: N-(6-(4-chlorophenyl)-5-(3-(difluoromethyl)-8-methyl-[1,2,4]triazolo[4,3-b]pyridazin-6-yl)-1-methyl-4-oxo-1,4,5,6-tetrahydropyrrolo[3,4-b]pyrrol-3-yl)-3-(dimethylamino)propanamide;

Example 111: 1-(6-(4-chlorophenyl)-5-(3-(difluoromethyl)-8-methyl-[1,2,4]triazolo[4,3-b]pyridazin-6-yl)-1-methyl-4-oxo-1,4,5,6-tetrahydropyrrolo[3,4-b]pyrrol-3-yl)-3-methylurea;

Example 112: 6-(4-chlorophenyl)-5-(1,4-dimethyl-1H-benzo[d][1,2,3]triazol-6-yl)-N-(2-(dimethylamino)ethyl)-1-methyl-4-oxo-1,4,5,6-tetrahydropyrrolo[3,4-b]pyrrole-3-carboxamide;

Example 113: N-(6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrol-3-yl)acetamide;

Example 114: 1-(6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrol-3-yl)-3-methylurea;

Example 115: N-(6-(4-chlorophenyl)-5-(1,4-dimethyl-1H-benzo[d][1,2,3]triazol-6-yl)-1-methyl-4-oxo-1,4,5,6-tetrahydropyrrolo[3,4-b]pyrrol-3-yl)-3-(dimethylamino)propanamide;

Example 116: N-(6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)-2-(dimethylamino)acetamide;

Example 117: 3-(1-acetylazetidin-3-yl)-6-(4-chlorophenyl)-5-(3,8-dimethyl-[1,2,4]triazolo[4,3-a]pyridin-6-yl)-1-methyl-5,6-dihydropyrrolo[3,4-b]pyrrol-4(1H)-one;

Example 118: 6-(4-chlorophenyl)-5-(3,8-dimethyl-[1,2,4]triazolo[4,3-a]pyridin-6-yl)-1-methyl-3-(1-methylazetidin-3-yl)-5,6-dihydropyrrolo[3,4-b]pyrrol-4(1H)-one;

Example 119: 6-(4-chlorophenyl)-3-cyclopropyl-2-(3,6-dihydro-2H-pyran-4-yl)-5-(3,8-dimethyl-[1,2,4]triazolo[4,3-a]pyridin-6-yl)-1-methyl-5,6-dihydropyrrolo[3,4-b]pyrrol-4(1H)-one;

Example 120: 6-(4-chlorophenyl)-3-cyclopropyl-5-(3,8-dimethyl-[1,2,4]triazolo[4,3-a]pyridin-6-yl)-2-(2-methoxypyridin-3-yl)-1-methyl-5,6-dihydropyrrolo[3,4-b]pyrrol-4(1H)-one;

Example 121: 6-(4-chlorophenyl)-3-cyclopropyl-5-(3,8-dimethyl-[1,2,4]triazolo[4,3-a]pyridin-6-yl)-1-methyl-2-(tetrahydro-2H-pyran-4-yl)-5,6-dihydropyrrolo[3,4-b]pyrrol-4(1H)-one;

Example 122: 6-(4-chlorophenyl)-3-cyclopropyl-5-(3,8-dimethyl-[1,2,4]triazolo[4,3-a]pyridin-6-yl)-1,2-dimethyl-5,6-dihydropyrrolo[3,4-b]pyrrol-4(1H)-one;

Example 123: Ethyl 6-(4-chlorophenyl)-2-(3,6-dihydro-2H-pyran-4-yl)-5-(3,8-dimethyl-[1,2,4]triazolo[4,3-a]pyridin-6-yl)-3-methyl-4-oxo-5,6-dihydropyrrolo[3,4-b]pyrrole-1(4H)-carboxylate;

Example 124: Ethyl 6-(4-chlorophenyl)-5-(3,8-dimethyl-[1,2,4]triazolo[4,3-a]pyridin-6-yl)-2-(2-methoxypyridin-3-yl)-3-methyl-4-oxo-5,6-dihydropyrrolo[3,4-b]pyrrole-1(4H)-carboxylate;

Example 125: Ethyl 6-(4-chlorophenyl)-3-cyclopropyl-5-(3,8-dimethyl-[1,2,4]triazolo[4,3-a]pyridin-6-yl)-4-oxo-5,6-dihydropyrrolo[3,4-b]pyrrole-1(4H)-carboxylate;

Example 126: 6-(4-chlorophenyl)-5-(3,8-dimethyl-[1,2,4]triazolo[4,3-a]pyridin-6-yl)-3-methyl-1-(1-methyl-2-oxopyrrolidin-3-yl)-5,6-dihydropyrrolo[3,4-b]pyrrol-4(1H)-one;

Example 127: 2-(6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrol-1(4H)-yl)-N-methylacetamide;

Example 128: 6-(4-chlorophenyl)-5-(3,8-dimethyl-[1,2,4]triazolo[4,3-a]pyridin-6-yl)-1-(2-(dimethylamino)ethyl)-3-methyl-5,6-dihydropyrrolo[3,4-b]pyrrol-4(1H)-one;

Example 129: 2-(6-(4-chlorophenyl)-5-(3,8-dimethyl-[1,2,4]triazolo[4,3-a]pyridin-6-yl)-3-methyl-4-oxo-5,6-dihydropyrrolo[3,4-b]pyrrol-1(4H)-yl)-N,N-dimethylacetamide;

Example 130: 3-(azetidin-3-yl)-6-(4-chlorophenyl)-5-(3,7-dimethyl-3H-[1,2,3]triazolo[4,5-b]pyridin-5-yl)-1-methyl-5,6-dihydropyrrolo[3,4-b]pyrrol-4(1H)-one;

Example 131: 6-(4-chlorophenyl)-5-(3,8-dimethyl-[1,2,4]triazolo[4,3-b]pyridazin-6-yl)-1-methyl-5,6-dihydropyrrolo[3,4-b]pyrrol-4(1H)-one;

Example 132: 6-(4-chlorophenyl)-5-(3-(difluoromethyl)-8-methyl-[1,2,4]triazolo[4,3-a]pyridin-6-yl)-N,1-dimethyl-4-oxo-1,4,5,6-tetrahydropyrrolo[3,4-b]pyrrole-3-carboxamide;

Example 133: N-(6-(4-chlorophenyl)-5-(3-(difluoromethyl)-8-methyl-[1,2,4]triazolo[4,3-a]pyridin-6-yl)-1-methyl-4-oxo-1,4,5,6-tetrahydropyrrolo[3,4-b]pyrrol-3-yl)acetamide;

Example 134: N-(6-(4-chlorophenyl)-5-(3-(difluoromethyl)-8-methyl-[1,2,4]triazolo[4,3-a]pyridin-6-yl)-1-methyl-4-oxo-1,4,5,6-tetrahydropyrrolo[3,4-b]pyrrol-3-yl)-2-(dimethylamino)acetamide;

Example 135: (R)-6-(4-chlorophenyl)-5-(3,8-dimethyl-[1,2,4]triazolo[4,3-a]pyridin-6-yl)-2-(2-methoxypyridin-3-yl)-1-methyl-5,6-dihydropyrrolo[3,4-b]pyrrol-4(1H)-one;

Example 136: (R)—N-(6-(4-chlorophenyl)-5-(3,8-dimethyl-[1,2,4]triazolo[4,3-a]pyridin-6-yl)-1-methyl-4-oxo-1,4,5,6-tetrahydropyrrolo[3,4-b]pyrrol-3-yl)acetamide; and Example 137: (R)-6-(4-chlorophenyl)-2-(3,6-dihydro-2H-pyran-4-yl)-5-(3,8-dimethyl-[1,2,4]triazolo[4,3-a]pyridin-6-yl)-1-methyl-5,6-dihydropyrrolo[3,4-b]pyrrol-4(1H)-one.

\* \* \* \* \*